(12) United States Patent
Swinney et al.

(10) Patent No.: US 10,231,932 B2
(45) Date of Patent: Mar. 19, 2019

(54) PROCESS OF PREPARING PHARMACEUTICAL COMPOSITIONS FOR THE TREATMENT OF CFTR MEDIATED DISEASES

(71) Applicant: VERTEX PHARMACEUTICALS INCORPORATED, Boston, MA (US)

(72) Inventors: Kelly Ann Swinney, Boston, MA (US); Patricia Nell Hurter, Harvard, MA (US); David E. Nadig, Dorchester, MA (US); David Smith, Newton, MA (US); Vance Hayden Thomas, Duxbury, MA (US); Martin Paul Warman, Hingham, MA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 179 days.

(21) Appl. No.: 15/035,969

(22) PCT Filed: Oct. 31, 2014

(86) PCT No.: PCT/US2014/063506
§ 371 (c)(1),
(2) Date: May 11, 2016

(87) PCT Pub. No.: WO2015/073231
PCT Pub. Date: May 21, 2015

(65) Prior Publication Data
US 2016/0354316 A1  Dec. 8, 2016

Related U.S. Application Data

(60) Provisional application No. 61/903,010, filed on Nov. 12, 2013, provisional application No. 61/929,604, filed on Jan. 21, 2014, provisional application No. 61/000,659, filed on May 20, 2014.

(51) Int. Cl.
| | | |
|---|---|---|
| A61K 9/14 | (2006.01) | |
| A61K 9/16 | (2006.01) | |
| A61K 9/20 | (2006.01) | |
| A61K 31/47 | (2006.01) | |
| A61K 45/06 | (2006.01) | |
| A61K 31/443 | (2006.01) | |

(52) U.S. Cl.
CPC .......... *A61K 9/2095* (2013.01); *A61K 9/1652* (2013.01); *A61K 9/1682* (2013.01); *A61K 9/1694* (2013.01); *A61K 9/2027* (2013.01); *A61K 9/2054* (2013.01); *A61K 9/2077* (2013.01); *A61K 31/443* (2013.01); *A61K 31/47* (2013.01); *A61K 45/06* (2013.01); *A61K 9/146* (2013.01)

(58) Field of Classification Search
None
See application file for complete search history.

(56) References Cited

U.S. PATENT DOCUMENTS

| | | |
|---|---|---|
| 3,758,475 A | 9/1973 | Hardtmann et al. |
| 4,501,729 A | 2/1985 | Boucher et al. |
| 5,739,345 A | 4/1998 | Fujita et al. |
| 5,876,700 A | 3/1999 | Boucher, Jr. et al. |
| 5,948,814 A | 9/1999 | Hwang et al. |
| 5,981,714 A | 11/1999 | Cheng et al. |
| 6,046,211 A | 4/2000 | Hansen, Jr. et al. |
| 6,426,331 B1 | 7/2002 | McKinney et al. |
| 6,479,483 B2 | 11/2002 | Bös et al. |
| 6,499,984 B1 | 12/2002 | Ghebre-Sellassie et al. |
| 6,627,646 B2 | 9/2003 | Bakale et al. |
| 6,770,637 B2 | 8/2004 | Godel et al. |
| 7,005,436 B2 | 2/2006 | Lloyd et al. |
| 7,223,778 B2 | 5/2007 | Ping et al. |
| 7,297,700 B2 | 11/2007 | Kelly et al. |
| 7,407,976 B2 | 8/2008 | Miller et al. |
| 7,446,117 B2 | 11/2008 | Beswick et al. |
| 7,476,744 B2 | 1/2009 | Ferro et al. |
| 7,482,469 B2 | 1/2009 | Palin et al. |
| 7,495,103 B2 | 2/2009 | Hadida-Ruah et al. |
| 7,553,855 B2 | 6/2009 | Young et al. |
| 7,585,885 B2 | 9/2009 | Shepherd et al. |
| 7,598,412 B2 | 10/2009 | Hadida Ruah et al. |
| 7,645,789 B2 | 1/2010 | Hadida Ruah et al. |

(Continued)

FOREIGN PATENT DOCUMENTS

| | | |
|---|---|---|
| AU | 2006311650 B2 | 2/2012 |
| CA | 2539250 A1 | 4/2005 |

(Continued)

OTHER PUBLICATIONS

Abadi, A. et al. (1999) Synthesis of 4-alkyl (aryl)-6-aryl-3-cyano-2(1H)-pyridinones and their 2-imino isosteres as nonsteroidal cardiotonic agents *Il Farmaco*, 54:195-201.

(Continued)

*Primary Examiner* — Mary Lynn F Theisen
(74) *Attorney, Agent, or Firm* — Finnegan, Henderson, Farabow, Garrett & Dunner LLP

(57) ABSTRACT

Processes of preparing pharmaceutical compositions comprising 3-(6-(1-(2,2-difluorobenzo[d][1,3]dioxol-5-yl) cyclopropanecarboxamido)-3-methylpyridin-2-yl)benzoic acid (Compound 1) in Form I and a solid dispersion comprising substantially amorphous N-(5-hydroxy-2,4-ditert-butyl-phenyl)-4-oxo-1H-quinoline-3-carboxamide (Compound 2), methods of treating, lessening the severity of or symptomatically treating CFTR mediated diseases, such as cystic fibrosis, methods of administering, and kits thereof are disclosed.

8 Claims, 26 Drawing Sheets

(56) References Cited

U.S. PATENT DOCUMENTS

| | | |
|---|---|---|
| 7,659,268 B2 | 2/2010 | Hadida-Ruah et al. |
| 7,671,221 B2 | 3/2010 | Hadida Ruah et al. |
| 7,691,902 B2 | 4/2010 | Hadida Ruah et al. |
| 7,741,321 B2 | 6/2010 | Hadida Ruah et al. |
| 7,754,739 B2 | 7/2010 | Hadida Ruah et al. |
| 7,776,905 B2 | 8/2010 | Hadida Ruah et al. |
| 7,846,951 B2 | 12/2010 | Miller et al. |
| 7,893,094 B2 | 2/2011 | Pollard et al. |
| 7,956,052 B2 | 6/2011 | Hadida Ruah et al. |
| 7,973,038 B2 | 7/2011 | Hadida Ruah et al. |
| 7,973,169 B2 | 7/2011 | Hadida Ruah et al. |
| 7,977,322 B2 | 7/2011 | Ruah et al. |
| 7,999,113 B2 | 8/2011 | Hadida-Ruah et al. |
| 8,012,999 B2 | 9/2011 | Hadida Ruah et al. |
| 8,039,491 B2 | 10/2011 | Hadida Ruah et al. |
| 8,076,357 B2 | 12/2011 | Young et al. |
| 8,101,767 B2 | 1/2012 | Ruah et al. |
| 8,124,781 B2 | 2/2012 | Siesel |
| 8,163,772 B2 | 4/2012 | DeMattei et al. |
| 8,188,283 B2 | 5/2012 | Binch et al. |
| 8,227,615 B2 | 7/2012 | Hadida-Ruah et al. |
| 8,232,302 B2 | 7/2012 | Miller et al. |
| 8,242,149 B2 | 8/2012 | Ruah et al. |
| 8,299,099 B2 | 10/2012 | Ruah et al. |
| 8,314,239 B2 | 11/2012 | Binch et al. |
| 8,314,256 B2 | 11/2012 | Ruah et al. |
| 8,318,733 B2 | 11/2012 | Hadida-Ruah et al. |
| 8,324,207 B2 | 12/2012 | Hadida Ruah et al. |
| 8,324,242 B2 | 12/2012 | Ruah et al. |
| 8,344,147 B2 | 1/2013 | Ambhaikar et al. |
| 8,354,427 B2 | 1/2013 | Van Goor |
| 8,362,253 B2 | 1/2013 | DeMattei et al. |
| 8,367,660 B2 | 2/2013 | Binch et al. |
| 8,389,727 B2 | 3/2013 | Zhang et al. |
| 8,399,479 B2 | 3/2013 | Binch et al. |
| 8,404,849 B2 | 3/2013 | Sun et al. |
| 8,404,865 B2 | 3/2013 | Ambhaikar et al. |
| 8,410,132 B2 | 4/2013 | Binch et al. |
| 8,410,274 B2 | 4/2013 | Hurter et al. |
| 8,415,387 B2 | 4/2013 | Ruah et al. |
| 8,431,605 B2 | 4/2013 | Hadida Ruah et al. |
| 8,436,014 B2 | 5/2013 | Zhang et al. |
| 8,461,156 B2 | 6/2013 | Hadida Ruah et al. |
| 8,461,342 B2 | 6/2013 | Siesel |
| 8,461,352 B2 | 6/2013 | Ambhaikar et al. |
| 8,471,029 B2 | 6/2013 | Arekar et al. |
| 8,476,442 B2 | 7/2013 | DeMattei et al. |
| 8,507,524 B2 | 8/2013 | Ruah et al. |
| 8,507,534 B2 | 8/2013 | Keshavarz-Shokri et al. |
| 8,507,687 B2 | 8/2013 | Keshavarz-Shokri et al. |
| 8,513,282 B2 | 8/2013 | Binch et al. |
| 8,524,767 B2 | 9/2013 | Miller et al. |
| 8,524,910 B2 | 9/2013 | Hadida Ruah et al. |
| 8,541,453 B2 | 9/2013 | Hadida-Ruah et al. |
| 8,552,006 B2 | 10/2013 | Binch et al. |
| 8,552,034 B2 | 10/2013 | Verwijs et al. |
| 8,563,573 B2 | 10/2013 | Ruah et al. |
| 8,563,593 B2 | 10/2013 | Alargova et al. |
| 8,575,209 B2 | 11/2013 | Ruah et al. |
| 8,586,615 B2 | 11/2013 | Hadida-Ruah et al. |
| 8,592,602 B2 | 11/2013 | Siesel |
| 8,598,181 B2 | 12/2013 | Hadida Ruah et al. |
| 8,598,205 B2 | 12/2013 | Binch et al. |
| 8,604,203 B2 | 12/2013 | Binch et al. |
| 8,609,703 B2 | 12/2013 | Ruah et al. |
| 8,614,325 B2 | 12/2013 | Yang et al. |
| 8,614,327 B2 | 12/2013 | Sheth et al. |
| 8,623,894 B2 | 1/2014 | DeMattei et al. |
| 8,623,905 B2 | 1/2014 | Ruah et al. |
| 8,629,162 B2 | 1/2014 | Hadida-Ruah et al. |
| 8,633,189 B2 | 1/2014 | Binch et al. |
| 8,642,609 B2 | 2/2014 | Makings et al. |
| 8,653,103 B2 | 2/2014 | Keshavarz-Shokri et al. |
| 8,674,108 B2 | 3/2014 | Luisi et al. |
| 8,710,075 B2 | 4/2014 | Binch et al. |
| 8,716,338 B2 | 5/2014 | Young |
| 8,722,704 B2 | 5/2014 | Hadida Ruah et al. |
| 8,741,922 B2 | 6/2014 | Zhang et al. |
| 8,741,925 B2 | 6/2014 | Hadida-Ruah et al. |
| 8,741,933 B2 | 6/2014 | Hadida Ruah et al. |
| 8,741,939 B2 | 6/2014 | Hadida Ruah et al. |
| 8,742,122 B2 | 6/2014 | Keshavarz-Shokri et al. |
| 8,748,612 B2 | 6/2014 | Binch et al. |
| 8,754,222 B2 | 6/2014 | Ambhaikar et al. |
| 8,754,224 B2 | 6/2014 | Hurter et al. |
| 8,759,335 B2 | 6/2014 | Hadida Ruah et al. |
| 8,765,957 B2 | 7/2014 | DeMattei et al. |
| 8,785,476 B2 | 7/2014 | Arekar et al. |
| 8,785,640 B2 | 7/2014 | Binch et al. |
| 8,796,308 B2 | 8/2014 | Yang et al. |
| 8,796,312 B2 | 8/2014 | Hadida Ruah et al. |
| 8,802,700 B2 | 8/2014 | Sheth et al. |
| 8,802,844 B2 | 8/2014 | Gallardo-Godoy et al. |
| 8,802,868 B2 | 8/2014 | Keshavarz-Shokri et al. |
| 8,816,093 B2 | 8/2014 | Siesel |
| 8,822,451 B2 | 9/2014 | Ruah et al. |
| 8,829,204 B2 | 9/2014 | Hadida-Ruah et al. |
| 8,835,639 B2 | 9/2014 | DeMattei et al. |
| 8,846,718 B2 | 9/2014 | Keshavarz-Shokri et al. |
| 8,846,753 B2 | 9/2014 | Hadida Ruah et al. |
| 8,853,254 B2 | 10/2014 | Hadida Ruah et al. |
| 8,853,415 B2 | 10/2014 | Hadida Ruah et al. |
| 8,883,206 B2 | 11/2014 | Doukou et al. |
| 8,884,018 B2 | 11/2014 | Ambhaikar et al. |
| 8,889,875 B2 | 11/2014 | Ruah et al. |
| 8,912,199 B2 | 12/2014 | Hadida Ruah et al. |
| 8,952,049 B2 | 2/2015 | Ruah et al. |
| 8,952,050 B2 | 2/2015 | Ruah et al. |
| 8,962,856 B2 | 2/2015 | Hadida-Ruah et al. |
| 8,969,382 B2 | 3/2015 | Binch et al. |
| 8,969,386 B2 | 3/2015 | Hadida-Ruah et al. |
| 8,969,574 B2 | 3/2015 | Keshavarz-Shokri et al. |
| 8,993,600 B2 | 3/2015 | Hadida Ruah et al. |
| 8,999,976 B2 | 4/2015 | Binch et al. |
| 9,012,473 B2 | 4/2015 | Hadida Ruah et al. |
| 9,012,496 B2 | 4/2015 | Alargova et al. |
| 9,012,652 B2 | 4/2015 | Siesel |
| 9,035,072 B2 | 5/2015 | Belmont et al. |
| 9,045,425 B2 | 6/2015 | Luisi et al. |
| 9,051,303 B2 | 6/2015 | Keshavarz-Shokri et al. |
| 9,051,324 B2 | 6/2015 | Binch et al. |
| 9,079,916 B2 | 7/2015 | Hadida Ruah et al. |
| 9,090,619 B2 | 7/2015 | Hadida-Ruah et al. |
| 9,102,672 B2 | 8/2015 | Hadida-Ruah et al. |
| 9,139,530 B2 | 9/2015 | Hurter et al. |
| 9,150,552 B2 | 10/2015 | Keshavarz-Shokri et al. |
| 9,192,606 B2 | 11/2015 | Young |
| 9,216,969 B2 | 12/2015 | Ruah et al. |
| 9,241,934 B2 | 1/2016 | Verwijs et al. |
| 9,249,131 B2 | 2/2016 | Hadida Ruah et al. |
| 9,254,291 B2 | 2/2016 | Looker et al. |
| 9,314,455 B2 | 4/2016 | Keshavarz-Shokri et al. |
| 9,321,725 B2 | 4/2016 | Miller et al. |
| 9,351,962 B2 | 5/2016 | Hadida Ruah et al. |
| 9,371,287 B2 | 6/2016 | DeMattei et al. |
| 9,399,648 B2 | 7/2016 | Gallardo-Godoy |
| 9,434,717 B2 | 9/2016 | Keshavarz-Shokri et al. |
| 9,504,683 B2 | 11/2016 | Hadida Ruah et al. |
| 9,522,145 B2 | 12/2016 | Hadida Ruah et al. |
| 9,550,761 B2 | 1/2017 | Hadida-Ruah et al. |
| 9,670,163 B2 | 6/2017 | Hurter et al. |
| 9,701,639 B2 | 7/2017 | Strohmeier et al. |
| 9,725,440 B2 | 8/2017 | Hadida-Ruah et al. |
| 9,732,080 B2 | 8/2017 | Hadida-Ruah et al. |
| 9,751,839 B2 | 9/2017 | DeMattei et al. |
| 9,751,890 B2 | 9/2017 | Hadida Ruah et al. |
| 9,758,510 B2 | 9/2017 | Hadida Ruah et al. |
| 9,776,968 B2 | 10/2017 | Siesel |
| 9,840,499 B2 | 12/2017 | Keshavarz-Shokri et al. |
| 9,931,334 B2 | 4/2018 | Hurter et al. |
| 9,974,781 B2 | 5/2018 | Hadida Ruah et al. |
| 10,022,352 B2 | 7/2018 | Hadida Ruah et al. |
| 10,058,546 B2 | 8/2018 | Alargova et al. |
| 10,071,979 B2 | 9/2018 | Tanoury et al. |

(56) References Cited

U.S. PATENT DOCUMENTS

| | | |
|---|---|---|
| 10,081,621 B2 | 9/2018 | Keshavarz-Shokri et al. |
| 2002/0115619 A1 | 8/2002 | Rubenstein et al. |
| 2003/0125315 A1 | 7/2003 | Mjalli et al. |
| 2004/0110832 A1 | 6/2004 | Mjalli et al. |
| 2004/0220191 A1 | 11/2004 | Schwink et al. |
| 2005/0013861 A1 | 1/2005 | Sherwood et al. |
| 2005/0070718 A1 | 3/2005 | Lubisch et al. |
| 2005/0113379 A1 | 5/2005 | Ge et al. |
| 2005/0113423 A1 | 5/2005 | Van Goor et al. |
| 2006/0003005 A1 | 1/2006 | Cao et al. |
| 2006/0069110 A1 | 3/2006 | Andersen et al. |
| 2006/0173050 A1 | 8/2006 | Liu et al. |
| 2007/0078120 A1 | 4/2007 | Ban et al. |
| 2007/0142411 A1 | 6/2007 | Hagan et al. |
| 2008/0138803 A1 | 6/2008 | Galvan-Goldman (nee Galvan) et al. |
| 2008/0260820 A1 | 10/2008 | Borrelly et al. |
| 2009/0105272 A1 | 4/2009 | Grootenhuis et al. |
| 2009/0176839 A1 | 7/2009 | Keshavarez-Shokri et al. |
| 2009/0246820 A1 | 10/2009 | Singh et al. |
| 2010/0036130 A1 | 2/2010 | Siesel |
| 2010/0074949 A1 | 3/2010 | Rowe et al. |
| 2010/0125090 A1 | 5/2010 | Hadida Ruah et al. |
| 2010/0144798 A1 | 6/2010 | Van Goor et al. |
| 2010/0256184 A1 | 10/2010 | Rowe et al. |
| 2011/0064811 A1 | 3/2011 | Hurter et al. |
| 2011/0098311 A1 | 4/2011 | Van Goor et al. |
| 2011/0177999 A1 | 7/2011 | Singh et al. |
| 2011/0251253 A1 | 10/2011 | Keshavarz-Shokri et al. |
| 2011/0257223 A1 | 10/2011 | Goor et al. |
| 2011/0288122 A1 | 11/2011 | Van Goor et al. |
| 2012/0035179 A1 | 2/2012 | Hadida-Ruah et al. |
| 2012/0046330 A1 | 2/2012 | Alargova et al. |
| 2012/0061869 A1 | 3/2012 | Boeckx et al. |
| 2012/0064157 A1 | 3/2012 | Doukou et al. |
| 2012/0122921 A1 | 5/2012 | DeMattei et al. |
| 2012/0122922 A1 | 5/2012 | Young et al. |
| 2012/0184583 A1 | 7/2012 | Van Goor et al. |
| 2012/0220625 A1 | 8/2012 | Rowe et al. |
| 2012/0232059 A1 | 9/2012 | Hadida-Ruah et al. |
| 2012/0258983 A1 | 10/2012 | Rowe et al. |
| 2013/0012536 A1 | 1/2013 | Hadida Ruah et al. |
| 2013/0018071 A1 | 1/2013 | Arekar et al. |
| 2013/0085158 A1 | 4/2013 | Keshavarz-Shokri et al. |
| 2013/0090354 A1 | 4/2013 | Van Goor et al. |
| 2013/0095181 A1 | 4/2013 | Verwijs et al. |
| 2013/0131107 A1 | 5/2013 | Van Goor et al. |
| 2013/0143919 A1 | 6/2013 | Van Goor et al. |
| 2013/0158071 A1 | 6/2013 | Van Goor et al. |
| 2013/0186801 A1 | 7/2013 | Verwijs et al. |
| 2013/0224293 A1 | 8/2013 | Dokou et al. |
| 2013/0231368 A1 | 9/2013 | Zhang et al. |
| 2013/0245010 A1 | 9/2013 | Hadida Ruah et al. |
| 2013/0245011 A1 | 9/2013 | Hadida Ruah et al. |
| 2013/0303484 A1 | 11/2013 | Grootenhuis et al. |
| 2013/0331567 A1 | 12/2013 | Hadida-Ruah et al. |
| 2014/0023706 A1 | 1/2014 | Verwijs et al. |
| 2014/0080825 A1 | 3/2014 | Hadida-Ruah et al. |
| 2014/0094499 A1 | 4/2014 | Alargova et al. |
| 2014/0112988 A1 | 4/2014 | Rowe et al. |
| 2014/0121208 A1 | 5/2014 | Van Goor et al. |
| 2014/0142138 A1 | 5/2014 | Van Goor et al. |
| 2014/0155431 A1 | 6/2014 | Hadida-Ruah et al. |
| 2014/0155626 A1 | 6/2014 | Hadida-Ruah et al. |
| 2014/0163011 A1 | 6/2014 | Hadida-Ruah et al. |
| 2014/0163068 A1 | 6/2014 | Verwijs et al. |
| 2014/0221424 A1 | 8/2014 | Zha |
| 2014/0235668 A1 | 8/2014 | Binch et al. |
| 2014/0243289 A1 | 8/2014 | Grootenhuis et al. |
| 2014/0303204 A1 | 10/2014 | Binch et al. |
| 2014/0303205 A1 | 10/2014 | Yang et al. |
| 2014/0315948 A1 | 10/2014 | Rowe et al. |
| 2014/0323521 A1 | 10/2014 | Van Goor et al. |
| 2014/0329855 A1 | 11/2014 | Arekar et al. |
| 2014/0336393 A1 | 11/2014 | Ambhaikar et al. |
| 2014/0343098 A1 | 11/2014 | Sheth et al. |
| 2014/0350281 A1 | 11/2014 | DeMattei et al. |
| 2015/0010628 A1 | 1/2015 | Dokou et al. |
| 2015/0024047 A1 | 1/2015 | Dokou et al. |
| 2015/0031722 A1 | 1/2015 | Hadida-Ruah et al. |
| 2015/0065487 A1 | 3/2015 | Hadida-Ruah et al. |
| 2015/0065497 A1 | 3/2015 | Hadida-Ruah et al. |
| 2015/0065500 A1 | 3/2015 | Hadida-Ruah et al. |
| 2015/0080431 A1 | 3/2015 | Van Goor et al. |
| 2015/0094304 A1 | 4/2015 | Ruah et al. |
| 2015/0119441 A1 | 4/2015 | Hadida Ruah et al. |
| 2015/0150879 A2 | 6/2015 | Van Goor et al. |
| 2015/0166516 A1 | 6/2015 | Hadida-Ruah et al. |
| 2015/0174098 A1 | 6/2015 | Ruah et al. |
| 2015/0182517 A1 | 7/2015 | Alargova et al. |
| 2015/0203478 A1 | 7/2015 | Keshavarz-Shokri et al. |
| 2015/0218122 A1 | 8/2015 | Tanoury et al. |
| 2015/0231142 A1 | 8/2015 | Van Goor et al. |
| 2015/0246031 A1 | 9/2015 | Dokou et al. |
| 2015/0293078 A1 | 10/2015 | Singh et al. |
| 2015/0320736 A1 | 11/2015 | Phenix et al. |
| 2015/0336898 A1 | 11/2015 | Grootenhuis et al. |
| 2015/0336956 A1 | 11/2015 | Hadida-Ruah et al. |
| 2016/0022664 A2 | 1/2016 | Van Goor et al. |
| 2016/0022665 A2 | 1/2016 | Van Goor et al. |
| 2016/0039800 A1 | 2/2016 | Young |
| 2016/0067239 A9 | 3/2016 | Van Goor et al. |
| 2016/0095858 A1 | 4/2016 | Miller et al. |
| 2016/0096807 A1 | 4/2016 | Strohmeier et al. |
| 2016/0143898 A1 | 5/2016 | Hadida Ruah et al. |
| 2016/0166540 A1 | 6/2016 | Looker et al. |
| 2016/0200712 A1 | 7/2016 | Siesel |
| 2016/0213648 A1 | 7/2016 | Duncton et al. |
| 2016/0221952 A1 | 8/2016 | Yang et al. |
| 2016/0221995 A1 | 8/2016 | Keshavarz-Shokri et al. |
| 2016/0228414 A1 | 8/2016 | Hadida Ruah et al. |
| 2016/0229806 A1 | 8/2016 | Hurter et al. |
| 2016/0237079 A1 | 8/2016 | Hadida Ruah et al. |
| 2016/0271105 A1 | 9/2016 | Hadida Ruah et al. |
| 2016/0303096 A1 | 10/2016 | Verwijs et al. |
| 2016/0318931 A1 | 11/2016 | Hadida Ruah et al. |
| 2016/0324788 A1 | 11/2016 | Verwijs |
| 2016/0324846 A1 | 11/2016 | Verwijs et al. |
| 2016/0332997 A1 | 11/2016 | Hadida Ruah et al. |
| 2017/0087144 A1 | 3/2017 | Rowe et al. |
| 2017/0096396 A1 | 4/2017 | DeMattei et al. |
| 2017/0100340 A1 | 4/2017 | Dokou et al. |
| 2017/0107205 A1 | 4/2017 | Hadida Ruah et al. |
| 2017/0107206 A1 | 4/2017 | Hadida Ruah et al. |
| 2017/0107225 A1 | 4/2017 | Hadida Ruah et al. |
| 2018/0008546 A1 | 1/2018 | Verwijs et al. |
| 2018/0127398 A1 | 5/2018 | Keshavarz-Shokri et al. |
| 2018/0153874 A1 | 6/2018 | Van Goor et al. |
| 2018/0162842 A1 | 6/2018 | Hadida Ruah et al. |

FOREIGN PATENT DOCUMENTS

| | | |
|---|---|---|
| CA | 2605300 A1 | 10/2006 |
| CA | 2736545 A1 | 4/2010 |
| CN | 1335771 A | 2/2002 |
| CN | 1356988 A | 7/2002 |
| CN | 1938279 A | 3/2007 |
| CN | 101006076 A | 7/2007 |
| CN | 101198333 A | 6/2008 |
| CN | 101287732 A | 10/2008 |
| CN | 101460489 A | 6/2009 |
| CN | 102058889 A | 5/2011 |
| CN | 102164587 A | 8/2011 |
| CN | 102438578 A | 5/2012 |
| EP | 0081756 A1 | 6/1983 |
| EP | 0574174 A2 | 12/1993 |
| EP | 0591830 A1 | 4/1994 |
| EP | 1026149 A1 | 8/2000 |
| EP | 2231606 B1 | 2/2013 |
| EP | 2615085 A1 | 7/2013 |
| JP | 58-121274 A | 7/1983 |
| JP | 5-78356 A | 3/1993 |
| JP | 8-301870 A | 11/1996 |
| JP | 2002-114777 A | 4/2002 |

(56) References Cited

FOREIGN PATENT DOCUMENTS

| | | |
|---|---|---|
| JP | 2003-501420 A | 1/2003 |
| JP | 2003-155285 A | 5/2003 |
| JP | 2003-519698 A | 6/2003 |
| JP | 2003-221386 A | 8/2003 |
| JP | 2004-520394 A | 7/2004 |
| JP | 2005-053902 A | 3/2005 |
| JP | 2005-508904 A | 4/2005 |
| JP | 2005-525389 A | 8/2005 |
| JP | 2005-529114 A | 9/2005 |
| JP | 2006-507247 A | 3/2006 |
| JP | 2006-508016 A | 3/2006 |
| JP | 2006-512338 A | 4/2006 |
| JP | 2007-511572 A | 5/2007 |
| JP | 2007-518791 A | 7/2007 |
| JP | 2007-519740 A | 7/2007 |
| JP | 2007-533740 A | 11/2007 |
| JP | 2008-504097 A | 2/2008 |
| JP | 2008-516639 A | 5/2008 |
| JP | 2011-529101 A | 12/2011 |
| JP | 2011-530598 A | 12/2011 |
| JP | 5165586 B2 | 3/2013 |
| JP | 5317184 B2 | 10/2013 |
| JP | 5497633 B2 | 5/2014 |
| JP | 2015-504920 A | 2/2015 |
| JP | 5666525 B2 | 2/2015 |
| JP | 5702149 B2 | 2/2015 |
| RU | 96121599 A | 2/1999 |
| RU | 2154064 C2 | 8/2000 |
| WO | WO 1995/06046 A1 | 3/1995 |
| WO | WO 1996/10027 A1 | 4/1996 |
| WO | WO 1996/19444 A1 | 6/1996 |
| WO | WO 1997/36876 A1 | 10/1997 |
| WO | WO 1998/07420 A1 | 2/1998 |
| WO | WO 1998/28980 A1 | 7/1998 |
| WO | WO 1998/35681 A1 | 8/1998 |
| WO | WO 1998/47868 A1 | 10/1998 |
| WO | WO 1999/41405 A1 | 8/1999 |
| WO | WO 1999/64394 A1 | 12/1999 |
| WO | WO 2000/16798 A1 | 3/2000 |
| WO | WO 2000/35452 A1 | 6/2000 |
| WO | WO 2000/50398 A2 | 8/2000 |
| WO | WO 2000/50401 A1 | 8/2000 |
| WO | WO 2000/75120 A1 | 12/2000 |
| WO | WO 2001/46165 A2 | 6/2001 |
| WO | WO 2001/51919 A2 | 7/2001 |
| WO | WO 2001/54690 A1 | 8/2001 |
| WO | WO 2001/56989 A2 | 8/2001 |
| WO | WO 2001/81317 A1 | 11/2001 |
| WO | WO 2001/92235 A1 | 12/2001 |
| WO | WO 2002/16324 A1 | 2/2002 |
| WO | WO 2002/22601 A1 | 3/2002 |
| WO | WO 2002/30875 A1 | 4/2002 |
| WO | WO 2002/34739 A1 | 5/2002 |
| WO | WO 2002/38107 A2 | 5/2002 |
| WO | WO 2002/44183 A2 | 6/2002 |
| WO | WO 2002/62804 A1 | 8/2002 |
| WO | WO 2002/79134 A1 | 10/2002 |
| WO | WO 2002/85458 A2 | 10/2002 |
| WO | WO 2002/96421 A1 | 12/2002 |
| WO | WO 2003/006016 A2 | 1/2003 |
| WO | WO 2003/007888 A2 | 1/2003 |
| WO | WO 2003/007945 A1 | 1/2003 |
| WO | WO 2003/022852 A2 | 3/2003 |
| WO | WO 2003/042191 A1 | 5/2003 |
| WO | WO 2003/055482 A1 | 7/2003 |
| WO | WO 2003/063797 A2 | 8/2003 |
| WO | WO 2003/082186 A2 | 10/2003 |
| WO | WO 2003/084997 A1 | 10/2003 |
| WO | WO 2003/088908 A2 | 10/2003 |
| WO | WO 2003/105788 A2 | 12/2003 |
| WO | WO 2004/024691 A1 | 3/2004 |
| WO | WO 2004/035571 A1 | 4/2004 |
| WO | WO 2004/041163 A2 | 5/2004 |
| WO | WO 2004/047974 A1 | 6/2004 |
| WO | WO 2004/054505 A2 | 7/2004 |
| WO | WO 2004/063179 A1 | 7/2004 |
| WO | WO 2004/072038 A1 | 8/2004 |
| WO | WO 2004/099168 A2 | 11/2004 |
| WO | WO 2005/000300 A1 | 1/2005 |
| WO | WO 2005/023806 A2 | 3/2005 |
| WO | WO 2005/026137 A2 | 3/2005 |
| WO | WO 2005/030702 A1 | 4/2005 |
| WO | WO 2005/030755 A1 | 4/2005 |
| WO | WO 2005/039589 A2 | 5/2005 |
| WO | WO 2005/044797 A1 | 5/2005 |
| WO | WO 2005/049018 A1 | 6/2005 |
| WO | WO 2005/049034 A2 | 6/2005 |
| WO | WO 2005/075435 A1 | 8/2005 |
| WO | WO 2005/080348 A1 | 9/2005 |
| WO | WO 2005/080381 A1 | 9/2005 |
| WO | WO 2005/100353 A1 | 10/2005 |
| WO | WO 2005/108391 A1 | 11/2005 |
| WO | WO 2005/115399 A2 | 12/2005 |
| WO | WO 2005/123569 A1 | 12/2005 |
| WO | WO 2006/002421 A2 | 1/2006 |
| WO | WO 2006/003504 A1 | 1/2006 |
| WO | WO 2006/014012 A2 | 2/2006 |
| WO | WO 2006/040520 A1 | 4/2006 |
| WO | WO 2006/051394 A1 | 5/2006 |
| WO | WO 2006/063999 A1 | 6/2006 |
| WO | WO 2006/067931 A1 | 6/2006 |
| WO | WO 2006/080884 A1 | 8/2006 |
| WO | WO 2006/082952 A1 | 8/2006 |
| WO | WO 2006/108127 A2 | 10/2006 |
| WO | WO 2006/108695 A2 | 10/2006 |
| WO | WO 2006/113704 A2 | 10/2006 |
| WO | WO 2006/113919 A2 | 10/2006 |
| WO | WO 2006/115834 A1 | 11/2006 |
| WO | WO 2006/116218 A1 | 11/2006 |
| WO | WO 2006/129199 A1 | 12/2006 |
| WO | WO 2006/130403 A1 | 12/2006 |
| WO | WO 2006/136829 A2 | 12/2006 |
| WO | WO 2007/021982 A2 | 2/2007 |
| WO | WO 2007/028654 A1 | 3/2007 |
| WO | WO 2007/039420 A1 | 4/2007 |
| WO | WO 2007/045462 A2 | 4/2007 |
| WO | WO 2007/054480 A1 | 5/2007 |
| WO | WO 2007/056341 A1 | 5/2007 |
| WO | WO 2007/067506 A | 6/2007 |
| WO | WO 2007/075946 A1 | 7/2007 |
| WO | WO 2007/079139 A2 | 7/2007 |
| WO | WO 2007/079257 A2 | 7/2007 |
| WO | WO 2007/087066 A2 | 8/2007 |
| WO | WO 2007/117715 A2 | 10/2007 |
| WO | WO 2007/134279 A2 | 11/2007 |
| WO | WO 2008/065068 A2 | 6/2008 |
| WO | WO 2008/127399 A2 | 10/2008 |
| WO | WO 2008/137787 A2 | 11/2008 |
| WO | WO 2008/141119 A2 | 11/2008 |
| WO | WO 2008/147952 A1 | 12/2008 |
| WO | WO 2009/006315 A1 | 1/2009 |
| WO | WO 2009/023509 A2 | 2/2009 |
| WO | WO 2009/033561 A1 | 3/2009 |
| WO | WO 2009/036412 A1 | 3/2009 |
| WO | WO 2009/038683 A2 | 3/2009 |
| WO | WO 2009/038913 A2 | 3/2009 |
| WO | WO 2009/073757 A1 | 6/2009 |
| WO | WO 2009/074749 A2 | 6/2009 |
| WO | WO 2009/076141 A2 | 6/2009 |
| WO | WO 2009/076142 A2 | 6/2009 |
| WO | WO 2009/076593 A1 | 6/2009 |
| WO | WO 2009/123896 A1 | 10/2009 |
| WO | WO 2010/013035 A1 | 2/2010 |
| WO | WO 2010/019239 A2 | 2/2010 |
| WO | WO 2010/037066 A2 | 4/2010 |
| WO | WO 2010/048526 A2 | 4/2010 |
| WO | WO 2010/048564 A2 | 4/2010 |
| WO | WO 2010/053471 A1 | 5/2010 |
| WO | WO 2010/054138 A2 | 5/2010 |
| WO | WO 2010/128359 A1 | 11/2010 |
| WO | WO 2010/138484 A2 | 12/2010 |
| WO | WO 2011/127241 A2 | 10/2011 |
| WO | WO 2011/133951 A1 | 10/2011 |
| WO | WO 2011/133953 A1 | 10/2011 |

(56) References Cited

FOREIGN PATENT DOCUMENTS

| WO | WO 2011/133956 A1 | 10/2011 |
|---|---|---|
| WO | WO 2001/83517 A1 | 11/2011 |
| WO | WO 2013/112804 A1 | 8/2013 |
| WO | WO 2013/185112 A1 | 12/2013 |
| WO | WO 2014/014841 A1 | 1/2014 |
| WO | WO 2014/055501 A1 | 4/2014 |
| WO | WO 2014/071122 A1 | 5/2014 |
| WO | WO 2016/086103 A1 | 6/2016 |
| WO | WO 2016/086136 A1 | 6/2016 |
| WO | WO 2016/087665 A2 | 6/2016 |
| WO | WO 2016/185423 A1 | 11/2016 |

OTHER PUBLICATIONS

Amaral, M. D. and C.M. Farinha (2013) "Rescuing Mutant CFTR: A Multi-task Approach to a Better Outcome in Treating Cystic Fibrosis" *Curr Pharm Des*, 19:3497-3508.

Aventis Pharmaceuticals, Inc. (May 12, 2003) Prescribing Information for Allegra® (10 pages).

Batt, D.G. and G.C. Houghton (May 1995) "Polyfunctional pyridines from nitroacetamidine and β-diketones. A useful synthesis of substituted imidazo [4,5-b] pyridines and related compounds" *J Heterocycl Chem*, 32(3):963-969.

Bavin, M. (Aug. 1989) "Polymorphism in Process Development" *Chemistry & Industry*, 16:527-529.

Bazant, V. et al. (Jan. 1968) "Properties of sodium-bis-(2-methoxyethoxy)aluminumhydride. I. Reduction of some organic functional groups" *Tetrahedron Letters*, 9(29):3303-3306.

Bell, T.W. et al. (Oct. 16, 1995) "Highly Effective Hydrogen-Bonding Receptors for Guanine Derivatives" *Angewandte Chemie—International Edition*, 34(19):2163-2165.

Bernstein, J. (2002) *Polymorphism in Molecular Crystals*. Oxford: Oxford Science Publications; Chapters 1 and 7, pp. 1-28 and 240-256.

Bernstein, J. (2002) *Polymorphism in Molecular Crystals*. Oxford: Oxford Science Publications; pp. 9-10.

Bhalerao, U.T. et al. (Jul. 1995) "A mild and efficient method for the dehydrogenation of dihydropyrido-pyrimidinones and related compounds by using active $MnO_2$" *Indian J Chem*, 34B:587-590.

Bhattacharya, S. et al. (2009) "Thermoanalytical and Crystallographic Methods" in *Polymorphism in Pharmaceutical Solids*. 2nd edition. Harry G. Brittain (ed.) New York, NY: Informa Healthcare USA, Inc.; pp. 318-335.

Bombieri, C. et al. (1998) "Complete mutational screening of the CFTR gene in 120 patients with pulmonary disease" *Hum Genet*, 103:718-722.

Boyle, M.P. et al. (Oct. 1, 2011) "VX-809, an Investigational CFTR Corrector, in Combination With VX-770, an Investigational CFTR Potentiator, in Subjects With CF and Homozygous for the F508del-CFTR Mutation" *Pediatric Pulmonology*, 46:287, Abstract 212.

Braga, D. et al. (2009) "Crystal Polymorphism and Multiple Crystal Forms" *Struct Bond*, 132:25-27.

Brittain (Ed.) (1999) *Polymorphism on Pharmaceutical Science*. NY:Marcel Dekker, Inc.; pp. 1-2, 183-226, 235-238.

Bryn, S. et al. (1995) "Pharmaceutical Solids: A Strategic Approach to Regulatory Considerations" *Pharmaceutical Research*, 12(7):945-954.

Cabeza, J. A. et al. (2004) "Triruthenium, Hexaruthenium, and Triosmium Carbonyl Derivatives of 2-Amino-6-phenylpyridine" *Organometallics*, 23(5):1107-1115.

Caira, M.R. (1998) "Crystalline Polymorphism of Organic Compounds" in *Topics in Current Chemistry*, vol. 198, pp. 163-208.

CAPLUS Database Accession No. 1960:17025; Document No. 54:17025. Ridi, M. (1959) *Annali di Chimica*, 49:944-957 (2 pages).

CAPLUS Database Accession No. 1970:435253; Document No. 73:352253. Van Allan, J.A. et al. (1970) *J Heterocycl Chem*, 7(3):495-507 (1 page).

CAPLUS Database Accession No. 1979:420373; Document No. 91:20373. Nantka-Namirski, P. et al. (1978) *Polish Journal of Pharmacology and Pharmacy*, 30(4):569-572 (2 pages).

CAPLUS Database Accession No. 1988:186521; Document No. 108:186521. Mertens, H. et al. (1987) *Archiv der Pharmazie*, 320(11):1143-1149 (2 pages).

CAPLUS Database Accession No. 1991:6375; Document No. 114:6375. Jure, M. et al. (1990) *Latvijas PSR Zinatnu Akademijas Vestis, Kimijas Serija*, 4:439-444 (3 pages).

CAPLUS Database Accession No. 1994:244582; Document No. 120:244582. Troscheutz, R. et al. (1994) *Archiv der Pharmazie*, 327(2):85-89 (1 page).

CAPLUS Database Accession No. 2005:406839; Document No. 143:248209; RN 134643-28-0. Spitzner (2005) *Science of Synthesis*, 15:11-284 (1 page).

Carnegie Mellon, Dept. of Physics (2002) "CMU Seed Fund Project on Detection and Control of Pharmaceutical Polymorphism" [online]. Retrieved from the Internet: http://andrew.cmu.edu/user/suter/polymorph.html; on Apr. 3, 2008, 3 pages.

Cerny, M. et al. (Mar. 1969) "Properties of sodium bis(2-methoxyethoxy)aluminum hydride. III. Reduction of carboxylic acids and their derivatives" *Collection of Czechoslovak Chemical Communications, Institute of Organic Chemistry & Biochemistry*, 34(3):1025-1032.

Clancy, J.P. et al. (Jan. 2012) "Results of a phase IIa study of VX-809, an investigational CFTR corrector compound, in subjects with cystic fibrosis homozygous for the F508del-CFTR mutation" *Thorax*, 67(1):12-18. NIH Public Access Author Manuscript; available in PMC Aug. 19, 2013 (16 pages).

*Concise Encyclopedia Chemistry*, NY: Walter de Gruyter, 1993, pp. 872-873.

Corning Inc. (2013) "Corning® Gentest™ ATPase Assay Kit. Colorimetric Reagent Kit for ABC Transporter Membrane ATPase Assays" Product information, 2 pages.

Costa, M. et al. (2005 Jun) "Diabetes: a major co-morbidity of cystic fibrosis" *Diabetes Metab*, 31(3 Pt 1):221-232 (French; English summary on p. 221).

Cowart, M. et al. (Jan. 2001) "Structure-activity studies of 5-substituted pyridopyrimidines as adenosine kinase inhibitors" *Bioorg Med Chem Lett*, 11(1):83-86.

Cystic Fibrosis Foundation (2006) *Annual Report*. (58 pages).

Dahl, M. et al. (Oct. 9, 2005) "Asthma and COPD in cystic fibrosis intron-8 5T carriers. A population-based study" *Respiratory Research*, 6:113, doi:10.1186/1465-9921-6-113, 9 pages.

Dahl, M. and B.G. Nordestgaard (2009) "Markers of early disease and prognosis in COPD" *Intl J COPD*, 4:157-167.

Damasio, A.R. (1996) "Alzheimer's Disease and Related Dementias" in *Cecil Textbook of Medicine*. 20th edition. J. Claude Bennett and F. Plum (Eds.). Philadelphia: W.B. Saunders Co.; vol. 2, pp. 1992-1996.

Danswan, G. et al. (1989) "Synthesis of (imidazo[1,2-C]pyrimidin-2-yl)phenylmethanones and 6-benzoylpyrrolo[2,3-D]pyrimidinones" *J Heterocyclic Chem*, 26(2):293-299.

Davidovich et al. (2004) "Detection of Polymorphism by Powder X-Ray Diffraction: Interference by Preferred Orientation" *American Pharmaceutical Review*, 7(1):10, 12, 14, 16 and 100.

Dhenge, R.M. et al. (2010) "Twin screw wet granulation: Granule properties" *Chemical Engineering Journal*, 164:322-329.

Doelker, E. (2002) "Modifications Cyrisallines et Transformations Polymorphes au Cours des Operations Galeniques (Crystalline Modifications and Polymorphous Changes During Drug Manufacture" English translation of *Ann. Pharm. Fr.*, 60:161-176 (40 pages).

Doelker, E. (1999) "Physicochemical Behaviors of Active Substances Their Consequences for the Feasibility and the Stability of Pharmaceutical Forms" *S.T.P. Pharma Pratiques*, 9(5):399-409. French with English translation. Yes.

Dornow, A. and P. Karlson (1940) "Über eine neue Synthese von 2-Amino-pyridin-Derivaten" *Berichte der Deutschen Chemischen Gesellschaft A/B*, 73(5):542-546.

Dornow, A. and E. Neuse (1951) "Über die Reaktion von Amidinen mit β-Dicarbonyl-Verbindungen" *Chemische Berichte*, 84:296-304 (German).

(56) References Cited

OTHER PUBLICATIONS

Dörwald, F.Z. (2005) *Side Reactions in Organic Synthesis*. Weinheim, Germany: Wiley-VCH; Preface, pp. 1-15 and Chapter 8, pp. 279-308.
Elkady, M. et al. (1980) "Some reactions of β-aroylacrylic acids" *Revue Roumanie de Chimie*, 25:1361-1366.
Evens, G. and P. Caluwe (1975) "Pyrido[2,3-d]pyrimidines. Latent 2-Aminonicotinaldehydes" *J Org Chem*, 40(10):1438-1439.
Farhanullah et al. (2003) "Synthesis of Aminonicotinonitriles and Diaminopyridines through Base-Catalyzed Ring Transformation of 2H-Pyran-2-ones" *J Org Chem*, 68(7):2983-2985.
Ferec, C. et al. (2012) "Assessing the Disease-Liability of Mutations in CFTR" *Cold Spring Harbor Perspect Med*, 2:a009480 (13 pages).
Florence, A.T. (2011) *Physicochemical Principles of Pharmacy*. Chapter 1, pp. 7-42.
Flume, P.A. (2012) "Ivacaftor in Subjects With Cystic Fibrosis Who Are Homozygous for the F508del-CFTR Mutation" *Chest*, 142(3):718-724.
Galietta, L.J.V. and O. Moran (2004) "Identification of CFTR activators and inhibitors: chance or design?" *Curr Opin Pharmacol*, 4:497-503.
Genomembrane Co. Ltd. (2015) "ABC Transporter and Assay" [online]. Retrieved from: http://www.genomembrane.com/E_ABC_Transporter_and_Assay.html; on Aug. 4, 2015 (3 pages).
Giardina, G.A.M. et al. (1999) "Replacement of the quinoline system in 2-phenyl-4-quinolinecarboxamide NK-3 receptor antagonists" *Il Farmaco*, 54:364-374.
Giron, D. (2001) "Investigations of polymorphism and pseudopolymorphism in pharmaceuticals by combined thermoanalytical techniques" *J Thermal Analysis Calorimetry*, 64:37-60.
Google.com (2016) "'new assay' cystic fibrosis transmembrane conductance regulator" Partial results of Internet search [online]. Retrieved from https://www.google.com; on Feb. 2, 2016 (2 pages).
Goshayev, M. et al. (1973) "Amination of 2-phenylpyridine under different conditions" *Izvestiya Akademii Nauk Turkmenskoi SSR, Seriya Giziko-Tekhnicheskikh, Khimicheskikh I Geologicheskikh Nauk*, 1973:108-109 (English abstract on p. 109).
Haleblian et al. (1969) "Pharmaceutical applications of polymorphism" *J Pharm Sci*, 58(8):911-929.
Hancock, B.C. and M. Parks (Apr. 2000) "What is the true solubility advantage for amorphous pharmaceuticals?" *Pharm Res*, 17(4):397-404.
HCAPLUS Database Accession No. 2005:823671 (2011) "Preparation of mainly N-thiazolyl carboxamides as modulators of ATP-binding cassette transporters" (3 pages).
Hirayama (Jul. 25, 2008) Yuuki kagoubutsu no kettshou sakusei handobuttku—genri to nouhou—(Handbook of preparation of crystal of organic compound—principle and know-how). Maruzen Co., Ltd, pp. 59-60 (Japanese).
Hisano, T. et al. (1982) "Raction of Aromatic N-Oxides with Dipolarophiles. V. 1,3-Cycloaddition of 2-Substituted Pyridine N-Oxides with Phenyl Isocyanates" *Chem Pharm Bull*, 30(10):3776-3781.
International Patent Application No. PCT/US2006/043289, filed Nov. 8, 2006, by Vertex Pharmaceuticals Inc.: International Search Report and Written Opinion, dated Mar. 9, 2007.
International Patent Application No. PCT/US2006/049412, filed Dec. 28, 2006, by Vertex Pharmaceuticals Inc.: International Search Report and Written Opinion, dated Sep. 4, 2007.
International Patent Application No. PCT/US2008/063144, filed May 9, 2008, by Vertex Pharmaceuticals Inc.: International Search Report and Written Opinion, dated Mar. 24, 2009.
International Patent Application No. PCT/US2008/083517, filed Nov. 14, 2008, by Vertex Pharmaceuticals Inc.: International Search Report and Written Opinion dated Feb. 19, 2009.
International Patent Application No. PCT/US2008/085456, filed Dec. 4, 2008, by Vertex Pharmaceuticals Inc.: International Search Report and Written Opinion, dated Feb. 26, 2009.
International Patent Application No. PCT/US2008/085458, filed Dec. 4, 2008, by Vertex Pharmaceuticals Inc.: International Search Report and Written Opinion, dated Aug. 7, 2009.
International Patent Application No. PCT/US2009/035064, filed Feb. 25, 2009, by Vertex Pharmaceuticals Inc.: International Search Report and Written Opinion, dated Oct. 12, 2009.
International Patent Application No. PCT/US2009/038203, filed Mar. 25, 2009, by Vertex Pharmaceuticals Inc.: International Search Report and Written Opinion, dated Jul. 9, 2009.
International Patent Application No. PCT/US2009/058677, filed Sep. 29, 2009, by Vertex Pharmaceuticals Inc.: International Search Report and Written Opinion, dated Mar. 23, 2010.
International Patent Application No. PCT/US2011/031519, filed Apr. 7, 2011, by Vertex Pharmaceuticals Inc.: International Search Report and Written Opinion, dated Dec. 16, 2011.
International Patent Application No. PCT/US2011/031588, filed Apr. 7, 2011, by Vertex Pharmaceuticals Inc.: International Search Report and Written Opinion, dated Dec. 16, 2011.
International Patent Application No. PCT/US2011/033687, filed Apr. 22, 2011, by Vertex Pharmaceuticals Inc.: International Search Report and Written Opinion dated Aug. 30, 2011.
International Patent Application No. PCT/US2011/033689, filed Apr. 22, 2011, by Vertex Pharmaceuticals Inc.: International Search Report and Written Opinion dated Aug. 30, 2011.
International Patent Application No. PCT/US2013/023100, filed Jan. 25, 2013, by Vertex Pharmaceuticals Inc.: International Search Report and Written Opinion, dated May 7, 2013.
International Patent Application No. PCT/US2013/067952, filed Nov. 1, 2013, by Vertex Pharmaceuticals Inc.: International Search Report and Written Opinion, dated Feb. 5, 2014.
International Patent Application No. PCT/US2014/063506, filed Oct. 31, 2014, by Vertex Pharmaceuticals Inc.: International Search Report and Written Opinion, dated Jan. 21, 2015.
Ito, K. et al. (1989) "A New Route to 2-Amino- or 2-Hydroxy-3-pyridinecarboxylic Acid Derivatives" *J Heterocyclic Chem*, 26:773-778.
Itoh, T. and T. Mase (May 16, 2005) "Direct synthesis of heterobiaryl compounds containing an unprotected $NH_2$ group via Suzuki-Miyaura reaction" *Tetrahedron Lett*, 46(20):3573-3577.
Ivanisevic, I. et al. (Aug./Sep. 2011) "Uses of X-Ray Powder Diffraction in the Pharmaceutical Industry" *Pharmaceutical Formulation & Quality*, pp. 30-33.
Ivanova, L.A. (1991) English translation of: *Dosage form technology: a guide in 2 volumes*. vol. 2—M: Medicine, pp. 144-146 (translation 4 pages).
Jalgaonkar, S.V. et al. (2010) "ABC Membrane Transporters: Target for Drugs and Diseases" *Global J Pharmc*, 4(2):75-82.
Jain, N.K. and M.N. Mohammedi (1986) "Polymorphism in Pharmacy" *Indian Drugs*, 23(6):315-329.
Jonat, S. (2004) "Investigation of Compacted Hydrophilic and Hydrophobic Colloidal Silicon Dioxides as Glidants for Pharmaceutical Excipients" *Powder Technology*, 141:31-43.
Jones, P.M. and A.M. George (2004) "The ABC transporter structure and mechanism: perspectives on recent research" *Cell Mol Life Sci*, 61(6):682-699.
Jones, A.M. and J.M. Helm (2009) "Emerging Treatments in Cystic Fibrosis" *Drugs*, 69(14):1903-1910.
Jure, M. et al. (1990) "Synthesis of 3-Alkyl-5-Phenyl-7-Trifluoromethylimidazo[4,5-b]pyridin-2-ones" *Latvijas PSR Zinatnu Akademijas Vestis, Kimijas Serija*, 1990(4):439-444 (English summary on p. 444).
Kaczmarek, L. et al. (Aug. 1, 1992) "An Excellent Method for the Mild and Safe Oxidation of N-Heteroaromatic Compounds and Tertiary Amines" *Chem Ber*, 125(8):1965-1966.
Kaminski, W. et al. (2006) "ABC A-subfamily transporters: Structure, function and disease" *Biochim Biophys Acta*, 1762(5):510-524.
Kanth, S. et al. (2005) "Multistep Synthesis of Pyrido[3',2':4,5]pyrrolo[3,2-d][1,3]oxazin-4(5H)-one from 2-Aminonicotinonitriles" *Heterocycles*, 65(6):1415-1423.
Katoh, A. et al. (1984) "Ring Transformation Reactions of 1-Substituted 2(1H)-Pyrimidinones and Related compounds with Active Methylene Compounds" *Chem Pharm Bull*, 32(8):2942-2946.

(56) References Cited

OTHER PUBLICATIONS

*Kirk-Othmer Encyclopedia of Chemical Technology.* vol. 8. John Wiley & Sons, Inc., 2002; pp. 95-147.
Koitz, G. et al. (1981) "Synthese and Fluoreszenzeigenschaften von cyansubstituierten 2-Aminopyridinen" *Monatshefte für Chemie*, 112:973-985. (German; English abstract on p. 973).
Lachman, L. et al. (1990) *The Theory and Practice of Industrial Pharmacy.* 3rd Edition. Bombay, India: Varghese Publication House; pp. 221-222.
Layzer, R.B. (1996) "Section Five—Degenerative Diseases of the Nervous System" in *Cecil Textbook of Medicine.* 20th edition. J. Claude Bennett and F. Plum (Eds.). Philadelphia: W.B. Saunders Co.; vol. 2, pp. 2050-2057.
Levin, M.H. et al. (Apr. 2005) "CFTR-Regulated Chloride Transport at the Ocular Surface in Living Mice Measured by Potential Differences" *Invest Ophthalmol Vis Sci*, 46(4):1428-1434.
Lin, S. et al. (Dec. 2010) "Identification of Synergistic Combinations of F508del Cystic Fibrosis Transmembrane Conductance Regulator (CFTR) Modulators" *ASSAY Drug Dev Tech*, 8(6):669-684.
Liu, X. et al. (2011) "Progress in the Study on Physical Stability and Anti-aging of Solid Dispersion" *Chin JMAP*, 28(8):710-717. Chinese with English abstract on p. 710.
Liu, Y. et al. (2005) "Expression Profiling of ABC Transporters in a Drug-Resistant Breast Cancer Cell Line Using AmpArray" *Mol Pharmacol*, 68(2):430-438.
Mathe, S. and A. Rassat (Jan. 29, 1998) "Synthesis of 1,1,1-Ethanetriacetonitrile, Precursor of 6-Substituted-4-methyl-2-aminopyridines" *Tetrahedron Lett*, 39:383-384.
Mertens, H. et al. (1986) "Synthese von 2-Amino-3-nitropyridinen und -1,4-dihydropyridinen" *Liebigs Ann Chem*, 1986:380-383 (German; English abstract on p. 380).
Mertens, H. and R. Troschütz (1987) "Synthese von $N^2$-substituierten 2-Amino-3-nitropyridinen als Vorstufen von Pyrido[2,3-b]pyrazinen (3-Desazapteridinen)" *Arch Pharm (Weinheim)*, 320:1143-1149 (German; English abstract on p. 1143).
Muzaffar, N.A. and M.A. Sheikh (1979) "Polymorphism and Drug Availability. A Review" *J Pharmacy (Lahore)*, 1(1):59-66.
Narsaiah, B. et al. (1994) "A novel synthetic route to 2-amino-3-cyano-4-trifluoromethyl-6-substituted pyridines" *J Fluorine Chem*, 67:87-90.
Ngiam, N.S.P. et al. (2006) "Cystic fibrosis transmembrane conductance regulator (CFTR) gene mutations in Asians with chronic pulmonary disease: A pilot study" *J Cystic Fibrosis*, 5:159-164.
Nitta, M. et al. (1991) "On the Reaction of (Vinylimino)phosphoranes. Part 17. Preparation of N-Vinylcarbodiimides and Their [4+2] Cycloaddition with Several Dienophiles to Give Pyridine Ring System" *Bull Chem Soc Japan*, 64(4):1325-1331.
Noone, P.G. et al. (2001) "'CFTR-opathies': disease phenotypes associated with cystic fibrosis transmembrane regulator gene mutations" *Respiratory Research*, 2(6):328-332.
Notice of Allowance and Fee(s) Due for U.S. Appl. No. 13/290,491, dated Oct. 25, 2012.
Notice of Allowance and Fee(s) Due for U.S. Appl. No. 13/871,349, dated Aug. 12, 2014.
Notice of Allowance and Fee(s) Due for U.S. Appl. No. 13/871,349, dated Apr. 17, 2015.
Notice of Allowance and Fee(s) Due for U.S. Appl. No. 13/871,349, dated Oct. 13, 2015.
Notice of Allowance and Fee(s) Due for U.S. Appl. No. 13/887,839, dated Jul. 7, 2014.
Notice of Allowance and Fee(s) Due for U.S. Appl. No. 13/887,839, dated Oct. 16, 2014.
Notice of Allowance and Fee(s) Due for U.S. Appl. No. 13/887,839, dated Feb. 2, 2015.
Notice of Allowance and Fee(s) Due for U.S. Appl. No. 13/887,839, dated Sep. 30, 2015.
Notice of Allowance and Fee(s) Due for U.S. Appl. No. 14/031,360, dated Aug. 14, 2014.
Notice of Allowance and Fee(s) Due for U.S. Appl. No. 14/298,245, dated Jul. 21, 2015.
Notice of Allowance and Fee(s) Due for U.S. Appl. No. 14/298,245, dated Nov. 12, 2015.
Notice of Allowance and Fee(s) Due for U.S. Appl. No. 14/326,930, dated Aug. 14, 2015.
Notice of Allowance and Fee(s) Due for U.S. Appl. No. 14/326,930, dated Dec. 8, 2015.
Notice of Allowance and Fee(s) Due for U.S. Appl. No. 14/334,902, dated Oct. 19, 2015.
Notice of Allowance and Fee(s) Due for U.S. Appl. No. 14/334,902, dated Feb. 18, 2016.
Notice of Allowance and Fee(s) Due for U.S. Appl. No. 14/532,791, dated Jul. 24, 2015.
Notice of Allowance and Fee(s) Due for U.S. Appl. No. 14/532,791, dated Nov. 6, 2015.
Notice of Allowance and Fee(s) Due for U.S. Appl. No. 14/532,791, dated Mar. 1, 2016.
Notice of Allowance and Fee(s) Due for U.S. Appl. No. 14/567,475, dated Sep. 21, 2015.
Notice of Allowance and Fee(s) Due for U.S. Appl. No. 14/567,475, dated Jan. 5, 2016.
Notice of Allowance and Fee(s) Due for U.S. Appl. No. 14/579,098, dated Feb. 1, 2016.
Notice of Allowability for U.S. Appl. No. 14/579,098, dated Apr. 18, 2016.
Notice of Allowance and Fee(s) Due for U.S. Appl. No. 14/579,098, dated May 12, 2016.
Notice of Allowance and Fee(s) Due for U.S. Appl. No. 14/656,043, dated Aug. 4, 2016.
Notice of Allowance and Fee(s) Due for U.S. Appl. No. 14/687,286, dated Feb. 10, 2016.
Notice of Allowance and Fee(s) Due for U.S. Appl. No. 14/687,286, dated May 19, 2016.
Notice of Allowance and Fee(s) Due for U.S. Appl. No. 14/687,286, dated Sep. 28, 2016.
Notice of Allowance and Fee(s) Due for U.S. Appl. No. 14/877,914, dated Jul. 27, 2016.
Notice of Allowance and Fee(s) Due for U.S. Appl. No. 14/877,914, dated Nov. 14, 2016.
Notice of Allowance and Fee(s) Due for U.S. Appl. No. 14/925,804, dated May 17, 2016.
Notice of Allowance and Fee(s) Due for U.S. Appl. No. 15/001,036, dated Feb. 10, 2017.
Notice of Allowance and Fee(s) Due for U.S. Appl. No. 15/073,591, dated Sep. 28, 2016.
Ochiai, Michiko et al., United States Court of Appeals for the Federal Circuit 71 F.3d 1565; 1995, U.S. Patent and Trademark Office Board of Patent Appeals and Interferences. (U.S. Appl. No. 07/462,492).
Okiyoneda, T. and G.L. Lukacs (Oct. 15, 2012) "Fixing cystic fibrosis by correcting CFTR domain assembly" *J Cell Biol*, 199(2):199-204.
Otsuka, M. et al. (1999) "Effect of Polymorphic Forms of Bulk Powders on Pharmaceutical Properties of Carbamazepine Granules" *Chem Pharm Bull*, 47(6):852-856.
Paranjape, S.M. et al. (2008) "Atypical Cystic fibrosis and CFTR-Related Diseases" *Clinic Rev Allerg Immunol*, 35(3):116-123.
Patani, G. et al. (1996) "Bioisosterism: A Rational Approach in Drug Design" *Chem Rev*, 96(8):3147-3176.
Qiao, J. X. et al. (Nov. 2, 2004) "5-Amidinobenzo[b]thiophenes as dual inhibitors of factors IXa and Xa" *Bioorg Med Chem Lett*, 15(1):29-35.
Registry Database RN 477866-05-0 (Dec. 31, 2002) "3-Pyridinecarboxylic acid, 5-cyano-2-phenyl-6-[(phenylmethyl)amino]-" Retrieved from STN [online]; retrieved on Nov. 28, 2016 (1 page).
Registry Database RN 478068-14-3 (Jan. 3, 2003) "3,4,5-Pyridinetricarbonitrile, 2-amino-6-(4-bromophenyl)-" Retrieved from STN [online]; retrieved on Nov. 28, 2016 (1 page).
Registry Database RN 478068-16-5 (Jan. 3, 2003) "3,4,5-Pyridinetricarbonitrile, 2-amino-6-[4-(trifluoromethyl)phenyl]-" Retrieved from STN [online]; retrieved on Nov. 28, 2016 (1 page).

(56) References Cited

OTHER PUBLICATIONS

Registry Database RN 478081-23-1 (Jan. 3, 2003) "3,4,5-Pyridinetricarbonitrile, 2-amino-6-(4-methylphenyl)-" Retrieved from STN [online]; retrieved on Nov. 28, 2016 (1 page).
Registry Database RN 881299-60-1 (Apr. 20, 2006) "3-Pyridinecarbonitrile, 6-(4-methoxyphenyl)-2-[(1-phenylethyl)amino]-" Retrieved from STN [online]; retrieved on Nov. 28, 2016 (1 page).
Registry Database RN 881300-29-4 (Apr. 20, 2006) "3-Pyridinecarbonitrile, 6-(4-methoxyphenyl)-2-(phenylamino)-" Retrieved from STN [online]; retrieved on Nov. 28, 2016 (1 page).
Registry Database RN 912772-80-6 (Nov. 9, 2006) "2,5 Pyridinediamine, 6-phenyl-" Retrieved from STN [online]; retrieved on Nov. 28, 2016 (1 page).
Registry Database RN 912772-97-5 (Nov. 9, 2006) "2-Pyridinamine, 5-nitro-6-phenyl-" Retrieved from STN [online]; retrieved on Nov. 28, 2016 (1 page).
Registry Database RN 925921-90-0 (Mar. 9, 2007) "2-Pyridinamine, 4-chloro-6-(2-methoxyphenyl)-" Retrieved from STN [online]; retrieved on Nov. 28, 2016 (1 page).
Registry Database RN 929400-78-2 (Apr. 8, 2007) "3-Pyridinecarbonitrile, 2-(cyclohexyllamino)-6-(4-methoxyphenyl)-" Retrieved from STN [online]; retrieved on Nov. 28, 2016 (1 page).
Registry Database RN 929443-65-2 (Apr. 9, 2007) "3-Pyridinecarbonitrile, 2-(cycloheptylamino)-6-(4-methoxyphenyl)-" Retrieved from STN [online]; retrieved on Nov. 28, 2016 (1 page).
Registry Database RN 929443-63-0 (Apr. 9, 2007) "3-Pyridinecarbonitrile, 6-(4-methoxyphenyl)-2-(4-piperidinylamino)-" Retrieved from STN [online]; retrieved on Nov. 28, 2016 (1 page).
Ridi, M. (1959) "Richerch sopra derivati della piridina. Nota II. Richerche sopra sistemi 3 H-1,2,6,7,9-pentaazafenalenci, piri-do(3,4-d)piridazinici e pirido(2,3-d)pirimidinici" *Annali di Chimica*, 49:944-957 (Italian).
Robins, R.K. and G.H. Hitchings (1958) "Studies on Condensed Pyrimidine Systems. XIX. A New Synthesis of Pyrido [2,3-d] pyrimidines. The Condensation of 1,3-Diketones and 3-Ketoaldehydes with 4-Aminopyrimidines" *J Am Chem*, 80(13):3449-3457.
Rodon, J. et al. (2010) "Combining Targeted Therapies: Practical Issues to Consider at the Bench and Bedside" *The Oncologist*, 15:37-50.
Rodríguez-Spong, B. et al. (2004) "General principles of a pharmaceutical solid polymorphism: a supramolecular perspective" *Adv Drug Delivery Reviews*, 56:241-274.
Rouhi, A.M. (2003) "The Right Stuff. From research and development to the clinic, getting drug crystals right is full of pitfalls" *Chem Eng News*, 81(8):32-35.
Rowe, S.M. et al. (2005) "Cystic Fibrosis" *N Engl J Med*, 352(19):1992-2001.
Rowland, M. and T.N. Tozer (1995) *Clinical Pharmacokinetics. Concepts and Applications.* p. 123.
Saito, T. et al. (1993) "Lewis Acid-Induced Hetero Diels-Alder Reaction of Conjugated Carbodiimides" *Chem Lett*, pp. 1127-1130.
Saito, T. et al. (1998) "Thermal or Lewis acid-promoted electrocyclisation and hetero Diels-Alder cycloaddition of α,β-unsaturated (conjugated) carbodiimides: a facile synthesis of nitrogen-containing heterocycles" *J Chem Soc Perkin Trans*, 1:3065-3080.
Schmidt, H-W. et al. (1980) "Synthesen mit Nitrilen; 59[1]. Ein einfacher Weg zu 2-Amino-3,4,5-tricyanopyridinen" *Synthesis*, 1980(6):471-472. (German).
Schultheiss, N. et al. (2009) "Pharmaceutical Cocrystals and Their Physiochemical Properties" *Crystal Growth & Design*, 9(6):2950-2967.
Shah, U. and L. Augsburger (2002) "Multiple Sources of Sodium Starch Glycolate, NF: Evaluation of Functional Equivalence and Development of Standard Performance Tests" *Pharmaceutical Development and Technology*, 7(3):345-359.
Silverman, R.B. (1993) *The Organic Chemistry of Drug Design and Drug Action.* Academic Press Inc.; pp. 72-76.
Silverman, R.B (2004) *The Organic Chemistry of Drug Design and Drug Action.* 2nd Ed. Elsevier Academic Press; pp. 26 and 29-32.

Singhal, D. and W. Curatolo (2004) "Drug Polymorphism and dosage form design: a practical perspective" *Advanced Drug Delivery Reviews*, 56:335-347.
Stankovic, M. et al. (2008) "The CFTR M470V gene variant as a potential modifier of COPD severity: study of Serbian population" *Genetic Testing*, 12(3):357-362.
Suloeva, E. et al. (2001) "Synthesis of 5-Phenyl-7-trifluoromethyl-2,3-dihydroimidazo[1,2-a]pyridines" *Chem Heterocyclic Compounds*, 37:329-337.
Taday, P.F. et al. (2003) "Using Terahertz Pulse Spectroscopy to Study the Crystalline Structure of a Drug: A Case Study of the Polymorphs of Ranitidine Hydrochloride" *J Pharm Sci*, 92(4):831-838.
Takata, N. (2009) "Cocrystal" *Pharm Tech Japan*, 25(12):155-166 (Japanese with English abstract).
The Associated Press (Sep. 24, 2003) "FDA mulls drug to slow late-stage Alzheimer's" CNN.com/HEALTH [online]. Retrieved from: http://www.cnn.com/2003/HEALTH/conditions/09/24/alzheimers.drug.ap/index.html, on Sep. 24, 2003 (2 pages).
Troschütz, R. (1979) "6-Substituierte 2-Aminonicotinsäure-ethylester" *Archiv der Pharmazie*, 312:455-457 (German).
Troschütz, R. and Lückel (1992) "Synthese von substituierten 2-Amino-3-nitropyridinen aus 1,3-Biselektrophilen und 2-Nitroethen-1,1-diamin" *Archiv der Pharmazie*, 325(12):785-789 (German; English abstract on p. 785).
Troschütz, R. and T. Dennstedt (1994) "Synthese von substituierten 2-Aminonicotinonitrilen" *Archiv der Pharmazie*, 327:33-40 (German; English abstract on p. 33).
Troschütz, R. and T. Dennstedt (1994) "Substituierte 2-Aminonicotinonitrile" *Archiv der Pharmazie*, 327:85-89 (German; English abstract on p. 85).
Tzetis, M. et al. (2001) "CFTR gene mutations—including three novel nucleotide substitutions—and haplotype background in patients with asthma, disseminated bronchiectasis and chronic obstructive pulmonary disease" *Hum. Genet.*, 108:216-221.
U.S. Department of Health and Human Services, Food and Drug Administration (FDA) (May 1999) *Guideline for Industry. Container Closure Systems for Packaging Human Drugs and Biologics.* (56 pages).
U.S. Appl. No. 13/632,835, filed Oct. 1, 2012.
U.S. Appl. No. 14/179,762, filed Feb. 13, 2014.
U.S. Appl. No. 14/444,451, filed Jul. 28, 2014.
U.S. Appl. No. 15/234,877, filed Aug. 11, 2016, by Hadida-Ruah et al.
U.S. Appl. No. 15/342,999, filed Nov. 3, 2016, by Alargova et al.
*U.S. Pharmacopia #23, National Formulary #18*, (1995), pp. 1843-1844.
Ulicky, L and T.J. Kemp (Eds.) (1992) *Comprehensive Dictionary of Physical Chemistry.* Czecho-Slovakia: ALFA/Ellis Horwood Ltd.; p. 21.
Van Goor, F. et al. (2006) "Rescue of ΔF580-CFTR trafficking and gating in human cystic fibrosis airway primary cultures by small molecules" *Am J Physiol Lung Cell Mol Physiol*, 290(6):L1117-L1130.
Vanallan, J.A. et al. (Jun. 1970) "Reactions of Some 4-Methylene-4H-pyran Derivatives with Primary and Secondary Amines" *J Heterocyclic Chem*, 7:495-507.
Vertex Pharmaceuticals, Inc. (May 17, 2006) "Vertex Pharmaceuticals Initiates Phase I Development for VX-770 in Cystic Fibrosis. FDA Grants Fast Track Designation to VX-770" Press Release [online]. Retrieved from: http://investors.vrtx.com/releasedetail.cfm?ReleaseID=233045; on Jan. 19, 2015 (2 pages).
Vertex Pharmaceuticals, Inc. (Mar. 2011) "Study of VX-809 Alone and in Combination With VX-770 in Cystic Fibrosis (CF) Patients Homozygous for the F508del-CFTR Mutation" ClinicalTrials.gov[online]. Retrieved from: http://clinicaltrials.gov/archive/NCT01225211/2011_03_01; Identifier: NCT01225211.
Vertex Pharmaceuticals, Inc. (Jun. 25, 2015) Summary Review of Regulatory Action for Lumacaftor/ivacaftor Tablets. U.S. FDA, Center for Drug Evaluation and Research, Division of Pulmonary, Allergy, and Rheumatology, Products, CDER; Director Badrul A. Chowdhury, MD, PhD.; Application No. 206038Orig1s000 (18 pages).

(56) References Cited

OTHER PUBLICATIONS

Wang, Y. et al. (2006) "Specific Rescue of Cystic Fibrosis Transmembrane Conductance Regulator Processing Mutants Using Pharmacological Chaperones" *Mol Pharmacol*, 70(1):297-302.
Wikipedia (Jul. 13, 2008) "ATP-binding cassette transporter" [online]. [Retrieved on Sep. 24, 2008]; Retrieved from the Internet: http://en.wikipedia.org/wiki/ATP-binding_cassette_transporter (6 pages).
Wikipedia (2009) "ATP-binding cassette transporter" [online]. [Retrieved on Jul. 10, 2009]; retrieved from the Internet: http://en.wikipedia.org/wiki/ATP-binding_cassette_transporter (20 pages).
Wikipedia (2011) "Solid solution" [online]. Retrieved from: http://www.wikipedia.com; Retrieved on Sep. 20, 2011, 3 pages.
Yin, J. et al. (Jun. 2007) "A general and efficient 2-amination of pyridines and quinolines" *J Org Chem*, 72(12):4554-4557.
Yogi, S. et al. (1986) "Synthesis of Stable 1,2-Diazocines, 4,7-Disubstituted 3,8-Diaryl-1,2-diazacycloocta-2,4,6,8-tetraenes, and Their Termolysis" *Bull Chem Soc Jpn*, 59:1087-1094.
Yurugi, S. et al. (1972) "Studies on the Synthesis of N-Heterocyclic Compounds. XII. Syntheses of Pyrido[3,4-d]pyridazine and Pyrido[2,3-d]pyridazine Derivatives" *Yakugaku Zasshi* (*Journal of the Pharmaceutical Society of Japan*), 92(11):1333-1338. Japanese with English abstract on p. 1333.
Zhang, W. et al. (Mar. 2012) "Recent advances and new perspectives in targeting CFTR for therapy of cystic fibrosis and enterotoxin-induced secretory diarrheas" *Future Med Chem*, 4(3):329-345. NIH Author Manuscript; available in PMC Jan. 1, 2013 (28 pages).
Zhu, J. et al. (2006) "Solid-phase synthesis of 4-biaryl-piperidine-4-caroxamides" *Tetrahedron Lett*, 47:7267-7270.
Abramzon, A.A. (1981) *Surfactant Active Agents: Properties and Applications*. 2nd ed. , p. 3 (Russian).
Andrews, J. et al. (1999) *An Introduction to Environmental Chemistry*. Blackwell Science; p. 117 (Russian).
Bauer, K.H. et al. (1999) *Lehrbuch der Pharmazeutischen Technologie*. Stuttgart: Wissenschaftliche Verlagsgesellschaft mbH; pp. 313-316, with English translation (13 pages total).
Bombieri et al., "Recommendations for the classification of diseases of CFTR-related disorders," *J. Cyst Fibros* 10:2 S86-S102 (2011).
European Medicines Agency (Sep. 24, 2015) "Orkambi" *Assessment Report*. Procedure No. EMEA/H/C/003954/0000 (104 pages).
European Patent Application No. 11715637.2 (Patent No. 2555755), filed Apr. 7, 2011, by Vertex Pharmaceuticals Inc.: Notice of Opposition by Alfred E. Tiefenbacher (GmbH & Co. KG), May 18, 2017 (19 pages).
Keleb, E.I. et al. (2004) "Twin screw granulation as a simple and efficient tool for continuous wet granulation" *Intl J Pharmaceutics*, 273:183-194.
Kharkevich, D.A. (2006) *Pharmacology: Textbook*. 9th edition. M: GEOTAR-Media; p. 66 (Russian).
Notice of Allowance and Fee(s) Due for U.S. Appl. No. 14/027,791, dated Jul. 31, 2015.
Notice of Allowance and Fee(s) Due for U.S. Appl. No. 14/687,286, dated Dec. 1, 2017.
Notice of Allowance and Fee(s) Due for U.S. Appl. No. 14/687,286, dated May 9, 2018.
Notice of Allowance and Fee(s) Due for U.S. Appl. No. 14/920,041, dated Jul. 21, 2017.
Notice of Allowance and Fee(s) Due for U.S. Appl. No. 15/001,036, dated May 1, 2018.
Notice of Allowance and Fee(s) Due for U.S. Appl. No. 15/152,092, dated May 17, 2018.
Notice of Allowance and Fee(s) Due for U.S. Appl. No. 14/676,205, dated May 24, 2018.
Notice of Opposition for EP Patent No. 2555755, mailed May 18, 2017.
Pettit, R.S. (2012) "Cystic Fibrosis Transmembrane Conductance Regulator-Modifying Medications: The Future of Cystic Fibrosis Treatment" *Ann Pharmacother*, 46(7/8):1065-1075.
Rathore, A.S. et al. (May 18, 2010) "Process analytical technology (PAT) for biopharmaceutical products" *Anal Bioanal Chem*, 398(1):137-154.
Santa Cruz Biotechnology, Inc. "Polyvinylpyrrolidone" Material Safety Data Sheet, Catalog No. sc-203204; Issue Date: Apr. 5, 2009, Print Date: Feb. 17, 2011 (8 pages).
Third Party Observation for EP Patent Application No. 20130792149, filed Jun. 13, 2018.
U.S. Appl. No. 15/043,049, filed Feb. 12, 2016.
U.S. Appl. No. 15/898,683, filed Feb. 19, 2018, by Frederick F. Van Goor, et al.
U.S. Appl. No. 15/937,564, filed Mar. 27, 2018, by Frederick F. Van Goor, et al.
U.S. Appl. No. 15/949,404, filed Apr. 10, 2018, by Sara Sabina Hadida Ruah.
*U.S. Pharmacopeia #28, National Formulary #23* (2005), p. 2711.
Van Goor, F. et al. (2011) "Correction of the F508del-CFTR protein processing defect in vitro by the investigational drug VX-809" *Proc Natl Acad Sci USA*, 108(46):18843-18848.
Vertex Pharmaceuticals, Inc. (2016) "ORKAMBI® (lumacaftor/ivacaftor tablets" Highlights of Prescribing Information, Revised Sep. 2016 (16 pages).
Wikipedia (Aug. 6, 2009) "Pharmaceutical formulation" [online]. Retrieved on Jan. 22, 2010, from the Internet: http://en.wikipedia.org/w/index.php?title=Pharmaceutical_formulation&oldid-30640 . . . (3 pages).
Xu, L. et al. (Feb. 2, 2009) "Multiple compounds determination and fingerprint analysis of Lidanpaishi tablet and keli by high-performance liquid chromatography" *Anal Chim Acta*, 633(1):136-148.

PROCESS OF PREPARING PHARMACEUTICAL COMPOSITIONS FOR THE TREATMENT OF CFTR MEDIATED DISEASES

TECHNICAL FIELD OF INVENTION

The invention relates to a process of preparing pharmaceutical compositions comprising 3-(6-(1-(2,2-difluorobenzo[d][1,3]dioxol-5-yl) cyclopropanecarboxamido)-3-methylpyridin-2-yl)benzoic acid (Compound 1) Form I and a solid dispersion comprising substantially amorphous N-(5-hydroxy-2,4-ditert-butyl-phenyl)-4-oxo-1H-quinoline-3-carboxamide (Compound 2), methods of treatment, methods of administering, and kits thereof.

BACKGROUND

Cystic fibrosis (CF) is a recessive genetic disease that affects approximately 30,000 children and adults in the United States and approximately 30,000 children and adults in Europe. Despite progress in the treatment of CF, there is no cure.

In patients with CF, mutations in CFTR endogenously expressed in respiratory epithelia leads to reduced apical anion secretion causing an imbalance in ion and fluid transport. The resulting decrease in anion transport contributes to enhanced mucus accumulation in the lung and the accompanying microbial infections that ultimately cause death in CF patients. In addition to respiratory disease, CF patients typically suffer from gastrointestinal problems and pancreatic insufficiency that, if left untreated, results in death. In addition, the majority of males with cystic fibrosis are infertile and fertility is decreased among females with cystic fibrosis. In contrast to the severe effects of two copies of the CF associated gene, individuals with a single copy of the CF associated gene exhibit increased resistance to cholera and to dehydration resulting from diarrhea—perhaps explaining the relatively high frequency of the CF gene within the population.

Sequence analysis of the CFTR gene of CF chromosomes has revealed a variety of disease causing mutations (Cutting, G. R. et al. (1990) Nature 346:366-369; Dean, M. et al. (1990) Cell 61:863:870; and Kerem, B-S. et al. (1989) Science 245:1073-1080; Kerem, B-S et al. (1990) Proc. Natl. Acad. Sci. USA 87:8447-8451). To date, greater than 1000 disease causing mutations in the CF gene have been identified (http://www.genet.sickkids.on.ca/cftr/app). The most prevalent mutation is a deletion of phenylalanine at position 508 of the CFTR amino acid sequence, and is commonly referred to as ΔF508-CFTR. This mutation occurs in approximately 70% of the cases of cystic fibrosis and is associated with a severe disease.

The deletion of residue 508 in ΔF508-CFTR prevents the nascent protein from folding correctly. This results in the inability of the mutant protein to exit the ER, and traffic to the plasma membrane. As a result, the number of channels present in the membrane is far less than observed in cells expressing wild-type CFTR. In addition to impaired trafficking, the mutation results in defective channel gating. Together, the reduced number of channels in the membrane and the defective gating lead to reduced anion transport across epithelia leading to defective ion and fluid transport. (Quinton, P. M. (1990), FASEB J. 4: 2709-2727). Studies have shown, however, that the reduced numbers of ΔF508-CFTR in the membrane are functional, albeit less than wild-type CFTR. (Dalemans et al. (1991), Nature Lond. 354: 526-528; Denning et al., supra; Pasyk and Foskett (1995), J. Cell. Biochem. 270: 12347-50). In addition to ΔF508-CFTR, other disease causing mutations in CFTR that result in defective trafficking, synthesis, and/or channel gating could be up- or down-regulated to alter anion secretion and modify disease progression and/or severity.

Compound 1 in salt form is disclosed in International PCT Publication WO2007056341 and U.S. Pat. No. 7,741,321 as an inducer of CFTR activity and thus as a useful treatment for CFTR-mediated diseases such as cystic fibrosis. Compound 1 Form I, which is a substantially crystalline and salt-free form, is disclosed in International PCT Publication WO2009073757 and U.S. Pat. No. 8,507,534. Compound 2 is disclosed in International PCT Publication WO2006002421 and U.S. Pat. No. 7,495,103 as an inducer of CFTR activity and thus as useful treatment for CFTR-mediated diseases such as cystic fibrosis. A solid dispersion comprising substantially amorphous Compound 2 is disclosed in International PCT Publication WO2010019239 and United States Published Patent Application No. US20100074949. All above applications and patents are incorporated in their entirety by reference herein.

Compounds which are CFTR potentiators, such as Compound 2, and compounds which are CFTR correctors, such as Compound 1, have been shown independently to have utility in the treatment of CFTR related diseases, such as cystic fibrosis.

Accordingly, there is a need for novel treatments of CFTR mediated diseases which involve CFTR corrector and potentiator compounds.

Particularly, there is a need for combination therapies to treat CFTR mediated diseases, such as cystic fibrosis, which include CFTR potentiator and corrector compounds.

More particularly, there is a need for combination therapies to treat CFTR mediated diseases, such as cystic fibrosis, which include CFTR potentiator compounds, such as substantially amorphous Compound 2, in combination with CFTR corrector compounds, such as Compound 1 Form I.

Compound 1 as part of a combination with Compound 2 has been granted a Breakthrough Therapy Designation from the Food and Drug Administration (FDA) for the treatment of cystic fibrosis, one of only two such grants at the time of the filing of this application (the other being for Compound 2). This demonstrates a significant unmet need for the effective treatment of the cause of cystic fibrosis over symptomatic treatments. Additionally, a common challenge for drugs approved by the FDA is the occasional lack of drug availability for patients in need thereof. Accordingly, a significant unmet need exists for the presently disclosed Compound 1 and Compound 2 formulations and processes for preparing them in a continuous and controlled manner.

Additionally, patient compliance with treatment schedules and dosage amounts is largely dependent on ease of drug administration. A pharmaceutical composition comprising fixed dosage amounts of a CFTR corrector and CFTR potentiator, wherein the solid forms of said corrector and potentiator are stable, is a significant breakthrough for the treatment of CFTR mediated diseases such as cystic fibrosis.

SUMMARY

The invention features a process of preparing pharmaceutical compositions comprising 3-(6-(1-(2,2-difluorobenzo[d][1,3]dioxol-5-yl) cyclopropanecarboxamido)-3-methylpyridin-2-yl)benzoic acid, Compound 1 Form I, which has the structure below:

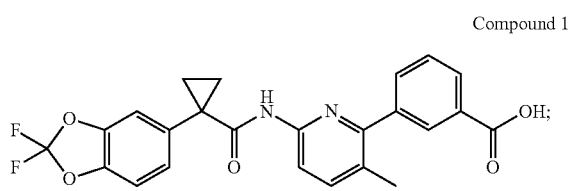 [SMILES: Cc1ccc(NC(=O)C2(c3ccc4c(c3)OC(F)(F)O4)CC2)nc1-c1cccc(C(=O)O)c1]

Compound 1 and
a solid dispersion of substantially amorphous N-(5-hydroxy-2,4-ditert-butyl-phenyl)-4-oxo-1H-quinoline-3-carboxamide, Compound 2, which has the structure below:

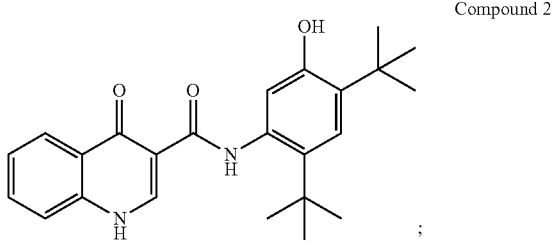 [SMILES: CC(C)(C)c1cc(C(C)(C)C)c(NC(=O)c2c[nH]c3ccccc3c2=O)cc1O]

Compound 2 methods of treatment, methods of administering, and kits thereof.

In one aspect, the present invention features a process of preparing a pharmaceutical composition comprising:
 a. Compound 1 Form I;
 b. a solid dispersion comprising substantially amorphous Compound 2;
 c. a filler;
 d. a disintegrant;
 e. a surfactant; and
 f. a binder;
referred to as PC-I.

In one embodiment, the process of preparing pharmaceutical compositions of the present invention comprise 30 to 55 percent by weight Compound 1 Form I, and 10 to 45 percent by weight solid dispersion comprising substantially amorphous Compound 2.

In one embodiment, the filler is selected from cellulose, modified cellulose, sodium carboxymethyl cellulose, ethyl cellulose hydroxymethyl cellulose, hydroxypropylcellulose, cellulose acetate, microcrystalline cellulose, dibasic calcium phosphate, sucrose, lactose, corn starch, potato starch, or any combination thereof. In another embodiment, the filler is microcrystalline cellulose, and is present in an amount ranging from 10 to 20 percent by weight.

In one embodiment, the disintegrant is selected from agar-agar, algins, calcium carbonate, carboxymethylcellulose, cellulose, hydroxypropylcellulose, low substituted hydroxypropylcellulose, clays, croscarmellose sodium, crospovidone, gums, magnesium aluminum silicate, methylcellulose, polacrilin potassium, sodium alginate, sodium starch glycolate, maize starch, potato starch, tapioca starch, or any combination thereof. In another embodiment, the disintegrant is croscarmellose sodium, and is present in an amount ranging from 1 to 3 percent by weight.

In one embodiment, the surfactant is selected from sodium lauryl sulfate, sodium stearyl fumerate, polyoxyethylene 20 sorbitan mono-oleate, or any combination thereof. In another embodiment, the surfactant is sodium lauryl sulfate, and is present in an amount ranging from 0.5 to 2 percent by weight.

In one embodiment, the binder is selected from polyvinylpyrrolidone, dibasic calcium phosphate, sucrose, corn starch, modified cellulose, or any combination thereof. In another embodiment, the binder is polyvinylpyrrolidone, and is present in an amount ranging from 0 to 5 percent by weight.

In one embodiment, the present invention features a process of preparing a pharmaceutical composition having the following formulation:

|  | % by wgt. |
| --- | --- |
| Compound 1 Form I | 35-50 |
| Solid dispersion comprising substantially amorphous Compound 2 | 25-40 |
| Microcrystalline cellulose | 10-20 |
| Croscarmellose sodium | 1-3 |
| Sodium lauryl sulfate | 0.5-2 |
| Polyvinylpyrrolidone | 0-5 | referred to as PC-II.

In another aspect, the present invention features a process of preparing a pharmaceutical composition comprising:
 a. Compound 1 Form I;
 b. a solid dispersion comprising substantially amorphous Compound 2;
 c. a filler;
 d. a disintegrant;
 e. a surfactant;
 f. a binder; and
 g. a lubricant;
referred to as PC-III.

In one embodiment, the process of preparing pharmaceutical compositions of present invention comprise about 100 to 250 mg of Compound 1 Form I, and about 100 to 150 mg of substantially amorphous Compound 2. In another embodiment, the pharmaceutical compositions of the present invention comprise about 200 mg of Compound 1 Form I, and about 125 mg of substantially amorphous Compound 2. In another embodiment, the pharmaceutical compositions of the present invention comprise about 150 mg of Compound 1 Form I, and about 125 mg of substantially amorphous Compound 2.

In one embodiment, the process of preparing pharmaceutical compositions of the present invention comprise 25 to 50 percent by weight Compound 1 Form I, and 15 to 35 percent by weight a solid dispersion comprising substantially amorphous Compound 2.

In one embodiment, the filler is selected from cellulose, modified cellulose, sodium carboxymethyl cellulose, ethyl cellulose hydroxymethyl cellulose, hydroxypropylcellulose, cellulose acetate, microcrystalline cellulose, dibasic calcium phosphate, sucrose, lactose, corn starch, potato starch, or any combination thereof. In another embodiment, the filler is microcrystalline cellulose, and is present in an amount ranging from 20 to 30 percent by weight.

In one embodiment, the disintegrant is selected from agar-agar, algins, calcium carbonate, carboxymethylcellulose, cellulose, hydroxypropylcellulose, low substituted hydroxypropylcellulose, clays, croscarmellose sodium, crospovidone, gums, magnesium aluminum silicate, methylcellulose, polacrilin potassium, sodium alginate, sodium starch glycolate, maize starch, potato starch, tapioca starch, or any combination thereof. In another embodiment, the disintegrant is croscarmellose sodium, and is present in an amount ranging from 3 to 10 percent by weight.

In one embodiment, the surfactant is selected from sodium lauryl sulfate, sodium stearyl fumerate, polyoxyethylene 20 sorbitan mono-oleate, or any combination thereof. In another embodiment, the surfactant is sodium lauryl sulfate, and is present in an amount ranging from 0.5 to 2 percent by weight.

In one embodiment, the binder is selected from polyvinylpyrrolidone, dibasic calcium phosphate, sucrose, corn starch, modified cellulose, or any combination thereof. In another embodiment, the binder is polyvinylpyrrolidone, and is present in an amount ranging from 0 to 5 percent by weight.

In one embodiment, the lubricant is selected from magnesium stearate, calcium stearate, zinc stearate, sodium stearate, stearic acid, aluminum stearate, leucine, glyceryl behenate, hydrogenated vegetable oil or any combination thereof. In another embodiment, the lubricant is magnesium stearate, and is present in an amount ranging from 0.5 to 2 percent by weight.

In one embodiment, the present invention features a process of preparing a pharmaceutical composition having the following formulation:

|  | % by wgt. |
| --- | --- |
| Compound 1 Form I | 25-50 |
| A solid dispersion comprising substantially amorphous Compound 2 | 15-35 |
| Microcrystalline cellulose | 20-30 |
| Croscarmellose sodium | 3-10 |
| Sodium lauryl sulfate | 0.5-2 |
| Polyvinylpyrrolidone | 0-5 |
| Magnesium stearate | 0.5-2 | referred to as PC-IV.

In one embodiment, the process of preparing pharmaceutical compositions of the present invention further comprise a colorant and optionally a wax. In another embodiment, the colorant is present in an amount ranging from 2 to 4 percent by weight. In another embodiment, the wax is carnauba wax present in an amount ranging from 0 to 0.020 percent by weight.

In one embodiment, the process of preparing pharmaceutical compositions of the present invention are solid oral pharmaceutical compositions. In another embodiment, the solid oral pharmaceutical compositions are a granular pharmaceutical composition or tablet.

In one embodiment, the process of preparing granular pharmaceutical compositions of the present invention have the following formulation:

|  | % by wgt. |
| --- | --- |
| Compound 1 Form I | 43 |
| Solid dispersion comprising substantially amorphous Compound 2 | 34 |
| Microcrystalline cellulose | 17 |
| Croscarmellose sodium | 2 |
| Sodium lauryl sulfate | 1 |
| Polyvinylpyrrolidone | 3 | referred to as PC-V.

In one embodiment, the process of preparing granular pharmaceutical compositions of the present invention have the following formulation:

|  | % by wgt. |
| --- | --- |
| Compound 1 Form I | 38 |
| Solid dispersion comprising substantially amorphous Compound 2 | 40 |
| Microcrystalline cellulose | 16 |
| Croscarmellose sodium | 2 |
| Sodium lauryl sulfate | 1 |
| Polyvinylpyrrolidone | 3 | referred to as PC-VI.

In one embodiment, the process of preparing granular pharmaceutical compositions of the present invention have the following formulation:

|  | % by wgt. |
| --- | --- |
| Compound 1 Form I | 51 |
| Solid dispersion comprising substantially amorphous Compound 2 | 27 |
| Microcrystalline cellulose | 16 |
| Croscarmellose sodium | 2 |
| Sodium lauryl sulfate | 1 |
| Polyvinylpyrrolidone | 3 | referred to as PC-VII.

In one embodiment, the process of preparing tablets of the present invention have the following formulation:

|  | % by wgt. |
| --- | --- |
| Compound 1 Form I | 35 |
| Solid dispersion comprising substantially amorphous Compound 2 | 28 |
| Microcrystalline cellulose | 26 |
| Croscarmellose sodium | 6 |
| Sodium lauryl sulfate | 1 |
| Polyvinylpyrrolidone | 3 |
| Magnesium stearate | 1 | referred to as PC-VIII.

In one embodiment, the process of preparing tablets of the present invention have the following formulation:

|  | % by wgt. |
| --- | --- |
| Compound 1 Form I | 31 |
| Solid dispersion comprising substantially amorphous Compound 2 | 32 |
| Microcrystalline cellulose | 26 |
| Croscarmellose sodium | 6 |
| Sodium lauryl sulfate | 1 |
| Polyvinylpyrrolidone | 3 |
| Magnesium stearate | 1 | referred to as PC-IX.

In one embodiment, the process of preparing tablets of the present invention have the following formulation:

|  | % by wgt. |
| --- | --- |
| Compound 1 Form I | 41 |
| Solid dispersion comprising substantially amorphous Compound 2 | 22 |
| Microcrystalline cellulose | 26 |
| Croscarmellose sodium | 6 |

|  | % by wgt. |
| --- | --- |
| Sodium lauryl sulfate | 1 |
| Polyvinylpyrrolidone | 3 |
| Magnesium stearate | 1 | referred to as PC-X.

In one embodiment, the process of preparing tablets of the present invention have the following formulation:

|  | mg |
| --- | --- |
| Compound 1 Form I | 200 |
| Solid dispersion comprising substantially amorphous Compound 2 | 156 |
| Microcrystalline cellulose | 150 |
| Croscarmellose sodium | 34 |
| Sodium lauryl sulfate | 4 |
| Polyvinylpyrrolidone | 15 |
| Magnesium stearate | 6 | referred to as PC-XI.

In one embodiment, the process of preparing tablets of the present invention have the following formulation:

|  | mg |
| --- | --- |
| Compound 1 Form I | 150 |
| Solid dispersion comprising substantially amorphous Compound 2 | 156 |
| Microcrystalline cellulose | 129 |
| Croscarmellose sodium | 30 |
| Sodium lauryl sulfate | 4 |
| Polyvinylpyrrolidone | 13 |
| Magnesium stearate | 5 | referred to as PC-XII.

In one embodiment, the process of preparing tablets of the present invention have the following formulation:

|  | mg |
| --- | --- |
| Compound 1 Form I | 200 |
| Solid dispersion comprising substantially amorphous Compound 2 | 104 |
| Microcrystalline cellulose | 128 |
| Croscarmellose sodium | 29 |
| Sodium lauryl sulfate | 4 |
| Polyvinylpyrrolidone | 13 |
| Magnesium stearate | 5 | referred to as PC-XIII.

In one embodiment, the process of preparing tablets of the present invention have the following formulation:

|  | % by wgt. |
| --- | --- |
| Compound 1 Form I | 34 |
| Solid dispersion comprising substantially amorphous Compound 2 | 27 |
| Microcrystalline cellulose | 25 |
| Croscarmellose sodium | 6 |
| Sodium lauryl sulfate | 1 |

|  | % by wgt. |
| --- | --- |
| Polyvinylpyrrolidone | 3 |
| Magnesium stearate | 1 |
| Colorant | 3 | referred to as PC-XIV.

In one embodiment, the process of preparing tablets of the present invention have the following formulation:

|  | % by wgt. |
| --- | --- |
| Compound 1 Form I | 30 |
| Solid dispersion comprising substantially amorphous Compound 2 | 31 |
| Microcrystalline cellulose | 25 |
| Croscarmellose sodium | 6 |
| Sodium lauryl sulfate | 1 |
| Polyvinylpyrrolidone | 3 |
| Magnesium stearate | 1 |
| Colorant | 3 | referred to as PC-XV.

In one embodiment, the process of preparing tablets of the present invention have the following formulation:

|  | % by wgt. |
| --- | --- |
| Compound 1 Form I | 40 |
| Solid dispersion comprising substantially amorphous Compound 2 | 21 |
| Microcrystalline cellulose | 25 |
| Croscarmellose sodium | 6 |
| Sodium lauryl sulfate | 1 |
| Polyvinylpyrrolidone | 3 |
| Magnesium stearate | 1 |
| Colorant | 3 | referred to as PC-XVI.

In one embodiment, the process of preparing tablets of the present invention have the following formulation:

|  | mg |
| --- | --- |
| Compound 1 Form I | 200 |
| Solid dispersion comprising substantially amorphous Compound 2 | 156 |
| Microcrystalline cellulose | 150 |
| Croscarmellose sodium | 34 |
| Sodium lauryl sulfate | 4 |
| Polyvinylpyrrolidone | 15 |
| Magnesium stearate | 6 |
| Colorant | 17 | referred to as PC-XVII.

In one embodiment, the process of preparing tablets of the present invention have the following formulation:

|  | mg |
| --- | --- |
| Compound 1 Form I | 200 |
| Substantially amorphous Compound 2 | 125 |
| Microcrystalline cellulose | 150 |
| Croscarmellose sodium | 34 |
| Sodium lauryl sulfate | 4 |

|  | mg |
|---|---|
| Polyvinylpyrrolidone | 15 |
| Magnesium stearate | 6 |
| Colorant | 17 | referred to as PC-XVIII

In one embodiment, the process of preparing tablets of the present invention have the following formulation:

|  | mg |
|---|---|
| Compound 1 Form I | 150 |
| Solid dispersion comprising substantially amorphous Compound 2 | 156 |
| Microcrystalline cellulose | 129 |
| Croscarmellose sodium | 29 |
| Sodium lauryl sulfate | 4 |
| Polyvinylpyrrolidone | 13 |
| Magnesium stearate | 5 |
| Colorant | 15 | referred to as PC-XIX.

In one embodiment, the process of preparing tablets of the present invention have the following formulation:

|  | mg |
|---|---|
| Compound 1 Form I | 200 |
| Solid dispersion comprising substantially amorphous Compound 2 | 104 |
| Microcrystalline cellulose | 128 |
| Croscarmellose sodium | 29 |
| Sodium lauryl sulfate | 4 |
| Polyvinylpyrrolidone | 13 |
| Magnesium stearate | 5 |
| Colorant | 14 | referred to as PC-XX.

In one embodiment, the process of preparing tablets of the present invention have the following formulation:

|  | mg |
|---|---|
| Compound 1 Form I | 200 |
| Solid dispersion comprising substantially amorphous Compound 2 | 83 |
| Microcrystalline cellulose | 128 |
| Croscarmellose sodium | 29 |
| Sodium lauryl sulfate | 4 |
| Polyvinylpyrrolidone | 13 |
| Magnesium stearate | 5 |
| Colorant | 14 | referred to as PC-XXI.

In one embodiment, the process of preparing tablets of the present invention have the following formulation:

| Component | % by wgt. |
|---|---|
| Compound 1 Form I | 20-40 |
| Solid dispersion comprising substantially amorphous Compound 2 | 30-40 |
| Microcrystalline cellulose | 20-30 |
| Croscarmellose sodium | 1-10 |
| Polyvinylpyrrolidone | 1-5 |
| Sodium lauryl sulfate | 0.1-1 |
| Magnesium stearate | 0.5-1.5 | referred to as PC-XXII.

In one embodiment, the process of preparing tablets of the present invention have the following formulation:

| Compound 1/Compound 2 100 mg/125 mg | | | |
|---|---|---|---|
| Component | % in Granule | % in Tablet | mg/Tablet |
| Compound 1 Form I | 30 | 25 | 100 |
| Solid dispersion comprising substantially amorphous Compound 2 | 47 | 38 | 156 |
| Microcrystalline cellulose | 17 | 13 | 55 |
| Croscarmellose sodium | 2 | 2 | 7 |
| Polyvinylpyrrolidone | 3 | 3 | 11 |
| Sodium lauryl sulfate | 1 | 1 | 3 |
| Total Granules | 100 | 82 | 332 |
| Croscarmellose sodium |  | 4 | 18 |
| Microcrystalline cellulose |  | 13 | 53 |
| Magnesium stearate |  | 1 | 4 |
| Total Tablet |  | 100 | 407 | referred to as PC-XXIII.

In one embodiment, the process of preparing tablets of the present invention have the following formulation:

| Compound 1/Compound 2 150 mg/125 mg | | | |
|---|---|---|---|
| Component | % in Granule | % in Tablet | mg/Tablet |
| Compound 1 Form I | 38 | 31 | 150 |
| Solid dispersion comprising substantially amorphous Compound 2 | 40 | 32 | 156 |
| Microcrystalline cellulose | 16 | 13 | 65 |
| Croscarmellose sodium | 2 | 2 | 8 |
| Polyvinylpyrrolidone | 3 | 3 | 13 |
| Sodium lauryl sulfate | 1 | 1 | 4 |
| Total Granules | 100 | 82 | 396 |
| Croscarmellose sodium |  | 4 | 22 |
| Microcrystalline cellulose |  | 13 | 64 |
| Magnesium stearate |  | 1 | 5 |
| Total Tablet |  | 100 | 487 | referred to as PC-XXIV.

In one embodiment, the process of preparing tablets of the present invention have the following formulation:

| Compound 1/Compound 2 75 mg/125 mg | | | |
|---|---|---|---|
| Component | % in Granule | % in Tablet | mg/Tablet |
| Compound 1 Form I | 25 | 20 | 75 |
| Solid dispersion comprising substantially amorphous Compound 2 | 52 | 43 | 156 |

-continued

Compound 1/Compound 2 75 mg/125 mg

| Component | % in Granule | % in Tablet | mg/Tablet |
|---|---|---|---|
| Microcrystalline cellulose | 17 | 13 | 49 |
| Croscarmellose sodium | 2 | 2 | 6 |
| Polyvinylpyrrolidone | 3 | 3 | 10 |
| Sodium lauryl sulfate | 1 | 1 | 3 |
| Total Granules | 100 | 82 | 299 |
| Croscarmellose sodium | | 4 | 17 |
| Microcrystalline cellulose | | 13 | 48 |
| Magnesium stearate | | 1 | 4 |
| Core Tablet | | 100 | 368 |
| Pink Opadry | | 3 | 11 |
| Film Coated Tablet | | | 379 |

Referred to as PC-XXV.

In one aspect, the present invention features a method of treating, lessening the severity of, or symptomatically treating cystic fibrosis in a patient comprising administering to the patient an effective amount of the pharmaceutical composition, granular pharmaceutical composition, or tablet of the present invention.

In embodiment, the present invention features a method of treating, lessening the severity of, or symptomatically treating cystic fibrosis in a patient comprising administering to the patient an effective amount of the pharmaceutical composition, granular pharmaceutical composition, or tablet of any one of formulations PC-I through PC-XXV.

In one embodiment, the patient has a ΔF508 CFTR mutation. In another embodiment, the patient is homozygous in ΔF508. In another embodiment, the patient is heterozygous in ΔF508. In another embodiment, two tablets are administered to the patient per day.

In one aspect, the present invention features a method of preparing a granular pharmaceutical composition comprising wet granulating the following components:
 a. Compound 1 Form I;
 b. a solid dispersion comprising substantially amorphous Compound 2;
 c. a filler;
 d. a disintegrant;
 e. a surfactant; and
 f. a binder.

In one aspect the present invention features a method of preparing a tablet comprising compressing:
 i) a plurality of granular pharmaceutical compositions comprising the following components:
  a. Compound 1 Form I;
  b. a solid dispersion comprising substantially amorphous Compound 2;
  c. a filler;
  d. a disintegrant;
  e. a surfactant; and
  f. a binder;
 ii) a disintegrant;
 iii) a filler; and
 iv) a lubricant.

In one aspect, the present invention features a kit comprising pharmaceutical compositions, granular pharmaceutical compositions, or tablets of the present invention, and a separate therapeutic agent or pharmaceutical composition thereof.

In one embodiment, the pharmaceutical compositions, granular pharmaceutical compositions, or tablets of the present invention, and the separate therapeutic agent or pharmaceutical composition thereof are in separate containers. In another embodiment, the separate containers are bottles. In another embodiment, the separate containers are vials. In another embodiment, the separate containers are blister packs.

In another aspect, the invention provides a continuous or semi-continuous process for making the pharmaceutical compositions described herein by a twin screw wet granulation process comprising the steps of screening and weighing Compound 1, Compound 2, and excipients; mixing Compound 1, Compound 2, and excipients in a blender and feeding the blend into a continuous granulator while adding a granulation fluid comprising surfactant and a binder at a suitable rate for a suitable amount of time and chopping the mixture into granules; drying the granules; blending the granules with extra-granular excipients for a suitable amount of time; compressing the blend into tablets; coating the tablets; and, optionally, printing a monogram on one or both tablet faces.

DETAILED DESCRIPTION

Definitions

Figure 1:
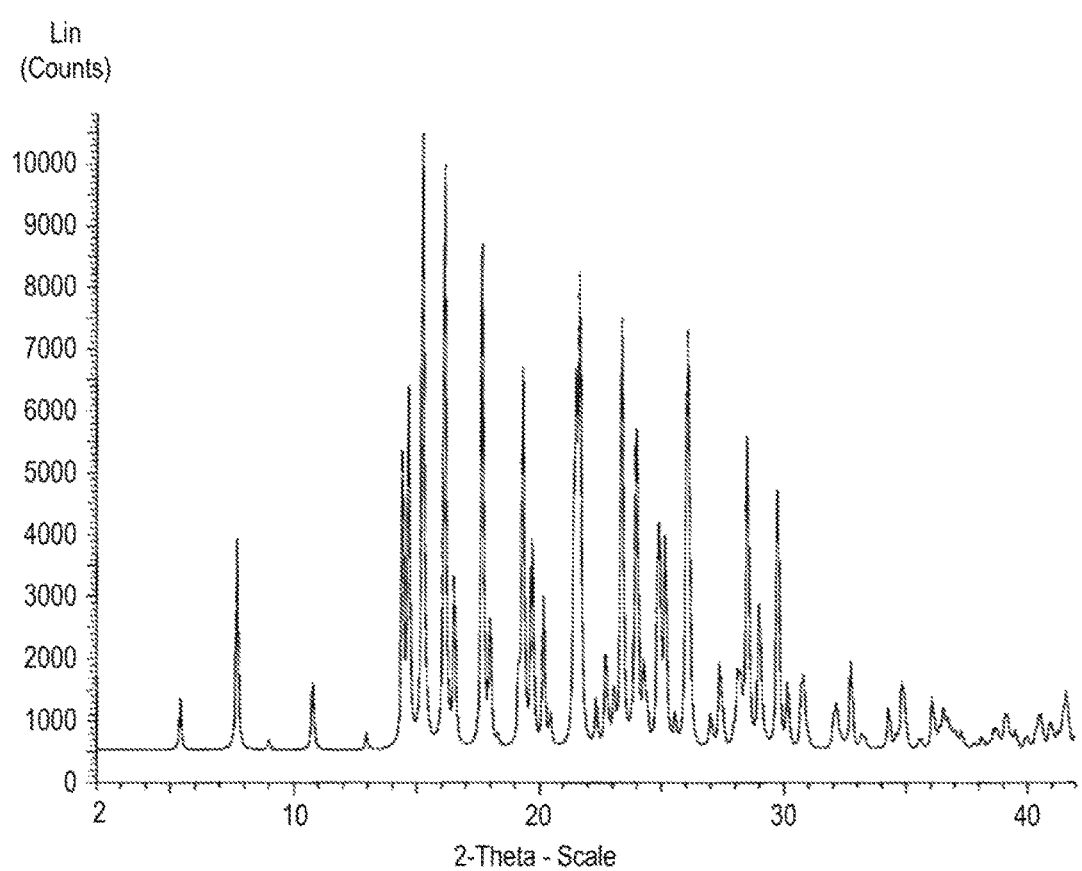
FIG. 1 is an X-ray diffraction pattern calculated from a single crystal structure of Compound 1 Form I.

As used herein, "CFTR" stands for cystic fibrosis transmembrane conductance regulator.

As used herein, a "ΔF508 mutation" or "F508-del mutation" is a specific mutation within the CFTR protein. The mutation is a deletion of the three nucleotides that comprise the codon for amino acid phenylalanine at position 508, resulting in CFTR protein that lacks this phenylalanine residue.

As used herein, a patient who is "homozygous" for a particular mutation, e.g. ΔF508, has the same mutation on each allele.

As used herein, a patient who is "heterozygous" for a particular mutation, e.g. ΔF508, has this mutation on one allele, and a different mutation on the other allele.

As used herein, the term "CFTR corrector" refers to a compound that increases the amount of functional CFTR protein to the cell surface, resulting in enhanced ion transport.

As used herein, the term "CFTR potentiator" refers to a compound that increases the channel activity of CFTR protein located at the cell surface, resulting in enhanced ion transport.

As used herein, the term "active pharmaceutical ingredient" or "API" refers to a biologically active compound.

As used herein, the term "PAT" stands for process analytical technology.

As used herein, the term "CU" stands for content uniformity.

The terms "solid form", "solid forms" and related terms, when used herein refer to Compound 1 or Compound 2, in a particular solid form e.g. crystals, amorphous states, and the like.

As used herein, the term "substantially amorphous" refers to a solid material having little or no long range order in the position of its molecules. For example, substantially amorphous materials have less than about 15% crystallinity (e.g., less than about 10% crystallinity or less than about 5% crystallinity). It is also noted that the term 'substantially amorphous' includes the descriptor, 'amorphous', which refers to materials having no (0%) crystallinity.

As used herein, the term "substantially crystalline" (as in the phrase substantially crystalline Compound 1 Form I refers to a solid material having predominantly long range order in the position of its molecules. For example, substantially crystalline materials have more than about 85% crystallinity (e.g., more than about 90% crystallinity or more than about 95% crystallinity). It is also noted that the term 'substantially crystalline' includes the descriptor, 'crystalline', which refers to materials having 100% crystallinity.

The term "crystalline" and related terms used herein, when used to describe a substance, component, product, or form, means that the substance, component or product is substantially crystalline as determined by X-ray diffraction. (See, e.g., Remington: The Science and Practice of Pharmacy, 21st Ed., Lippincott Williams & Wilkins, Baltimore, Md. (2003); The United States Pharmacopeia, 23$^{rd}$ ed., 1843-1844 (1995)).

As used herein, an "excipient" includes functional and non-functional ingredients in a pharmaceutical composition.

As used herein, a "disintegrant" is an excipient that hydrates a pharmaceutical composition and aids in tablet dispersion. As used herein, a "diluent" or "filler" is an excipient that adds bulkiness to a pharmaceutical composition.

As used herein, a "surfactant" is an excipient that imparts pharmaceutical compositions with enhanced solubility and/or wettability.

As used herein, a "binder" is an excipient that imparts a pharmaceutical composition with enhanced cohesion or tensile strength (e.g., hardness).

As used herein, a "glidant" is an excipient that imparts a pharmaceutical compositions with enhanced flow properties.

As used herein, a "colorant" is an excipient that imparts a pharmaceutical composition, e.g. a tablet, with a desired color. Examples of colorants include commercially available pigments such as FD&C Blue #1 Aluminum Lake, FD&C Blue #2, other FD&C Blue colors, titanium dioxide, iron oxide, and/or combinations thereof. In one embodiment, the tablet provided by the invention is pink.

As used herein, a "lubricant" is an excipient that is added to pharmaceutical compositions that are pressed into tablets. The lubricant aids in compaction of granules into tablets and ejection of a tablet of a pharmaceutical composition from a die press.

As used herein, "cubic centimeter" and "cc" are used interchangeably to represent a unit of volume. Note that 1 cc=1 mL.

As used herein, "kiloPond" and "kP" are used interchangeably and refer to the measure of force where a kP=approximately 9.8 Newtons.

As used herein, "friability" refers to the property of a tablet to remain intact and hold its form despite an external force of pressure. Friability can be quantified using the mathematical expression presented in equation 1:

$$\% \text{ friability} = 100 \times \frac{(W_0 - W_f)}{W_0} \quad (1)$$

wherein $W_0$ is the original weight of the tablet and W is the final weight of the tablet after it is put through the friabilator. Friability is measured using a standard USP testing apparatus that tumbles experimental tablets for 100 or 400 revolutions. Some tablets of the invention have a friability of less than 5.0%. In another embodiment, the friability is less than 2.0%. In another embodiment, the target friability is less than 1.0% after 400 revolutions.

As used herein, "mean particle diameter" Is the average particle diameter as measured using techniques such as laser light scattering, image analysis, or sieve analysis. In one embodiment, the granules used to prepare the pharmaceutical compositions provided by the invention have a mean particle diameter of less than 1.0 mm.

As used herein, "bulk density" is the mass of particles of material divided by the total volume the particles occupy. The total volume includes particle volume, inter-particle void volume and internal pore volume. Bulk density is not an intrinsic property of a material; it can change depending on how the material is processed. In one embodiment, the granules used to prepare the pharmaceutical compositions provided by the invention have a bulk density of about 0.5-0.7 g/cc.

An "effective amount" or "therapeutically effective amount" of a compound of the invention may vary according to factors such as the disease state, age, and weight of the subject, and the ability of the compound of the invention to elicit a desired response in the subject. Dosage regimens may be adjusted to provide the optimum therapeutic response. An effective amount is also one in which any toxic or detrimental effects (e.g., side effects) of the compound of the invention are outweighed by the therapeutically beneficial effects.

As used herein, and unless otherwise specified, the terms "therapeutically effective amount" and "effective amount" of a compound mean an amount sufficient to provide a therapeutic benefit in the treatment or management of a disease or disorder, or to delay or minimize one or more symptoms associated with the disease or disorder. A "therapeutically effective amount" and "effective amount" of a compound mean an amount of therapeutic agent, alone or in combination with one or more other agent(s), which provides a therapeutic benefit in the treatment or management of the disease or disorder. The terms "therapeutically effective amount" and "effective amount" can encompass an amount that improves overall therapy, reduces or avoids symptoms or causes of disease or disorder, or enhances the therapeutic efficacy of another therapeutic agent.

"Substantially pure" as used in the phrase "substantially pure Compound 1 Form I" means greater than about 90% purity. In another embodiment, substantially pure refers to greater than about 95% purity. In another embodiment, substantially pure refers to greater than about 98% purity. In another embodiment, substantially pure refers to greater than about 99% purity.

With respect to Compound 1 Form I, or a solid dispersion comprising substantially amorphous Compound 2, the terms "about" and "approximately", when used in connection with doses, amounts, or weight percent of ingredients of a composition or a dosage form, mean a dose, amount, or weight percent that is recognized by one of ordinary skill in the art to provide a pharmacological effect equivalent to that obtained from the specified dose, amount, or weight percent. Specifically the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, 0.1%, or 0.05% of a given value or range.

Pharmaceutical Compositions

The invention provides pharmaceutical compositions comprising Compound 1 Form I and a solid dispersion comprising substantially amorphous Compound 2. In some embodiments of this aspect, the amount of Compound 1 Form I that is present in the pharmaceutical composition is 100 mg, 125 mg, 150 mg, 200 mg, 250 mg, 300 mg, or 400 mg. In some embodiments of this aspect, wgt. percent of Compound 1 Form I present in the pharmaceutical composition is from 10 to 75 percent. In these and other embodiments, Compound 1 Form I is present as substantially pure Compound 1 Form I. In some embodiments of this aspect, the amount of substantially amorphous Compound 2 that is present in the pharmaceutical composition is 100 mg, 125 mg, 150 mg, 200 mg, or 250 mg. In some embodiments of this aspect, wgt. percent of substantially amorphous Compound 2 that is present in the pharmaceutical composition is from 10 to 75 percent. In these and other embodiments, substantially amorphous Compound 2 is present as substantially pure and amorphous Compound 2. "Substantially pure" means greater than ninety percent pure; preferably greater than 95 percent pure; more preferably greater than 99.5 percent pure.

Thus in one aspect, the invention provides a pharmaceutical composition comprising:
a. Compound 1 Form I;
b. a solid dispersion of substantially amorphous Compound 2;
c. a filler;
d. a disintegrant;
e. a surfactant; and
f. a binder.

In one embodiment of this aspect, the pharmaceutical composition comprises 25 mg of Compound 1 Form I. In another embodiment of this aspect, the pharmaceutical composition comprises 50 mg of Compound 1 Form I. In another embodiment of this aspect, the pharmaceutical composition comprises 100 mg of Compound 1 Form I. In another embodiment of this aspect, the pharmaceutical composition comprises 125 mg of Compound 1 Form I. In another embodiment of this aspect, the pharmaceutical composition comprises 150 mg of Compound 1 Form I. In another embodiment of this aspect, the pharmaceutical composition comprises 200 mg of Compound 1 Form I. In another embodiment of this aspect, the pharmaceutical composition comprises 250 mg of Compound 1 Form I. In another embodiment of this aspect, the pharmaceutical composition comprises 400 mg of Compound 1 Form I.

In one embodiment of this aspect, the pharmaceutical composition comprises 25 mg of substantially amorphous Compound 2. In another embodiment of this aspect, the pharmaceutical composition comprises 50 mg of substantially amorphous Compound 2. In another embodiment of this aspect, the pharmaceutical composition comprises 100 mg of substantially amorphous Compound 2. In another embodiment of this aspect, the pharmaceutical composition comprises 125 mg of substantially amorphous Compound 2. In another embodiment of this aspect, the pharmaceutical composition comprises 150 mg of substantially amorphous Compound 2. In another embodiment of this aspect, the pharmaceutical composition comprises 200 mg of substantially amorphous Compound 2. In another embodiment of this aspect, the pharmaceutical composition comprises 250 mg of substantially amorphous Compound 2.

In some embodiments, the pharmaceutical compositions comprises Compound 1 Form I, wherein Compound 1 Form I is present in an amount of at least 15 wt % (e.g., at least 20 wt %, at least 30 wt %, at least 40 wt %, at least 50 wt %, or at least 60 wt %) by weight of the composition.

In some embodiments, the pharmaceutical compositions comprises substantially amorphous Compound 2, wherein the substantially amorphous Compound 2 is present in an amount of at least 15 wt % (e.g., at least 20 wt %, at least 30 wt %, at least 40 wt %, at least 50 wt %, or at least 60 wt %) by weight of the composition.

In some embodiments, the pharmaceutical composition comprises Compound 1 Form I, a solid dispersion comprising substantially amorphous Compound 2, a filler, a disintegrant, a surfactant, and a binder. In this embodiment, the composition comprises from about 25 wt % to about 55 wt % (e.g., about 30-50 wt %) of Compound 1 Form I by weight of the composition, and more typically, from 40 wt % to about 45 wt % of Compound 1 Form I by weight of the composition. In this embodiment, the composition comprises from about 15 wt % to about 40 wt % (e.g., about 20-35 wt %) of substantially amorphous Compound 2 by weight of the composition, and more typically, from 25 wt % to about 30 wt % of substantially amorphous Compound 2 by weight of the composition.

The concentration of Compound 1 Form I and substantially amorphous Compound 2 in the composition depends on several factors such as the amount of pharmaceutical composition needed to provide a desired amount of Compound 1 Form I and substantially amorphous Compound 2 and the desired dissolution profile of the pharmaceutical composition.

In another embodiment, the pharmaceutical composition comprises Compound 1 Form I, in which Compound 1 Form I in its solid form has a mean particle diameter, measured by light scattering (e.g., using a Malvern Mastersizer available from Malvern Instruments in England) of 0.1 microns to 10 microns. In another embodiment, the particle size of Compound 1 Form I is 1 micron to 5 microns. In another embodiment, Compound 1 Form I has a particle size D50 of 2.0 microns.

As indicated, in addition to Compound 1 Form I and a solid dispersion of substantially amorphous Compound 2, in some embodiments of the invention, the pharmaceutical compositions which are oral formulations also comprise one or more excipients such as fillers, disintegrants, surfactants, diluents, binders, glidants, lubricants, colorants, or fragrances and any combination thereof.

Fillers suitable for the invention are compatible with the ingredients of the pharmaceutical composition, i.e., they do not substantially reduce the solubility, the hardness, the chemical stability, the physical stability, or the biological activity of the pharmaceutical composition. Exemplary fillers include: celluloses, modified celluloses, (e.g. sodium carboxymethyl cellulose, ethyl cellulose hydroxymethyl cellulose, hydroxypropylcellulose), cellulose acetate, microcrystalline cellulose, calcium phosphates, dibasic calcium phosphate, starches (e.g. corn starch, potato starch), sugars (e.g., sorbitol) lactose, sucrose, or the like), or any combination thereof.

Thus, in one embodiment, the pharmaceutical composition comprises at least one filler in an amount of at least 5 wt % (e.g., at least about 20 wt %, at least about 30 wt %, or at least about 40 wt %) by weight of the composition. For example, the pharmaceutical composition comprises from about 10 wt % to about 60 wt % (e.g., from about 20 wt % to about 55 wt %, from about 25 wt % to about 50 wt %, or from about 27 wt % to about 45 wt %) of filler, by weight of the composition. In another example, the pharmaceutical composition comprises at least about 20 wt % (e.g., at least 30 wt % or at least 40 wt %) of microcrystalline cellulose, for example MCC Avicel PH102, by weight of the composition. In yet another example, the pharmaceutical composition comprises from about 10 wt % to about 60 wt % (e.g., from about 20 wt % to about 55 wt % or from about 25 wt % to about 45 wt %) of microcellulose, by weight of the composition.

Disintegrants suitable for the invention enhance the dispersal of the pharmaceutical composition and are compatible with the ingredients of the pharmaceutical composition, i.e., they do not substantially reduce the chemical stability, the physical stability, the hardness, or the biological activity of the pharmaceutical composition. Exemplary disintegrants include croscarmellose sodium, sodium starch glycolate, or a combination thereof.

Thus, in one embodiment, the pharmaceutical composition comprises disintegrant in an amount of about 10 wt % or less (e.g., about 7 wt % or less, about 6 wt % or less, or about 5 wt % or less) by weight of the composition. For example, the pharmaceutical composition comprises from about 1 wt % to about 10 wt % (e.g., from about 1.5 wt % to about 7.5 wt % or from about 2.5 wt % to about 6 wt %) of disintegrant, by weight of the composition. In another example, the pharmaceutical composition comprises about 10 wt % or less (e.g., 7 wt % or less, 6 wt % or less, or 5 wt % or less) of croscarmellose sodium, by weight of the composition. In yet another example, the pharmaceutical composition comprises from about 1 wt % to about 10 wt % (e.g., from about 1.5 wt % to about 7.5 wt % or from about 2.5 wt % to about 6 wt %) of croscarmellose sodium, by weight of the composition. In some examples, the pharmaceutical composition comprises from about 0.1% to about 10 wt % (e.g., from about 0.5 wt % to about 7.5 wt % or from about 1.5 wt % to about 6 wt %) of disintegrant, by weight of the composition. In still other examples, the pharmaceutical composition comprises from about 0.5% to about 10 wt % (e.g., from about 1.5 wt % to about 7.5 wt % or from about 2.5 wt % to about 6 wt %) of disintegrant, by weight of the composition.

Surfactants suitable for the invention enhance the wettability of the pharmaceutical composition and are compatible with the ingredients of the pharmaceutical composition, i.e., they do not substantially reduce the chemical stability, the physical stability, the hardness, or the biological activity of the pharmaceutical composition. Exemplary surfactants include sodium lauryl sulfate (SLS), sodium stearyl fumarate (SSF), polyoxyethylene 20 sorbitan mono-oleate (e.g., Tween™), any combination thereof, or the like.

Thus, in one embodiment, the pharmaceutical composition comprises a surfactant in an amount of about 10 wt % or less (e.g., about 5 wt % or less, about 2 wt % or less, about 1 wt % or less, about 0.8 wt % or less, or about 0.6 wt % or less) by weight of the composition. For example, the pharmaceutical composition includes from about 10 wt % to about 0.1 wt % (e.g., from about 5 wt % to about 0.2 wt % or from about 2 wt % to about 0.3 wt %) of surfactant, by weight of the composition. In another example, the pharmaceutical composition comprises 10 wt % or less (e.g., about 5 wt % or less, about 2 wt % or less, about 1 wt % or less, about 0.8 wt % or less, or about 0.6 wt % or less) of sodium lauryl sulfate, by weight of the composition. In yet another example, the pharmaceutical composition comprises from about 10 wt % to about 0.1 wt % (e.g., from about 5 wt % to about 0.2 wt % or from about 2 wt % to about 0.3 wt %) of sodium lauryl sulfate, by weight of the composition.

Binders suitable for the invention enhance the tablet strength of the pharmaceutical composition and are compatible with the ingredients of the pharmaceutical composition, i.e., they do not substantially reduce the chemical stability, the physical stability, or the biological activity of the pharmaceutical composition. Exemplary binders include polyvinylpyrrolidone, dibasic calcium phosphate, sucrose, corn (maize) starch, modified cellulose (e.g., hydroxymethyl cellulose), or any combination thereof.

Thus, in one embodiment, the pharmaceutical composition comprises a binder in an amount of at least about 0.1 wt % (e.g., at least about 1 wt %, at least about 3 wt %, at least about 4 wt %, or at least about 5 wt %) by weight of the composition. For example, the pharmaceutical composition comprises from about 0.1 wt % to about 10 wt % (e.g., from about 1 wt % to about 10 wt % or from about 2 wt % to about 7 wt %) of binder, by weight of the composition. In another example, the pharmaceutical composition comprises at least about 0.1 wt % (e.g., at least about 1 wt %, at least about 2 wt %, at least about 3 wt %, or at least about 4 wt %) of polyvinylpyrrolidone, by weight of the composition. In yet another example, the pharmaceutical composition comprises a glidant in an amount ranging from about 0.1 wt % to about 10 wt % (e.g., from about 1 wt % to about 8 wt % or from about 2 wt % to about 5 wt %) of polyvinylpyrrolidone, by weight of the composition.

Diluents suitable for the invention may add necessary bulk to a formulation to prepare tablets of the desired size and are generally compatible with the ingredients of the pharmaceutical composition, i.e., they do not substantially reduce the solubility, the hardness, the chemical stability, the physical stability, or the biological activity of the pharmaceutical composition. Exemplary diluents include: sugars, for example, confectioner's sugar, compressible sugar, dextrates, dextrin, dextrose, lactose, mannitol, sorbitol, cellulose, and modified celluloses, for example, powdered cellulose, talc, calcium phosphate, starch, or any combination thereof.

Thus, in one embodiment, the pharmaceutical composition comprises a diluent in an amount of 40 wt % or less (e.g., 35 wt % or less, 30 wt % or less, or 25 wt % or less, or 20 wt % or less, or 15 wt % or less, or 10 wt % or less) by weight of the composition. For example, the pharmaceutical composition comprises from about 40 wt % to about 1 wt % (e.g., from about 35 wt % to about 5 wt % or from about 30 wt % to about 7 wt %, from about 25 wt % to about 10 wt %, from about 20 wt % to about 15 wt %) of diluent, by weight of the composition. In another example, the pharmaceutical composition comprises 40 wt % or less (e.g., 35 wt % or less, 25 wt % or less, or 15 wt % or less) of mannitol, by weight of the composition. In yet another example, the pharmaceutical composition comprises from about 35 wt % to about 1 wt % (e.g., from about 30 wt % to about 5 wt % or from about 25 wt % to about 10 wt %) of mannitol, by weight of the composition.

Glidants suitable for the invention enhance the flow properties of the pharmaceutical composition and are compatible with the ingredients of the pharmaceutical composition, i.e., they do not substantially reduce the solubility, the hardness, the chemical stability, the physical stability, or the biological activity of the pharmaceutical composition. Exemplary glidants include colloidal silicon dioxide, talc, or a combination thereof.

Thus, in one embodiment, the pharmaceutical composition comprises a glidant in an amount of 2 wt % or less (e.g., 1.75 wt %, 1.25 wt % or less, or 1.00 wt % or less) by weight of the composition. For example, the pharmaceutical composition comprises from about 2 wt % to about 0.05 wt % (e.g., from about 1.5 wt % to about 0.07 wt % or from about 1.0 wt % to about 0.09 wt %) of glidant, by weight of the composition. In another example, the pharmaceutical composition comprises 2 wt % or less (e.g., 1.75 wt %, 1.25 wt % or less, or 1.00 wt % or less) of colloidal silicon dioxide, by weight of the composition. In yet another example, the pharmaceutical composition comprises from about 2 wt % to about 0.05 wt % (e.g., from about 1.5 wt % to about 0.07 wt % or from about 1.0 wt % to about 0.09 wt %) of colloidal silicon dioxide, by weight of the composition.

In some embodiments, the pharmaceutical composition can include an oral solid pharmaceutical dosage form which can comprise a lubricant that can prevent adhesion of a granulate-bead admixture to a surface (e.g., a surface of a mixing bowl, a compression die and/or punch). A lubricant can also reduce interparticle friction within the granulate and improve the compression and ejection of compressed pharmaceutical compositions from a die press. The lubricant is also compatible with the ingredients of the pharmaceutical composition, i.e., they do not substantially reduce the solubility, the hardness, or the biological activity of the pharmaceutical composition. Exemplary lubricants include magnesium stearate, calcium stearate, zinc stearate, sodium stearate, stearic acid, aluminum stearate, leucine, glyceryl behenate, hydrogenated vegetable oil or any combination thereof. In one embodiment, the pharmaceutical composition comprises a lubricant in an amount of 5 wt % or less (e.g., 4.75 wt %, 4.0 wt % or less, or 3.00 wt % or less, or 2.0 wt % or less) by weight of the composition. For example, the pharmaceutical composition comprises from about 5 wt % to about 0.10 wt % (e.g., from about 4.5 wt % to about 0.5 wt % or from about 3 wt % to about 1 wt %) of lubricant, by weight of the composition. In another example, the pharmaceutical composition comprises 5 wt % or less (e.g., 4.0 wt % or less, 3.0 wt % or less, or 2.0 wt % or less, or 1.0 wt % or less) of magnesium stearate, by weight of the composition. In yet another example, the pharmaceutical composition comprises from about 5 wt % to about 0.10 wt % (e.g., from about 4.5 wt % to about 0.15 wt % or from about 3.0 wt % to about 0.50 wt %) of magnesium stearate, by weight of the composition.

Pharmaceutical compositions of the invention can optionally comprise one or more colorants, flavors, and/or fragrances to enhance the visual appeal, taste, and/or scent of the composition. Suitable colorants, flavors, or fragrances are compatible with the ingredients of the pharmaceutical composition, i.e., they do not substantially reduce the solubility, the chemical stability, the physical stability, the hardness, or the biological activity of the pharmaceutical composition. In one embodiment, the pharmaceutical composition comprises a colorant, a flavor, and/or a fragrance. In one embodiment, the pharmaceutical compositions provided by the invention are purple.

In some embodiments, the pharmaceutical composition includes or can be made into tablets and the tablets can be coated with a colorant and optionally labeled with a logo, other image and/or text using a suitable ink. In still other embodiments, the pharmaceutical composition includes or can be made into tablets and the tablets can be coated with a colorant, waxed, and optionally labeled with a logo, other image and/or text using a suitable ink. Suitable colorants and inks are compatible with the ingredients of the pharmaceutical composition, i.e., they do not substantially reduce the solubility, the chemical stability, the physical stability, the hardness, or the biological activity of the pharmaceutical composition. The suitable colorants and inks can be any color and are water based or solvent based. In one embodiment, tablets made from the pharmaceutical composition are coated with a colorant and then labeled with a logo, other image, and/or text using a suitable ink. For example, tablets comprising pharmaceutical composition as described herein can be coated with about 3 wt % (e.g., less than about 6 wt % or less than about 4 wt %) of film coating comprising a colorant. The colored tablets can be labeled with a logo and text indicating the strength of the active ingredient in the tablet using a suitable ink. In another example, tablets comprising pharmaceutical composition as described herein can be coated with about 3 wt % (e.g., less than about 6 wt % or less than about 4 wt %) of a film coating comprising a colorant.

In another embodiment, tablets made from the pharmaceutical composition are coated with a colorant, waxed, and then labeled with a logo, other image, and/or text using a suitable ink. For example, tablets comprising pharmaceutical composition as described herein can be coated with about 3 wt % (e.g., less than about 6 wt % or less than about 4 wt %) of film coating comprising a colorant. The colored tablets can be waxed with Carnauba wax powder weighed out in the amount of about 0.01% w/w of the starting tablet core weight. The waxed tablets can be labeled with a logo and text indicating the strength of the active ingredient in the tablet using a suitable ink. In another example, tablets comprising pharmaceutical composition as described herein can be coated with about 3 wt % (e.g., less than about 6 wt % or less than about 4 wt %) of a film coating comprising a colorant The colored tablets can be waxed with Carnauba wax powder weighed out in the amount of about 0.01% w/w of the starting tablet core weight. The waxed tablets can be labeled with a logo and text indicating the strength of the active ingredient in the tablet using a pharmaceutical grade ink such as a black ink (e.g., Opacode® S-1-17823, a solvent based ink, commercially available from Colorcon, Inc. of West Point, Pa.).

One exemplary pharmaceutical composition comprises from about 15 wt % to about 70 wt % (e.g., from about 15 wt % to about 60 wt %, from about 15 wt % to about 50 wt %, or from about 20 wt % to about 70 wt %, or from about 30 wt % to about 70 wt %) of Compound 1 Form I, by weight of the composition; and from about 15 wt % to about 40 wt % (e.g., about 20-35 wt %) of substantially amorphous Compound 2 by weight of the composition, and more typically, from 25 wt % to about 30 wt % of substantially amorphous Compound 2 by weight of the composition. The aforementioned compositions can also include one or more pharmaceutically acceptable excipients, for example, from about 20 wt % to about 50 wt % of a filler; from about 1 wt % to about 5 wt % of a disintegrant; from about 2 wt % to about 0.3 wt % of a surfactant; and from about 0.1 wt % to about 5 wt % of a binder.

Another exemplary pharmaceutical composition comprises from about 15 wt % to about 70 wt % (e.g., from about 15 wt % to about 60 wt %, from about 15 wt % to about 50 wt %, or from about 15 wt % to about 40 wt % or from about 20 wt % to about 70 wt %, or from about 30 wt % to about 70 wt %, or from about 40 wt % to about 70 wt %, or from about 50 wt % to about 70 wt %) of Compound 1 Form I by weight of the composition, from about 15 wt % to about 40 wt % (e.g., about 20-35 wt %) of substantially amorphous Compound 2 by weight of the composition, and more typically, from 25 wt % to about 30 wt % of substantially amorphous Compound 2 by weight of the composition, and one or more excipients, for example, from about 20 wt % to about 50 wt % of a filler; from about 1 wt % to about 5 wt % of a disintegrant; from about 2 wt % to about 0.3 wt % of a surfactant; from about 0.1 wt % to about 5 wt % of a binder; and from about 2 wt % to about 0.1 wt % of a lubricant.

Another exemplary pharmaceutical composition comprises from about 15 wt % to about 70 wt % (e.g., from about 15 wt % to about 60 wt %, from about 15 wt % to about 50 wt %, or from about 15 wt % to about 40 wt % or from about 20 wt % to about 70 wt %, or from about 30 wt % to about 70 wt %, or from about 40 wt % to about 70 wt %, or from about 50 wt % to about 70 wt %) of Compound 1 Form I by weight of the composition, from about 15 wt % to about 40 wt % (e.g., about 20-35 wt %) of substantially amorphous Compound 2 by weight of the composition, and more typically, from 25 wt % to about 30 wt % of substantially amorphous Compound 2 by weight of the composition, and one or more excipients, for example, from about 20 wt % to about 50 wt % of a filler; from about 1 wt % to about 5 wt % of a disintegrant; from about 2 wt % to about 0.3 wt % of a surfactant; from about 0.1 wt % to about 5 wt % of a binder; from about 2 wt % to about 0.1 wt % of a lubricant;

from about 2 wt % to about 4 wt % colorant; and about 0.005 wt % to about 0.015 wt % wax.

In one embodiment, the invention is a granular pharmaceutical composition comprising:
 a. about 43 wt % of Compound 1 Form I by weight of the composition;
 b. about 34 wt % of a solid dispersion comprising substantially amorphous Compound 2 by weight of the composition;
 c. about 17 wt % of microcrystalline cellulose by weight of the composition;
 d. about 2 wt % of croscarmellose sodium by weight of the composition;
 e. about 1 wt % of sodium lauryl sulfate by weight of the composition; and
 f. about 3 wt % of polyvinylpyrrolidone by weight of the composition.

In one embodiment, the invention is a tablet comprising:
 a. about 35 wt % of Compound 1 Form I by weight of the composition;
 b. about 28 wt %/o of a solid dispersion comprising substantially amorphous Compound 2 by weight of the composition;
 c. about 26 wt % of microcrystalline cellulose by weight of the composition;
 d. about 6 wt % of croscarmellose sodium by weight of the composition;
 e. about 3 wt % of polyvinylpyrrolidone by weight of the composition;
 f. about 1 wt % of sodium lauryl sulfate by weight of the composition; and
 g. about 1 wt % of magnesium stearate by weight of the composition.

In one embodiment, the invention is a tablet comprising:
 a. about 34 wt % of Compound 1 Form I by weight of the composition;
 b. about 27 wt % of a solid dispersion comprising substantially amorphous Compound 2 by weight of the composition;
 c. about 26 wt % of microcrystalline cellulose by weight of the composition;
 d. about 6 wt % of croscarmellose sodium by weight of the composition;
 e. about 2 wt % of polyvinylpyrrolidone by weight of the composition
 f. about 1 wt % of sodium lauryl sulfate by weight of the composition;
 g. about 1 wt % of magnesium stearate by weight of the composition;
 h. about 3 wt % of a colorant by weight of the composition; and
 i. about 0.010 wt % of a wax by weight of the composition.

Another tablet of the invention comprises:
 a. about 150 to 250 mg of Compound 1 Form I;
 b. about 100 to 150 mg of substantially amorphous Compound 2;
 c. about 125 to 175 mg of microcrystalline cellulose;
 d. about 20 to 40 mg of croscarmellose sodium;
 e. about 10 to 20 mg of polyvinylpyrrolidone;
 f. about 2 to 6 mg of sodium lauryl sulfate; and
 g. about 3 to 7 mg of magnesium stearate.

Another tablet of the invention comprises:
 a. about 200 mg of Compound 1 Form I;
 b. about 125 mg of substantially amorphous Compound 2;
 c. about 150 mg of microcrystalline cellulose;
 d. about 34 mg of croscarmellose sodium;
 e. about 15 mg of polyvinylpyrrolidone;
 f. about 4 mg of sodium lauryl sulfate; and
 g. about 6 mg of magnesium stearate.

Another tablet of the invention comprises:
 a. about 200 mg of Compound 1 Form I;
 b. about 125 mg of substantially amorphous Compound 2;
 c. about 150 mg of microcrystalline cellulose;
 d. about 34 mg of croscarmellose sodium;
 e. about 15 mg of polyvinylpyrrolidone;
 f. about 4 mg of sodium lauryl sulfate;
 g. about 6 mg of magnesium stearate;
 h. about 17 mg of a colorant; and
 i. about 0.06 mg of a wax.

In one embodiment, the invention is a granular pharmaceutical composition comprising:
 a. about 38 wt % of Compound 1 Form I by weight of the composition;
 b. about 40 wt % of a solid dispersion comprising substantially amorphous Compound 2 by weight of the composition;
 c. about 16 wt % of microcrystalline cellulose by weight of the composition;
 d. about 2 wt % of croscarmellose sodium by weight of the composition;
 e. about 1 wt % of sodium lauryl sulfate by weight of the composition; and
 f. about 3 wt % of polyvinylpyrrolidone by weight of the composition.

In one embodiment, the invention is a tablet comprising:
 a. about 31 wt % of Compound 1 Form I by weight of the composition;
 b. about 32 wt % of a solid dispersion comprising substantially amorphous Compound 2 by weight of the composition;
 c. about 26 wt % of microcrystalline cellulose by weight of the composition;
 d. about 6 wt % of croscarmellose sodium by weight of the composition;
 e. about 3 wt % of polyvinylpyrrolidone by weight of the composition
 f. about 1 wt % of sodium lauryl sulfate by weight of the composition;
 g. about 1 wt % of magnesium stearate by weight of the composition; and
 h. about 3 wt % of a colorant by weight of the composition.

Another tablet of the invention comprises:
 a. about 100 to 200 mg of Compound 1 Form I;
 b. about 100 to 150 mg of substantially amorphous Compound 2;
 c. about 100 to 150 mg of microcrystalline cellulose;
 d. about 20 to 40 mg of croscarmellose sodium;
 e. about 10 to 20 mg of polyvinylpyrrolidone;
 f. about 2 to 6 mg of sodium lauryl sulfate; and
 g. about 3 to 7 mg of magnesium stearate.

Another tablet of the invention comprises:
 a. about 150 mg of Compound 1 Form I;
 b. about 125 mg of substantially amorphous Compound 2;
 c. about 129 mg of microcrystalline cellulose;
 d. about 29 mg of croscarmellose sodium;
 e. about 13 mg of polyvinylpyrrolidone;
 f. about 4 mg of sodium lauryl sulfate;
 g. about 5 mg of magnesium stearate; and
 h. about 15 mg of a colorant.

The pharmaceutical compositions of the invention can be processed into a tablet form, capsule form, pouch form, lozenge form, or other solid form that is suited for oral administration. Thus in some embodiments, the pharmaceutical compositions are in tablet form.

Another aspect of the invention provides a pharmaceutical formulation consisting of a tablet that includes Compound 1 Form I, a solid dispersion comprising substantially amorphous Compound 2, and excipients (e.g., a filler, a disintegrant, a surfactant, a binder, a colorant, a lubricant, or any combination thereof), each of which is described above and in the Examples below, wherein the tablet has a dissolution of at least about 50% (e.g., at least about 60%, at least about 70%, at least about 80%, at least about 90%, or at least about 99%) in about 30 minutes.

In one example, the pharmaceutical composition consists of a tablet that includes Compound 1 Form I in an amount ranging from 25 mg to 400 mg, for example, 25 mg, or 50 mg, or 75 mg, or 100 mg, or 150 mg, 200 mg, 250 mg, 300 mg, or 400 mg, substantially amorphous Compound 2 in an amount ranging from 25 mg to 250 mg, for example, 25 mg, or 50 mg, or 75 mg, or 100 mg, or 150 mg, 200 mg, 250 mg, and one or more excipients (e.g., a filler, a disintegrant, a surfactant, a binder, a colorant, a lubricant, or any combination thereof) each of which is described above and in the Examples below, wherein the tablet has a dissolution of from about 50% to about 100% (e.g., from about 55% to about 95% or from about 60% to about 90%) in about 30 minutes.

Dissolution can be measured with a standard USP Type II apparatus that employs a dissolution media of 0.1% CTAB dissolved in 900 mL of DI water, buffered at pH 6.8 with 50 mM potassium phosphate monoasic, stirring at about 50-75 rpm at a temperature of about 37° C. A single experimental tablet is tested in each test vessel of the apparatus. Dissolution can also be measured with a standard USP Type II apparatus that employs a dissolution media of 0.7% sodium lauryl sulfate dissolved in 900 mL of 50 mM sodium phosphate buffer (pH 6.8), stirring at about 65 rpm at a temperature of about 37° C. A single experimental tablet is tested in each test vessel of the apparatus. Dissolution can also be measured with a standard USP Type II apparatus that employs a dissolution media of 0.5% sodium lauryl sulfate dissolved in 900 mL of 50 mM sodium phosphate buffer (pH 6.8), stirring at about 65 rpm at a temperature of about 37° C. A single experimental tablet is tested in each test vessel of the apparatus.

Methods for Making Compound 1 Form I and a Solid Dispersion Comprising Substantially Amorphous Compound 2

Compound 1

Compound 1 is used as the starting point for Compound 1 Form I and can be prepared by coupling an acid chloride moiety with an amine moiety according to Schemes 1-4.

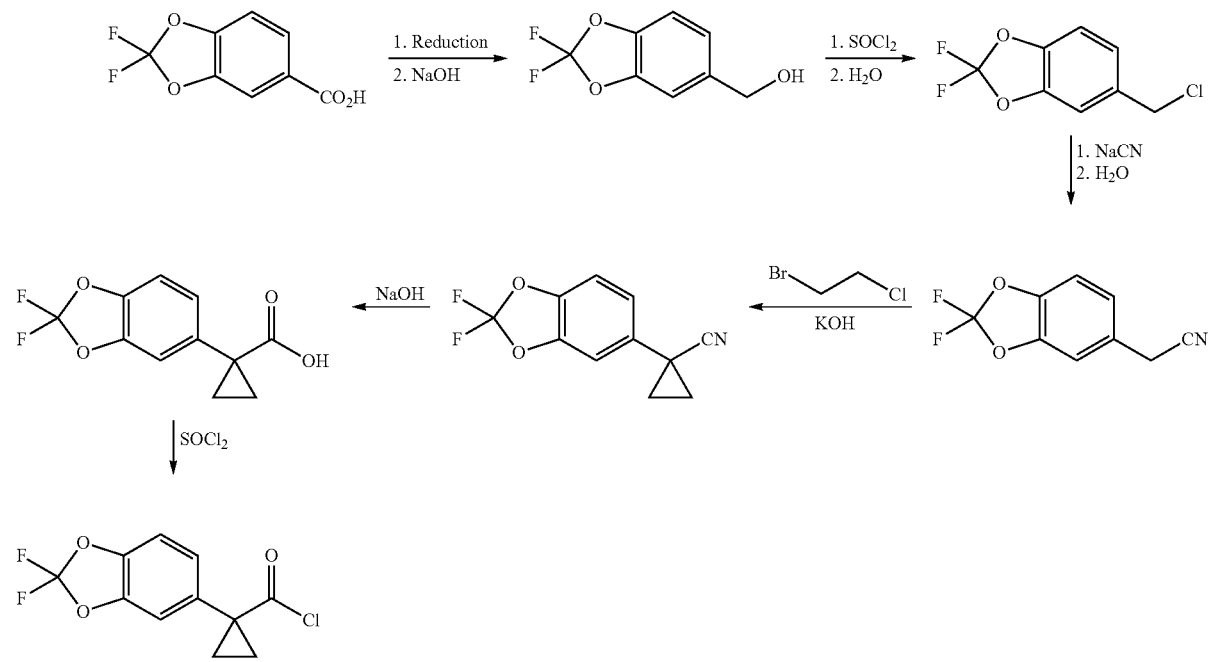

Scheme 1. Synthesis of the acid chloride moiety.

Scheme 1 depicts the preparation of 1-(2,2-difluorobenzo[d][1,3]dioxol-5-yl)cyclopropanecarbonyl chloride, which is used in Scheme 3 to make the amide linkage of Compound 1.

The starting material, 2,2-difluorobenzo[d][1,3]dioxole-5-carboxylic acid, is commercially available from Saltigo (an affiliate of the Lanxess Corporation). Reduction of the carboxylic acid moiety in 2,2-difluorobenzo[d][1,3]dioxole-5-carboxylic acid to the primary alcohol, followed by conversion to the corresponding chloride using thionyl chloride ($SOCl_2$), provides 5-(chloromethyl)-2,2-difluorobenzo[d][1,3]dioxole, which is subsequently converted to 2-(2,2-difluorobenzo[d][1,3]dioxol-5-yl)acetonitrile using sodium cyanide. Treatment of 2-(2,2-difluorobenzo[d][1,3]dioxol-5-yl)acetonitrile with base and 1-bromo-2-chloroethane provides 1-(2,2-difluorobenzo[d][1,3]dioxol-5-yl)cyclopropanecarbonitrile. The nitrile moiety in 1-(2,2-difluorobenzo[d][1,3]dioxol-5-yl)cyclopropanecarbonitrile is converted to a carboxylic acid using base to give 1-(2,2-difluorobenzo[d][1,3]dioxol-5-yl)cyclopropanecarboxylic acid, which is converted to the desired acid chloride using thionyl chloride.

Scheme 2. Alternative synthesis of the acid chloride moiety.

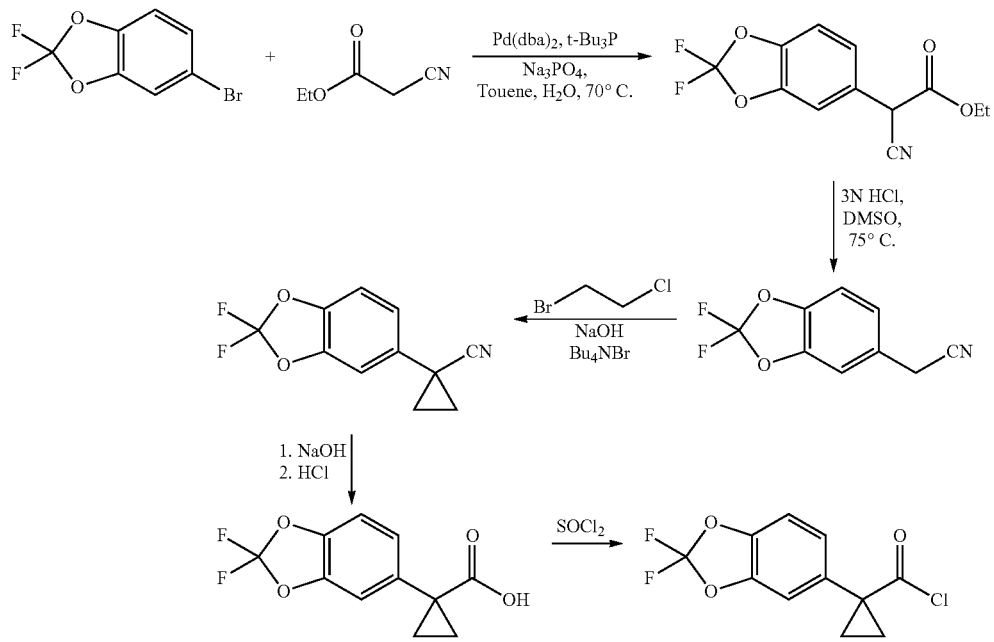

Scheme 2 depicts an alternative synthesis of the requisite acid chloride. 5-bromomethyl-2,2-difluoro-1,3-benzodioxole is coupled with ethyl cyanoacetate in the presence of a palladium catalyst to form the corresponding alpha cyano ethyl ester. Saponification of the ester moiety to the carboxylic acid gives the cyanoethyl compound. Alkylation of the cyanoethyl compound with 1-bromo-2-chloro ethane in the presence of base gives the cyanocyclopropyl compound. Treatment of the cyanocyclopropyl compound with base gives the carboxylate salt, which is converted to the carboxylic acid by treatment with acid. Conversion of the carboxylic acid to the acid chloride is then accomplished using a chlorinating agent such as thionyl chloride or the like.

Scheme 3. Synthesis of the amine moiety.

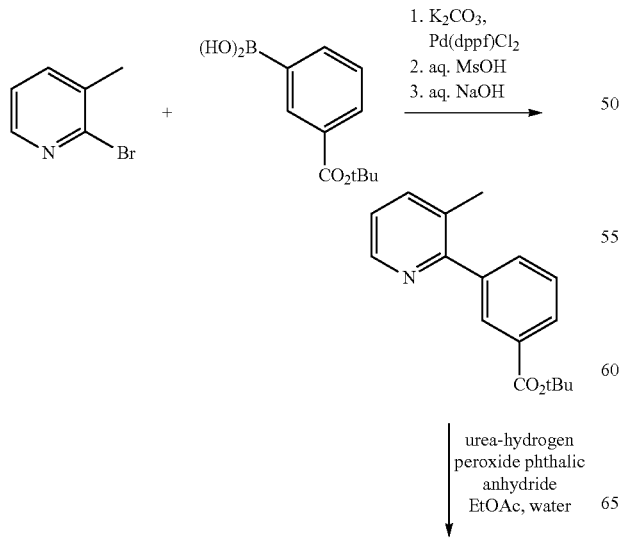

-continued

Scheme 3 depicts the preparation of the requisite tert-butyl 3-(6-amino-3-methylpyridin-2-yl)benzoate, which is coupled with 1-(2,2-difluorobenzo[d][1,3]dioxol-5-yl)cyclopropanecarbonyl chloride in Scheme 3 to give Compound 1. Palladium-catalyzed coupling of 2-bromo-3-methylpyridine with 3-(tert-butoxycarbonyl)phenylboronic acid gives tert-butyl 3-(3-methylpyridin-2-yl)benzoate, which is subsequently converted to the desired compound.

Scheme 4. Formation of an acid salt of 3-(6-(1-(2,2-difluorobenzo[d[[1,3]dioxol-5-yl) cyclopropanecarboxamido)-3-methylpyridin-2-yl)benzoic acid.

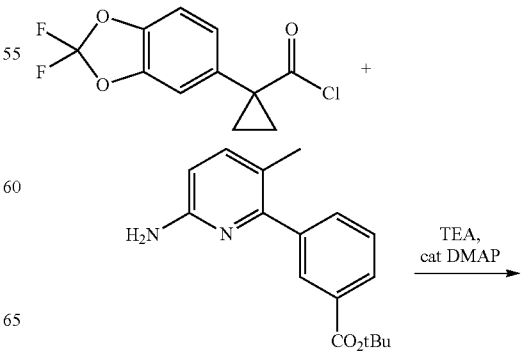

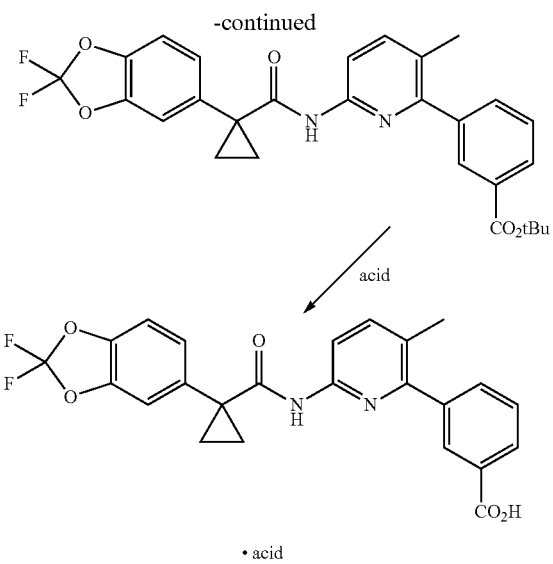

Scheme 4 depicts the coupling of 1-(2,2-difluorobenzo[d][1,3]dioxol-5-yl)cyclopropanecarbonyl chloride with tert-butyl 3-(6-amino-3-methylpyridin-2-yl)benzoate using triethyl amine and 4-dimethylaminopyridine to initially provide the tert-butyl ester of Compound 1.

Compound 1 Form I

Compound 1 Form I is prepared by dispersing or dissolving a salt form, such as the HCl salt, of Compound 1 in an appropriate solvent for an effective amount of time. Treatment of the tert-butyl ester with an acid such as HCl, gives the HCL salt of Compound 1, which is typically a crystalline solid. Compound 1 Form I may also be prepared directly from the t-butyl ester precursor by treatment with an appropriate acid, such as formic acid.

The HCl salt of 3-(6-(1-(2,2-difluorobenzo[d][1,3]dioxol-5-yl) cyclopropanecarboxamido)-3-methylpyridin-2-yl)benzoic acid can be used to make Form I by dispersing or dissolving the HCl salt of 3-(6-(1-(2,2-difluorobenzo[d][1,3]dioxol-5-yl) cyclopropanecarboxamido)-3-methylpyridin-2-yl)benzoic acid in an appropriate solvent for an effective amount of time. Other salts of 3-(6-(1-(2,2-difluorobenzo[d][1,3]dioxol-5-yl) cyclopropanecarboxamido)-3-methylpyridin-2-yl)benzoic acid may be used, such as, for example, salts derived from other mineral or organic acids. The other salts result from acid-mediated hydrolysis of the t-butyl ester moiety. Salts derived from other acids may include, for example, nitric, sulfuric, phosphoric, boric, acetic, benzoic and malonic. These salt forms of 3-(6-(1-(2,2-difluorobenzo[d][1,3]dioxol-5-yl) cyclopropanecarboxamido)-3-methylpyridin-2-yl)benzoic acid may or may not be soluble, depending upon the solvent used, but lack of solubility does not hinder formation of Compound 1 Form I. For example, in one embodiment, the appropriate solvent may be water or an alcohol/water mixture such as 50% methanol/water mixture, even though the HCl salt form of 3-(6-(1-(2,2-difluorobenzo[d][1,3]dioxol-5-yl) cyclopropanecarboxamido)-3-methylpyridin-2-yl)benzoic acid is only sparingly soluble in water. In one embodiment, the appropriate solvent is water.

The effective amount of time for formation of Compound 1 Form I from the salt of 3-(6-(1-(2,2-difluorobenzo[d][1,3]dioxol-5-yl) cyclopropanecarboxamido)-3-methylpyridin-2-yl)benzoic acid can be any time between 2 to 24 hours or greater. It is recognized that the amount of time needed is inversely proportional to the temperature. That is, the higher the temperature the less time needed to affect dissociation of acid to form Compound 1 Form I. When the solvent is water, stirring the dispersion for approximately 24 hours at room temperature provides Compound 1 Form I in an approximately 98% yield. If a solution of the salt of 3-(6-(1-(2,2-difluorobenzo[d][1,3]dioxol-5-yl) cyclopropanecarboxamido)-3-methylpyridin-2-yl)benzoic acid is desired for process purposes, an elevated temperature may be used. After stirring the solution for an effective amount of time at the elevated temperature, recrystallization upon cooling provides substantially pure Compound 1 Form I. In one embodiment, substantially pure refers to greater than about 90% purity. In another embodiment, substantially pure refers to greater than about 95% purity. In another embodiment, substantially pure refers to greater than about 98% purity. In another embodiment, substantially pure refers to greater than about 99% purity. The temperature selected depends in part on the solvent used and is well within the determination capabilities of one of ordinary skill in the art. In one embodiment, the temperature is between room temperature and about 80° C. In another embodiment, the temperature is between room temperature and about 40° C. In another embodiment, the temperature is between about 40° C. and about 60° C. In another embodiment, the temperature is between about 60° C. and about 80° C.

Compound 1 Form I may also be formed directly from 3-(6-(1-(2,2-difluorobenzo[d][1,3]dioxol-5-yl) cyclopropanecarboxamido)-3-methylpyridin-2-yl)-t-butylbenzoate (cf. Scheme 3), which is a precursor to the salt of Compound 1. Thus, 3-(6-(1-(2,2-difluorobenzo[d][1,3]dioxol-5-yl) cyclopropanecarboxamido)-3-methylpyridin-2-yl)-t-butylbenzoate is allowed to undergo reaction with an appropriate acid, such as, for example, formic acid under appropriate reaction conditions to give Compound 1 Form I.

Compound 1 Form I may be further purified by recrystallization from an organic solvent. Examples of organic solvents include, but are not limited to, toluene, cumene, anisol, 1-butanol, isopropyl acetate, butyl acetate, isobutyl acetate, methyl t-butyl ether, methyl isobutyl ketone and 1-propanol-water mixtures. The temperature may be as described above. For example, Compound 1 Form I is dissolved in l-butanol at 75° C. until it is completely dissolved. Cooling down the solution to 10° C. at a rate of 0.2° C./min yields crystals of Compound 1 Form I which may be isolated by filtration.

In one embodiment, Compound 1 Form I is characterized by one or more peaks at 15.2 to 15.6 degrees, 16.1 to 16.5 degrees, and 14.3 to 14.7 degrees in an X-ray powder diffraction obtained using Cu K alpha radiation. In another embodiment, Compound 1 Form I is characterized by one or more peaks at 15.4, 16.3, and 14.5 degrees. In another embodiment, Compound 1 Form I is further characterized by a peak at 14.6 to 15.0 degrees. In another embodiment, Compound 1 Form I is further characterized by a peak at 14.8 degrees. In another embodiment, Compound 1 Form I is further characterized by a peak at 17.6 to 18.0 degrees. In another embodiment, Compound 1 Form I is further characterized by a peak at 17.8 degrees. In another embodiment, Compound 1 Form I is further characterized by a peak at 16.4 to 16.8 degrees. In another embodiment, Compound 1 Form I is further characterized by a peak at 16.4 to 16.8 degrees. In another embodiment, Compound 1 Form I is further characterized by a peak at 16.6 degrees. In another embodiment, Compound 1 Form I is further characterized by a peak at 7.6 to 8.0 degrees. In another embodiment, Compound 1 Form I is further characterized by a peak at 7.8 degrees. In another embodiment, Compound 1 Form I is further characterized by a peak at 25.8 to 26.2 degrees. In another embodiment, Compound 1 Form I is further characterized by a peak at 26.0 degrees. In another embodiment, Compound 1 Form I is further characterized by a peak at 21.4 to 21.8 degrees. In another embodiment, Compound 1 Form I is further characterized by a peak at 21.6 degrees. In another embodiment, Compound 1 Form I is further characterized by a peak at 23.1 to 23.5 degrees. In another embodiment, Compound 1 Form I is further characterized by a peak at 23.3 degrees. In some embodiments, Compound 1 Form I is characterized by a diffraction pattern substantially similar to that of FIG. 1. In some embodiments, Compound 1 Form I is characterized by a diffraction pattern substantially similar to that of FIG. 2.

In some embodiments, the particle size distribution of D90 is about 82 μm or less for Compound 1 Form I. In some embodiments, the particle size distribution of D50 is about 30 μm or less for Compound 1 Form I.

Compound 2

Compound 2 is the starting point for the solid dispersion comprising substantially amorphous Compound 2 and can be prepared by coupling a 4-oxo-dihydroquinoline carboxylic acid moiety with an amine moiety according to Schemes 5-7.

Scheme 5: Synthesis of the 4-oxo-dihydroquinoline carboxylic acid moiety.

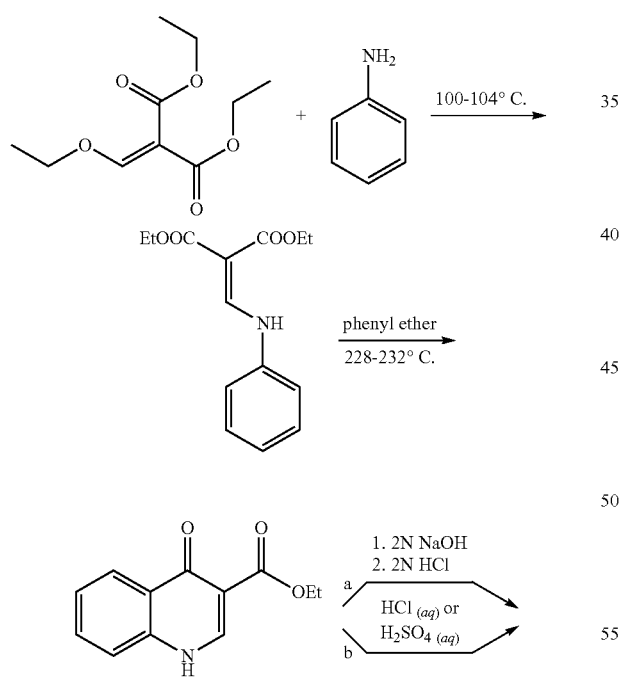

Scheme 6: Synthesis of the amine moiety.

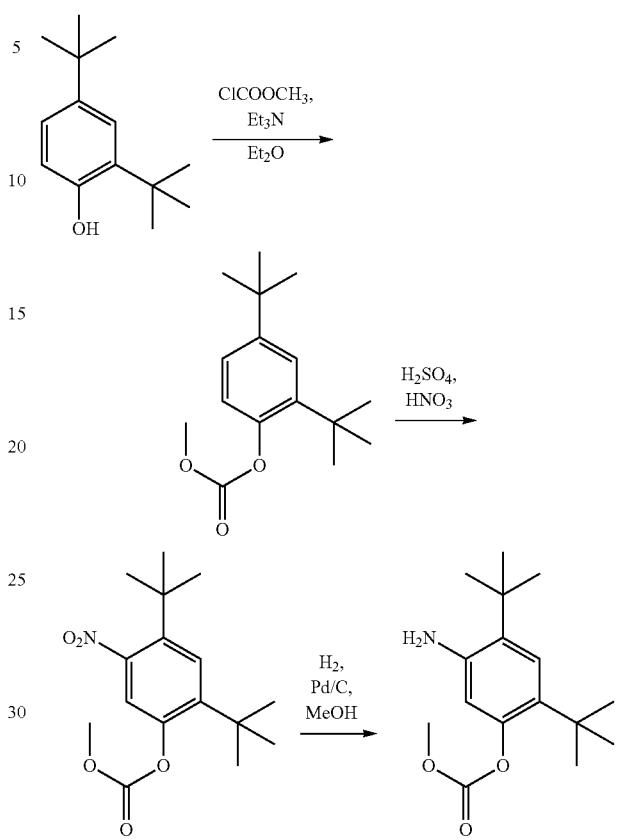

Scheme 7: Coupling of the 4-oxo-dihydroquinoline carboxylic acid moiety with the amine moiety.

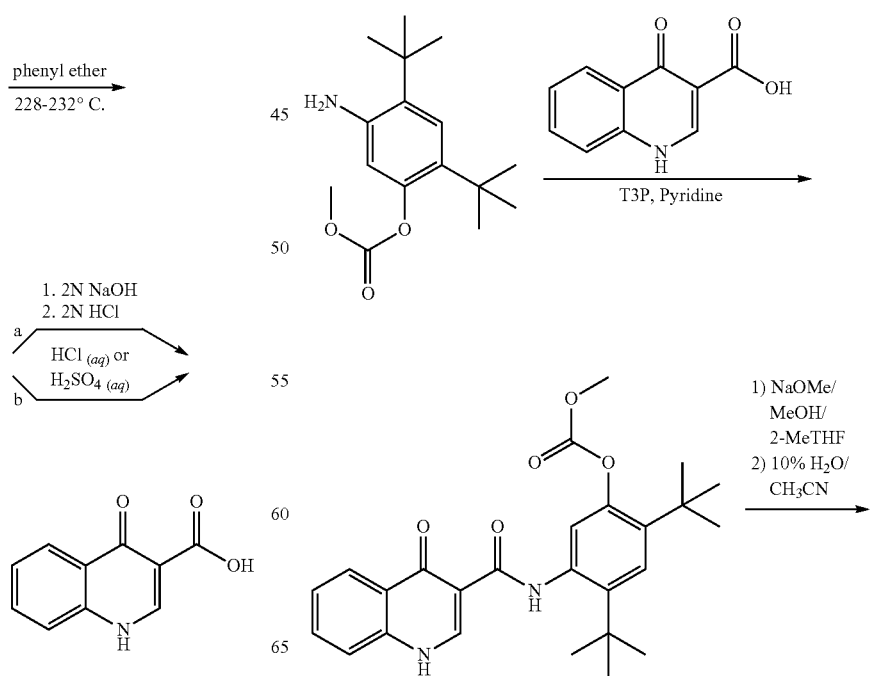

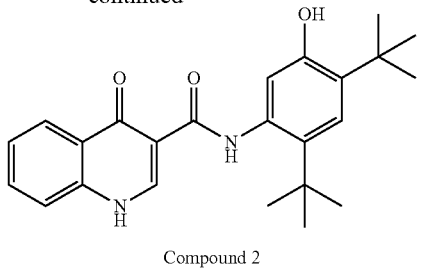

Compound 2

Solid Dispersion Comprising Substantially Amorphous Compound 2

Starting from Compound 2 the amorphous form of Compound 2 may be prepared by spray dried methods. Spray drying is a process that converts a liquid feed to a dried particulate form. Optionally, a secondary drying process such as fluidized bed drying or vacuum drying, may be used to reduce residual solvents to pharmaceutically acceptable levels. Typically, spray drying involves contacting a highly dispersed liquid suspension or solution, and a sufficient volume of hot air to produce evaporation and drying of the liquid droplets. The preparation to be spray dried can be any solution, coarse suspension, slurry, colloidal dispersion, or paste that may be atomized using the selected spray drying apparatus. In a standard procedure, the preparation is sprayed into a current of warm filtered air that evaporates the solvent and conveys the dried product to a collector (e.g. a cyclone). The spent air is then exhausted with the solvent, or alternatively the spent air is sent to a condenser to capture and potentially recycle the solvent. Commercially available types of apparatus may be used to conduct the spray drying. For example, commercial spray dryers are manufactured by Buchi Ltd. And Niro (e.g., the PSD line of spray driers manufactured by Niro) (see, US 2004/0105820; US 2003/0144257).

Spray drying typically employs solid loads of material from about 3% to about 30% by weight, (i.e., drug and excipients), for example about 4% to about 20% by weight, preferably at least about 10%. In general, the upper limit of solid loads is governed by the viscosity of (e.g., the ability to pump) the resulting solution and the solubility of the components in the solution. Generally, the viscosity of the solution can determine the size of the particle in the resulting powder product.

Techniques and methods for spray drying may be found in Perry's Chemical Engineering Handbook, 6$^{th}$ Ed., R. H. Perry, D. W. Green & J. O. Maloney, eds.), McGraw-Hill book co. (1984); and Marshall "Atomization and Spray-Drying" 50, Chem. Eng. Prog. Monogr. Series 2 (1954). In general, the spray drying is conducted with an inlet temperature of from about 60° C. to about 200° C., for example, from about 95° C. to about 185° C., from about 110° C. to about 182° C., from about 96° C. to about 180° C., e.g., about 145° C. The spray drying is generally conducted with an outlet temperature of from about 30° C. to about 90° C., for example from about 40° C. to about 80° C., about 45° C. to about 80° C. e.g., about 75° C. The atomization flow rate is generally from about 4 kg/h to about 12 kg/h, for example, from about 4.3 kg/h to about 10.5 kg/h, e.g., about 6 kg/h or about 10.5 kg/h. The feed flow rate is generally from about 3 kg/h to about 10 kg/h, for example, from about 3.5 kg/h to about 9.0 kg/h, e.g., about 8 kg/h or about 7.1 kg/h. The atomization ratio is generally from about 0.3 to 1.7, e.g., from about 0.5 to 1.5, e.g., about 0.8 or about 1.5.

Removal of the solvent may require a subsequent drying step, such as tray drying, fluid bed drying (e.g., from about room temperature to about 100° C.), vacuum drying, microwave drying, rotary drum drying or biconical vacuum drying (e.g., from about room temperature to about 200° C.).

In one embodiment, the spray dried dispersion is fluid bed dried.

In one process, the solvent includes a volatile solvent, for example a solvent having a boiling point of less than about 100° C. In some embodiments, the solvent includes a mixture of solvents, for example a mixture of volatile solvents or a mixture of volatile and non-volatile solvents. Where mixtures of solvents are used, the mixture can include one or more non-volatile solvents, for example, where the non-volatile solvent is present in the mixture at less than about 15%, e.g., less than about 12%, less than about 10%, less than about 8%, less than about 5%, less than about 3%, or less than about 2%.

Preferred solvents are those solvents where Compound 2 has a solubility of at least about 10 mg/ml, (e.g., at least about 15 mg/ml, 20 mg/ml, 25 mg/ml, 30 mg/ml, 35 mg/ml, 40 mg/ml, 45 mg/ml, 50 mg/ml, or greater). More preferred solvents include those where Compound 2 has a solubility of at least about 20 mg/ml.

Exemplary solvents that could be tested include acetone, cyclohexane, dichloromethane, N,N-dimethylacetamide (DMA), N,N-dimethylformamide (DMF), 1,3-dimethyl-2-imidazolidinone (DMI), dimethyl sulfoxide (DMSO), dioxane, ethyl acetate, ethyl ether, glacial acetic acid (HAc), methyl ethyl ketone (MEK), N-methyl-2-pyrrolidinone (NMP), methyl tert-butyl ether (MTBE), tetrahydrofuran (THF), pentane, acetonitrile, methanol, ethanol, isopropyl alcohol, isopropyl acetate, and toluene. Exemplary co-solvents include acetone/DMSO, acetone/DMF, acetone/water, MEK/water, THF/water, dioxane/water. In a two solvent system, the solvents can be present in of from about 0.1% to about 99.9%. In some preferred embodiments, water is a co-solvent with acetone where water is present from about 0.1% to about 15%, for example about 9% to about 11%, e.g., about 10%. In some preferred embodiments, water is a co-solvent with MEK where water is present from about 0.1% to about 15%, for example about 9% to about 11%, e.g., about 10%. In some embodiments the solvent solution include three solvents. For example, acetone and water can be mixed with a third solvent such as DMA, DMF, DMI, DMSO, or HAc. In instances where substantially amorphous Compound 2 is a component of a solid dispersion, preferred solvents dissolve both Compound 2 and the polymer. Suitable solvents include those described above, for example, MEK, acetone, water, methanol, and mixtures thereof.

The particle size and the temperature drying range may be modified to prepare an optimal spray dry dispersion. As would be appreciated by skilled practitioners, a small particle size would lead to improved solvent removal. Applicants have found however, that smaller particles can lead to fluffy particles that, under some circumstances do not provide optimal spray dry dispersions for downstream processing such as tableting. At higher temperatures, crystallization or chemical degradation of substantially amorphous Compound 2 may occur. At lower temperatures, a sufficient amount of the solvent may not be removed. The methods herein provide an optimal particle size and an optimal drying temperature.

In general, particle size is such that D10 (μm) is less than about 5, e.g., less than about 4.5, less than about 4.0, or less than about 3.5, D50 (μm) is generally less than about 17, e.g., less than about 16, less than about 15, less than about 14, less than about 13, and D90 (μm) is generally less than about 175, e.g., less than about 170, less than about 170, less than about 150, less than about 125, less than about 100, less than about 90, less than about 80, less than about 70, less than about 60, or less than about less than about 50. In general bulk density of the spray dried particles is from about 0.08 g/cc to about 0.20 g/cc, e.g., from about 0.10 to about 0.15 g/cc, e.g., about 0.11 g/cc or about 0.14 g/cc. Tap density of the spray dried particles generally ranges from about 0.08 g/cc to about 0.20 g/cc, e.g., from about 0.10 to about 0.15 g/cc, e.g., about 0.11 g/cc or about 0.14 g/cc, for 10 taps; 0.10 g/cc to about 0.25 g/cc, e.g., from about 0.11 to about 0.21 g/cc, e.g., about 0.15 g/cc, about 0.19 g/cc, or about 0.21 g/cc for 500 taps; 0.15 g/cc to about 0.27 g/cc, e.g., from about 0.18 to about 0.24 g/cc, e.g., about 0.18 g/cc, about 0.19 g/cc, about 0.20 g/cc, or about 0.24 g/cc for 1250 taps; and 0.15 g/cc to about 0.27 g/cc, e.g., from about 0.18 to about 0.24 g/cc, e.g., about 0.18 g/cc, about 0.21 g/cc, about 0.23 g/cc, or about 0.24 g/cc for 2500 taps.

Polymers

Spray dried dispersions including amorphous Compound 2 and a polymer (or solid state carrier) also are included herein. For example, Compound 2 is present as an amorphous compound as a component of a solid amorphous dispersion. The solid amorphous dispersion, generally includes substantially amorphous Compound 2 and a polymer. Exemplary polymers include cellulosic polymers such as HPMC or HPMCAS and pyrrolidone containing polymers such as PVP/VA. In some embodiments, the solid amorphous dispersion includes one or more additional excipients, such as a surfactant.

In one embodiment, a polymer is able to dissolve in aqueous media. The solubility of the polymers may be pH-independent or pH-dependent. The latter include one or more enteric polymers. The term "enteric polymer" refers to a polymer that is preferentially soluble in the less acidic environment of the intestine relative to the more acid environment of the stomach, for example, a polymer that is insoluble in acidic aqueous media but soluble when the pH is above 5-6. An appropriate polymer should be chemically and biologically inert. In order to improve the physical stability of the spray dry dispersions, the glass transition temperature (T) of the polymer should be as high as possible. For example, preferred polymers have a glass transition temperature at least equal to or greater than the glass transition temperature of the drug (i.e., Compound 2). Other preferred polymers have a glass transition temperature that is within about 10 to about 15° C. of the drug (i.e., Compound 2). Examples of suitable glass transition temperatures of the polymers include at least about 90° C., at least about 95° C., at least about 100° C., at least about 105° C., at least about 110° C., at least about 115° C., at least about 120° C., at least about 125° C., at least about 130° C., at least about 135° C., at least about 140° C., at least about 145° C., at least about 150° C., at least about 155° C., at least about 160° C., at least about 165° C., at least about 170° C., or at least about 175° C. (as measured under dry conditions). Without wishing to be bound by theory, it is believed that the underlying mechanism is that a polymer with a higher $T_g$ generally has lower molecular mobility at room temperature, which can be a crucial factor in stabilizing the physical stability of the amorphous spray dry dispersion.

Additionally, the hygroscopicity of the polymers should be as low, e.g., less than about 10%. For the purpose of comparison in this application, the hygroscopicity of a polymer or composition is characterized at about 60% relative humidity. In some preferred embodiments, the polymer has less than about 10% water absorption, for example less than about 9%, less than about 8%, less than about 7%, less than about 6%, less than about 5%, less than about 4%, less than about 3%, or less than about 2% water absorption. The hygroscopicity can also affect the physical stability of the spray dry dispersions. Generally, moisture adsorbed in the polymers can greatly reduce the $T_g$ of the polymers as well as the resulting spray dry dispersions, which will further reduce the physical stability of the spray dry dispersions as described above.

In one embodiment, the polymer is one or more water-soluble polymer(s) or partially water-soluble polymer(s). Water-soluble or partially water-soluble polymers include but are not limited to, cellulose derivatives (e.g., hydroxypropylmethylcellulose (HPMC), hydroxypropylcellulose (HPC)) or ethylcellulose; polyvinylpyrrolidones (PVP); polyethylene glycols (PEG); polyvinyl alcohols (PVA); acrylates, such as polymethacrylate (e.g., Eudragit® E); cyclodextrins (e.g., β-cyclodextin) and copolymers and derivatives thereof, including for example PVP-VA (polyvinylpyrollidone-vinyl acetate).

In some embodiments, the polymer is hydroxypropylmethylcellulose (HPMC), such as HPMCAS, HPMC E50, HPMCE15, or HPMC60SH50).

As discussed herein, the polymer can be a pH-dependent enteric polymer. Such pH-dependent enteric polymers include, but are not limited to, cellulose derivatives (e.g., cellulose acetate phthalate (CAP)), hydroxypropyl methyl cellulose phthalates (HPMCP), hydroxypropyl methyl cellulose acetate succinate (HPMCAS), carboxymethylcellulose (CMC) or a salt thereof (e.g., a sodium salt such as (CMC-Na)); cellulose acetate trimellitate (CAT), hydroxypropylcellulose acetate phthalate (HPCAP), hydroxypropylmethyl-cellulose acetate phthalate (HPMCAP), and methylcellulose acetate phthalate (MCAP), or polymethacrylates (e.g., Eudragit® S). In some embodiments, the polymer is hydroxypropyl methyl cellulose acetate succinate (HPMCAS). In some embodiments, the polymer is hydroxypropyl methyl cellulose acetate succinate HG grade (HPMCAS-HG).

In yet another embodiment, the polymer is a polyvinylpyrrolidone co-polymer, for example, a vinylpyrrolidone/vinyl acetate co-polymer (PVP/VA).

In embodiments where Compound 2 forms a spray dry dispersion with a polymer, for example with an HPMC, HPMCAS, or PVP/VA polymer, the amount of polymer relative to the total weight of the spray dry dispersion ranges from about 0.1% to 99% by weight. Unless otherwise specified, percentages of drug, polymer and other excipients as described within a dispersion are given in weight percentages. The amount of polymer is typically at least about 20%, and preferably at least about 30%, for example, at least about 35%, at least about 40%, at least about 45%, or about 50% (e.g., 49.5%). The amount is typically about 99% or less, and preferably about 80% or less, for example about 75% or less, about 70% or less, about 65% or less, about 60% or less, or about 55% or less. In one embodiment, the polymer is in an amount of up to about 50% of the total weight of the dispersion (and even more specifically, between about 40% and 50%, such as about 49%, about 49.5%, or about 50%). HPMC and HPMCAS are available in a variety of grades from ShinEtsu, for example, HPMCAS is available in a number of varieties, including AS-LF, AS-MF, AS-HF, AS-LG, AS-MG, AS-HG. Each of these grades vary with the percent substitution of acetate and succinate.

In some embodiments, substantially amorphous Compound 2 and polymer are present in roughly equal amounts, for example each of the polymer and the drug make up about half of the percentage weight of the dispersion. For example, the polymer is present in about 49.5% and the drug is present in about 50%.

In some embodiments, substantially amorphous Compound 2 and the polymer combined represent 1% to 20% w/w total solid content of the non-spray dry dispersion prior to spray drying. In some embodiments, substantially amorphous Compound 2 and the polymer combined represent 5% to 15% w/w total solid content of the non-spray dry dispersion prior to spray drying. In some embodiments, substantially amorphous Compound 2 and the polymer combined represent about 11% w/w total solid content of the non-spray dry dispersion prior to spray drying.

In some embodiments, the dispersion further includes other minor ingredients, such as a surfactant (e.g., SLS). In some embodiments, the surfactant is present in less than about 10% of the dispersion, for example less than about 9%, less than about 8%, less than about 7%, less than about 6%, less than about 5%, less than about 4%, less than about 3%, less than about 2%, about 1%, or about 0.5%.

In embodiments including a polymer, the polymer should be present in an amount effective for stabilizing the spray dry dispersion. Stabilizing includes inhibiting or preventing, the crystallization of substantially amorphous Compound 2. Such stabilizing would inhibit the conversion Compound 2 from amorphous to crystalline form. For example, the polymer would prevent at least a portion (e.g., about 5%, about 10%, about 15%, about 20%, about 25%, about 30%, about 35%, about 40%, about 45%, about 50%, about 55%, about 60%, about 65%, about 70%, about 75%, or greater) of Compound 2 from converting from an amorphous to a crystalline form. Stabilization can be measured, for example, by measuring the glass transition temperature of the spray dry dispersion, measuring the rate of relaxation of the amorphous material, or by measuring the solubility or bioavailability of Compound 2.

Suitable polymers for use in combination with Compound 2, for example to form a spray dry dispersion such as an amorphous spray dry dispersion, should have one or more of the following properties:

The glass transition temperature of the polymer should have a temperature of no less than about 10-15° C. lower than the glass transition temperature of substantially amorphous Compound 2. Preferably; the glass transition temperature of the polymer is greater than the glass transition temperature of substantially amorphous Compound 2, and in general at least 50° C. higher than the desired storage temperature of the drug product. For example, at least about 100° C., at least about 105° C., at least about 105° C., at least about 110° C., at least about 120° C., at least about 130° C., at least about 140° C., at least about 150° C., at least about 160° C., at least about 160° C., or greater.

The polymer should be relatively non-hygroscopic. For example, the polymer should, when stored under standard conditions, absorb less than about 10% water, for example, less than about 9%, less than about 8%, less than about 7%, less than about 6%, or less than about 5%, less than about 4%, or less than about 3% water. Preferably the polymer will, when stored under standard conditions, be substantially free of absorbed water.

The polymer should have similar or better solubility in solvents suitable for spray drying processes relative to that of Compound 2. In preferred embodiments, the polymer will dissolve in one or more of the same solvents or solvent systems as Compound 2. It is preferred that the polymer is soluble in at least one non-hydroxy containing solvent such as methylene chloride, acetone, or a combination thereof.

The polymer, when combined with substantially amorphous Compound 2, for example in a spray dry dispersion or in a liquid suspension, should increase the solubility of Compound 2 in aqueous and physiologically relative media either relative to the solubility of Compound 2 in the absence of polymer or relative to the solubility of Compound 2 when combined with a reference polymer. For example, the polymer could increase the solubility of amorphous Compound 2 by reducing the amount of amorphous Compound 2 that converts to crystalline Compound 2, either from a solid amorphous dispersion or from a liquid suspension.

The polymer should decrease the relaxation rate of the amorphous substance.

The polymer should increase the physical and/or chemical stability of substantially amorphous Compound 2.

The polymer should improve the manufacturability of substantially amorphous Compound 2.

The polymer should improve one or more of the handling, administration or storage properties of substantially amorphous Compound 2.

The polymer should not interact unfavorably with other pharmaceutical components, for example excipients.

The suitability of a candidate polymer (or other component) can be tested using the spray drying methods (or other methods) described herein to form an amorphous composition. The candidate composition can be compared in terms of stability, resistance to the formation of crystals, or other properties, and compared to a reference preparation, e.g., a preparation of neat amorphous Compound 2 or crystalline Compound 2. For example, a candidate composition could be tested to determine whether it inhibits the time to onset of solvent mediated crystallization, or the percent conversion at a given time under controlled conditions, by at least 50%, 75%, 100%, or 110% as well as the reference preparation, or a candidate composition could be tested to determine if it has improved bioavailability or solubility relative to crystalline Compound 2.

Surfactants

The spray dry dispersion may include a surfactant. A surfactant or surfactant mixture would generally decrease the interfacial tension between the spray dry dispersion and an aqueous medium. An appropriate surfactant or surfactant mixture may also enhance aqueous solubility and bioavailability of Compound 2 from a spray dry dispersion. The surfactants for use in connection with the present invention include, but are not limited to, sorbitan fatty acid esters (e.g., Spans®), polyoxyethylene sorbitan fatty acid esters (e.g., Tweens®), sodium lauryl sulfate (SLS), sodium dodecylbenzene sulfonate (SDBS) dioctyl sodium sulfosuccinate (Docusate), dioxycholic acid sodium salt (DOSS), Sorbitan Monostearate, Sorbitan Tristearate, hexadecyltrimethyl ammonium bromide (HTAB), Sodium N-lauroylsarcosine, Sodium Oleate, Sodium Myristate, Sodium Stearate, Sodium Palmitate, Gelucire 44/14, ethylenediamine tetraacetic acid (EDTA), Vitamin E d-alpha tocopheryl polyethylene glycol 1000 succinate (TPGS), Lecithin, MW 677-692, Glutanic acid monosodium monohydrate, Labrasol, PEG 8 caprylic/capric glycerides, Transcutol, diethylene glycol monoethyl ether, Solutol HS-15, polyethylene glycol/hydroxystearate, Taurocholic Acid, Pluronic F68, Pluronic F108, and Pluronic F127 (or any other polyoxyethylene-polyoxypropylene co-polymers (Pluronics®) or saturated polyglycolized glycerides (Gelucirs®)). Specific example of such surfactants that may be used in connection with this invention include, but are not limited to, Span 65, Span 25, Tween 20, Capryol 90, Pluronic F108, sodium lauryl sulfate (SLS), Vitamin E TPGS, pluronics and copolymers. SLS is generally preferred.

The amount of the surfactant (e.g., SLS) relative to the total weight of the spray dry dispersion may be between 0.1-15%. Preferably, it is from about 0.5% to about 10%, more preferably from about 0.5 to about 5%, e.g., about 0.5 to 4%, about 0.5 to 3%, about 0.5 to 2%, about 0.5 to 1%, or about 0.5%.

In certain embodiments, the amount of the surfactant relative to the total weight of the spray dry dispersion is at least about 0.1%, preferably about 0.5%. In these embodiments, the surfactant would be present in an amount of no more than about 15%, and preferably no more than about 12%, about 11%, about 10%, about 9%, about 8%, about 7%, about 6%, about 5%, about 4%, about 3%, about 2% or about 1%. An embodiment wherein the surfactant is in an amount of about 0.5% by weight is preferred.

Candidate surfactants (or other components) can be tested for suitability for use in the invention in a manner similar to that described for testing polymers.

Methods for Making the Pharmaceutical Compositions

The pharmaceutical compositions of the invention can be produced by, wet granulation, compacting or compressing an admixture or composition, for example, a powder or granules, under pressure to form a stable three-dimensional shape (e.g., a tablet). As used herein, "tablet" includes compressed pharmaceutical dosage unit forms of all shapes and sizes, whether coated or uncoated.

The term "tablet" as used herein refers to a physically discrete unit of agent appropriate for the patient to be treated. In general, a compacted mixture has a density greater than that of the mixture prior to compaction. A dosage tablet of the invention can have almost any shape including concave and/or convex faces, rounded or angled corners, and a rounded to rectilinear shape. In some embodiments, the compressed tablets of the invention comprise a rounded tablet having flat faces. The tablets of the invention can be prepared by any compaction and compression method known by persons of ordinary skill in the art of forming compressed solid pharmaceutical dosage forms. In particular embodiments, the formulations provided herein may be prepared using conventional methods known to those skilled in the field of pharmaceutical formulation, as described, e.g., in pertinent textbooks. See, e.g., Remington: The Science and Practice of Pharmacy, 21st Ed., Lippincott Williams & Wilkins, Baltimore, Md. (2003); Ansel et al., Pharmaceutical Dosage Forms And Drug Delivery Systems, 7th Edition, Lippincott Williams & Wilkins, (1999); The Handbook of Pharmaceutical Excipients, 4$^{th}$ edition, Rowe et al., Eds., American Pharmaceuticals Association (2003); Gibson, Pharmaceutical Preformulation And Formulation, CRC Press (2001), these references hereby incorporated herein by reference in their entirety.

Granulation and Compression

In some embodiments, the ingredients are weighed according to the formula set herein. Next, all of the intragranular ingredients are sifted and mixed well. The ingredients can be lubricated with a suitable lubricant, for example, magnesium stearate. The next step can comprise compaction/slugging of the powder admixture and sized ingredients. Next, the compacted or slugged blends are milled into granules and sifted to obtain the desired size. Next, the granules can be further lubricated with, for example, magnesium stearate. Next the granular composition of the invention can be compressed on suitable punches into various pharmaceutical formulations in accordance with the invention. Optionally the tablets can be coated with a film, colorant or other coating.

Another aspect of the invention provides a method for producing a pharmaceutical composition comprising providing an admixture of a composition comprising Compound 1 Form I, a solid dispersion comprising substantially amorphous Compound 2 and one or more excipients selected from: a filler, a diluent, a binder, a surfactant, a lubricant, a disintegrant, and compressing the composition into a tablet having a dissolution of at least about 50% in about 30 minutes.

In another embodiment, a wet granulation process is performed to yield the pharmaceutical formulation of the invention from an admixture of powdered and liquid ingredients. For example, a pharmaceutical composition comprising an admixture of a composition comprising Compound 1 Form I, a solid dispersion comprising substantially amorphous Compound 2, and one or more excipients selected from: a filler, a binder, a surfactant, or a disintegrant, are weighed as per the formula set herein. Next, all of the intragranular ingredients are sifted and mixed in a high shear or low shear granulator using water or water with a surfactant or water with a binder or water with a surfactant and a binder to granulate the powder blend. A fluid other than water can also be used with or without surfactant and/or binder to granulate the powder blend. Next, the wet granules can optionally be milled using a suitable mill. Next, water may optionally be removed from the admixture by drying the ingredients in any suitable manner. Next, the dried granules can optionally be milled to the required size. Next, extra granular excipients can be added by blending (for example a filler, a diluent, and a disintegrant). Next, the sized granules can be further lubricated with magnesium stearate and a disintegrant, for example, croscarmellose sodium. Next the granular composition of the invention can be sifted for sufficient time to obtain the correct size and then compressed on suitable punches into various pharmaceutical formulations in accordance with the invention. Optionally, the tablets can be coated with a film, colorant or other coating. Surprisingly, wet granulation can be carried out without substantial loss of the solid state forms of Compound 1 Form I or substantially amorphous Compound 2.

In a particularly favored embodiment, the pharmaceutical compositions of the present invention are prepared by a continuous twin screw wet granulation (TSWG) process. Continuous manufacturing delivers high quality and highly consistent product with on-line monitoring and control. Continuous manufacturing also facilitates quality by design development with a "data rich" design space and an easier to understand impact of upstream variables on the downstream process and final product quality. In addition, the pharmaceutical compositions of the present invention can be finalized early on commercial scale equipment which avoids scale-up risks and formulation changes late in development. Finally, continuous manufacturing has commercial manufacturing advantages such as improved process control, reduced product handling, and real time release efficiencies. The overall result is a more robust, controllable, and scalable process that has fewer process checks resulting in increased product quality and therefore greater patient safety. These advantages address Janet Woodcock's (director of the Center for Drug Evaluation and Research (CDER)) concerns that chemistry, manufacturing, and controls (CMC) won't be able to keep up with rapid clinical development of highly effective therapies ("What we are seeing is that often the rate limiting step is going to be manufacturing," Jul. 24, 2013

Friends of Cancer hosted congressional briefing "Answering a Compelling Need: Expediting Life-Saving Treatments to Patients" to discuss the Food and Drug Administration's Breakthrough Therapy Designation).

Figure 3:
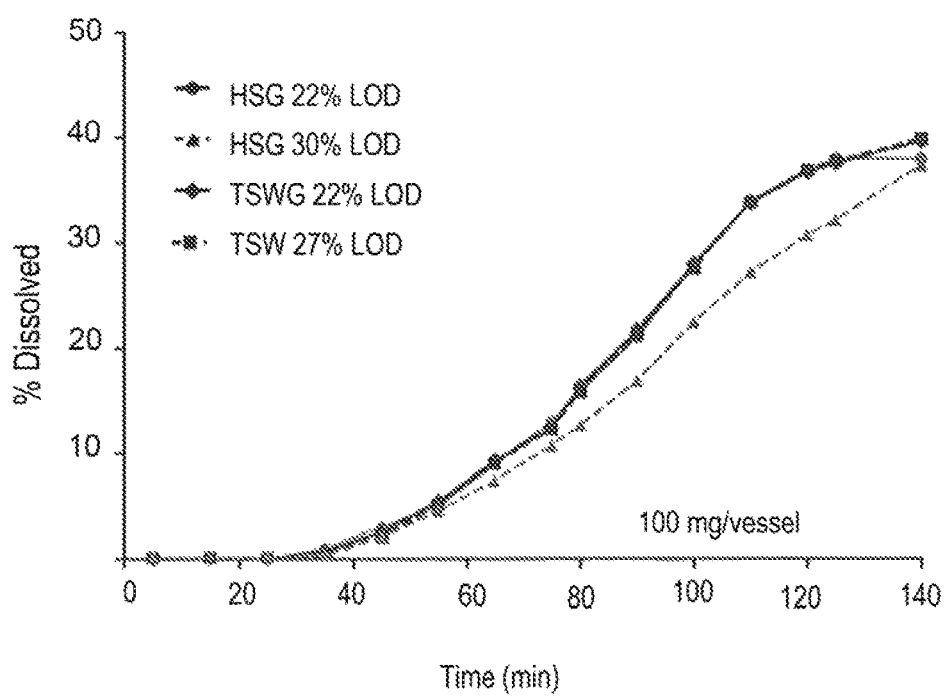
FIG. 3 is a graph depicting Compound 1 pH gradient dissolution profiles for a tablet made by a high shear granulation (HSG) process and a twin screw wet granulation (TSWG) process (LOD stands for loss on drying, a measure to define the amount of water in a powder/granule).

For example, high shear granulation (HSG), a common granulation technique is well known for the risk of over-granulation and poor process control. Scale-up of this process is very challenging and involves significant risk. Changing from a HSG process to a continuous TSWG process, allows scale-up using the same equipment to produce different batch sizes, by running for a longer time. This eliminates the scale-up risk commonly encountered with other granulation processes. Additionally, it was found that the TSWG process is more robust, being less sensitive to over-granulation. As can be seen in FIG. 3 for a Compound 1 tablet, the HSG process showed significant dissolution slow-down with increasing water content, while the TSWG process did not show a change for a similar range of water addition. Surprisingly, no performance changes were found with the tablet formulations comprising Compound 1 between 45-55 percent by weight and the tablet formulations comprising Compound 1 between 60-70 percent by weight using the twin screw wet granulation process. This was not the case with the HSG process. Additionally, this continuous and increased product quality process addresses a common complaint by the FDA regarding the lack of drug availability for patients in need thereof.

In one embodiment the continuous process starts with feeding individual excipients, Compound 1, and Compound 2 into a continuous in-line blender through loss-in-weight feeding. From this blender, the material is continuously conveyed and processed through twin screw wet granulation, drying, milling, extra-granular excipient addition, blending, compression and film coating.

Figure 26:
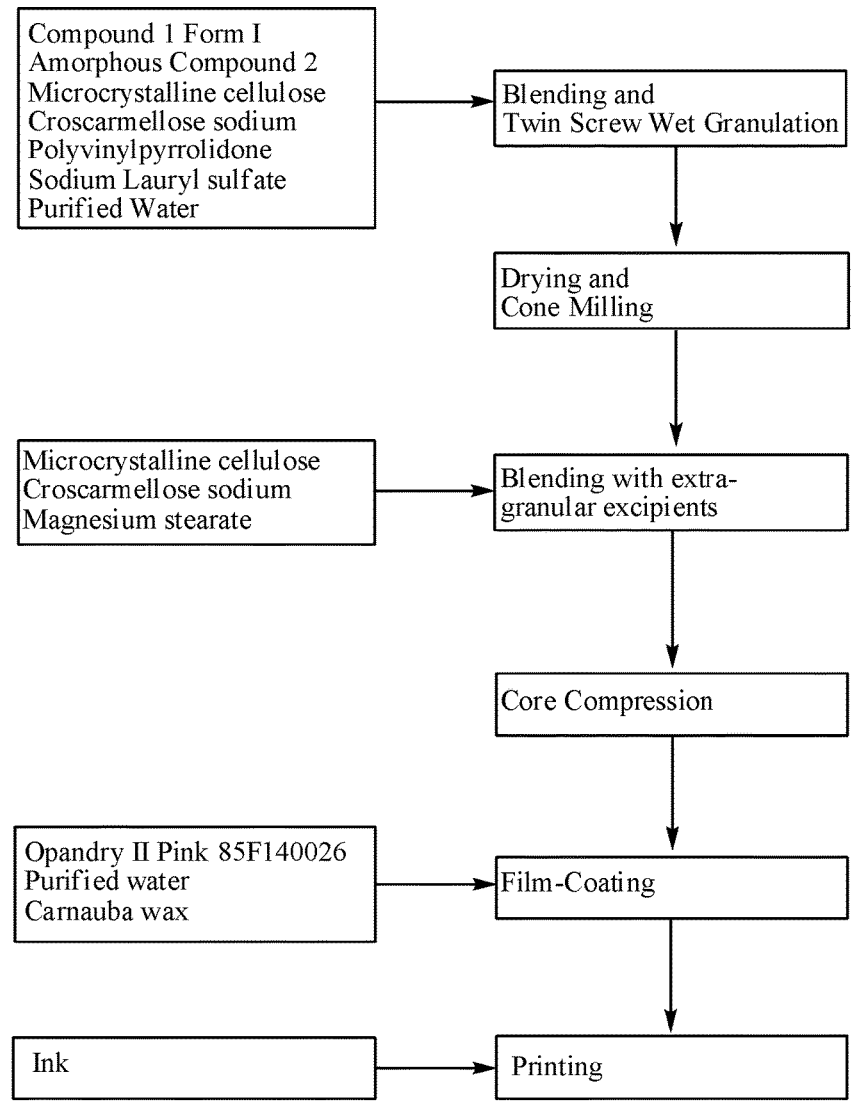
FIG. 26 depicts a flow chart, which describes a process for continuously preparing a tablet comprising Compound 1 and Compound 2.

For example, in one embodiment, a tablet comprising Compound 1 and Compound 2 may be prepared continuously according to the flow chart depicted in FIG. 26.

Each of the ingredients of this exemplary admixture is described above and in the Examples below. Furthermore, the admixture can comprise optional additives, such as, one or more colorants, one or more flavors, and/or one or more fragrances as described above and in the Examples below. In some embodiments, the relative concentrations (e.g., wt %) of each of these ingredients (and any optional additives) in the admixture are also presented above and in the Examples below. The ingredients constituting the admixture can be provided sequentially or in any combination of additions; and, the ingredients or combination of ingredients can be provided in any order. In one embodiment, the lubricant is the last component added to the admixture.

In another embodiment, the admixture comprises a composition of Compound 1 Form I, a solid dispersion of substantially amorphous Compound 2, and any one or more of the excipients; a binder, a surfactant, a diluent, a lubricant, a disintegrant, and a filler, wherein each of these ingredients is provided in a powder form (e.g., provided as particles having a mean or average diameter, measured by light scattering, of 250 µm or less (e.g., 150 µm or less, 100 µm or less, 50 µm or less, 45 µm or less, 40 µm or less, or 35 µm or less)).

In another embodiment, compressing the admixture into a tablet is accomplished by filling a form (e.g., a mold) with the admixture and applying pressure to admixture. This can be accomplished using a die press or other similar apparatus. In some embodiments, the admixture of Compound 1 Form I, a solid dispersion comprising substantially amorphous Compound 2, and excipients can be first processed into granular form. The granules can then be sized and compressed into tablets or formulated for encapsulation according to known methods in the pharmaceutical art. It is also noted that the application of pressure to the admixture in the form can be repeated using the same pressure during each compression or using different pressures during the compressions. In another example, the admixture of powdered ingredients or granules can be compressed using a die press that applies sufficient pressure to form a tablet having a dissolution of about 50% or more at about 30 minutes (e.g., about 55% or more at about 30 minutes or about 60% or more at about 30 minutes). For instance, the admixture is compressed using a die press to produce a tablet hardness of at least about 5 kP (at least about 5.5 kP, at least about 6 kP, at least about 7 kP, at least about 10 kP, or at least 15 kP). In some instances, the admixture is compressed to produce a tablet hardness of between about 5 and 20 kP.

In some embodiments, tablets comprising a pharmaceutical composition as described herein can be coated with about 3.0 wt % of a film coating comprising a colorant by weight of the tablet. In certain instances, the colorant suspension or solution used to coat the tablets comprises about 20% w/w of solids by weight of the colorant suspension or solution. In still further instances, the coated tablets can be labeled with a logo, other image or text.

In another embodiment, the method for producing a pharmaceutical composition comprises providing an admixture of a solid forms, e.g. an admixture of powdered and/or liquid ingredients, the admixture comprising Compound 1 Form I, a solid dispersion comprising substantially amorphous Compound 2, and one or more excipients selected from: a binder, a diluent, a surfactant, a lubricant, a disintegrant, and a filler; mixing the admixture until the admixture is substantially homogenous, and compressing or compacting the admixture into a granular form. Then the granular composition comprising Compound 1 Form I and a solid dispersion comprising substantially amorphous Compound 2 can be compressed into tablets or formulated into capsules as described above or in the Examples below. Alternatively, methods for producing a pharmaceutical composition comprises providing an admixture of Compound 1 Form I, a solid dispersion comprising substantially amorphous Compound 2, and one or more excipients, e.g. a binder, a diluent, a surfactant, a lubricant, a disintegrant, and a filler; mixing the admixture until the admixture is substantially homogenous, and compressing/compacting the admixture into a granular form using a high shear wet granule compaction process as set forth in the Examples below. Pharmaceutical formulations, for example a tablet as described herein, can be made using the granules prepared incorporating Compound 1 Form I and a solid dispersion comprising substantially amorphous Compound 2 in addition to the selected excipients described herein.

In some embodiments, the admixture is mixed by stirring, blending, shaking, or the like using hand mixing, a mixer, a blender, any combination thereof, or the like. When ingredients or combinations of ingredients are added sequentially, mixing can occur between successive additions, continuously throughout the ingredient addition, after the addition of all of the ingredients or combinations of ingredients, or any combination thereof. The admixture is mixed until it has a substantially homogenous composition.

In another embodiment, the present invention comprises jet milling a pharmaceutical composition comprising Compound 1 Form I and a solid dispersion comprising substantially amorphous Compound 2 in a suitable, conventional milling apparatus using air pressure suitable to produce particles having a significant particle size fraction between 0.1 microns and 50 microns. In another embodiment, the particle size is between 0.1 microns and 20 microns. In another embodiment, the particles size is between 0.1 microns and 10 microns. In another embodiment, the particle size is between 1.0 microns and 5 microns. In still another embodiment, the pharmaceutical composition has a particle size D50 of 2.0 microns.

Figure 4:
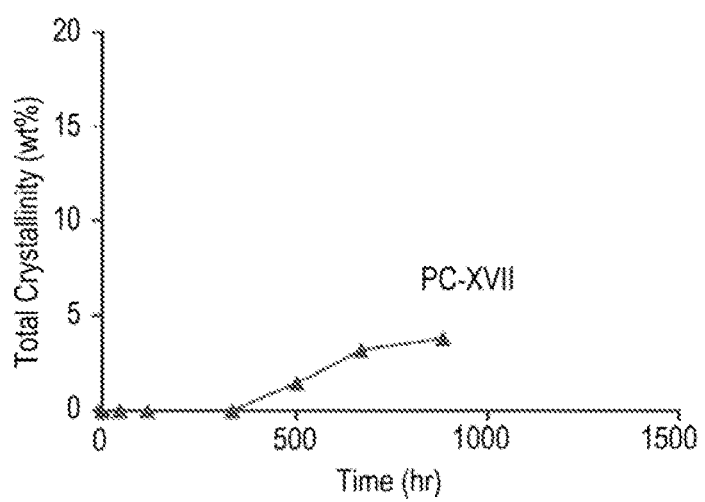
FIG. 4 is a graph depicting the stability of the substantially amorphous form of Compound 2 in tablet formulation PC-XVII at 50° C. after pre-equilibrating at 60% relative humidity by showing only a small amount of crystallinity over time.
Figure 5:
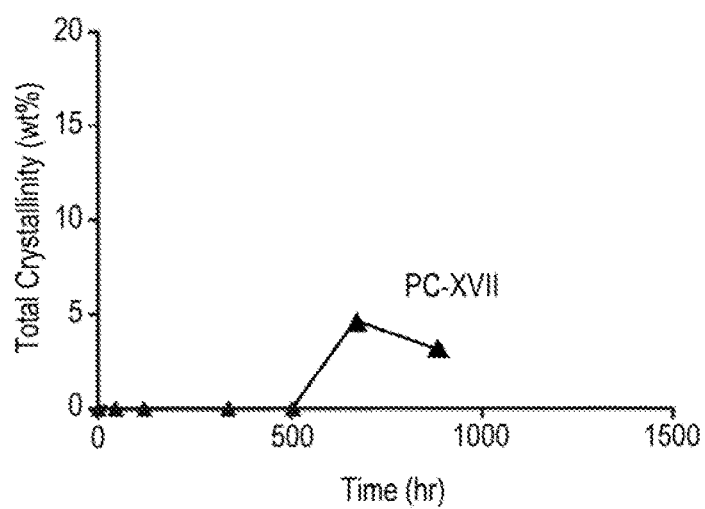
FIG. 5 is a graph depicting the stability of the substantially amorphous form of Compound 2 in tablet formulation PC-XVII at 60° C. after pre-equilibrating at 60% relative humidity by showing only a small amount of crystallinity over time.
Figure 6:
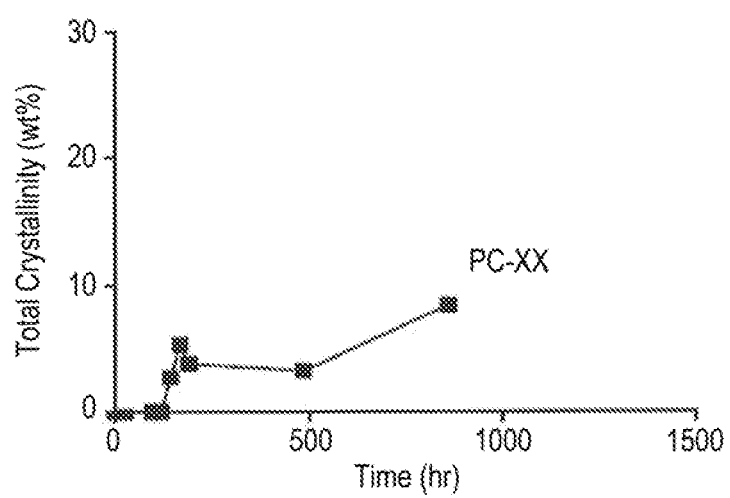
FIG. 6 is a graph depicting the stability of the substantially amorphous form of Compound 2 in tablet formulation PC-XX at 60° C. after pre-equilibrating at 60% relative humidity by showing only a small amount of crystallinity over time.
Figure 7:
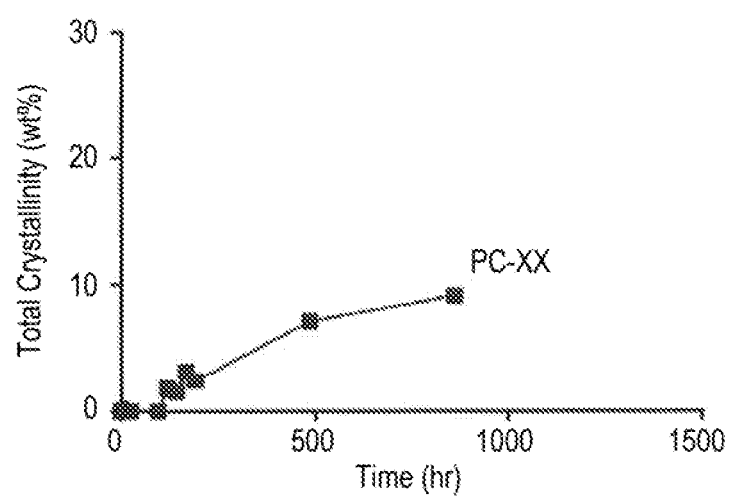
FIG. 7 is a graph depicting the stability of the substantially amorphous form of Compound 2 in tablet formulation PC-XX at 50° C. after pre-equilibrating at 60% relative humidity by showing only a small amount of crystallinity over time.

The formulations of the present invention provide a fixed dosage of two APIs for the effective treatment of cystic fibrosis, a combination that has received one of only two Breakthrough Therapy Designation from the FDA, and does so with surprising stability as measured by the small loss of the amorphous solid form of Compound 2. FIG. 4 depicts the small amount of crystallinity of Compound 2 over time in PC-XVII at 50° C. after pre-equilibration at 60% relative humidity. Even after close to 1000 hours under these conditions, less than 5% by weight of Compound 2 has crystallized. FIG. 5 shows for PC-XVII that even at the higher temperature of 60° C. after pre-equilibrating at 60% relative humidity, at close to 1000 hours under these conditions, less than 10% by weight of Compound 2 has crystallized. FIGS. 6 and 7 show similar results for PC-XIX. The present formulations, therefore, provide the convenience of a fixed dosage of two breakthrough API's in a surprisingly stable pharmaceutical composition. Such formulations increase patient compliance which directly relates to the effective treatment of diseases.

Dosage forms prepared as above can be subjected to in vitro dissolution evaluations according to Test 711 "Dissolution" in United States Pharmacopoeia 29, United States Pharmacopeial Convention, Inc., Rockville, Md., 2005 ("USP"), to determine the rate at which the active substance is released from the dosage forms. The content of active substance and the impurity levels are conveniently measured by techniques such as high performance liquid chromatography (HPLC).

In some embodiments, the invention includes use of packaging materials such as containers and closures of high-density polyethylene (HDPE), low-density polyethylene (LDPE) and or polypropylene and/or glass, glassine foil, aluminum pouches, and blisters or strips composed of aluminum or high-density polyvinyl chloride (PVC), optionally including a desiccant, polyethylene (PE), polyvinylidene dichloride (PVDC), PVC/PE/PVDC, and the like. These package materials can be used to store the various pharmaceutical compositions and formulations in a sterile fashion after appropriate sterilization of the package and its contents using chemical or physical sterilization techniques commonly employed in the pharmaceutical arts.

Methods for Administering the Pharmaceutical Compositions

In one aspect, the pharmaceutical compositions of the invention can be administered to a patient once daily or about every twenty four hours. Alternatively, the pharmaceutical compositions of the invention can be administered to a patient twice daily. Alternatively, the pharmaceutical composition of the invention can be administered about every twelve hours. These pharmaceutical compositions are administered as oral formulations containing about 25 mg, 50 mg, 100 mg, 125 mg, 150 mg, 200 mg, 250 mg, 300 mg, or 400 mg of Compound 1 Form I; and about 25 mg, 50 mg, 100 mg, 125 mg, 150 mg, 200 mg, or 250 mg of substantially amorphous Compound 2. In this aspect, in addition to Compound 1 Form I and substantially amorphous Compound 2, the pharmaceutical compositions comprise a filler; a disintegrant; a surfactant; a binder; and a lubricant (depending on whether the pharmaceutical composition is a granule or a tablet). For instance, a dose of 400 mg of Compound 1 Form I, may comprise two tablets of the invention each containing 200 mg of Compound 1 Form I. A dose of 250 mg of substantially amorphous Compound 2, may comprise two tablets of the invention each containing 125 mg of substantially amorphous Compound 2.

It will also be appreciated that the compound and pharmaceutically acceptable compositions and formulations of the invention can be employed in combination therapies; that is, Compound 1 Form I and a solid dispersion of substantially amorphous Compound 2 and pharmaceutically acceptable compositions thereof can be administered concurrently with, prior to, or subsequent to, one or more other desired therapeutics or medical procedures.

In one embodiment, the additional therapeutic agent is selected from a mucolytic agent, bronchodialator, an antibiotic, an anti-infective agent, an anti-inflammatory agent, a compound that induces CFTR activity other than Compound 1 Form I and substantially amorphous Compound 2, or a nutritional agent.

In one embodiment, the additional agent is (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide. In another embodiment, the additional agent is 4-(3-(1-(2,2-difluorobenzo[d][1,3]dioxol-5-yl)cyclopropanecarboxamido) isoquinolin-1-yl)benzoic acid. In another embodiment, the additional agent is selected from Table 1:

TABLE 1

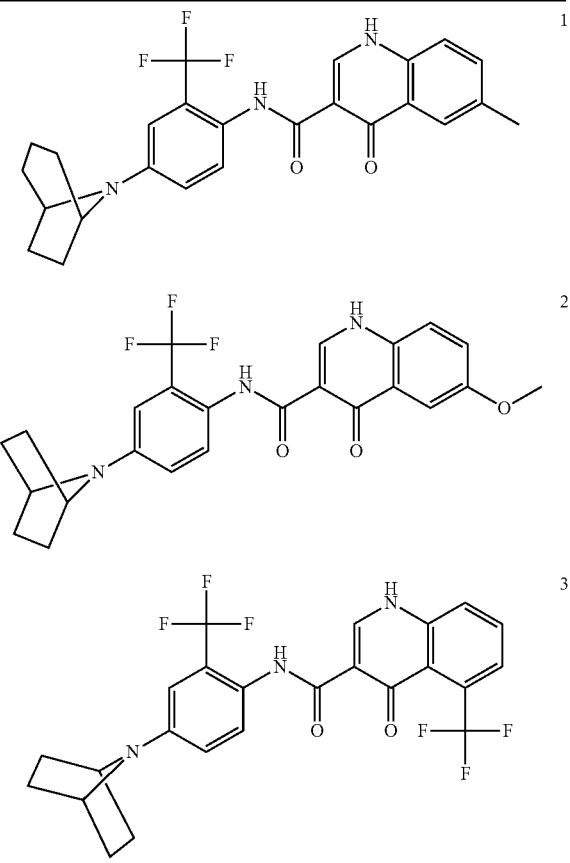

TABLE 1-continued
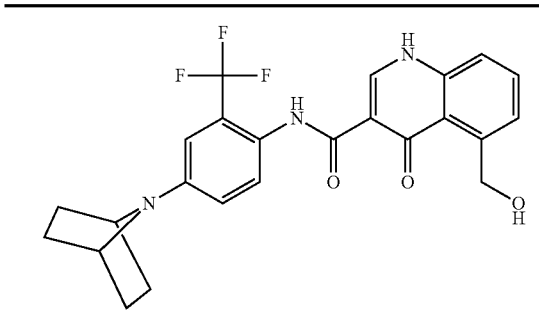 4
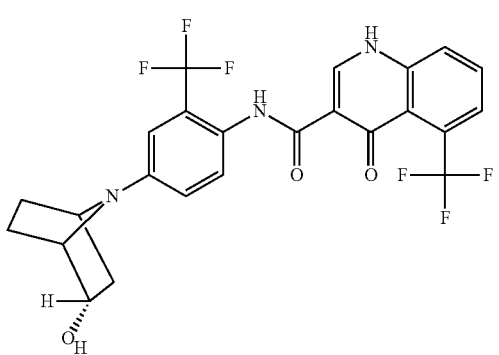 5
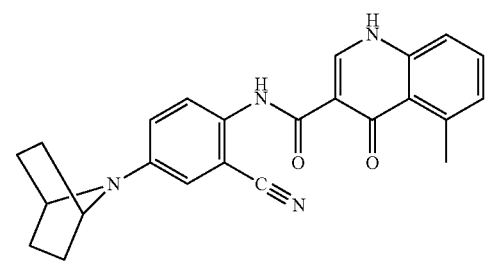 [SMILES: Cc1cccc2[nH]cc(C(=O)Nc3ccc(N4C5CCC4CC5)cc3C#N)c(=O)c12] 6
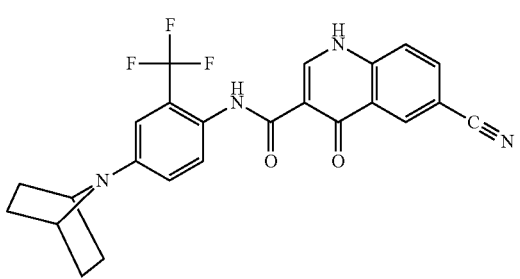 [SMILES: N#Cc1ccc2[nH]cc(C(=O)Nc3ccc(N4C5CCC4CC5)cc3C(F)(F)F)c(=O)c2c1] 7
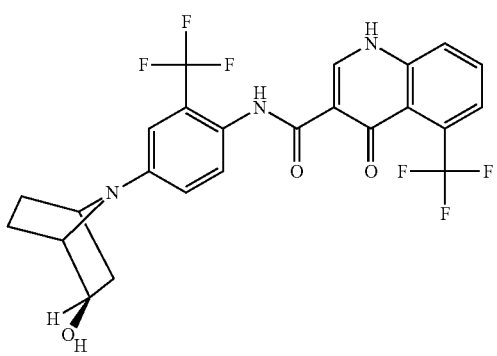 8
TABLE 1-continued
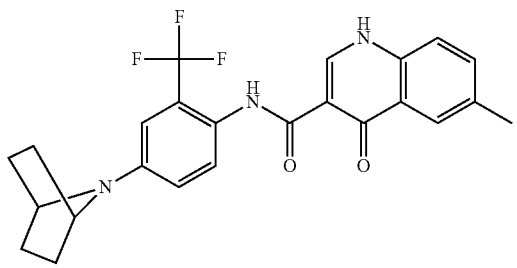 [SMILES: Cc1ccc2[nH]cc(C(=O)Nc3ccc(N4C5CCC4CC5)cc3C(F)(F)F)c(=O)c2c1] 9
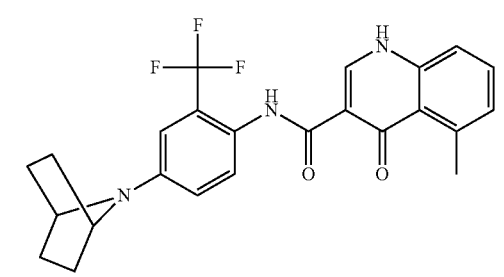 [SMILES: Cc1cccc2[nH]cc(C(=O)Nc3ccc(N4C5CCC4CC5)cc3C(F)(F)F)c(=O)c12] 10
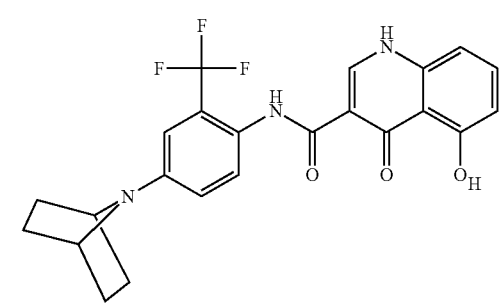 11
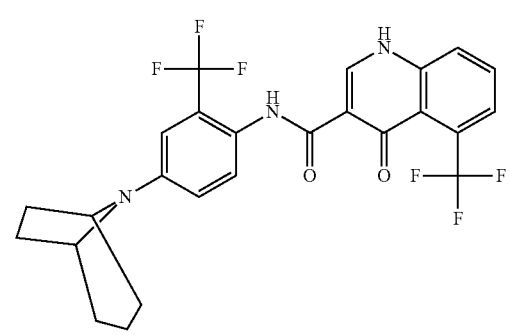 [SMILES: O=C(Nc1ccc(N2C3CCCC2CC3)cc1C(F)(F)F)c1c[nH]c2cccc(C(F)(F)F)c2c1=O] 12
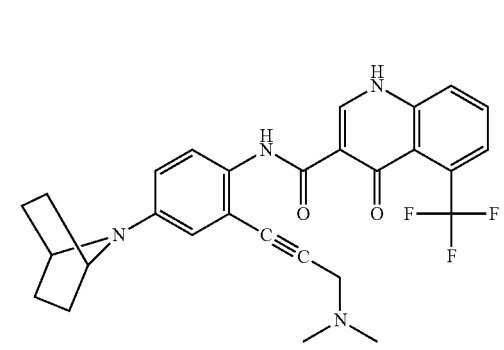 [SMILES: CN(C)CC#Cc1cc(N2C3CCC2CC3)ccc1NC(=O)c1c[nH]c2cccc(C(F)(F)F)c2c1=O] 13

TABLE 1-continued

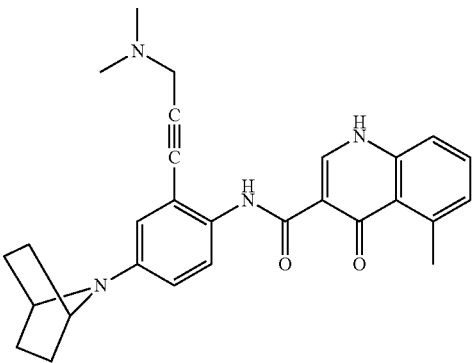 [SMILES: Cc1cccc2[nH]cc(C(=O)Nc3ccc(N4C5CCC4CC5)cc3C#CCN(C)C)c(=O)c12]

14

In another embodiment, the additional agent is any combination of the above agents. For example, the combination may comprise a pharmaceutical composition or tablet of the present invention comprising Compound 1 Form I and a solid dispersion of substantially amorphous Compound 2, and the additional therapeutic agent is (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide. In another example, the combination may comprise a pharmaceutical composition or tablet of the present invention comprising Compound 1 Form I and a solid dispersion of substantially amorphous Compound 2, and the additional therapeutic agent is 4-(3-(1-(2,2-difluorobenzo[d][1,3]dioxol-5-yl)cyclopropanecarboxamido) isoquinolin-1-yl)benzoic acid. In another example, the combination may comprise a pharmaceutical composition or tablet of the present invention comprising Compound 1 Form I and a solid dispersion of substantially amorphous Compound 2, and the additional therapeutic agent is any one of the compounds from Table 1, i.e. compounds 1 through 14 of Table 1, or any combination thereof.

In another embodiment, the additional agent is selected from Table 1:

TABLE 1

Compounds disclosed in U.S. Pat. No. 7,407,976 (Col 13, ln 35-col 66, ln 67; Compounds 1-100 in Table 1 at col 67, ln 1-col 127, ln 42)
Compounds disclosed in U.S. Pat. No. 7,645,789 (Col 16, ln 52-col 50, ln 22; Compounds 1-322 in Table 1 at col 50, ln 24-col 167, ln 42)
Compounds disclosedin U.S. Pat. No. 7,659,268 (Col 16, ln 20-col 70, ln 52; Compounds 1-528 in Table 1 at col 70, ln 53-col 331, ln 34)
Compounds disclosed in U.S. Pat. No. 7,671,221 (Col 16, ln 12-col 54, ln 48; Compounds 1-1216 in Table 1 at col 54, ln 49-col 699, ln 27)
Compounds disclosed in U.S. Pat. No. 7,691,902 (Col 16, ln 11-col 54, ln 29; Compounds 1-959 in Table 1 at col 54, ln 29-col 683, ln 44)
Compounds disclosed in U.S. Pat. No. 7,741,321 (Col 16, ln 25-col 72, ln 17; Compounds 1-422 in Table 1 at col 72, ln 20-col 279, ln 15)
Compounds disclosed in U.S. Pat. No. 7,754,739 (Col 16, ln 1-col 22, ln 47; Compounds 1-2 in Table 1 at col 18, ln 26-65)
Compounds disclosed in U.S. Pat. No. 7,776,905 (Col 16, ln 23-col 38, ln 40; Compounds 1-306 in Table 1 at col 38, ln 45-col 96, ln 40)
Compounds disclosed in U.S. Pat. No. 7,973,169 (Col 9, ln 16-col 40, ln 40; Compounds 1-289 in Table 1 at col. 40, ln 41-col 289, ln 39)
Compounds disclosed in U.S. Pat. No. 7,977,322 (Col 6, ln 26-col 37, ln 47; Compounds 1-498 in Table 1 at col 37, ln 50-col 141, ln 40)
Compounds disclosed in U.S. Pat. No. 7,999,113 (Col 6, ln 13-col 10, ln 67; Compounds 1-13 in Table 1 at col 11, ln 5-col 13, ln 65)
Compounds disclosed in U.S. Pat. No. 8,227,615 (Col 6, ln 10-col 29, ln 66; Compounds 1-78 in Table 1 at col 30, ln 1-col 46, ln 48)
Compounds disclosed in U.S. Pat. No. 8,299,099 (Col 6, ln 10-col 34, ln 18; Compounds 1-47 in Table 1 at col 34, ln 20-col 42, ln 35)
Compounds disclosed in US Published Application No. 2006-0052358 (Paragraphs [0034]-[0056]; [0077]-[0240]; Compounds 1-320 in Table 1 at paragraph [0241])
Compounds disclosed in US Published Application No. 2009-0143381 (Paragraphs [0102]-[0263]; Compounds 1-28 in Table 1 at paragraph [0264])
Compounds disclosed in US Published Application No. 2009-0170905 (Paragraphs [0012]-[0013]; [0030]-[0051])
Compounds disclosed in US Published Application No. 2009-0253736 (Paragraphs [0031]-[0162]; Compounds 1-15 in Table 1 at paragraph [0163])
Compounds disclosed in US Published Application No. 2011-0263654 (Paragraphs [0012]-[0013]; [0066]-[0141])
Compounds disclosed in US Published Application No. 2011-0251253 (Paragraphs [0012]-[0013]; [0054]-[0079])
Compounds disclosed in PCT application WO2008141119 (Paragraphs [0100]-[0339]; Compounds 1-117 in Table 1 at paragraph [0340])
Compounds disclosed in U.S. application No. 11/047,361
Compounds disclosed in US Published Application No. 2013-0116238 (Paragraphs [0028]-[0044]; [0117]-[0128]), or combinations thereof.

In another embodiment, the additional agent is selected from Table 2:

TABLE 2

Compounds disclosed in US Published Application No. 2005-0113423 (Paragraph [00146];
Compounds IA-1-IA-136 and Compounds I-1-I-21 in Tables 1 and 2 at paragraphs [0391]-[0392])
Compounds disclosed in US Published Application No. 2005-0059687 (Paragraphs [00100]-[00101];
Compounds 1-405 in Table 1 at paragraph [0169])
Compounds 1-108 disclosed in U.S. Pat. No. 7,598,412 (Col 22, ln 14-col 79, ln 20; Table 1)
Compounds 1-485 disclosed in U.S. Pat. No. 7,495,103 (Col 51, ln 1-col 63, ln 43; Table 1)
Compounds 1-718 disclosed in U.S. Pat. No. 8,354,427 (Col 51, ln 3-col 71, ln 46; Table 1)
Compounds 1-233 disclosed in US Published Application No. 2007-0105833 (Paragraph
[00145]; Table 1)
Compounds 1-26 disclosed in U.S. Pat. No. 8,242,149 (Col 46, ln 47-col 57, ln 37; Table 1)
Compounds 1-18 disclosed in U.S. Pat. No. 8,314,256 (Col 21, ln 1-col 26, ln 19)
Compounds 1-14 disclosed in U.S. Pat. No. 8,399,479 (Col 36, ln 20-col 38, ln 40; Table 1)
Compounds 1-18 disclosed in U.S. Pat. No. 8,188,283 (Col 38, ln 43-col 43, ln 36; Table 1)
Compounds 1-16 disclosed in US Published Application No. 2010-0249180 (Paragraph [0173]; Table 1)
Compounds 1-19 disclosed in US Published Application No. 2011-0008259 (Paragraph [0172]; Table 1)
Compounds 1-129 disclosed in U.S. Pat. No. 8,367,660 (Col 57, ln 31-col 81, ln 24; Table 1)

In one embodiment, the additional therapeutic agent is an antibiotic. Exemplary antibiotics useful herein include tobramycin, including tobramycin inhaled powder (TIP), azithromycin, cayston, aztreonam, including the aerosolized form of aztreonam, amikacin, including liposomal formulations thereof, ciprofloxacin, including formulations thereof suitable for administration by inhalation, levoflaxacin, including aerosolized formulations thereof, and combinations of two antibiotics, e.g., fosfomycin and tobramycin.

In another embodiment, the additional agent is a mucolyte. Exemplary mucolytes useful herein includes Pulmozyme®.

In another embodiment, the additional agent is a bronchodialator. Exemplary bronchodialtors include albuterol, metaprotenerol sulfate, pirbuterol acetate, salmeterol, or tetrabuline sulfate.

In another embodiment, the additional agent is effective in restoring lung airway surface liquid. Such agents improve the movement of salt in and out of cells, allowing mucus in the lung airway to be more hydrated and, therefore, cleared more easily. Exemplary such agents include hypertonic saline, denufosol tetrasodium ([[(3S,5R)-5-(4-amino-2-oxopyrimidin-1-yl)-3-hydroxyoxolan-2-yl]methoxy-hydroxyphosphoryl][[[(2R,3S,4R,5R)-5-(2,4-dioxopyrimidin-1-yl)-3,4-dihydroxyoxolan-2-yl]methoxy-hydroxyphosphoryl] oxy-hydroxyphosphoryl] hydrogen phosphate), or bronchitol (inhaled formulation of mannitol).

In another embodiment, the additional agent is an anti-inflammatory agent, i.e., an agent that can reduce the inflammation in the lungs. Exemplary such agents useful herein include ibuprofen, docosahexanoic acid (DHA), sildenafil, inhaled glutathione, pioglitazone, hydroxychloroquine, or simavastatin.

In another embodiment, the additional agent is a compound that augments or induces CFTR activity other than Compound 1 Form I or a solid dispersion comprising substantially amorphous Compound 2, i.e., an agent that has the effect of inducing or augmenting CFTR activity. Exemplary such agents include ataluren ("PTC 124®"; 3-[5-(2-fluorophenyl)-1,2,4-oxadiazol-3-yl]benzoic acid), sinapultide, lancovutide, depelestat (a human recombinant neutrophil elastase inhibitor), and cobiprostone (7-{(2R, 4aR, 5R, 7aR)-2-[(3S)-1,1-difluoro-3-methylpentyl]-2-hydroxy-6-oxooctahydrocyclopenta[b]pyran-5-yl}heptanoic acid).

In another embodiment, the additional agent is a nutritional agent. Exemplary nutritional agents include pancrelipase (pancreating enzyme replacement), including Pancrease®, Pancreacarb®, Ultrase®, or Creon®, Liprotomase® (formerly Trizytek®), Aquadeks®, or glutathione inhalation. In one embodiment, the additional nutritional agent is pancrelipase.

In another embodiment, the additional agent is a compound selected from gentamicin, curcumin, cyclophosphamide, 4-phenylbutyrate, miglustat, felodipine, nimodipine, Philoxin B, geniestein, Apigenin, cAMP/cGMP augmenters or inducers such as rolipram, sildenafil, milrinone, tadalafil, amrinone, isoproterenol, albuterol, and almeterol, deoxyspergualin, HSP 90 inhibitors, HSP 70 inhibitors, proteosome inhibitors such as epoxomicin, lactacystin, etc.

In another embodiment, the additional agent is a compound selected from 3-amino-6-(4-fluoro-phenyl)-5-trifluoromethyl-pyridine-2-carboxylic acid (3,3,3-trifluoro-2-hydroxy-2-methyl-propyl)-amide; 5-amino-6'-methyl-3-trifluoromethyl-[2,3]bipyridinyl-6-carboxylic acid (3,3,3-trifluoro-2-hydroxy-2-methyl-propyl)-amide; 3-amino-6-cyclopropyl-N-(3,3,3-trifluoro-2-hydroxy-2-methylpropyl)-5-(trifluoromethyl)picolinamide; 3-amino-6-methoxy-N-(3,3,3-trifluoro-2-hydroxy-2-(trifluoromethyl)propyl)-5-(trifluoro methyl)picolinamide; 3-amino-6-(4-fluoro-phenyl)-5-trifluoromethyl-pyridine-2-carboxylic acid ((S)-3,3,3-trifluoro-2-hydroxy-2-methyl-propyl)-amide; 3-amino-6-methoxy-5-trifluoromethyl-pyridine-2-carboxylic acid ((S-3,3,3-trifluoro-2-hydroxy-2-methyl-propyl)-amide; 3-amino-6-methoxy-5-trifluoromethyl-pyridine-2-carboxylic acid ((R)-3,3,3-trifluoro-2-hydroxy-2-methyl-propyl)-aide; 3-amino-6-(2,4-dichloro-phenyl)-5-trifluoromethyl-pyridine-2-carboxylic acid ((S)-3,3,3-trifluoro-2-hydroxy-2-methyl-propyl)-amide; 3-amino-6-(2,4-dichloro-phenyl)-5-trifluoromethyl-pyridine-2-carboxylic acid ((R)-3,3,3-trifluoro-2-hydroxy-2-methyl-propyl)-amide; 3-amino-6-(4-fluoro-phenyl)-5-trifluoromethyl-pyridine-2-carboxylic acid (2-hydroxy-2-methyl-propyl)-amide; 3-amino-5,6-bis-trifluoromethyl-pyridine-2-carboxylic acid ((S)-3,3,3-trifluoro-2-hydroxy-2-methyl-propyl)-amide; 3-amino-5,6-bis-trifluoromethyl-pyridine-2-carboxylic acid ((R)-3,3,3-trifluoro-2-hydroxy-2-methyl-propyl)-amide; (S)-3-amino-6-ethoxy-N-(3,3,3-trifluoro-2-hydroxy-2-methylpropyl)-5-(trifluoro methyl)picolinamide; 3-amino-6-methoxy-5-trifluoromethyl-pyridine-2-carboxylic acid ((S)-3,3,3-trifluoro-2-hydroxy-2-methyl-propyl)-amide; 3-amino-6-methoxy-5-trifluoromethyl-pyridine-2-carboxylic acid ((R)-3,3,3-trifluoro-2-hydroxy-2-methyl-propyl)-amide; 3-amino-6-(4-fluoro-phenyl)-5-trifluoromethyl-pyridine-2-carboxylic acid (3,3,3-trifluoro-2-hydroxy-2-methyl-propyl)-amide; 3-amino-5,6-bis-trifluoromethyl-pyridine-2- carboxylic acid ((S)-3,3,3-trifluoro-2-hydroxy-2-methyl-propyl)-amide; 3-amino-5,6-bis-trifluoromethyl-pyridine-2-carboxylic acid ((R)-3,3,3-trifluoro-2-hydroxy-2-methyl-propyl)-amide, or pharmaceutically acceptable salts thereof. In another embodiment, the additional agent is a compound disclosed in U.S. Pat. No. 8,247,436 and International PCT Publication WO 2011113894, incorporated herein in their entirety by reference.

In another embodiment, the additional agent may be an epithelial sodium channel (ENac) modulator disclosed in PCT publications WO2012035158, WO2009074575, WO2011028740, WO2009150137, WO2011079087, or WO2008135557, incorporated herein in their entirety by reference.

In other embodiments, the additional agent is a compound disclosed in WO 2004028480, WO 2004110352, WO 2005094374, WO 2005120497, or WO 2006101740, incorporated herein in their entirety by reference. In another embodiment, the additional agent is a benzo[c]quinolizinium derivative that exhibits CFTR inducing or augmenting activity or a benzopyran derivative that exhibits CFTR inducing or augmenting activity. In another embodiment, the additional agent is a compound disclosed in U.S. Pat. Nos. 7,202,262, 6,992,096, US20060148864, US20060148863, US20060035943, US20050164973, WO2006110483, WO2006044456, WO2006044682, WO2006044505, WO02006044503, WO2006044502, or WO2004091502, incorporated herein in their entirety by reference. In another embodiment, the additional agent is a compound disclosed in WO2004080972, WO2004111014, WO2005035514, WO2005049018, WO2006099256, WO2006127588, or WO2007044560, incorporated herein in their entirety by reference.

In one embodiment, 400 mg of Compound 1 Form I and 250 mg of substantially amorphous Compound 2 may be administered to a subject in need thereof. In these embodiments, the dosage amounts may be achieved by administration of one or more tablets of the invention. For example, administration of 400 mg of Compound 1 Form I and 250 mg of substantially amorphous Compound 2 may be achieved by administering two tablets each containing 200 mg of Compound 1 Form I, and 125 mg of substantially amorphous Compound 2. The duration of administration may continue until amelioration of the disease is achieved or until a subject's physician advises, e.g. duration of administration may be less than a week, 1 week, 2 weeks, 3 weeks, four weeks (28 days), or a month or longer. In one embodiment, two tablets each comprising 200 mg of Compound 1 Form I, and 125 mg of substantially amorphous Compound 2 may be administered to the patient per day. In a further embodiment, the two tablets may be administered at the same time or at different times during the day. In a further embodiment, one tablet is administered every 12 hours.

In one embodiment, 400 mg of Compound 1 Form I and 500 mg of substantially amorphous Compound 2 may be administered to a subject in need thereof. In these embodiments, the dosage amounts may be achieved by administration of two tablets each containing 200 mg of Compound 1 Form I, and 250 mg of substantially amorphous Compound 2. In one embodiment a tablet is administered once every 12 hours. In another embodiment, the dosage amount may also be achieved by administering two tablets, each containing 100 mg of Compound 1 Form I and 125 mg of substantially amorphous Compound 2, every 12 hours. In another embodiment, the dosage amounts may also be achieved by administering Compound 1 Form I and substantially amorphous Compound 2 in separate tablets. For example, the dosage amounts may be achieved by administering two tablets containing 200 mg of Compound 1 Form I, and four tablets containing 125 mg of substantially amorphous Compound 2 or two tablets containing 150 mg of substantially amorphous Compound 2 and two tablets containing 100 mg of substantially amorphous Compound 2. The duration of administration may continue until amelioration of the disease is achieved or until a subject's physician advises, e.g. duration of administration may be less than a week, 1 week, 2 weeks, 3 weeks, four weeks (28 days), or a month or longer. In one embodiment, two tablets comprising 200 mg of Compound 1 Form I, and four tablets comprising 125 mg of substantially amorphous Compound 2 may be administered to the patient per day. In one embodiment, two tablets comprising 200 mg of Compound 1 Form I may be administered to the patient per day, and two tablets comprising 150 mg and 100 mg of substantially amorphous Compound 2 may be administered to the patient twice per day. In a further embodiment, the two tablets may be administered at the same time or at different times during the day. In a further embodiment, one tablet comprising 200 mg of Compound 1 is administered every 12 hours, and two tablets comprising 150 mg and 100 mg of substantially amorphous Compound 2 are administered every 12 hours.

In one embodiment, 300 mg of Compound 1 Form I and 250 mg of substantially amorphous Compound 2 may be administered to a subject in need thereof. In these embodiments, the dosage amounts may be achieved by administration of one or more tablets of the invention. For example, administration of 300 mg of Compound 1 Form I and 250 mg of substantially amorphous Compound 2 may be achieved by administering two tablets each containing 150 mg of Compound 1 Form I, and 125 mg of substantially amorphous Compound 2. The duration of administration may continue until amelioration of the disease is achieved or until a subject's physician advises, e.g. duration of administration may be less than a week, 1 week, 2 weeks, 3 weeks, four weeks (28 days), or a month or longer. In one embodiment, two tablets each comprising 150 mg of Compound 1 Form I, and 125 mg of substantially amorphous Compound 2 may be administered to the patient per day. In a further embodiment, the two tablets may be administered at the same time or at different times during the day. In a further embodiment, one tablet is administered every 12 hours.

In one embodiment, 600 mg of Compound 1 Form I and 500 mg of substantially amorphous Compound 2 may be administered to a subject in need thereof. In these embodiments, the dosage amounts may be achieved by administration of one or more tablets of the invention. For example, administration of 600 mg of Compound 1 Form I and 500 mg of substantially amorphous Compound 2 may be achieved by administering two tablets, each containing 150 mg of Compound 1 Form I, and 125 mg of substantially amorphous Compound 2, every 12 hours. The duration of administration may continue until amelioration of the disease is achieved or until a subject's physician advises, e.g. duration of administration may be less than a week, 1 week, 2 weeks, 3 weeks, four weeks (28 days), or a month or longer. In one embodiment, four tablets each comprising 150 mg of Compound 1 Form I, and 125 mg of substantially amorphous Compound 2 may be administered to the patient per day. In a further embodiment, the four tablets may be administered at the same time or at different times during the day. In a further embodiment, two tablet is administered every 12 hours.

In one embodiment, 800 mg of Compound 1 Form I and 500 mg of substantially amorphous Compound 2 may be administered to a subject in need thereof. In these embodiments, the dosage amounts may be achieved by administration of one or more tablets of the invention. For example, administration of 800 mg of Compound 1 Form I and 500 mg of substantially amorphous Compound 2 may be achieved by administering four tablets each containing 200 mg of Compound 1 Form I, and 125 mg of substantially amorphous Compound 2. The duration of administration may continue until amelioration of the disease is achieved or until a subject's physician advises, e.g. duration of administration may be less than a week, 1 week, 2 weeks, 3 weeks, four weeks (28 days), or a month or longer. In one embodiment, four tablets each comprising 200 mg of Compound 1 Form I, and 125 mg of substantially amorphous Compound 2 may be administered to the patient per day. In a further embodiment, the four tablets may be administered at the same time or at different times during the day. In a further embodiment, two tablets are administered per dosing occasion, and there are two dosing occasions per day. In a further embodiment, 800 mg of Compound 1 and 500 mg of Compound 2 are administered to the patient by administering two tablets each comprising 200 mg of Compound 1 and 125 mg of Compound 2 twice a day (BID). In a further embodiment, 800 mg of Compound 1 and 500 mg of Compound 2 are administered to the patient by administering two tablets each comprising 200 mg of Compound 1 and 125 mg of Compound 2 every 12 hours (q12h).

In one embodiment, 600 mg of Compound 1 Form I and 250 mg of substantially amorphous Compound 2 may be administered to a subject in need thereof. In these embodiments, the dosage amounts may be achieved by administration of one or more tablets of the invention. For example, administration of 600 mg of Compound 1 Form I and 250 mg of substantially amorphous Compound 2 may be achieved by administering three tablets each containing 200 mg of Compound 1 Form I, and 83.3 mg of substantially amorphous Compound 2. The duration of administration may continue until amelioration of the disease is achieved or until a subject's physician advises, e.g. duration of administration may be less than a week, 1 week, 2 weeks, 3 weeks, four weeks (28 days), or a month or longer. In one embodiment, three tablets each comprising 200 mg of Compound 1 Form I, and 83.3 mg of substantially amorphous Compound 2 may be administered to the patient per day. In a further embodiment, the three tablets may be administered at the same time or at different times during the day. In a further embodiment, three tablets are administered at the same time.

In one embodiment, 600 mg of Compound 1 Form I and 500 mg of substantially amorphous Compound 2 may be administered to a subject in need thereof. In these embodiments, the dosage amounts may be achieved by administration of one or more tablets of the invention. For example, administration of 600 mg of Compound 1 Form I and 500 mg of substantially amorphous Compound 2 may be achieved by administering three tablets each containing 200 mg of Compound 1 Form I, and 83.3 mg of substantially amorphous Compound 2, followed by two additional tablets each comprising 125 mg of Compound 2. The duration of administration may continue until amelioration of the disease is achieved or until a subject's physician advises, e.g. duration of administration may be less than a week, 1 week, 2 weeks, 3 weeks, four weeks (28 days), or a month or longer. In one embodiment, 600 mg of Compound 1 may be administered daily (qd) and 250 mg of Compound 2 administered twice a day (bid) by administering three tablets each comprising 200 mg of Compound 1 Form I, and 83.3 mg of substantially amorphous Compound 2 daily (qd) and two tablets each comprising 125 mg of Compound 2 every 12 hours (q12h). In one embodiment, 600 mg of Compound 1 may be administered daily (qd) and 250 mg of Compound 2 administered every 12 hours (q12h) by administering three tablets each comprising 200 mg of Compound 1 Form I, and 83.3 mg of substantially amorphous Compound 2 daily (qd) and two tablets each comprising 125 mg of Compound 2 every 12 hours (q12h).

These combinations are useful for treating the diseases described herein including cystic fibrosis. These combinations are also useful in the kits described herein. In another aspect, the present invention features a kit comprising a pharmaceutical composition or tablet of the present invention comprising Compound 1 Form I and a solid dispersion comprising substantially amorphous Compound 2, and a separate additional therapeutic agent or pharmaceutical composition thereof. In another embodiment, the pharmaceutical composition or tablet of the present invention, separate additional therapeutic agent or pharmaceutical composition thereof are in separate containers. In another embodiment, the separate containers are bottles. In another embodiment, the separate containers are vials. In another embodiment, the separate containers are blister packs.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Therapeutic Uses of the Composition

In one aspect, the invention also provides a method of treating, lessening the severity of, or symptomatically treating a disease in a patient, the method comprising administering an effective amount of the pharmaceutical composition or tablet of the invention to the patient, preferably a mammal, wherein the disease is selected from cystic fibrosis, asthma, smoke induced COPD, chronic bronchitis, rhinosinusitis, constipation, pancreatitis, pancreatic insufficiency, male infertility caused by congenital bilateral absence of the vas deferens (CBAVD), mild pulmonary disease, idiopathic pancreatitis, allergic bronchopulmonary aspergillosis (ABPA), liver disease, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders such as Huntington's, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease, Straussler-Scheinker syndrome, COPD, dry-eye disease, or Sjogren's disease, osteoporosis, osteopenia, bone healing and bone growth (including bone repair, bone regeneration, reducing bone resorption and increasing bone deposition), Gorham's Syndrome, chloride channelopathies such as myotonia congenita (Thomson and Becker forms), Bartter's syndrome type III, Dent's disease, hyperekplexia, epilepsy, lysosomal storage disease, Angelman syndrome, and Primary Ciliary Dyskinesia (PCD), a term for inherited disorders of the structure and/or function of cilia, including PCD with situs inversus (also known as Kartagener syndrome), PCD without situs inversus and ciliary aplasia.

In one aspect, the invention also provides a method of treating, lessening the severity of, or symptomatically treating a disease in a patient comprising administering an effective amount of the pharmaceutical composition or tablet of the invention to the patient, preferably a mammal, wherein the disease is selected from generalized epilepsy with ferbrile seizures plus (GEFS+), general epilepsy with ferbile and aferbrile seizures, myotonia, paramyotonia congenital, potassium-aggravated myotonia, hyperkalemic periodic paralysis, LQTS, LQTS/Brugada syndrome, autosomal-dominant LQTS with deafness, autosomal-recessive LQTS, LQTS with dysmorphic features, congenital and acquired LQTS, Timothy syndrome, persistent hyperinsulinemic hypolglycemia of infancy, dilated cardiomyopathy, autosomal-dominant LQTS, Dent disease, Osteopetrosis, Bartter syndrome type III, central core disease, malignant hyperthermia, and catecholaminergic polymorphic tachycardia.

In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation N1303K, ΔI507, or R560T.

In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation G551D. In another embodiment, the patient is homozygous in G551D. In another embodiment, the patient is heterozygous in G551D wherein the other CFTR genetic mutation is any one of ΔF508, G542X, N1303K, W1282X, R117H, R553X, 1717-1G→A, 621+1G→T, 2789+5G→A, 3849+10kbC→T, R1162X, G85E, 3120+1G→A, ΔI507, 1898+1G→A, 3659delC, R347P, R560T, R334W, A455E, 2184delA, or 711+1G→T.

In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation ΔF508. In another embodiment, the patient is homozygous in ΔF508. In another embodiment, the patient is heterozygous in ΔF508 wherein the other CFTR genetic mutation is any one of G551D, G542X, N1303K, W1282X, R117H, R553X, 1717-1G→A, 621+1G→T, 2789+5G→A, 3849+10kbC→T, R1162X, G85E, 3120+1G→A, ΔI507, 1898+1G→A, 3659delC, R347P, R560T, R334W, A455E, 2184delA, or 71 l+1G→T.

In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from G178R, G551S, G970R, G1244E, S1255P, G1349D, S549N, S549R, S1251N, E193K, F1052V, G1069R, R117C, D110H, R347H, R352Q, E56K, P67L, L206W, A455E, D579G, S1235R, S945L, R1070W, F1074L, D110E, D1270N, D1152H, 1717-1G→A, 621+1G→T, 3120+1G→A, 1898+1 G→A, 711+1 G→T, 2622+1 G→A, 405+1 G→A, 406-1 G→A, 4005+1 G→A, 1812-1 G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C and 621+3A→G.

In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from G178R, G551S, G970R, G1244E, S1255P, G1349D, S549N, S549R, S1251N, E193K, F1052V and G1069R. In one embodiment of this aspect, the invention provides a method of treating CFTR comprising administering Compound 1 to a patient possessing a human CFTR mutation selected from G178R, G551S, G970R, G1244E, S1255P, G1349D, S549N, S549R and S1251N. In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from E193K, F1052V and G1069R. In some embodiments of this aspect, the method produces a greater than 10-fold increase in chloride transport relative to baseline chloride transport.

In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from R117C, D110H, R347H, R352Q, E56K, P67L, L206W, A455E, D579G, S1235R, S945L, R1070W, F1074L, D110E, D1270N and D1152H. In one embodiment of this aspect, the method produces an increase in chloride transport which is greater or equal to 10% above the baseline chloride transport.

In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C and 621+3A→G. In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from 1717-1 G→A, 1811+1.6kbA→G, 2789+5G→A, 3272-26A→G and 3849+10kbC→T. In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from 2789+5G→A and 3272-26A→G.

In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from G178R, G551S, G970R, G1244E, S1255P, G1349D, S549N, S549R, S1251N, E193K, F1052V, G1069R, R117C, D110H, R347H, R352Q, E56K, P67L, L206W, A455E, D579G, S1235R, S945L, R1070W, F1074L, D110E, D1270N, D1152H, 1717-1G→A, 621+1G→T, 3120+1G→A, 1898+1 G→A, 711+1 G→T, 2622+1 G→A, 405+1 G→A, 406-1 G→A, 4005+1 G→A, 1812-1 G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C and 621+3A→G, and a human CFTR mutation selected from ΔF508, R117H, and G551D.

In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from G178R, G551S, G970R, G1244E, S1255P, G1349D, S549N, S549R, S1251N, E193K, F1052V and G1069R, and a human CFTR mutation selected from ΔF508, R117H, and G551D. In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from G178R, G551S, G970R, G1244E, S1255P, G1349D, S549N, S549R and S1251N, and a human CFTR mutation selected from ΔF508, R117H, and G551D. In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from E193K, F1052V and G1069R, and a human CFTR mutation selected from ΔF508, R117H, and G551D. In some embodiments of this aspect, the method produces a greater than 10-fold increase in chloride transport relative to baseline chloride transport.

In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from R117C, D110H, R347H, R352Q, E56K, P67L, L206W, A455E, D579G, S1235R, S945L, R1070W, F1074L, D110E, D1270N and D1152H, and a human CFTR mutation selected from ΔF508, R117H, and G551D. In one embodiment of this aspect, the method produces an increase in chloride transport which is greater or equal to 10% above the baseline chloride transport.

In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from 1717-1G→A, 621+1G→T, 3120+1G→A, 1898+1G→A, 711+1G→T, 2622+1G→A, 405+1G→A, 406-1 G→A, 4005+1 G→A, 1812-1 G→A, 1525-1 G→A, 712-1 G→T, 1248+1 G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C and 621+3A→G, and a human CFTR mutation selected from ΔF508, R117H, and G551D. In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from 1717-1G→A, 1811+1.6kbA→G, 2789+5G→A, 3272-26A→G and 3849+10kbC→T, and a human CFTR mutation selected from ΔF508, R117H, and G551D. In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from 2789+5G→A and 3272-26A→G, and a human CFTR mutation selected from ΔF508, R117H.

In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from G178R, G551S, G970R, G1244E, S1255P, G1349D, S549N, S549R, S1251N, E193K, F1052V, G1069R, R117C, D10H, R347H, R352Q, E56K, P67L, L206W, A455E, D579G, S1235R, S945L, R1070W, F1074L, D110E, D1270N, D1152H, 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C and 621+3A→G, and a human CFTR mutation selected from ΔF508, R117H, and G551D.

In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from G178R, G551S, G970R, G1244E, S1255P, G1349D, S549N, S549R, S1251N, E193K, F1052V and G1069R. In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from G178R, G551S, G970R, G1244E, S1255P, G1349D, S549N, S549R and S1251N. In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from E193K, F1052V and G1069R. In some embodiments of this aspect, the method produces a greater than 10-fold increase in chloride transport relative to baseline chloride transport.

In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from R117C, D110H, R347H, R352Q, E56K, P67L, L206W, A455E, D579G, S1235R, S945L, R1070W, F1074L, D110E, D1270N and D1152H. In one embodiment of this aspect, the method produces an increase in chloride transport which is greater or equal to 10% above the baseline chloride transport.

In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C and 621+3A→G. In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from 1717-1G→A, 1811+1.6kbA→G, 2789+5G→A, 3272-26A→G and 3849+10kbC→T. In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from 2789+5G→A and 3272-26A→G.

In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from G178R, G551S, G970R, G1244E, S1255P, G1349D, S549N, S549R, S1251N, E193K, F1052V, G1069R, R117C, D110H, R347H, R352Q, E56K, P67L, L206W, A455E, D579G, S1235R, S945L, R1070W, F1074L, D110E, D1270N, D1152H, 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C and 621+3A→G, and a human CFTR mutation selected from ΔF508, R117H, and G551D, and one or more human CFTR mutations selected from ΔF508, R117H, and G551D.

In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from G178R, G551S, G970R, G1244E, S1255P, G1349D, S549N, S549R, S1251N, E193K, F1052V and G1069R, and one or more human CFTR mutations selected from ΔF508, RI 17H, and G551D. In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from G178R, G551S, G970R, G1244E, S1255P, G1349D, S549N, S549R and S1251N, and one or more human CFTR mutations selected from ΔF508, R117H, and G551D. In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from E193K, F1052V and G1069R, and one or more human CFTR mutations selected from ΔF508, R117H, and G551D. In some embodiments of this aspect, the method produces a greater than 10-fold increase in chloride transport relative to baseline chloride transport.

In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from R117C, D110H, R347H, R352Q, E56K, P67L, L206W, A455E, D579G, S1235R, S945L, R1070W, F1074L, D110E, D1270N and D1152H, and one or more human CFTR mutations selected from ΔF508, R117H, and G551D. In one embodiment of this aspect, the method produces an increase in chloride transport which is greater or equal to 10% above the baseline chloride transport.

In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C and 621+3A→G, and one or more human CFTR mutations selected from ΔF508, R117H, and G551D. In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from 1717-1G→A, 1811+1.6kbA→G, 2789+5G→A, 3272-26A→G and 3849+10kbC→T, and one or more human CFTR mutations selected from ΔF508, R117H, and G551D. In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation is selected from 2789+5G→A and 3272-26A→G, and one or more human CFTR mutations selected from ΔF508, R117H, and G551D.

In certain embodiments, the pharmaceutically acceptable composition or tablet of the present invention comprising Compound 1 Form I and a solid dispersion of substantially amorphous Compound 2 are useful for treating, lessening the severity of, or symptomatically treating cystic fibrosis in patients who exhibit residual CFTR activity in the apical membrane of respiratory and non-respiratory epithelia. The presence of residual CFTR activity at the epithelial surface can be readily detected using methods known in the art, e.g., standard electrophysiological, biochemical, or histochemical techniques. Such methods identify CFTR activity using in vivo or ex vivo electrophysiological techniques, measurement of sweat or salivary Cl⁻ concentrations, or ex vivo biochemical or histochemical techniques to monitor cell surface density. Using such methods, residual CFTR activity can be readily detected in patients heterozygous or homozygous for a variety of different mutations, including patients homozygous or heterozygous for the most common mutation, ΔF508, as well as other mutations such as the G551D mutation, or the R117H mutation. In certain embodiments, the pharmaceutically acceptable compositions or tablets comprising Compound 1 Form I and a solid dispersion comprising substantially amorphous Compound 2 are useful for treating, lessening the severity of, or symptomatically treating cystic fibrosis in patients who exhibit little to no residual CFTR activity. In certain embodiments, the pharmaceutically acceptable compositions or tablets comprising Compound 1 Form I and a solid dispersion comprising substantially amorphous Compound 2 are useful for treating, lessening the severity of, or symptomatically treating cystic fibrosis in patients who exhibit little to no residual CFTR activity in the apical membrane of respiratory epithelia.

In another embodiment, the compounds and compositions of the present invention are useful for treating or lessening the severity of cystic fibrosis in patients who have residual CFTR activity induced or augmented using pharmacological methods. In another embodiment, the compounds and compositions of the present invention are useful for treating or lessening the severity of cystic fibrosis in patients who have residual CFTR activity induced or augmented using or gene therapy. Such methods increase the amount of CFTR present at the cell surface, thereby inducing a hitherto absent CFTR activity in a patient or augmenting the existing level of residual CFTR activity in a patient.

In one embodiment, pharmaceutical compositions and tablets of the present invention comprising Compound 1 Form I and a solid dispersion comprising substantially amorphous Compound 2, as described herein, are useful for treating or lessening the severity of cystic fibrosis in patients within certain genotypes exhibiting residual CFTR activity, e.g., Class I mutations (not synthesized), class II mutation (misfolding), class III mutations (impaired regulation or gating), class IV mutations (altered conductance), or class V mutations (reduced synthesis).

In one embodiment, pharmaceutical compositions and tablets of the present invention comprising Compound 1 Form I and a solid dispersion comprising substantially amorphous Compound 2, as described herein, are useful for treating, lessening the severity of, or symptomatically treating cystic fibrosis in patients within certain clinical phenotypes, e.g., a moderate to mild clinical phenotype that typically correlates with the amount of residual CFTR activity in the apical membrane of epithelia. Such phenotypes include patients exhibiting pancreatic sufficiency.

In one embodiment, pharmaceutical compositions and tablets of the present invention comprising Compound 1 Form I and a solid dispersion comprising substantially amorphous Compound 2, as described herein, are useful for treating, lessening the severity of, or symptomatically treating patients diagnosed with pancreatic sufficiency, idiopathic pancreatitis and congenital bilateral absence of the vas deferens, or mild lung disease wherein the patient exhibits residual CFTR activity.

In one embodiment, pharmaceutical compositions and tablets of the present invention comprising Compound 1 Form I and a solid dispersion comprising substantially amorphous Compound 2, as described herein, are useful for treating, lessening the severity of, or symptomatically treating patients diagnosed with pancreatic sufficiency, idiopathic pancreatitis and congenital bilateral absence of the vas deferens, or mild lung disease wherein the patient has wild type CFTR.

In addition to cystic fibrosis, modulation of CFTR activity may be beneficial for other diseases not directly caused by mutations in CFTR, such as secretory diseases and other protein folding diseases mediated by CFTR. These include, but are not limited to, chronic obstructive pulmonary disease (COPD), dry eye disease, and Sjögren's Syndrome. COPD is characterized by airflow limitation that is progressive and not fully reversible. The airflow limitation is due to mucus hypersecretion, emphysema, and bronchiolitis. Activators of mutant or wild-type CFTR offer a potential treatment of mucus hypersecretion and impaired mucociliary clearance that is common in COPD. Specifically, increasing anion secretion across CFTR may facilitate fluid transport into the airway surface liquid to hydrate the mucus and optimized periciliary fluid viscosity. This would lead to enhanced mucociliary clearance and a reduction in the symptoms associated with COPD. Dry eye disease is characterized by a decrease in tear aqueous production and abnormal tear film lipid, protein and mucin profiles. There are many causes of dry eye, some of which include age, Lasik eye surgery, arthritis, medications, chemical/thermal burns, allergies, and diseases, such as cystic fibrosis and Sjögrens's syndrome. Increasing anion secretion via CFTR would enhance fluid transport from the corneal endothelial cells and secretory glands surrounding the eye to increase corneal hydration. This would help to alleviate the symptoms associated with dry eye disease. Sjögrens's syndrome is an autoimmune disease in which the immune system attacks moisture-producing glands throughout the body, including the eye, mouth, skin, respiratory tissue, liver, vagina, and gut. Symptoms, include, dry eye, mouth, and vagina, as well as lung disease. The disease is also associated with rheumatoid arthritis, systemic lupus, systemic sclerosis, and polymypositis/dermatomyositis. Defective protein trafficking is believed to cause the disease, for which treatment options are limited. Augmenters or inducers of CFTR activity may hydrate the various organs afflicted by the disease and help to elevate the associated symptoms.

In one embodiment, the invention relates to a method of augmenting or inducing anion channel activity in vitro or in vivo, comprising contacting the channel with any one of pharmaceutical compositions PC-I to PC-XXV. In another embodiment, the anion channel is a chloride channel or a bicarbonate channel. In another embodiment, the anion channel is a chloride channel.

The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

Anywhere in the present application where a name of a compound may not correctly describe the structure of the compound, the structure supersedes the name and governs.

Examples

XRPD (X-Ray Powder Diffraction)

The X-Ray diffraction (XRD) data of Compound 1 Form I were collected on a Bruker D8 DISCOVER powder diffractometer with HI-STAR 2-dimensional detector and a flat graphite monochromator. Cu sealed tube with Kα radiation was used at 40 kV, 35 mA. The samples were placed on zero-background silicon wafers at 25° C. For each sample, two data frames were collected at 120 seconds each at 2 different $\theta_2$ angles: 8° and 260. The data were integrated with GADDS software and merged with DIFFRACT$^{plus}$EVA software. Uncertainties for the reported peak positions are ±0.2 degrees.

Differential Scanning Calorimetry (DSC)

The Differential scanning calorimetry (DSC) data of Compound 1 Form I were collected using a DSC Q100 V9.6 Build 290 (TA Instruments, New Castle, Del.). Temperature was calibrated with indium and heat capacity was calibrated with sapphire. Samples of 3-6 mg were weighed into aluminum pans that were crimped using lids with 1 pin hole. The samples were scanned from 25° C. to 350° C. at a heating rate of 1.0° C./min and with a nitrogen gas purge of 50 ml/min. Data were collected by Thermal Advantage Q Series™ version 2.2.0.248 software and analyzed by Universal Analysis software version 4.1D (TA Instruments, New Castle, Del.). The reported numbers represent single analyses.

Compound 1 Form I Single Crystal Structure Determination

Diffraction data were acquired on Bruker Apex II diffractometer equipped with sealed tube Cu K-alpha source and an Apex II CCD detector. The structure was solved and refined using SHELX program (Sheldrick, G. M., Acta Cryst., (2008) A64, 112-122). Based on systemratic absences and intensities statistics the structure was solved and refined in P2$_1$/n space group.

Vitride® (sodium bis(2-methoxyethoxy)aluminum hydride [or NaAlH$_2$(OCH$_2$CH$_2$OCH$_3$)$_2$], 65 wgt % solution in toluene) was purchased from Aldrich Chemicals.

2,2-Difluoro-1,3-benzodioxole-5-carboxylic acid was purchased from Saltigo (an affiliate of the Lanxess Corporation).

Preparation of Compound 1

Preparation of (2,2-difluoro-1,3-benzodioxol-5-yl)-methanol

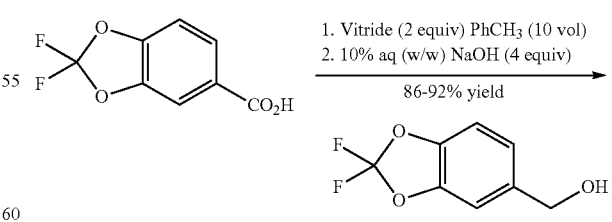

Commercially available 2,2-difluoro-1,3-benzodioxole-5-carboxylic acid (1.0 eq) was slurried in toluene (10 vol). Vitride® (2 eq) was added via addition funnel at a rate to maintain the temperature at 15-25° C. At the end of the addition, the temperature was increased to 40° C. for 2 hours (h), then 10% (w/w) aqueous (aq) NaOH (4.0 eq) was carefully added via addition funnel, maintaining the temperature at 40-50° C. After stirring for an additional 30 minutes (min), the layers were allowed to separate at 40° C. The organic phase was cooled to 20° C., then washed with water (2×1.5 vol), dried (Na₂SO₄), filtered, and concentrated to afford crude (2,2-difluoro-1,3-benzodioxol-5-yl)-methanol that was used directly in the next step.

Preparation of 5-chloromethyl-2,2-difluoro-1,3-benzodioxole

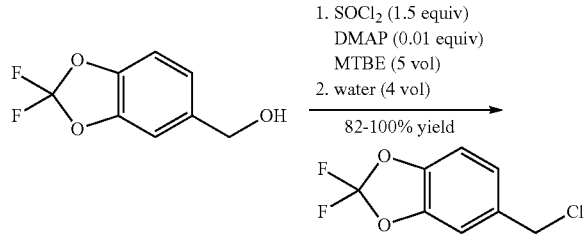

(2,2-difluoro-1,3-benzodioxol-5-yl)-methanol (1.0 eq) was dissolved in MTBE (5 vol). A catalytic amount of 4-(N,N-dimethyl)aminopyridine (DMAP) (1 mol %) was added and SOCl₂ (1.2 eq) was added via addition funnel. The SOCl₂ was added at a rate to maintain the temperature in the reactor at 15-25° C. The temperature was increased to 30° C. for 1 h, and then was cooled to 20° C. Water (4 vol) was added via addition funnel while maintaining the temperature at less than 30° C. After stirring for an additional 30 min, the layers were allowed to separate. The organic layer was stirred and 10% (w/v) aq NaOH (4.4 vol) was added. After stirring for 15 to 20 min, the layers were allowed to separate. The organic phase was then dried (Na₂SO₄), filtered, and concentrated to afford crude 5-chloromethyl-2,2-difluoro-1,3-benzodioxole that was used directly in the next step.

Preparation of (2,2-difluoro-1,3-benzodioxol-5-yl)-acetonitrile

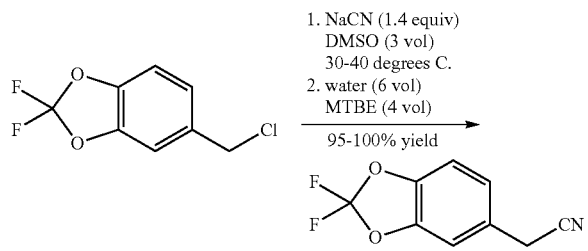

A solution of 5-chloromethyl-2,2-difluoro-1,3-benzodioxole (1 eq) in DMSO (1.25 vol) was added to a slurry of NaCN (1.4 eq) in DMSO (3 vol), while maintaining the temperature between 30-40° C. The mixture was stirred for 1 h, and then water (6 vol) was added, followed by methyl tert-butyl ether (MTBE) (4 vol). After stirring for 30 min, the layers were separated. The aqueous layer was extracted with MTBE (1.8 vol). The combined organic layers were washed with water (1.8 vol), dried (Na₂SO₄), filtered, and concentrated to afford crude (2,2-difluoro-1,3-benzodioxol-5-yl)-acetonitrile (95%) that was used directly in the next step.

Synthesis of (2,2-difluoro-1,3-benzodioxol-5-yl)-1-ethylacetate-acetonitrile

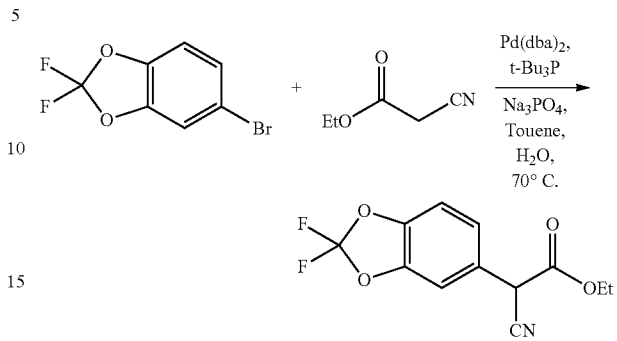

A reactor was purged with nitrogen and charged with 900 mL of toluene. The solvent was degassed via nitrogen sparge for no less than 16 h. To the reactor was then charged Na₃PO₄ (155.7 g, 949.5 mmol), followed by bis(dibenzylideneacetone) palladium (0) (7.28 g, 12.66 mmol). A 10% w/w solution of tert-butylphosphine in hexanes (51.23 g, 25.32 mmol) was charged over 10 min at 23° C. from a nitrogen purged addition funnel. The mixture was allowed to stir for 50 min, at which time 5-bromo-2,2-difluoro-1,3-benzodioxole (75 g, 316.5 mmol) was added over 1 min. After stirring for an additional 50 min, the mixture was charged with ethyl cyanoacetate (71.6 g, 633.0 mmol) over 5 min followed by water (4.5 mL) in one portion. The mixture was heated to 70° C. over 40 min and analyzed by HPLC every 1-2 h for the percent conversion of the reactant to the product. After complete conversion was observed (typically 100% conversion after 5-8 h), the mixture was cooled to 20-25° C. and filtered through a celite pad. The celite pad was rinsed with toluene (2×450 mL) and the combined organics were concentrated to 300 mL under vacuum at 60-65° C. The concentrate was charged with 225 mL DMSO and concentrated under vacuum at 70-80° C. until active distillation of the solvent ceased. The solution was cooled to 20-25° C. and diluted to 900 mL with DMSO in preparation for Step 2. ¹H NMR (500 MHz, CDCl₃) δ 7.16-7.10 (m, 2H), 7.03 (d, J=8.2 Hz, 1H), 4.63 (s, 1H), 4.19 (m, 2H), 1.23 (t, J=7.1 Hz, 3H).

Synthesis of (2,2-difluoro-1,3-benzodioxol-5-yl)-acetonitrile

The DMSO solution of (2,2-difluoro-1,3-benzodioxol-5-yl)-1-ethylacetate-acetonitrile from above was charged with 3 N HCl (617.3 mL, 1.85 mol) over 20 min while maintaining an internal temperature <40° C. The mixture was then heated to 75° C. over 1 h and analyzed by HPLC every 1-2 h for % conversion. When a conversion of >99% was observed (typically after 5-6 h), the reaction was cooled to 20-25° C. and extracted with MTBE (2×525 mL), with sufficient time to allow for complete phase separation during the extractions. The combined organic extracts were washed with 5% NaCl (2×375 mL). The solution was then transferred to equipment appropriate for a 1.5-2.5 Torr vacuum distillation that was equipped with a cooled receiver flask. The solution was concentrated under vacuum at <60° C. to remove the solvents. (2,2-Difluoro-1,3-benzodioxol-5-yl)-acetonitrile was then distilled from the resulting oil at 125-130° C. (oven temperature) and 1.5-2.0 Torr. (2,2-Difluoro-1,3-benzodioxol-5-yl)-acetonitrile was isolated as a clear oil in 66% yield from 5-bromo-2,2-difluoro-1,3-benzodioxole (2 steps) and with an HPLC purity of 91.5% AUC (corresponds to a w/w assay of 95%). $^1$H NMR (500 MHz, DMSO) δ 7.44 (br s, 1H), 7.43 (d, J=8.4 Hz, 1H), 7.22 (dd, J=8.2, 1.8 Hz, 1H), 4.07 (s, 2H).

Preparation of (2,2-difluoro-1,3-benzodioxol-5-yl)-cyclopropanecarbonitrile

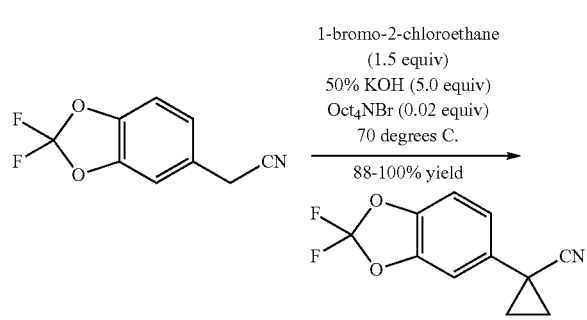

A mixture of (2,2-difluoro-1,3-benzodioxol-5-yl)-acetonitrile (1.0 eq), 50 wt % aqueous KOH (5.0 eq) 1-bromo-2-chloroethane (1.5 eq), and Oct$_4$NBr (0.02 eq) was heated at 70° C. for 1 h. The reaction mixture was cooled, then worked up with MTBE and water. The organic phase was washed with water and brine. The solvent was removed to afford (2,2-difluoro-1,3-benzodioxol-5-yl)-cyclopropanecarbonitrile.

Preparation of 1-(2,2-difluoro-1,3-benzodioxol-5-yl)-cyclopropanecarboxylic Acid

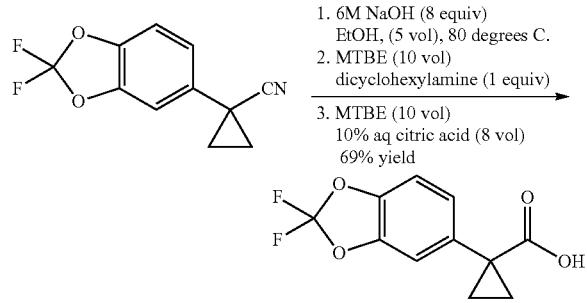

(2,2-difluoro-1,3-benzodioxol-5-yl)-cyclopropanecarbonitrile was hydrolyzed using 6 M NaOH (8 equiv) in ethanol (5 vol) at 80° C. overnight. The mixture was cooled to room temperature and the ethanol was evaporated under vacuum. The residue was taken up in water and MTBE, 1 M HCl was added, and the layers were separated. The MTBE layer was then treated with dicyclohexylamine (DCHA) (0.97 equiv). The slurry was cooled to 0° C., filtered and washed with heptane to give the corresponding DCHA salt. The salt was taken into MTBE and 10% citric acid and stirred until all the solids had dissolved. The layers were separated and the MTBE layer was washed with water and brine. A solvent swap to heptane followed by filtration gave 1-(2,2-difluoro-1,3-benzodioxol-5-yl)-cyclopropanecarboxylic acid after drying in a vacuum oven at 50° C. overnight.

Preparation of 1-(2,2-difluoro-1,3-benzodioxol-5-yl)-cyclopropanecarbonyl chloride

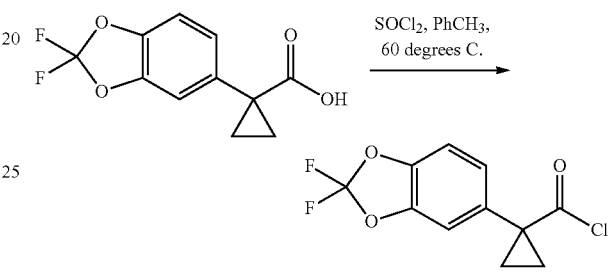

1-(2,2-difluoro-1,3-benzodioxol-5-yl)-cyclopropanecarboxylic acid (1.2 eq) is slurried in toluene (2.5 vol) and the mixture was heated to 60° C. SOCl$_2$ (1.4 eq) was added via addition funnel. The toluene and SOCl$_2$ were distilled from the reaction mixture after 30 minutes. Additional toluene (2.5 vol) was added and the resulting mixture was distilled again, leaving the product acid chloride as an oil, which was used without further purification.

Preparation of tert-butyl-3-(3-methylpyridin-2-yl)benzoate

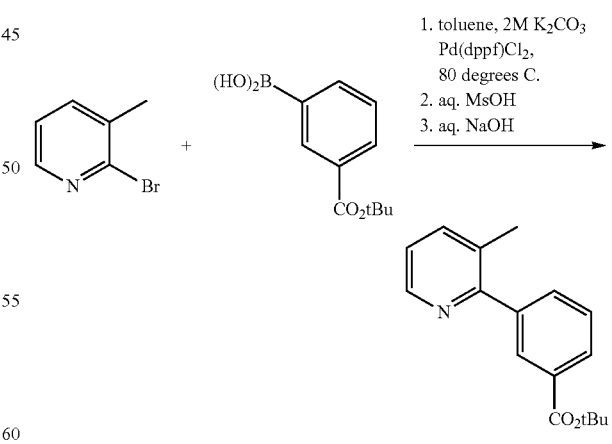

2-Bromo-3-methylpyridine (1.0 eq) was dissolved in toluene (12 vol). K$_2$CO$_3$ (4.8 eq) was added, followed by water (3.5 vol). The resulting mixture was heated to 65° C. under a stream of N$_2$ for 1 hour. 3-(t-Butoxycarbonyl)phenylboronic acid (1.05 eq) and Pd(dppf)Cl$_2$—CH$_2$Cl$_2$ (0.015 eq) were then added and the mixture was heated to 80° C. After 2 hours, the heat was turned off, water was added (3.5 vol), and the layers were allowed to separate. The organic phase was then washed with water (3.5 vol) and extracted with 10% aqueous methanesulfonic acid (2 eq MsOH, 7.7 vol). The aqueous phase was made basic with 50% aqueous NaOH (2 eq) and extracted with EtOAc (8 vol). The organic layer was concentrated to afford crude tert-butyl-3-(3-methylpyridin-2-yl)benzoate (82%) that was used directly in the next step.

Preparation of 2-(3-(tert-butoxycarbonyl)phenyl)-3-methylpyridine-1-oxide

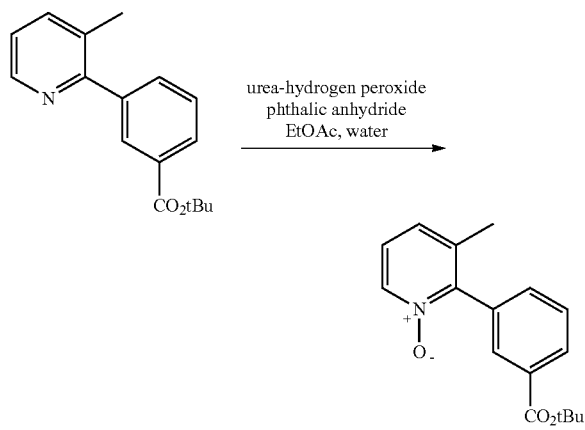

tert-Butyl-3-(3-methylpyridin-2-yl)benzoate (1.0 eq) was dissolved in EtOAc (6 vol). Water (0.3 vol) was added, followed by urea-hydrogen peroxide (3 eq). Phthalic anhydride (3 eq) was then added portionwise to the mixture as a solid at a rate to maintain the temperature in the reactor below 45° C. After completion of the phthalic anhydride addition, the mixture was heated to 45° C. After stirring for an additional 4 hours, the heat was turned off. 10% w/w aqueous Na$_2$SO$_3$ (1.5 eq) was added via addition funnel. After completion of Na$_2$SO$_3$ addition, the mixture was stirred for an additional 30 min and the layers separated. The organic layer was stirred and 10% wt/wt aqueous. Na$_2$CO$_3$ (2 eq) was added. After stirring for 30 minutes, the layers were allowed to separate. The organic phase was washed 13% w/v aq NaCl. The organic phase was then filtered and concentrated to afford crude 2-(3-(tert-butoxycarbonyl)phenyl)-3-methylpyridine-1-oxide (95%) that was used directly in the next step.

Preparation of tert-butyl-3-(6-amino-3-methylpyridin-2-yl)benzoate

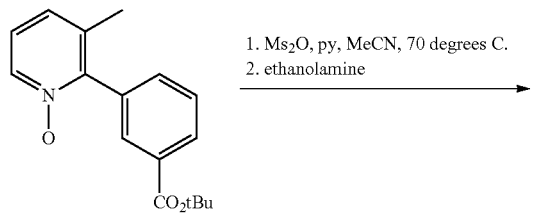

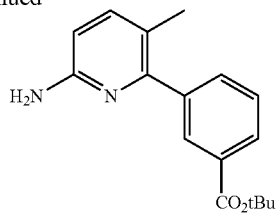

A solution of 2-(3-(tert-butoxycarbonyl)phenyl)-3-methylpyridine-1-oxide (1 eq) and pyridine (4 eq) in acetonitrile (8 vol) was heated to 70° C. A solution of methanesulfonic anhydride (1.5 eq) in MeCN (2 vol) was added over 50 min via addition funnel while maintaining the temperature at less than 75° C. The mixture was stirred for an additional 0.5 hours after complete addition. The mixture was then allowed to cool to ambient. Ethanolamine (10 eq) was added via addition funnel. After stirring for 2 hours, water (6 vol) was added and the mixture was cooled to 10° C. After stirring for 3 hours, the solid was collected by filtration and washed with water (3 vol), 2:1 acetonitrile/water (3 vol), and acetonitrile (2×1.5 vol). The solid was dried to constant weight (<1% difference) in a vacuum oven at 50° C. with a slight N$_2$ bleed to afford tert-butyl-3-(6-amino-3-methylpyridin-2-yl)benzoate as a red-yellow solid (53% yield).

Preparation of 3-(6-(1-(2,2-difluorobenzo[d][1,3]dioxol-5-yl)-cyclopropanecarboxamido)-3-methylpyridin-2-yl)-t-butylbenzoate

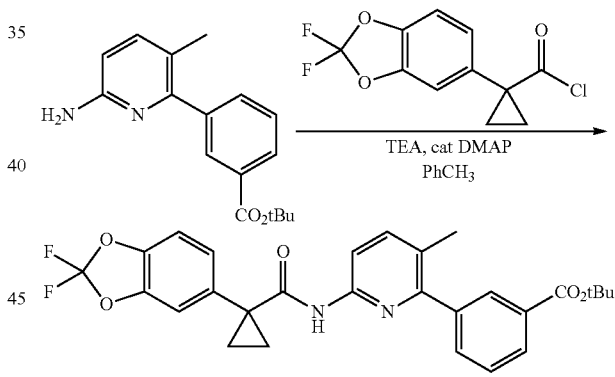

The crude acid chloride described above was dissolved in toluene (2.5 vol based on acid chloride) and added via addition funnel to a mixture of tert-butyl-3-(6-amino-3-methylpyridin-2-yl)benzoate (1 eq), DMAP, (0.02 eq), and triethylamine (3.0 eq) in toluene (4 vol based on tert-butyl-3-(6-amino-3-methylpyridin-2-yl)benzoate). After 2 hours, water (4 vol based on tert-butyl-3-(6-amino-3-methylpyridin-2-yl)benzoate) was added to the reaction mixture. After stirring for 30 minutes, the layers were separated. The organic phase was then filtered and concentrated to afford a thick oil of 3-(6-(1-(2,2-difluorobenzo[d][1,3]dioxol-5-yl)cyclopropanecarboxamido)-3-methylpyridin-2-yl)-t-butylbenzoate (quantitative crude yield). Acetonitrile (3 vol based on crude product) was added and distilled until crystallization occurs. Water (2 vol based on crude product) was added and the mixture stirred for 2 h. The solid was collected by filtration, washed with 1:1 (by volume) acetonitrile/water (2×1 volumes based on crude product), and partially dried on the filter under vacuum. The solid was dried to a constant weight (<1% difference) in a vacuum oven at 60° C. with a slight N₂ bleed to afford 3-(6-(1-(2,2-difluorobenzo[d][1,3]dioxol-5-yl) cyclopropanecarboxamido)-3-methylpyridin-2-yl)-t-butylbenzoate as a brown solid.

Preparation of 3-(6-(1-(2,2-difluorobenzo[d][1,3]dioxol-5-yl) cyclopropanecarboxamido)-3-methylpyridin-2-yl)benzoic acid.HCL Salt

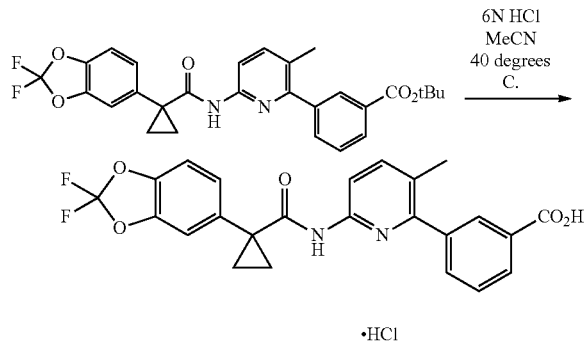

To a slurry of 3-(6-(1-(2,2-difluorobenzo[d][1,3]dioxol-5-yl) cyclopropanecarboxamido)-3-methylpyridin-2-yl)-t-butylbenzoate (1.0 eq) in MeCN (3.0 vol) was added water (0.83 vol) followed by concentrated aqueous HCl (0.83 vol). The mixture was heated to 45±5° C. After stirring for 24 to 48 h, the reaction was complete, and the mixture was allowed to cool to ambient. Water (1.33 vol) was added and the mixture stirred. The solid was collected by filtration, washed with water (2×0.3 vol), and partially dried on the filter under vacuum. The solid was dried to a constant weight (<1% difference) in a vacuum oven at 60° C. with a slight N₂ bleed to afford 3-(6-(1-(2,2-difluorobenzo[d][1,3]dioxol-5-yl) cyclopropanecarboxamido)-3-methylpyridin-2-yl)benzoic acid.HCl as an off-white solid.

Figure 8:
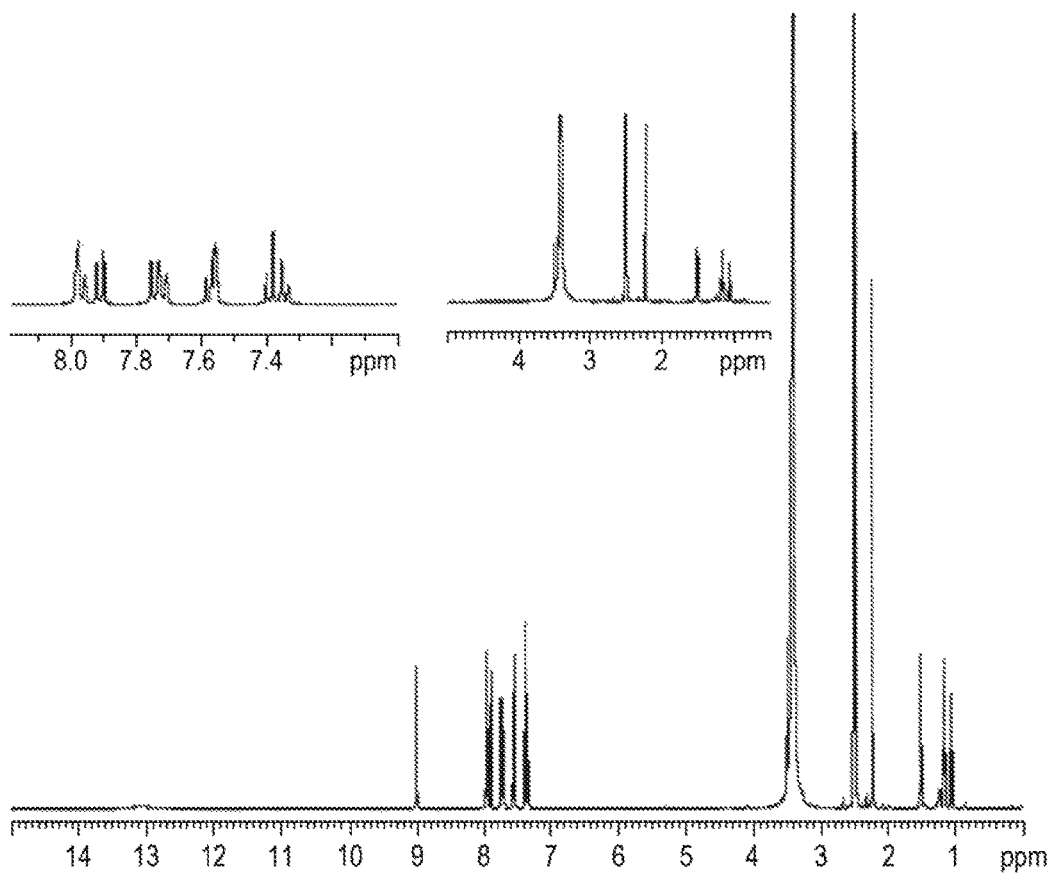
FIG. 8 is an ¹HNMR spectrum of Compound 1.
Figure 9:
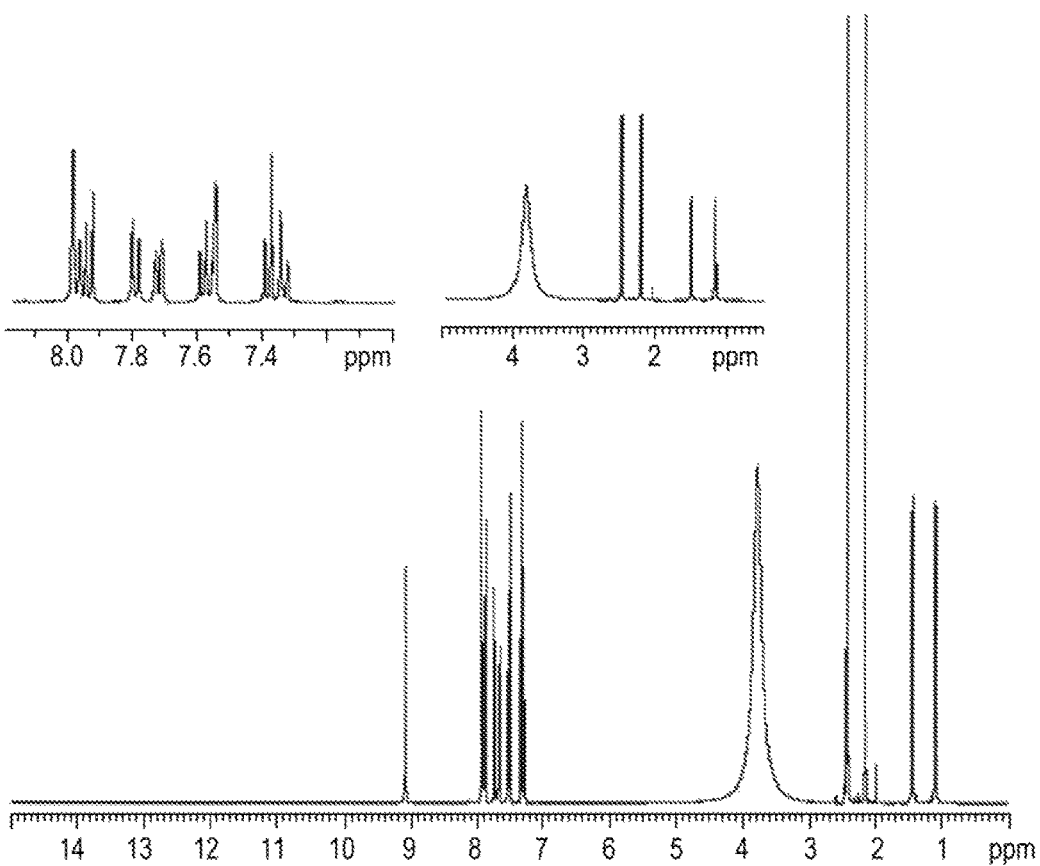
FIG. 9 is an ¹HNMR spectrum of Compound 1 HCl salt.

An ¹HNMR spectrum of Compound 1 is shown in FIG. 8 and FIG. 9 depicts an ¹HNMR spectrum of Compound 1 as an HCl salt.

Table 2 below recites the ¹HNMR data for Compound 1.

TABLE 2

| Compound No | LC/MS M + 1 | LC/RT minutes | NMR |
|---|---|---|---|
| 1 | 453.3 | 1.93 | ¹HNMR (400 MHz, DMSO-d6) 9.14 (s, 1H), 7.99-7.93 (m, 3H), 7.80-7.78 (m, 1H), 7.74-7.72 (m, 1H), 7.60-7.55 (m, 2H), 7.41-7.33 (m, 2H), 2.24 (s, 3H), 1.53-1.51 (m, 2H), 1.19-1.17 (m, 2H). |

Preparation of Compound 1 Form I

Preparation of Compound 1 Form I, Method A

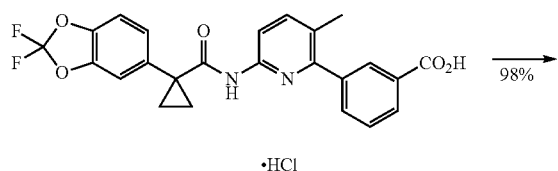

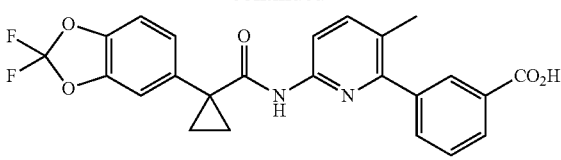

Form I

A slurry of 3-(6-(1-(2,2-difluorobenzo[d][1,3]dioxol-5-yl) cyclopropanecarboxamido)-3-methylpyridin-2-yl)benzoic acid.HCl (1 eq) in water (10 vol) was stirred at ambient temperature. A sample was taken after stirring for 24 h. The sample was filtered and the solid was washed with water (2 times). The solid sample was submitted for DSC analysis. When DSC analysis indicated complete conversion to Form I, the solid was collected by filtration, washed with water (2×1.0 vol), and partially dried on a filter under vacuum. The solid was then dried to a constant weight (<1% difference) in a vacuum oven at 60° C. with a slight N₂ bleed to afford Compound 1 Form I as an off-white solid (98% yield). ¹H NMR (400 MHz, DMSO-d6) 9.14 (s, 1H), 7.99-7.93 (m, 3H), 7.80-7.78 (m, 1H), 7.74-7.72 (m, 1H), 7.60-7.55 (m, 2H), 7.41-7.33 (m, 2H), 2.24 (s, 3H), 1.53-1.51 (m, 2H), 1.19-1.17 (m, 2H).

Preparation of Compound 1 Form I, Method B

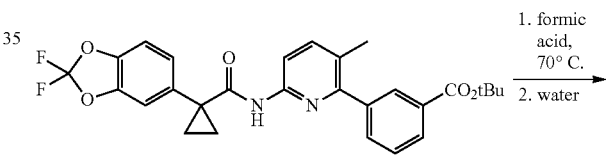

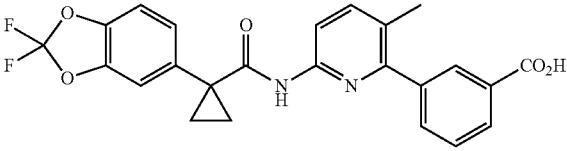

Form I

A solution of 3-(6-(1-(2,2-difluorobenzo[d][1,3]dioxol-5-yl) cyclopropanecarboxamido)-3-methylpyridin-2-yl)-t-butylbenzoate (1.0 eq) in formic acid (3.0 vol) was heated with stirring to 70±10° C., for 8 h. The reaction was deemed complete when no more than 1.0% AUC by chromatographic methods of 3-(6-(1-(2,2-difluorobenzo[d][1,3]dioxol-5-yl) cyclopropanecarboxamido)-3-methylpyridin-2-yl)-t-butylbenzoate) remained. The mixture was allowed to cool to ambient. The solution was added to water (6 vol), heated at 50° C., and the mixture was stirred. The mixture was then heated to 70±10° C. until the level of 3-(6-(1-(2,2-difluorobenzo[d][1,3]dioxol-5-yl) cyclopropanecarboxamido)-3-methylpyridin-2-yl)-t-butylbenzoate was no more than 0.8% (AUC). The solid was collected by filtration, washed with water (2×3 vol), and partially dried on the filter under vacuum. The solid was dried to a constant weight (<1% difference) in a vacuum oven at 60° C. with a slight $N_2$ bleed to afford Compound 1 Form I as an off-white solid.

Figure 10:
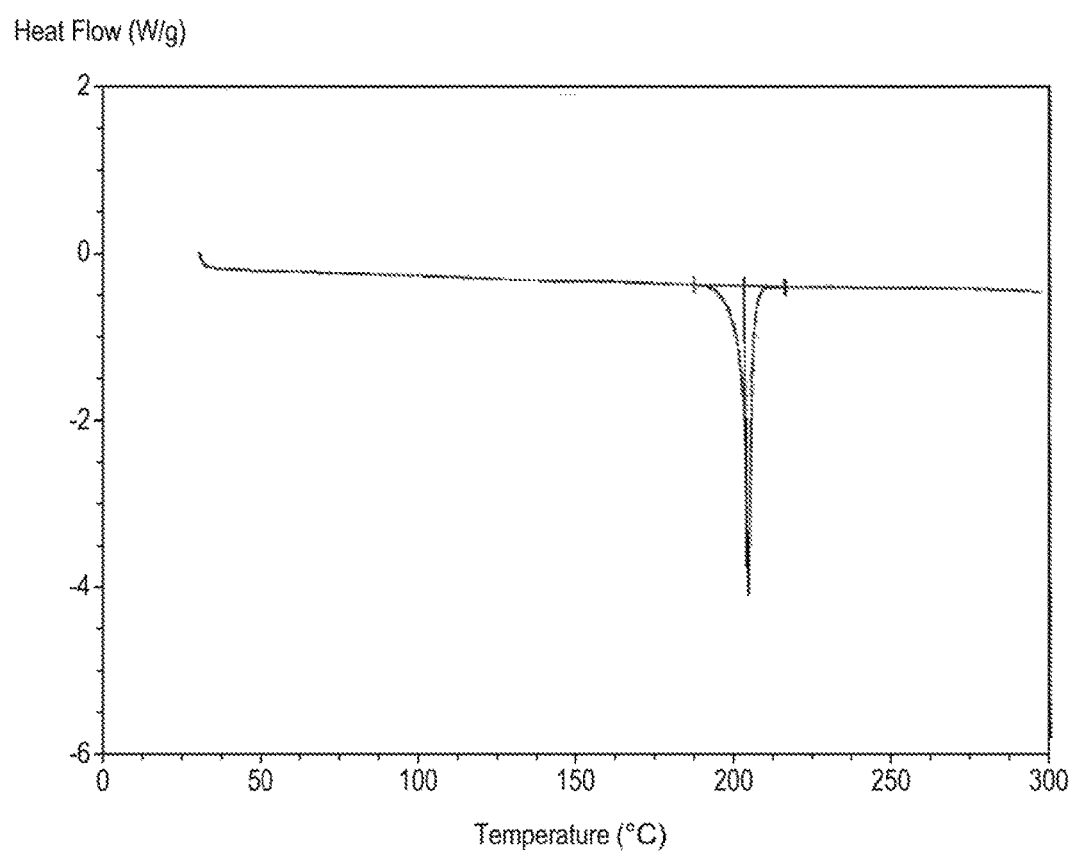
FIG. 10 is a differential scanning calorimetry (DSC) trace of Compound 1 Form I.

The DSC trace of Compound 1 Form I is shown in FIG. 10. Melting for Compound 1 Form I occurs at about 204° C.

An X-ray diffraction pattern was calculated from a single crystal structure of Compound 1 Form I and is shown in FIG. 1. Table 3 lists the calculated peaks for FIG. 1.

TABLE 3

| Peak Rank | 2θ Angle [degrees] | Relative Intensity [%] |
|---|---|---|
| 11 | 14.41 | 48.2 |
| 8 | 14.64 | 58.8 |
| 1 | 15.23 | 100.0 |
| 2 | 16.11 | 94.7 |
| 3 | 17.67 | 81.9 |
| 7 | 19.32 | 61.3 |
| 4 | 21.67 | 76.5 |
| 5 | 23.40 | 68.7 |
| 9 | 23.99 | 50.8 |
| 6 | 26.10 | 67.4 |
| 10 | 28.54 | 50.1 |

Figure 2:
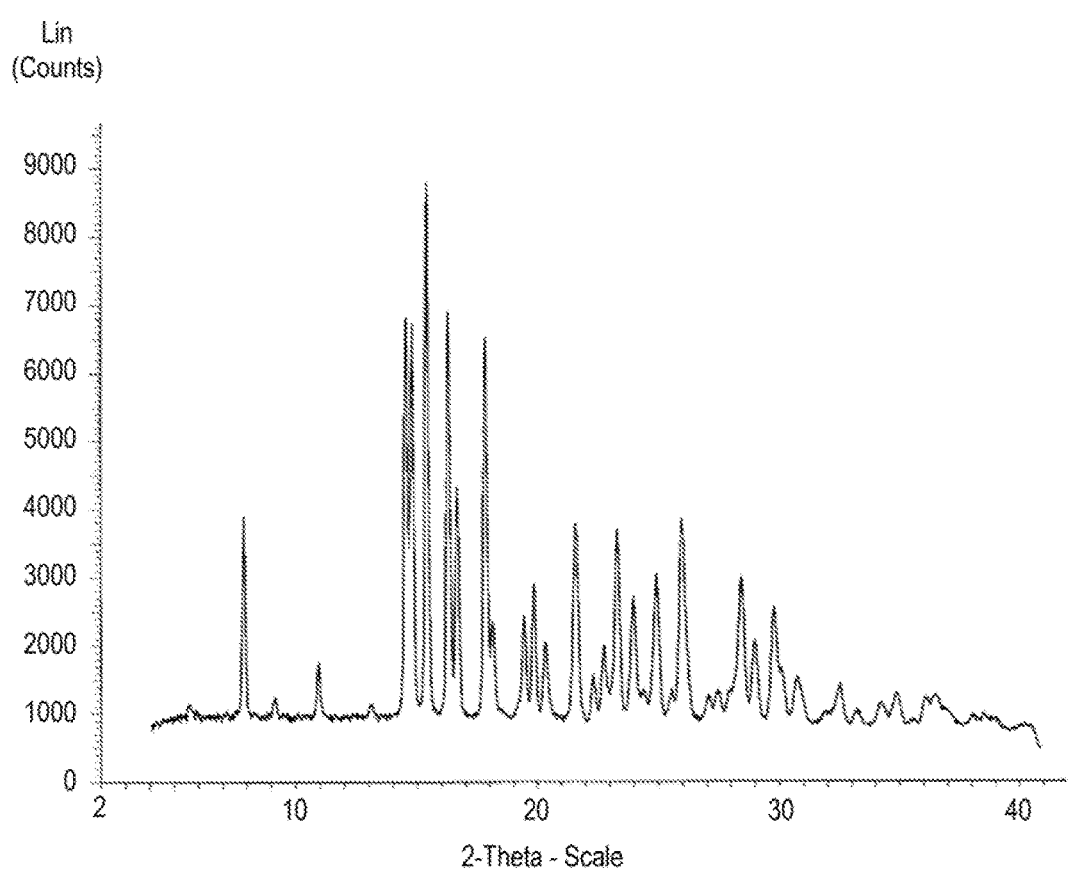
FIG. 2 is an actual X-ray powder diffraction pattern of Compound 1 Form I.

An actual X-ray powder diffraction pattern of Compound 1 Form I is shown in FIG. 2. Table 4 lists the actual peaks for FIG. 2.

TABLE 4

| Peak Rank | 2θ Angle [degrees] | Relative Intensity [%] |
|---|---|---|
| 7 | 7.83 | 37.7 |
| 3 | 14.51 | 74.9 |
| 4 | 14.78 | 73.5 |
| 1 | 15.39 | 100.0 |
| 2 | 16.26 | 75.6 |
| 6 | 16.62 | 42.6 |
| 5 | 17.81 | 70.9 |
| 9 | 21.59 | 36.6 |
| 10 | 23.32 | 34.8 |
| 11 | 24.93 | 26.4 |
| 8 | 25.99 | 36.9 |

Colorless crystals of Compound 1 Form I were obtained by cooling a concentrated 1-butanol solution from 75° C. to 10° C. at a rate of 0.2° C./min. A crystal with dimensions of 0.50×0.08×0.03 mm was selected, cleaned with mineral oil, mounted on a MicroMount and centered on a Bruker APEX II system. Three batches of 40 frames separated in reciprocal space were obtained to provide an orientation matrix and initial cell parameters. Final cell parameters were obtained and refined based on the full data set.

A diffraction data set of reciprocal space was obtained to a resolution of 0.82 Å using 0.5° steps using 30 s exposure for each frame. Data were collected at 100 (2) K. Integration of intensities and refinement of cell parameters were accomplished using APEXII software. Observation of the crystal after data collection showed no signs of decomposition.

Figure 11:
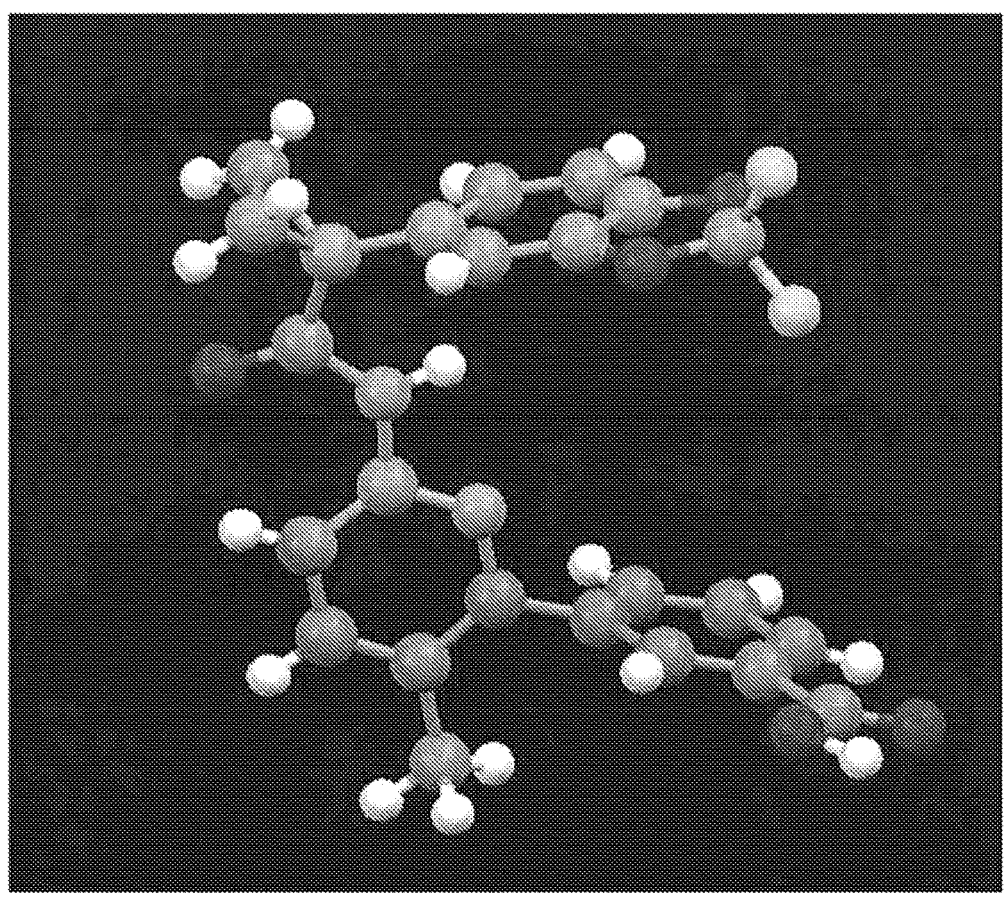
FIG. 11 is a conformational picture of Compound 1 Form I based on single crystal X-ray analysis.
Figure 12:
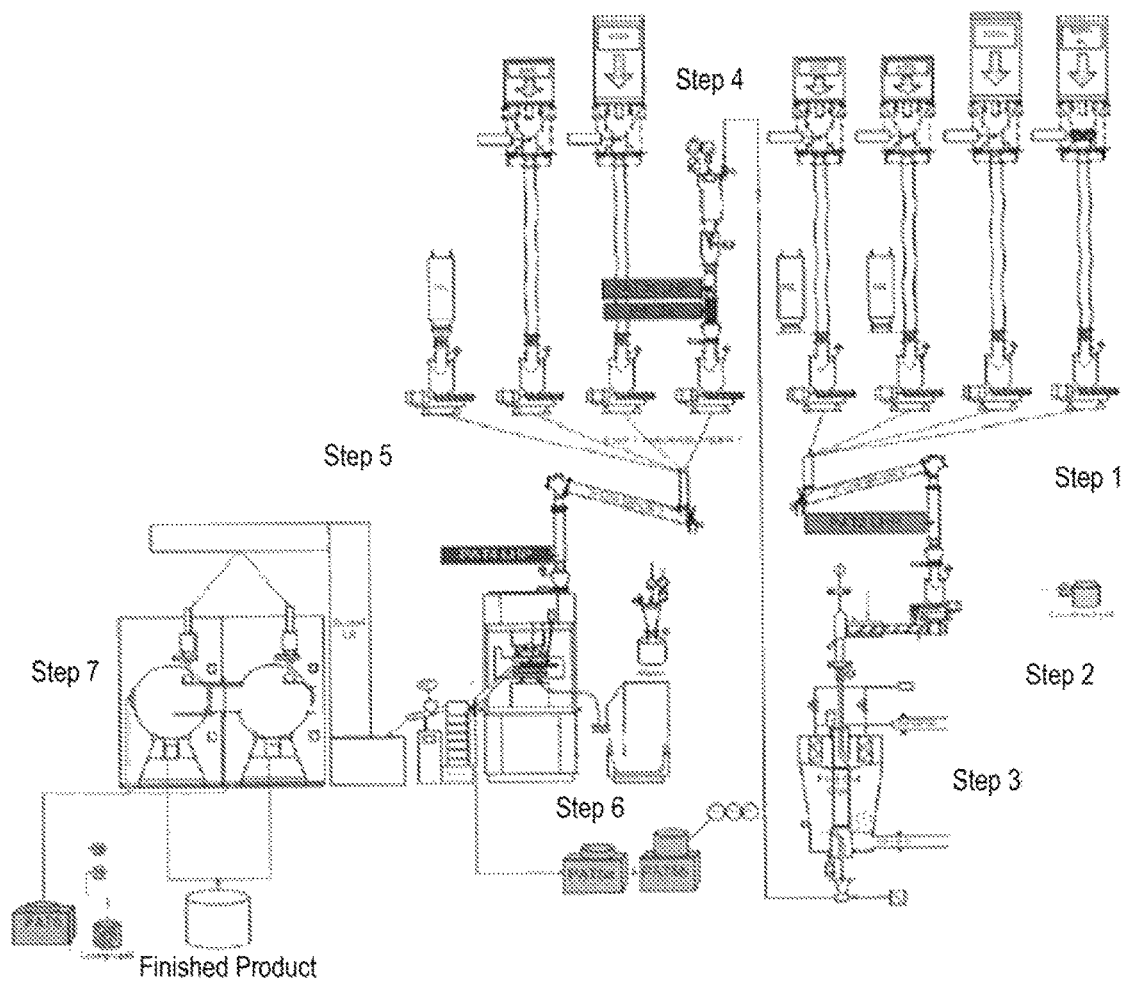
FIG. 12 is a schematic drawing of a process analytical technique (PAT) enabled continuous manufacturing process where in step 1) feeder/blender one, PAT1 NIR measures material attributes during screening of raw materials; step 2) twin screw granulator, PAT2 NIR measures composition and BU; step 3) fluidized bed dryer, PAT 3a NIR measures granule uniformity, LOD, solid state form and physical attributes of granules, PAT 3b laser diffraction measures particle size distribution; step 4) milling, PAT4 NIR measures composition and BU; step 5) feeder/blender two, PAT 5a Raman measures assay and CU, PAT 5b weight, hardness, thickness; step 6) compression, PAT6 Raman measures coat thickness; and step 7) coating.
Figure 13:
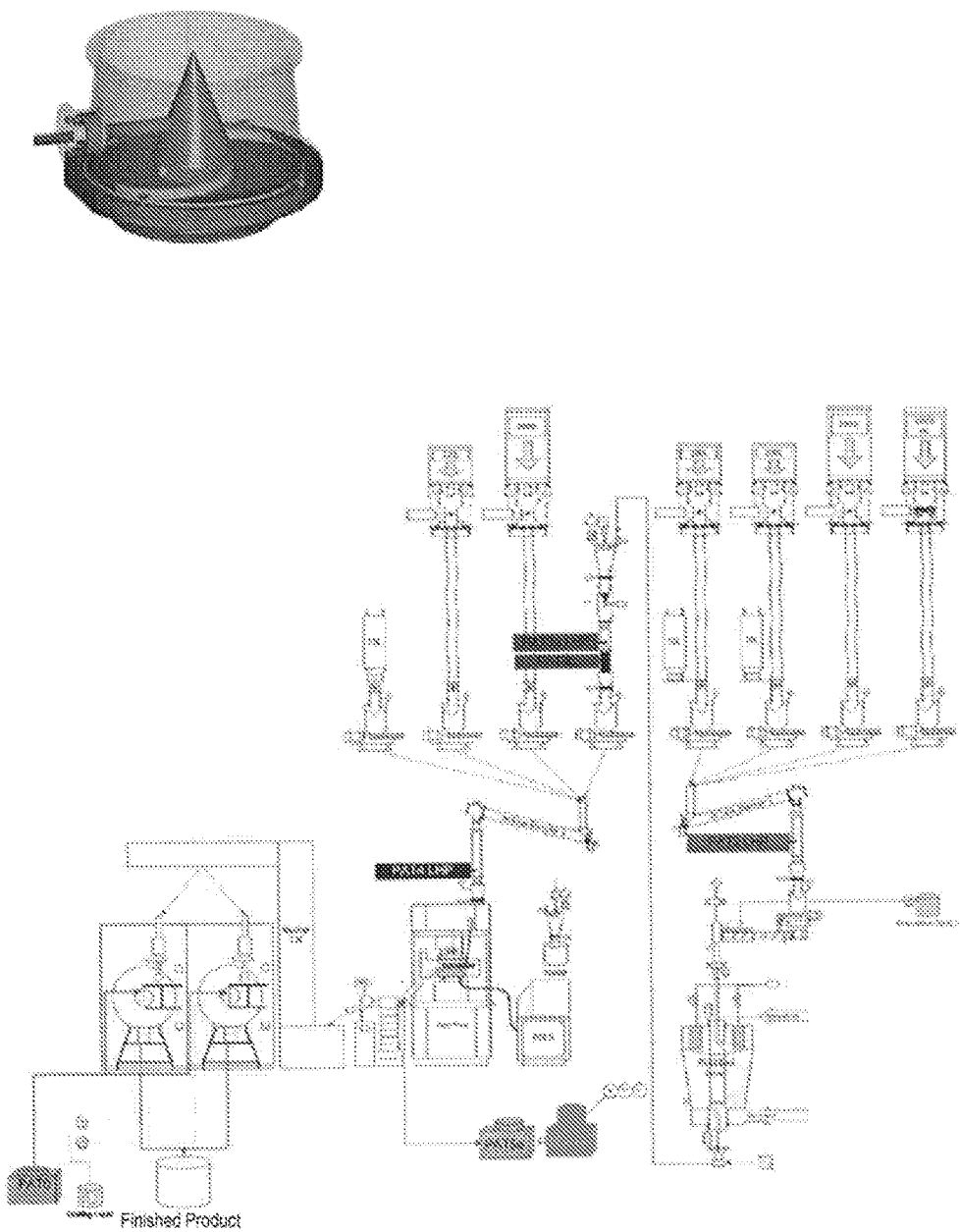
FIG. 13 is a schematic drawing showing a PAT inline Sentronics NIR located after blender one, granule mill, and extra granule blender. Each probe has 7 spots that cycle sequentially to maximize sampling and NIR with multiplexer-NIR ensuring robust and exhaustive sampling by controlled powder flow across the probe optics.
Figure 14:
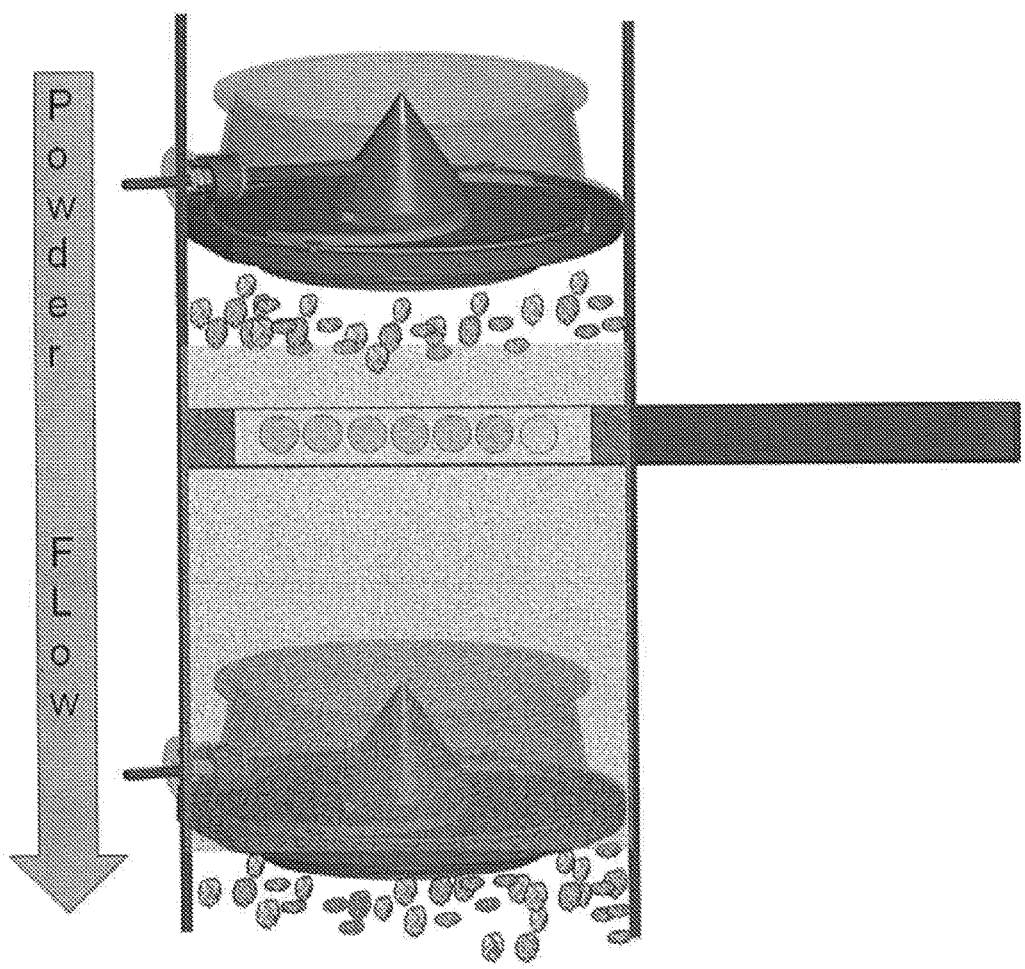
FIG. 14 is a depiction of NIR in flowing powder.
Figure 15:
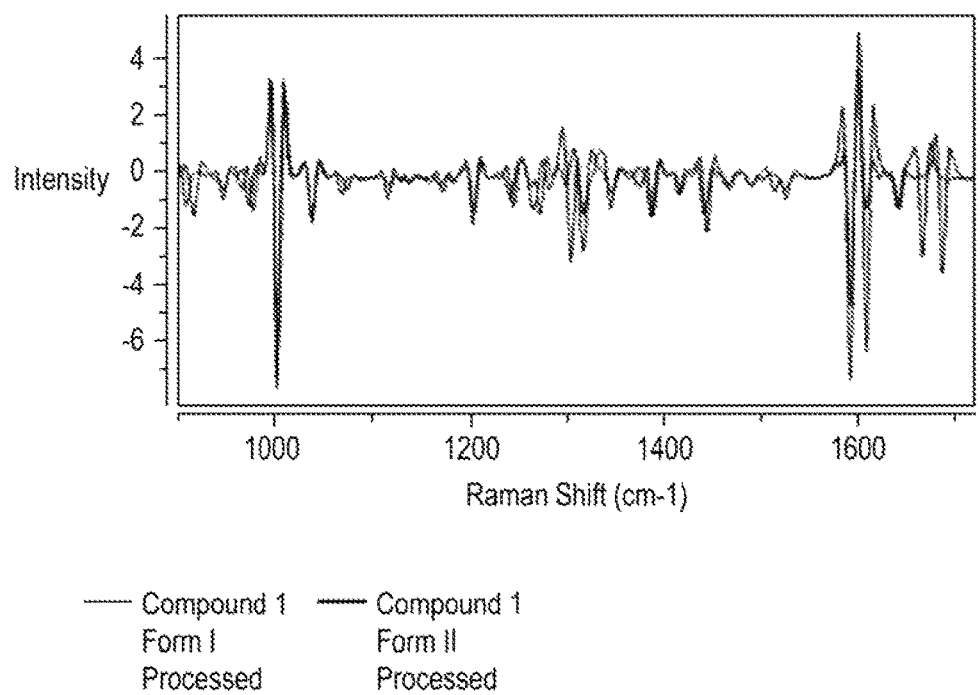
FIG. 15 is a Kaiser Raman spectrum of Compound 1 Form I and Compound 1 Form II (Compound 1 Form II is a different polymorph disclosed in US 201131588 incorporated herein in its entirety by reference) taken after tablet pressing. The Kaiser Raman spectrometer is mounted on the Kraemer UTS tablet tester.
Figure 16:
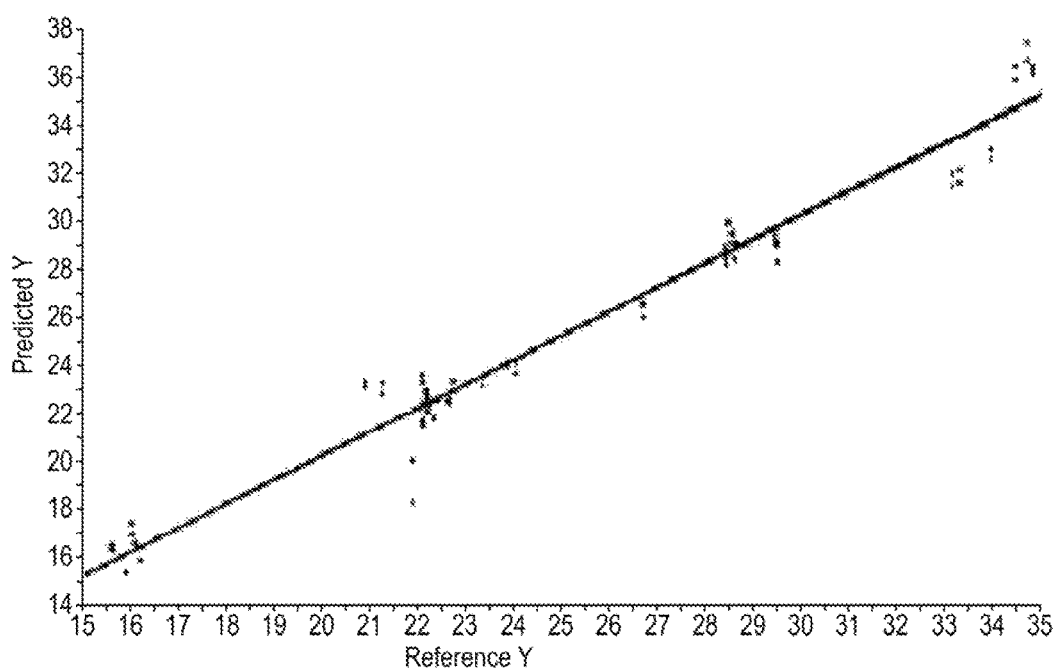
FIG. 16 is a graph showing good correlation between predicted and reference off-line NIR samplings of Compound 2 granules.
Figure 17:
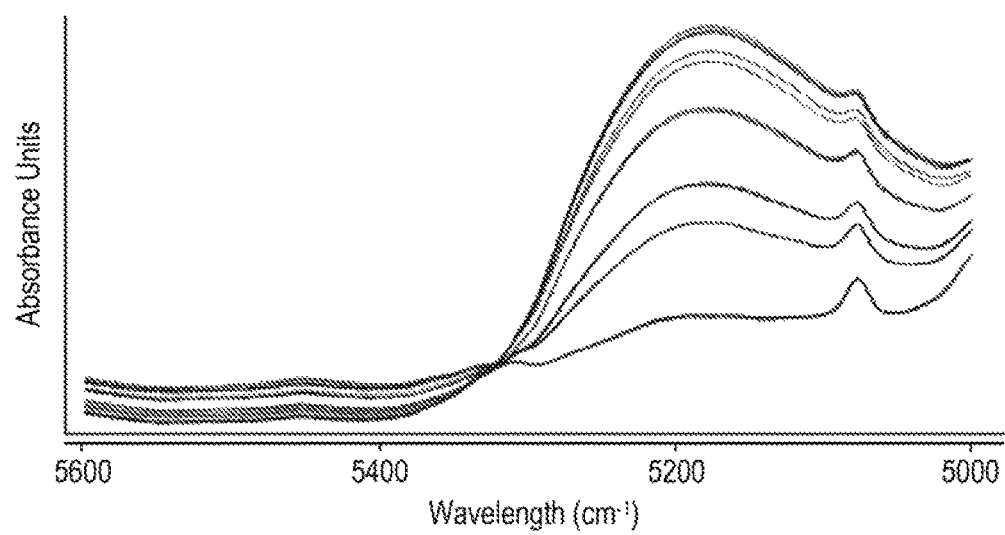
FIG. 17 is a series of NIR spectra measuring water content in samples of Compound 1 granules.
Figure 18:
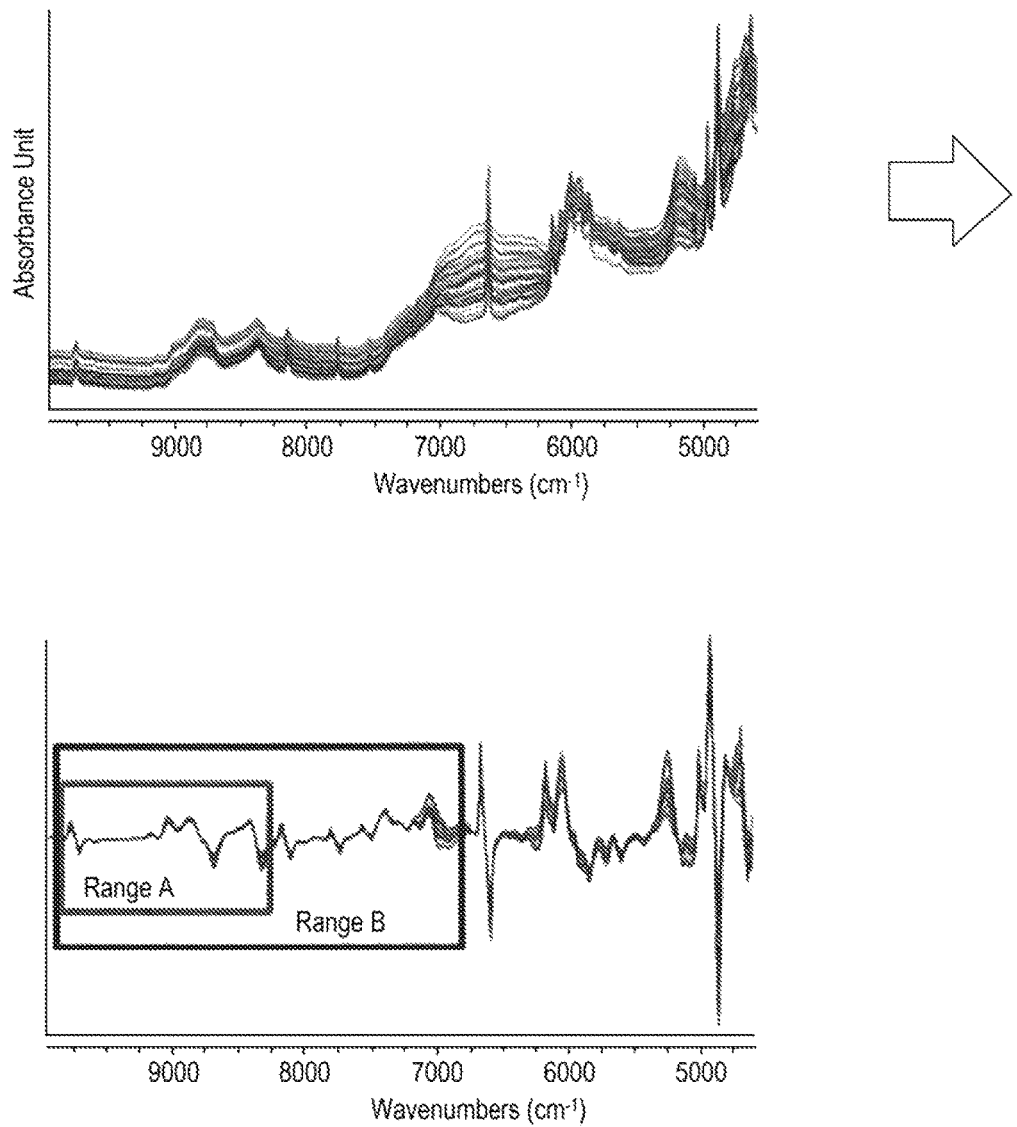
FIG. 18 is a series of NIR spectra measuring a range of compositions comprising different ratios of Compound 1 Form I and a solid dispersions comprising substantially amorphous Compound 2 on the left, and pretreated spectra on the right depicting Range A for identifying Compound 1 Form I and Range B for identifying amorphous Compound 2.
Figure 19:
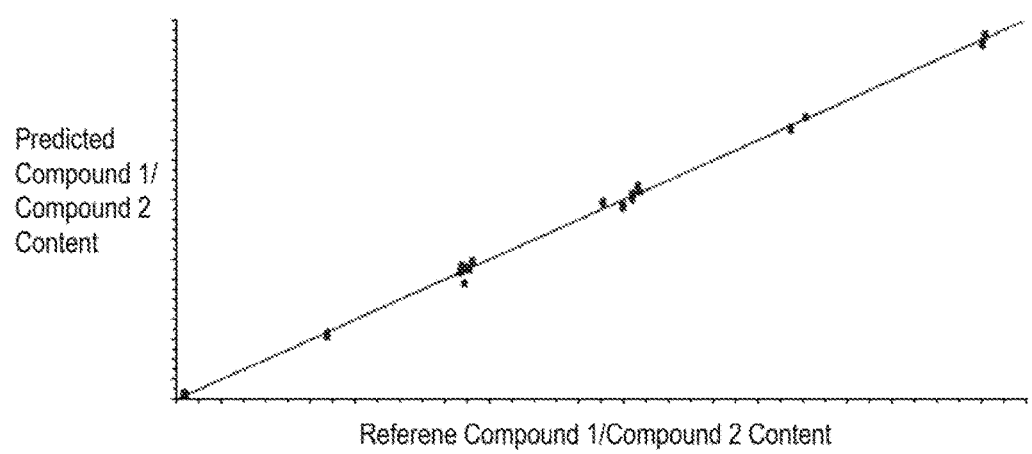
FIG. 19 depicts a calibration curve for predicted Compound 1 Form I content versus reference (actual) Compound 1 Form I content using partial least squares (PLS) techniques.
Figure 20:
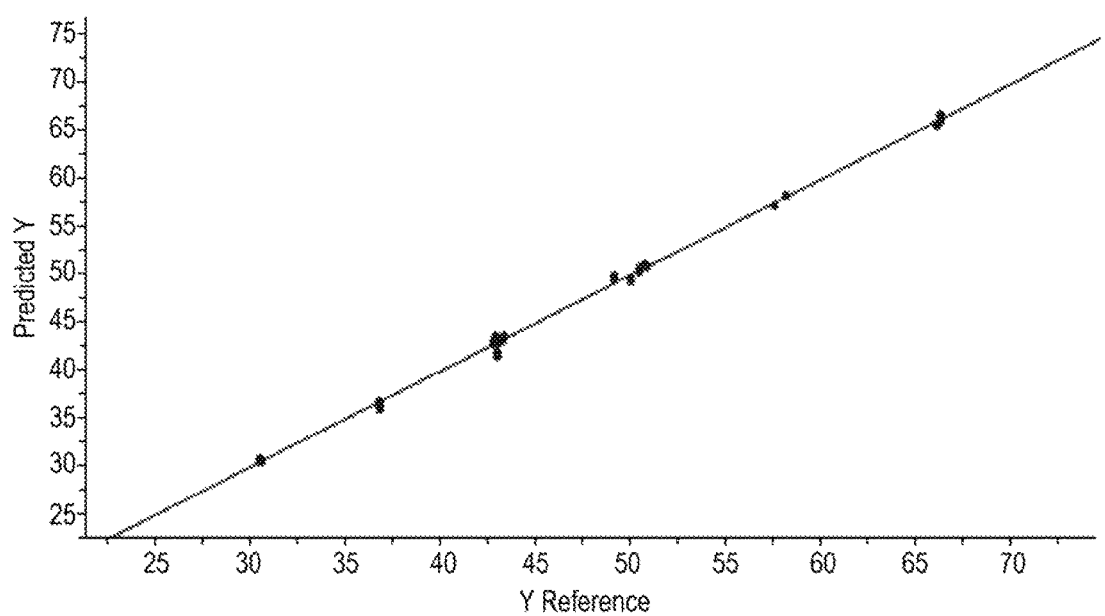
FIG. 20 depicts actual results of unknown samples comprising different contents of Compound 1 Form I (Y Reference) versus predicted content using the calibration curve calculated from FIG. 19 (Y Predicted).
Figure 21:
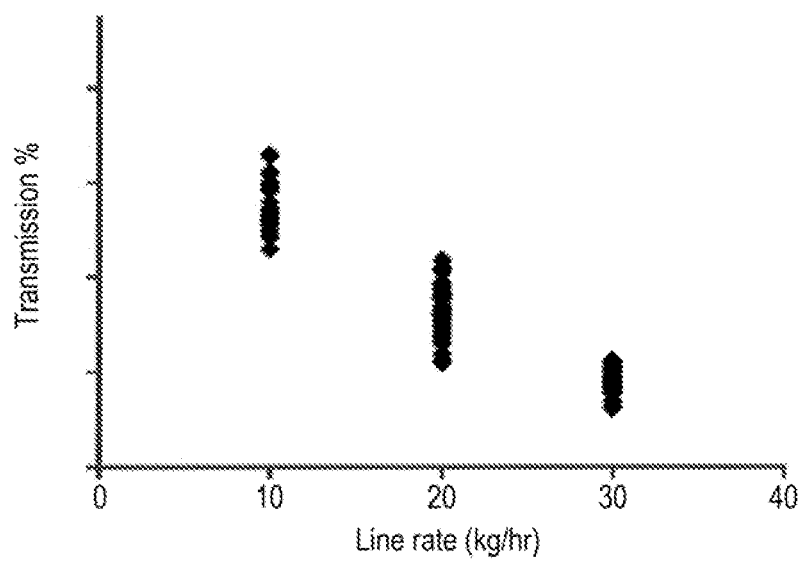
FIG. 21 depicts the transmission percent of a laser diffraction measurement in response to changes in line rate (flow velocity) for a composition comprising Compound 1 Form I and a solid dispersions comprising substantially amorphous Compound 2 showing the expected reduction in transmission percent as line rate increase.
Figure 22:
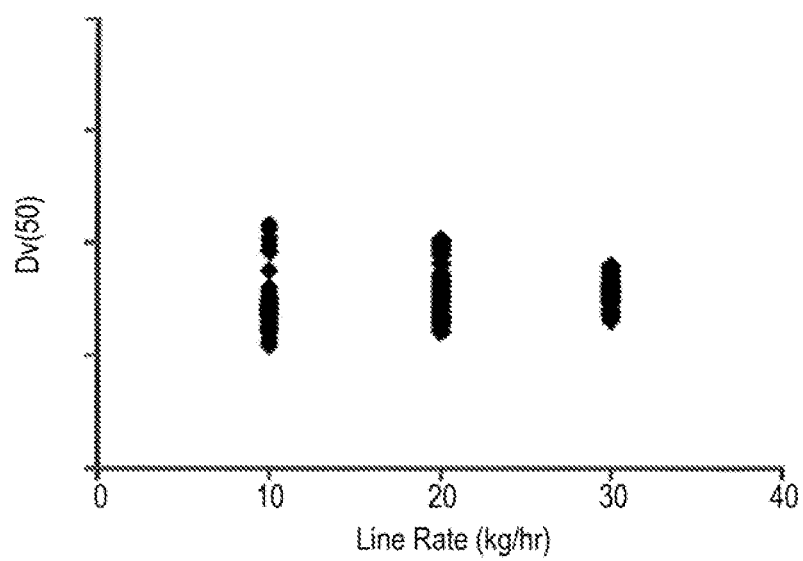
FIG. 22 depicts laser diffraction measurements of particles comprising Compound 1 Form I and a solid dispersions comprising substantially amorphous Compound 2 at different line rates showing that the average particle size (Dv(50) is not affected by line rate.
Figure 23:
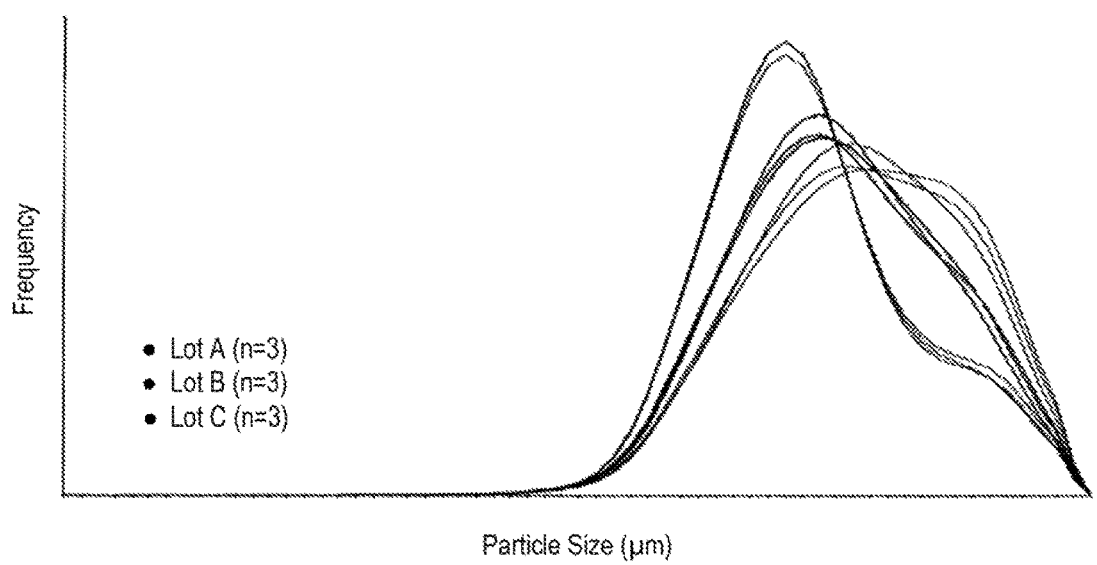
FIG. 23 depicts laser diffraction measurements of particles comprising Compound 1 Form I and a solid dispersions comprising substantially amorphous Compound 2 under different processing parameters showing that the particle size measurements are sensitive to such changes.
Figure 24:
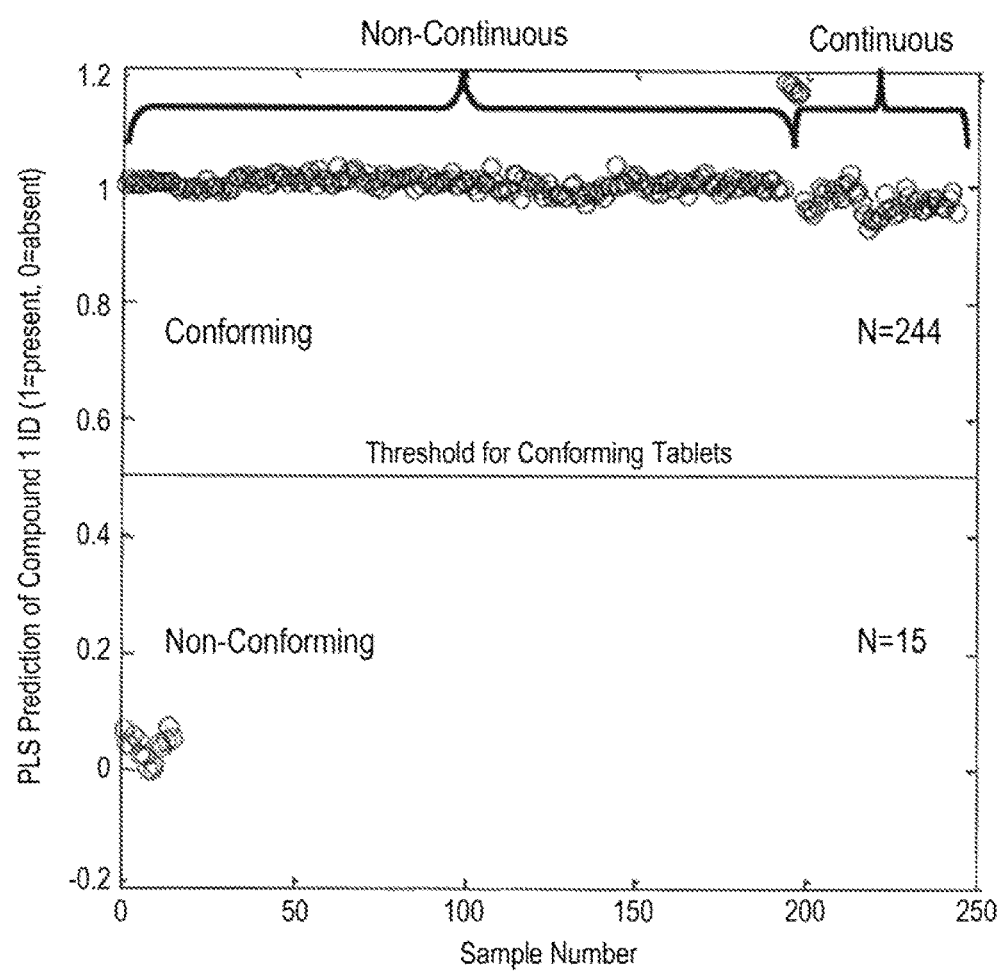
FIG. 24 depicts the predictive capabilities of process analytical technology models using Raman spectroscopy, both non-continuously and continuously, for monitoring Compound 1 solid form identity in a tablet.
Figure 25:
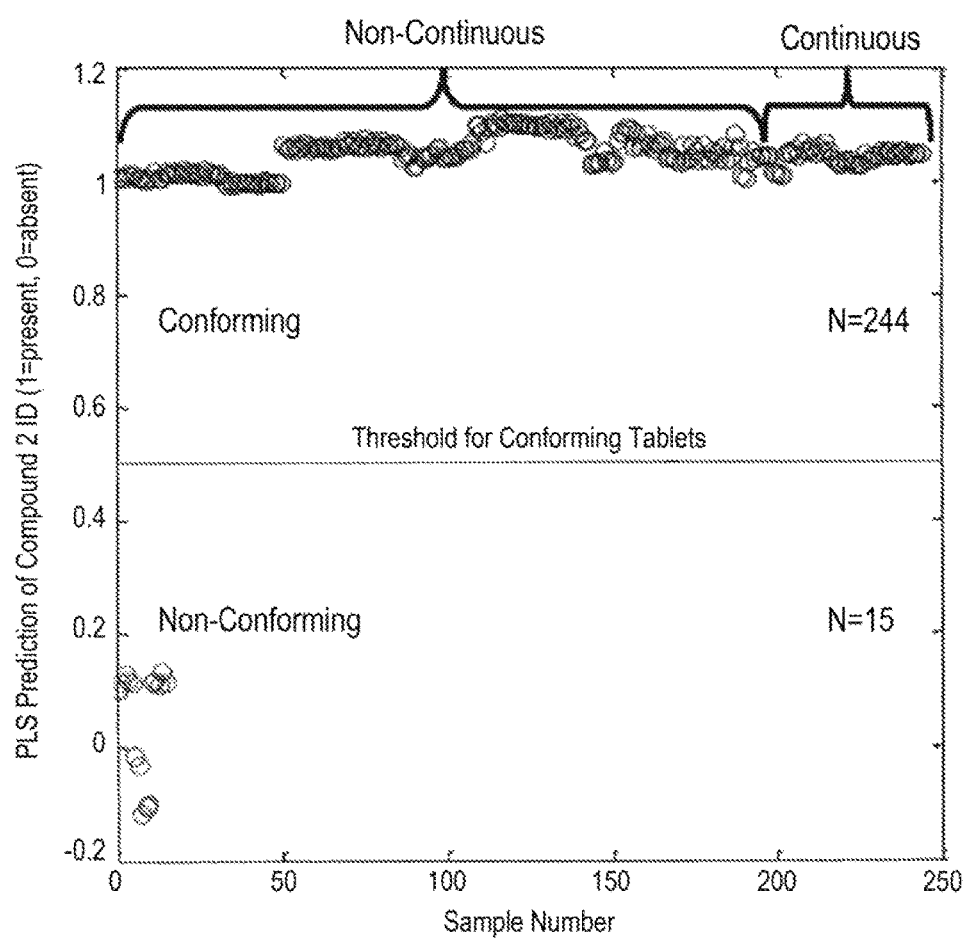
FIG. 25 depicts the predictive capabilities of process analytical technology models using Raman spectroscopy, both non-continuously and continuously, for monitoring Compound 2 solid form identity in a tablet.

A conformational picture of Compound 1 Form I based on single crystal X-ray analysis is shown in FIG. 11. Compound 1 Form I is monoclinic, $P_2 1/n$, with the following unit cell dimensions: a=4.9626(7) Å, b=12.299(2) Å, c=33.075 (4) Å, β=93.938(9) °, V=2014.0 Å$^3$, Z=4. Density of Compound 1 Form I calculated from structural data is 1.492 g/cm$^3$ at 100 K.

Preparation of Compound 2

Synthesis of
4-oxo-1,4-dihydroquinoline-3-carboxylic Acid (26)

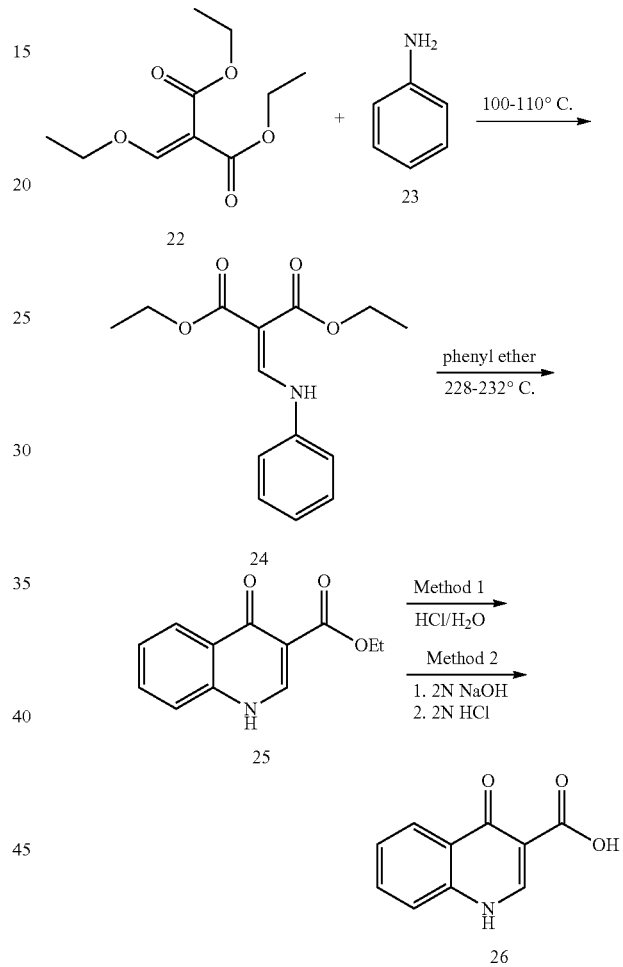

Procedure for the preparation of ethyl
4-oxo-1,4-dihydroquinoline-3-carboxylate (25)

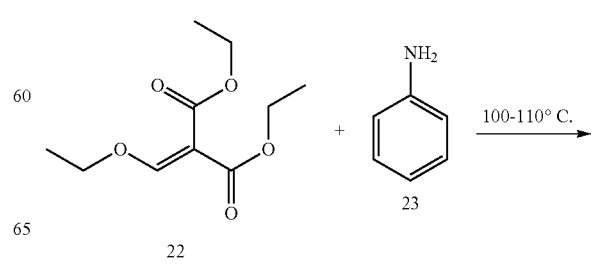

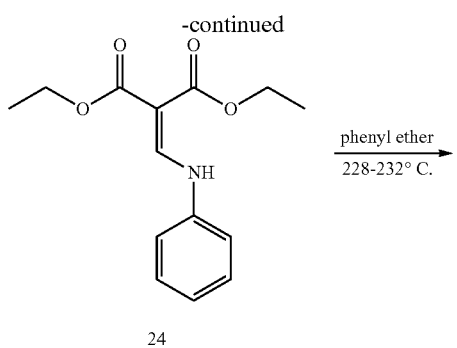

24

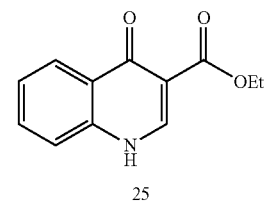

25

Compound 23 (4.77 g, 47.7 mmol) was added dropwise to compound 22 (10 g, 46.3 mmol) with subsurface N₂ flow to drive out ethanol below 30° C. for 0.5 hours. The solution was then heated to 100-110° C. and stirred for 2.5 hours. After cooling the mixture to below 60° C., diphenyl ether was added. The resulting solution was added dropwise to diphenyl ether that had been heated to 228-232° C. for 1.5 hours with subsurface N₂ flow to drive out ethanol. The mixture was stirred at 228-232° C. for another 2 hours, cooled to below 100° C. and then heptane was added to precipitate the product. The resulting slurry was stirred at 30° C. for 0.5 hours. The solids were then filtrated, and the cake was washed with heptane and dried in vacuo to give compound 25 as brown solid. ¹H NMR (DMSO-d₆; 400 MHz) δ 12.25 (s), δ 8.49 (d), δ 8.10 (m), δ 7.64 (m), δ 7.55 (m), δ 7.34 (m), δ 4.16 (q), δ 1.23 (t).

Procedure for the Preparation of
4-oxo-1,4-dihydroquinoline-3-carboxylic Acid (26)

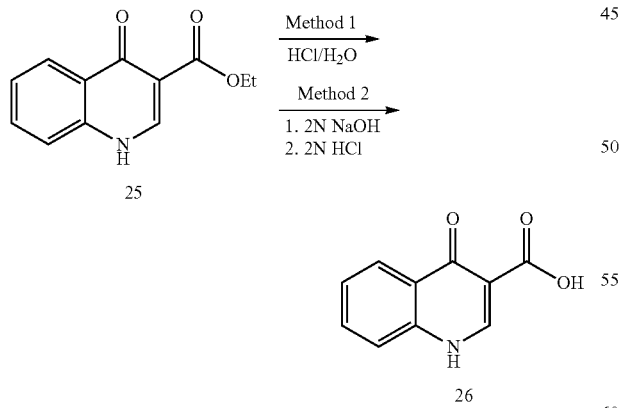

Method 1

Compound 25 (1.0 eq) was suspended in a solution of HCl (10.0 eq) and H₂O (11.6 vol). The slurry was heated to 85-90° C., although alternative temperatures are also suitable for this hydrolysis step. For example, the hydrolysis can alternatively be performed at a temperature of from about 75 to about 100° C. In some instances, the hydrolysis is performed at a temperature of from about 80 to about 95° C. In others, the hydrolysis step is performed at a temperature of from about 82 to about 93° C. (e.g., from about 82.5 to about 92.5° C. or from about 86 to about 89° C.). After stirring at 85-90° C. for approximately 6.5 hours, the reaction was sampled for reaction completion. Stirring may be performed under any of the temperatures suited for the hydrolysis. The solution was then cooled to 20-25° C. and filtered. The reactor/cake was rinsed with H₂O (2 vol×2). The cake was then washed with 2 vol H₂O until the pH ≥3.0. The cake was then dried under vacuum at 60° C. to give compound 26.

Method 2

Compound 25 (11.3 g, 52 mmol) was added to a mixture of 10% NaOH (aq) (10 mL) and ethanol (100 mL). The solution was heated to reflux for 16 hours, cooled to 20-25° C. and then the pH was adjusted to 2-3 with 8% HCl. The mixture was then stirred for 0.5 hours and filtered. The cake was washed with water (50 mL) and then dried in vacuo to give compound 26 as a brown solid. ¹H NMR (DMSO-d₆; 400 MHz) δ 15.33 (s), δ 13.39 (s), δ 8.87 (s), δ 8.26 (m), δ 7.87 (m), δ 7.80 (m), δ 7.56 (m).

Total Synthesis of N-(2,4-di-tert-butyl-5-hydroxyphenyl)-4-oxo-1,4-dihydroquinoline-3-carboxamide (Compound 2)

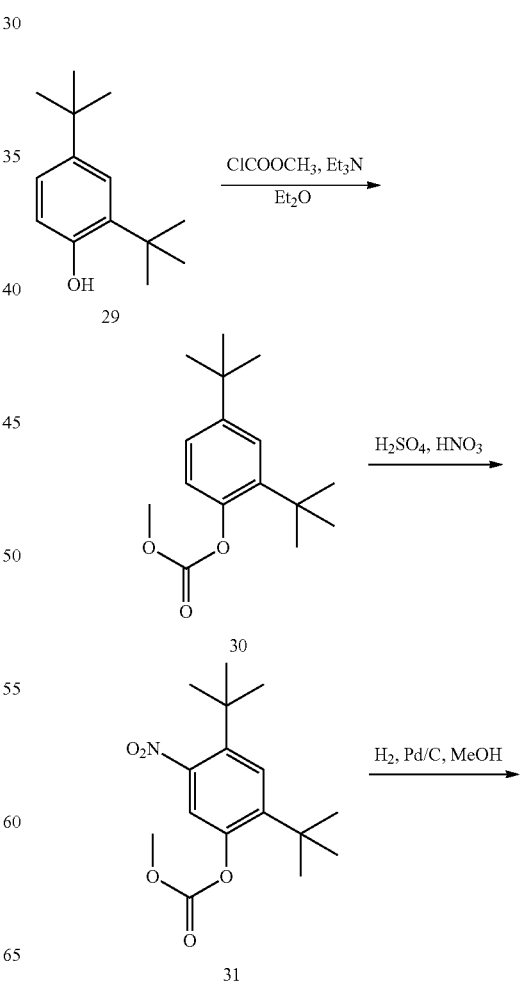

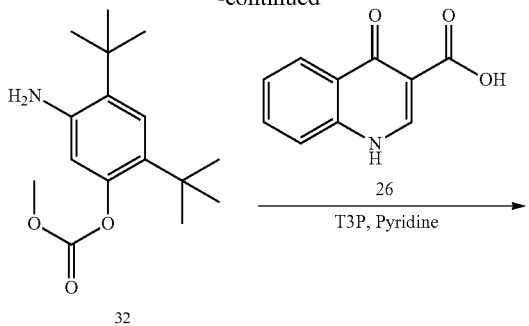

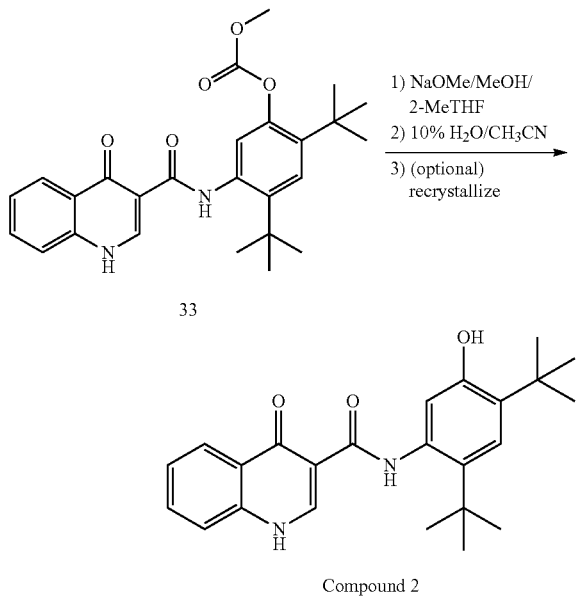

Compound 2

Procedure for the Preparation of
2,4-di-tert-butylphenyl methyl carbonate (30)

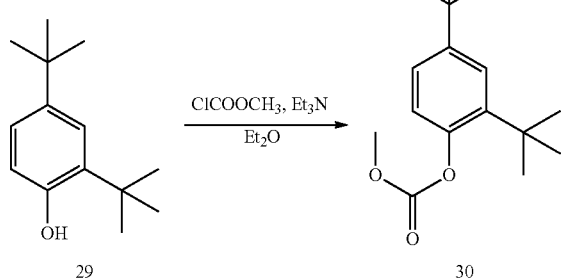

Method 1

To a solution of 2,4-di-tert-butyl phenol, 29, (10 g, 48.5 mmol) in diethyl ether (100 mL) and triethylamine (10.1 mL, 72.8 mmol), was added methyl chloroformate (7.46 mL, 97 mmol) dropwise at 0° C. The mixture was then allowed to warm to room temperature and stir for an additional 2 hours. An additional 5 mL triethylamine and 3.7 mL methyl chloroformate was then added and the reaction stirred overnight. The reaction was then filtered, the filtrate was cooled to 0° C., and an additional 5 mL triethylamine and 3.7 mL methyl chloroformate was then added and the reaction was allowed to warm to room temperature and then stir for an addition 1 hours. At this stage, the reaction was almost complete and was worked up by filtering, then washing with water (2×), followed by brine. The solution was then concentrated to produce a yellow oil and purified using column chromatography to give compound 30. $^1$H NMR (400 MHz, DMSO-$d_6$) δ 7.35 (d, J=2.4 Hz, 1H), 7.29 (dd, J=8.4, 2.4 Hz, 1H), 7.06 (d, J=8.4 Hz, 1H), 3.85 (s, 3H), 1.30 (s, 9H), 1.29 (s, 9H).

Method 2

To a reactor vessel charged with 4-dimethylaminopyridine (DMAP, 3.16 g, 25.7 mmol) and 2,4-ditert-butyl phenol (compound 29, 103.5 g, 501.6 mmol) was added methylene chloride (415 g, 313 mL) and the solution was agitated until all solids dissolved. Triethylamine (76 g, 751 mmol) was then added and the solution was cooled to 0-5° C. Methyl chloroformate (52 g, 550.3 mmol) was then added dropwise over 2.5-4 hours, while keeping the solution temperature between 0-5° C. The reaction mixture was then slowly heated to 23-28° C. and stirred for 20 hours. The reaction was then cooled to 10-15° C. and charged with 150 mL water. The mixture was stirred at 15-20° C. for 35-45 minutes and the aqueous layer was then separated and extracted with 150 mL methylene chloride. The organic layers were combined and neutralized with 2.5% HCl (aq) at a temperature of 5-20° C. to give a final pH of 5-6. The organic layer was then washed with water and concentrated in vacuo at a temperature below 20° C. to 150 mL to give compound 30 in methylene chloride.

Procedure for the Preparation of
5-nitro-2,4-di-tert-butylphenyl methyl carbonate
(31)

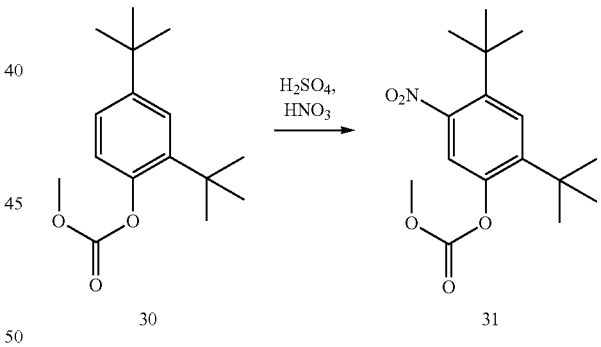

Method 1

To a stirred solution of compound 30 (6.77 g, 25.6 mmol) was added 6 mL of a 1:1 mixture of sulfuric acid and nitric acid at 0° C. dropwise. The mixture was allowed to warm to room temperature and stirred for 1 hour. The product was purified using liquid chromatography (ISCO, 120 g, 0-7% EtOAc/Hexanes, 38 min) producing about an 8:1-10:1 mixture of regioisomers of compound 31 as a white solid. $^1$H NMR (400 MHz, DMSO-$d_6$) δ 7.63 (s, 1H), 7.56 (s, 1H), 3.87 (s, 3H), 1.36 (s, 9H), 1.32 (s, 9H). HPLC ret. time 3.92 min 10-99% $CH_3CN$, 5 min run; ESI-MS 310 m/z (MH)$^+$.

Method 2

To compound 30 (100 g, 378 mmol) was added DCM (540 g, 408 mL). The mixture was stirred until all solids dissolved, and then cooled to −5-0° C. Concentrated sulfuric acid (163 g) was then added dropwise, while maintaining the initial temperature of the reaction, and the mixture was stirred for 4.5 hours. Nitric acid (62 g) was then added dropwise over 2-4 hours while maintaining the initial temperature of the reaction, and was then stirred at this temperature for an additional 4.5 hours. The reaction mixture was then slowly added to cold water, maintaining a temperature below 5° C. The quenched reaction was then heated to 25° C. and the aqueous layer was removed and extracted with methylene chloride. The combined organic layers were washed with water, dried using $Na_2SO_4$, and concentrated to 124-155 mL. Hexane (48 g) was added and the resulting mixture was again concentrated to 124-155 mL. More hexane (160 g) was subsequently added to the mixture. The mixture was then stirred at 23-27° C. for 15.5 hours, and was then filtered. To the filter cake was added hexane (115 g), the resulting mixture was heated to reflux and stirred for 2-2.5 hours. The mixture was then cooled to 3-7° C., stirred for an additional 1-1.5 hours, and filtered to give compound 31 as a pale yellow solid.

Procedure for the Preparation of 5-amino-2,4-di-tert-butylphenyl methyl carbonate (32)

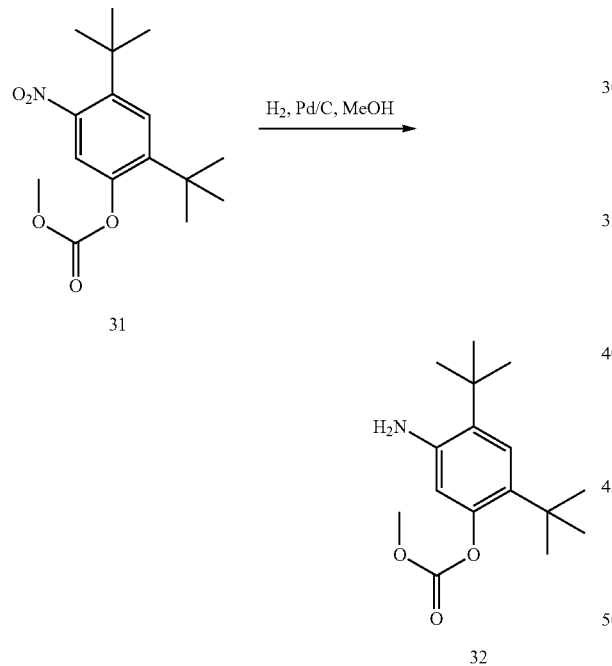

2,4-Di-tert-butyl-5-nitrophenyl methyl carbonate (1.00 eq) was charged to a suitable hydrogenation reactor, followed by 5% Pd/C (2.50 wt % dry basis, Johnson-Matthey Type 37). MeOH (15.0 vol) was charged to the reactor, and the system was closed. The system was purged with $N_2$ (g), and was then pressurized to 2.0 Bar with $H_2$ (g). The reaction was performed at a reaction temperature of 25° C.+/−5° C. When complete, the reaction was filtered, and the reactor/cake was washed with MeOH (4.00 vol). The resulting filtrate was distilled under vacuum at no more than 50° C. to 8.00 vol. Water (2.00 vol) was added at 45° C.+/−5° C. The resultant slurry was cooled to 0° C.+/−5. The slurry was held at 0° C.+/−5° C. for no less than 1 hour, and filtered. The cake was washed once with 0° C.+/−5° C. MeOH/$H_2O$ (8:2) (2.00 vol). The cake was dried under vacuum (−0.90 bar and −0.86 bar) at 35° C.-40° C. to give compound 32. $^1$H NMR (400 MHz, DMSO-$d_6$) δ 7.05 (s, 1H), 6.39 (s, 1H), 4.80 (s, 2H), 3.82 (s, 3H), 1.33 (s, 9H), 1.23 (s, 9H).

Once the reaction was complete, the resulting mixture was diluted with from about 5 to 10 volumes of MeOH (e.g., from about 6 to about 9 volumes of MeOH, from about 7 to about 8.5 volumes of MeOH, from about 7.5 to about 8 volumes of MeOH, or about 7.7 volumes of MeOH), heated to a temperature of about 35±5° C., filtered, washed, and dried, as described above.

Preparation of N-(2,4-di-tert-butyl-5-hydroxyphenyl)-4-oxo-1,4-dihydroquinoline-3-carboxamide (Compound 2)

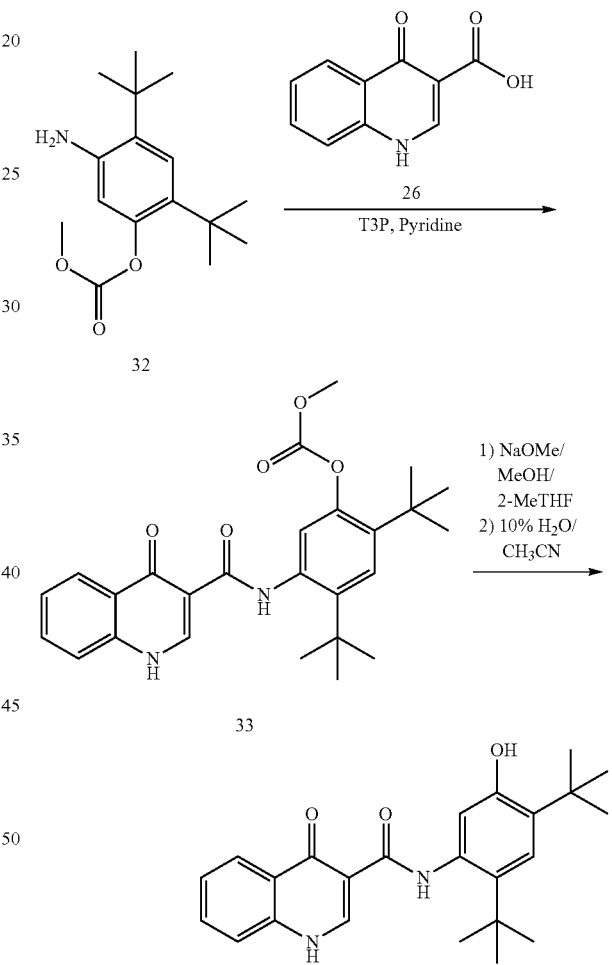

4-Oxo-1,4-dihydroquinoline-3-carboxylic acid, 26, (1.0 eq) and 5-amino-2,4-di-tert-butylphenyl methyl carbonate, 32, (1.1 eq) were charged to a reactor. 2-MeTHF (4.0 vol, relative to the acid) was added followed by T3P® 50% solution in 2-MeTHF (1.7 eq). The T3P charged vessel was washed with 2-MeTHF (0.6 vol). Pyridine (2.0 eq) was then added, and the resulting suspension was heated to 47.5+/−5.0° C. and held at this temperature for 8 hours. A sample was taken and checked for completion by HPLC. Once complete, the resulting mixture was cooled to 25.0° C.+/−2.5° C. 2-MeTHF was added (12.5 vol) to dilute the mixture. The reaction mixture was washed with water (10.0 vol) 2 times. 2-MeTHF was added to bring the total volume of reaction to 40.0 vol (~16.5 vol charged). To this solution was added NaOMe/MeOH (1.7 equiv) to perform the methanolysis. The reaction was stirred for no less than 1.0 hour, and checked for completion by HPLC. Once complete, the reaction was quenched with 1 N HCl (10.0 vol), and washed with 0.1 N HCl (10.0 vol). The organic solution was polish filtered to remove any particulates and placed in a second reactor. The filtered solution was concentrated at no more than 35° C. (jacket temperature) and no less than 8.0° C. (internal reaction temperature) under reduced pressure to 20 vol. $CH_3CN$ was added to 40 vol and the solution concentrated at no more than 35° C. (jacket temperature) and no less than 8.0° C. (internal reaction temperature) to 20 vol. The addition of $CH_3CN$ and concentration cycle was repeated 2 more times for a total of 3 additions of $CH_3CN$ and 4 concentrations to 20 vol. After the final concentration to 20 vol, 16.0 vol of $CH_3CN$ was added followed by 4.0 vol of $H_2O$ to make a final concentration of 40 vol of 10% $H_2O/CH_3CN$ relative to the starting acid. This slurry was heated to 78.0° C.+/−5.0° C. (reflux). The slurry was then stirred for no less than 5 hours. The slurry was cooled to 0.0° C.+/−5.0° C. over 5 hours, and filtered. The cake was washed with 0.0° C.+/−5.0° C. $CH_3CN$ (5 vol) 4 times. The resulting solid (Compound 2) was dried in a vacuum oven at 50.0° C.+/−5.0° C. $^1H$ NMR (400 MHz, DMSO-$d_6$) δ 12.8 (s, 1H), 11.8 (s, 1H), 9.2 (s, 1H), 8.9 (s, 1H), 8.3 (s, 1H), 7.2 (s, 1H), 7.9 (t, 1H), 7.8 (d, 1H), 7.5 (t, 1H), 7.1 (s, 1H), 1.4 (s, 9H), 1.4 (s, 9H).

Alternative Preparation of N-(2,4-di-tert-butyl-5-hydroxyphenyl)-4-oxo-1,4-dihydroquinoline-3-carboxamide (Compound 2)

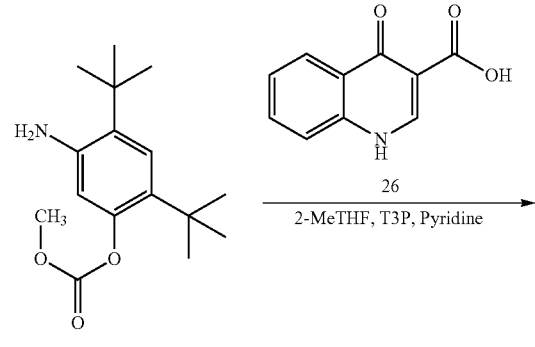

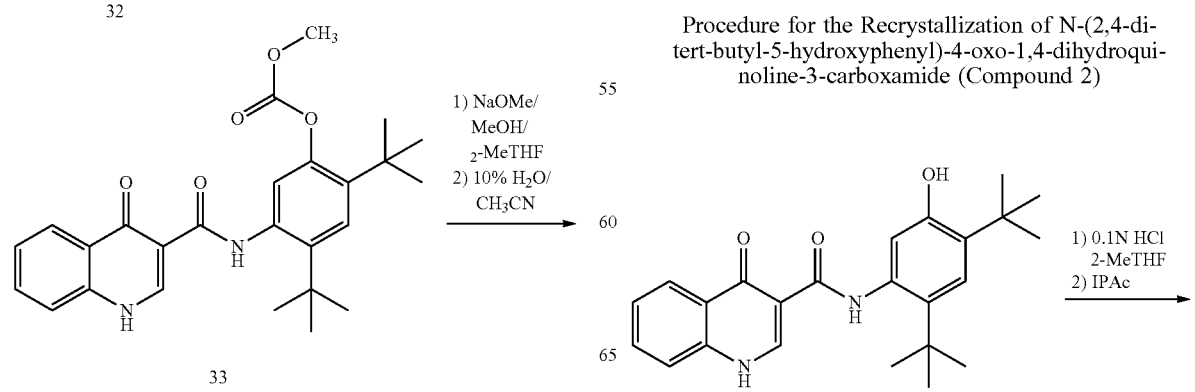

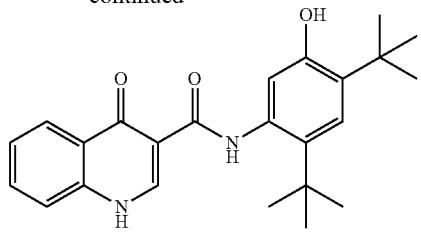

Compound 2

4-Oxo-1,4-dihydroquinoline-3-carboxylic acid, 26, (1.0 eq) and 5-amino-2,4-di-tert-butylphenyl methyl carbonate, 32, (1.1 eq) were charged to a reactor. 2-MeTHF (4.0 vol, relative to the acid) was added followed by T3P' 50% solution in 2-MeTHF (1.7 eq). The T3P charged vessel was washed with 2-MeTHF (0.6 vol). Pyridine (2.0 eq) was then added, and the resulting suspension was heated to 47.5+/−5.0° C. and held at this temperature for 8 hours. A sample was taken and checked for completion by HPLC. Once complete, the resulting mixture was cooled to 20° C.+/−5° C. 2-MeTHF was added (12.5 vol) to dilute the mixture. The reaction mixture was washed with water (10.0 vol) 2 times and 2-MeTHF (16.5 vol) was charged to the reactor. This solution was charged with 30% w/w NaOMe/MeOH (1.7 equiv) to perform the methanolysis. The reaction was stirred at 25.0° C.+/−5.0° C. for no less than 1.0 hour, and checked for completion by HPLC. Once complete, the reaction was quenched with 1.2 N HCl/$H_2O$ (10.0 vol), and washed with 0.1 N HCl/$H_2O$ (10.0 vol). The organic solution was polish filtered to remove any particulates and placed in a second reactor.

The filtered solution was concentrated at no more than 35° C. (jacket temperature) and no less than 8.0° C. (internal reaction temperature) under reduced pressure to 20 vol. $CH_3CN$ was added to 40 vol and the solution concentrated at no more than 35° C. (jacket temperature) and no less than 8.0° C. (internal reaction temperature) to 20 vol. The addition of $CH_3CN$ and concentration cycle was repeated 2 more times for a total of 3 additions of $CH_3CN$ and 4 concentrations to 20 vol. After the final concentration to 20 vol, 16.0 vol of $CH_3CN$ was charged followed by 4.0 vol of $H_2O$ to make a final concentration of 40 vol of 10% $H_2O/CH_3CN$ relative to the starting acid. This slurry was heated to 78.0° C.+/−5.0° C. (reflux). The slurry was then stirred for no less than 5 hours. The slurry was cooled to 20 to 25° C. over 5 hours, and filtered. The cake was washed with $CH_3CN$ (5 vol) heated to 20 to 25° C. 4 times. The resulting solid (Compound 2) was dried in a vacuum oven at 50.0° C.+/−5.0° C. $^1H$ NMR (400 MHz, DMSO-$d_6$) δ 12.8 (s, 1H), 11.8 (s, 1H), 9.2 (s, 1H), 8.9 (s, 1H), 8.3 (s, 1H), 7.2 (s, 1H), 7.9 (t, 1H), 7.8 (d, 1H), 7.5 (t, 1H), 7.1 (s, 1H), 1.4 (s, 9H), 1.4 (s, 9H).

Procedure for the Recrystallization of N-(2,4-di-tert-butyl-5-hydroxyphenyl)-4-oxo-1,4-dihydroquinoline-3-carboxamide (Compound 2)

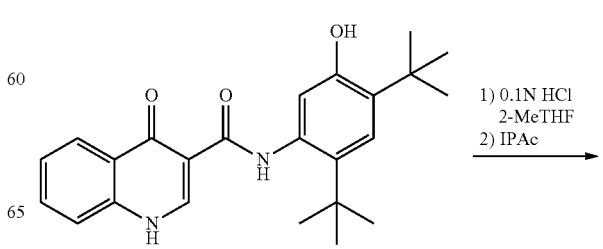

-continued

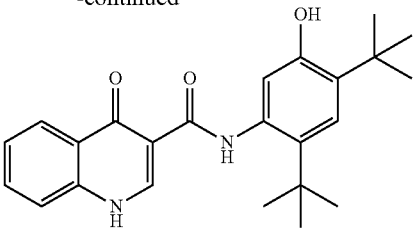

Compound 2 (1.0 eq) was charged to a reactor. 2-MeTHF (20.0 vol) was added followed by 0.1N HCl (5.0 vol). The biphasic solution was stirred and separated and the top organic phase was washed twice more with 0.1N HCl (5.0 vol). The organic solution was polish filtered to remove any particulates and placed in a second reactor. The filtered solution was concentrated at no more than 35° C. (jacket temperature) and no more than 8.0° C. (internal reaction temperature) under reduced pressure to 10 vol. Isopropyl acetate (IPAc) (10 vol) was added and the solution concentrated at no more than 35° C. (jacket temperature) and no more than 8.0° C. (internal reaction temperature) to 10 vol. The addition of IPAc and concentration was repeated 2 more times for a total of 3 additions of IPAc and 4 concentrations to 10 vol. After the final concentration, 10 vol of IPAc was charged and the slurry was heated to reflux and maintained at this temperature for 5 hours. The slurry was cooled to 0.0° C.+/−5° C. over 5 hours and filtered. The cake was washed with IPAc (5 vol) once. The resulting solid was dried in a vacuum oven at 50.0° C.+/−5.0° C.

Preparation of a Solid Dispersion Comprising Substantially Amorphous Compound 2

A solvent system of MEK and DI water, formulated according to the ratio 90 wt % MEK/10 wt % DI water, was heated to a temperature of 20-30° C. in a reactor, equipped with a magnetic stirrer and thermal circuit. Into this solvent system, hypromellose acetate succinate polymer (HPMCAS)(HG grade), SLS, and Compound 2 were added according to the ratio 19.5 wt % hypromellose acetate succinate/0.5 wt % SLS/80 wt % Compound 2. The resulting mixture contained 10.5 wt % solids. The actual amounts of ingredients and solvents used to generate this mixture are recited in Table 5, below:

TABLE 5

Solid Spray Dispersion Ingredients for Intermediate F.

|  | Units | Batch |
| --- | --- | --- |
| Compound 2 | Kg | 70.0 |
| HPMCAS | Kg | 17.1 |
| SLS | Kg | 0.438 |
| Total Solids | Kg | 87.5 |
| MEK | Kg | 671 |
| Water | Kg | 74.6 |
| Total Solvents | Kg | 746 |
| Total Spray Solution Weight | Kg | 833 |

The mixture temperature was adjusted to a range of 20-45° C. and mixed until it was substantially homogenous and all components were substantially dissolved.

A spray drier, Niro PSD4 Commercial Spray Dryer, fitted with pressure nozzle (Spray Systems Maximum Passage series SK-MFP having orifice/core size 54/21) equipped with anti-bearding cap, was used under normal spray drying mode, following the dry spray process parameters recited in Table 6, below.

TABLE 6

Dry spray process parameters used to generate Intermediate F.

| Parameter | Value |
| --- | --- |
| Feed Pressure | 20 bar |
| Feed Flow Rate | 92-100 Kg/hr |
| Inlet Temperature | 93-99° C. |
| Outlet Temperature | 53-57° C. |
| Vacuum Dryer Temperature | 80° C. for 2 hours then 110° C. (+/−5° C.) |
| Vacuum Drying Time | 20-24 hours |

A high efficiency cyclone separated the wet product from the spray gas and solvent vapors. The wet product contained 8.5-9.7% MEK and 0.56-0.83% Water and had a mean particle size of 17-19 um and a bulk density of 0.27-0.33 g/cc. The wet product was transferred to a 4000L stainless steel double cone vacuum dryer for drying to reduce residual solvents to a level of less than about 5000 ppm and to generate dry spray dry dispersion of amorphous Compound 2, containing <0.03% MEK and 0.3% Water.

Tablet Formation from a Fully Continuous Wet Granulation Process

Equipment/Process

Equipment

Fully Continuous Development and Launch Rig (DLR) or similar type of equipment.

Screening

Compound 1 Form I, the solid dispersion comprising substantially amorphous Compound 2, and excipients may be dispensed in separate intermediate bin containers (IBCs). These materials may be screened using a "bin-to-bin" screening operation. Appropriate screen sizes are mesh 20, mesh 40, or mesh 60.

Blending

The IBCs containing the screened Compound 1 Form I, the solid dispersion comprising substantially amorphous Compound 2, and excipients may be docked to the a feeder system, which can feed the materials in a controlled manner, e.g. using volumetric or gravimetric loss in weight feeders, into a continuous blender. The feed rates of the individual components is defined by the formulation composition and the overall line rate. The line rate may be 8 kg/hr to 30 kg/hr. The continuous blender can have different blade configurations to allow appropriate blending and the rotational speed of these blades may be between 80 RPM and 300 RPM.

Wet Granulation

A granulation solution may be prepared by dissolving 48 g sodium lauryl sulfate and 159 g polyvinylpyrrolidone in 1,626 g water in a stainless steel container, using an overhead stirrer with a stirring speed of 700 RPM. The granulation solution may be placed in a container from which the solution may be pumped into the twin screw granulator using a peristaltic pump with a mass flow meter and control, using a flow rate that is appropriate for the process. The blend may be granulated using a twin screw granulator such as the granulator that is part of the DLR. The blend may be added to the twin screw granulator using a Loss in Weight feeder, such as the K-Tron feeder on the DLR, with a feed rate of 8 kg/hr to 24 kg/hr. The twin screw granulator may be operated with a barrel temperature of 25 degrees Celsius and a screw speed of 200 to 950 RPM. The granulation process may be performed for three minutes for small batch sizes or several hours for large batch sizes.

Drying

The wet granules may be fed directly into a fluid bed dryer, such as the segmented fluid bed dryer on the DLR. The drying end-point may be chosen at a product temperature during discharge ranging from 40 to 55 degrees Celsius at which point the water content of the granules may be 2.1% w/w ("Loss on Drying, LOD") or less. The drying time may be 12 minutes, or shorter or longer, to reach the desired drying endpoint.

Milling

The dried granules may be milled to reduce the size of the granules. A cone mill such as the integrated Quadro U 10 CoMil may be used for this.

Blending

The granules may be blended with extra-granular excipients such as fillers and lubricant using loss in weight feeders and a continuous blender. The blending speed may be 80-300 RPM.

Compression

The compression blend may be compressed into tablets using a single station or rotary tablet press, such as the Courtoy Modul P press, which is part of the DLR system, using appropriately sized tooling. The weight of the tablets for a dose of 200 mg of Compound 1 Form I and 125 mg of substantially amorphous Compound 2 may be about 500 or 600 mg.

Film Coating

Tablets may be film coated using the innovative Omega film coater, which is part of the DLR system. This coater enables fast film coating of sub-batches of 1 to 4 kg to allow continuous manufacturing.

Printing

Film coated tablets may be printed with a monogram on one or both tablet faces with, for example, an Ackley ramp printer.

The continuous process described above in one embodiment is enhanced by PAT techniques as described in Table 7. There are 6 PAT positions each of which includes a manual sampling port. In process samples can be obtained for investigational reasons, as needed, and also for PAT model maintenance, transfer, and validation. The PAT systems may be used for real time release testing (RTRT) and may also be employed for in process controls (IPC) and feedback/feed-forward control.

TABLE 7

| Location | Technology | Processing Step | Proposed Purpose | Role |
|---|---|---|---|---|
| PAT 1 | NIR | Dispensing/Charging | Build an NIR raw material library | IPC |
| PAT 2 | NIR | Initial blend | Blend uniformity | IPC |
| PAT 3 | NIR | Wet Granulation | Granule uniformity Moisture | IPC RTRT/IPC |
| | Laser Diffraction | Wet Granulation | Particle size distribution | RTRT |
| PAT 4 | NIR | Final blend | Blend uniformity Moisture | RTRT RTRT |
| PAT 5 | Raman | Compression | API form Identification | RTRT RTRT |
| | Tablet Tester | Compression | Weight Thickness Hardness | RTRT/IPC IPC RTRT/IPC |

TABLE 7-continued

| Location | Technology | Processing Step | Proposed Purpose | Role |
|---|---|---|---|---|
| PAT 6 | Raman | Coating | Coating thickness | IPC |

Meeting specifications may be done by RTRT as described in Table 8.

TABLE 8

| Final Product Attribute | PAT Position | In-Process Material | Measurement |
|---|---|---|---|
| Identity | PAT 5a (Raman) | Uncoated Tablet | Confirms spectrum matches the reference standard spectra |
| Assay | PAT 4 (NIR) | Final Blend | API Concentration |
| | PAT 5b (Tablet Tester) | Uncoated Tablet | Tablet Weight |
| CU | PAT 4 (NIR) | Final Blend | Variance in API concentration |
| | PAT 5b (Tablet Tester) | Uncoated Tablet | Variance in tablet weight |
| Dissolution | May include: PAT 3b (Laser Diffraction) | Milled granules | May include: Granule Particle Size |
| | PAT 4 (NIR) | Final Blend | API Concentration |
| | PAT 5b (Tablet Tester) | Uncoated Tablet | Tablet Weight, Hardness |
| Moisture | PAT 4 | Final Blend | Water Content |
| Form | PAT 5a (Raman) | Uncoated Tablet | Form I & Absence of Form II |

There is a high probability of detecting non-conforming material. For example, if model classification criterion is set at a minimum of 95% confidence and 800 tablets are tested during batch manufacture, 40 hour run with a sampling rate of 1 tablet every 3 minutes equals 800 tablets. Then, probability of passing a non-conforming batch is extremely low: $<(0.05)^n$, where n=# of samples, therefore the probability is $<1.5\times10^{-1041}$. Probability of not detecting non-conforming tablets resulting from a short term event ($\geq 3$ minutes) is as follows: 1 tablet (3 min event)→0.05 (probability of detection >0.95); 2 tablets (6 minute event) →0.0025 (probability of detection >0.9975).

PAT measurements can serve as surrogates for conventional end-testing directly via combining measurements to express attributes conventionally (i.e. as assay, CU, dissolution, etc.). Validation can be performed using ICH Q2 as guidance. Sequential off-line to on-line method development allows for the assessment of CQAs in a material sparing manner. Ultimately, RTRT will lead to ensuring product quality at a higher confidence level than conventional testing.

Tablet Formation from Twin Screw Wet Granulation Process

Equipment/Process

Equipment

Twin Screw Wet Granulators: ConsiGma-1, ConsiGma-25 or Leistritz nano.

Screening/Weighing

Compound 1 Form I, the solid dispersion comprising substantially amorphous Compound 2, and excipients may be screened prior to or after weigh-out. Appropriate screen sizes are mesh 20, mesh 40, or mesh 60. Compound 1 Form I and/or the solid dispersion comprising substantially amorphous Compound 2 may be pre-blended with one or more of the excipients to simplify screening.

Blending

Compound 1 Form I, the solid dispersion comprising substantially amorphous Compound 2, and excipients may be added to the blender in different order. The blending may be performed in a Turbula blender, a v-shell blender, or a bin blender. The components may be blended for 10 minutes.

Wet Granulation

A granulation solution may be prepared by dissolving 48 g sodium lauryl sulfate and 159 g polyvinylpyrrolidone in 1,626 g water in a stainless steel container, using an overhead stirrer with a stirring speed of 700 RPM. The blend may be granulated using a twin screw granulator such as the ConsiGma-1. The granulation solution may be added to the twin screw granulator using a peristaltic pump, such as the pump on the ConsiGma-1, with a feed rate of 67 g/min. The blend may be added to the twin screw granulator using a Loss in Weight feeder, such as the Brabender feeder on the ConsiGma-1, with a feed rate of 10 kg/hr. The twin screw granulator may be operated with a barrel temperature of 25 degrees Celsius and a screw speed of 400 RPM. The granulation process may be performed for four minutes. The granulation process may be performed for a shorter or longer duration of time to produce a smaller or larger amount of wet granules.

Drying

The wet granules may be fed directly into a fluid bed dryer, such as the drying chamber on the ConsiGma-1 or the segmented fluid bed dryer on the CTL-25. The drying end-point may be chosen at a product temperature of 43 degrees Celsius at which point the water content of the granules may be 1.6% w/w ("Loss on Drying, LOD"). The drying time may be 12 minutes, or shorter or longer, to reach the desired drying endpoint. The drying may be performed with an air flow of 59 m$^3$/min and inlet temperature of 60 degrees Celsius. Alternatively, the wet granules coming from the twin screw granulator may be collected into a bin or container for a certain period of time after which the wet granules are transferred to a separate stand-alone fluid bed dryer, such as the Vector Multi 15.

Milling

The dried granules may be milled to reduce the size of the granules. A cone mill such as the Quadro 194 CoMil may be used for this.

Blending

The granules may be blended with extra-granular excipients such as fillers and lubricant using a V-shell blender or a bin blender. The blending time may be 5, 3 or 1 minute(s).

Compression

The compression blend may be compressed into tablets using a single station or rotary tablet press, such as the Courtoy Modul P press, using 0.55'×0.33' oval shaped tooling. The weight of the tablets for a dose of 200 mg of Compound 1 Form I and 125 mg of substantially amorphous Compound 2 may be about 500 or 600 mg.

Film Coating

Tablets may be film coated using a pan coater, such as, for example a Thomas Engineering Compu-Lab coater. A trace amount of Carnauba wax may be added to improve tablet appearance and process ability.

Printing

Film coated tablets may be printed with a monogram on one or both tablet faces with, for example, a Hartnett Delta printer.

Tablet Formation from Continuous Twin Screw Wet Granulation Process

Equipment/Process

Equipment Granulator: ConsiGma or Leistritz or Thermo Fisher twin screw granulator.

Screening/Weighing

Compound 1 and excipients may be screened prior to or after weigh-out. Possible screen sizes are mesh 20, mesh 40, or mesh 60. Compound 1 may be pre-blended with one or more of the excipients to simplify screening.

Blending

Compound 1 and excipients may be added to the blender in different order. The blending may be performed in a Turbula blender, a v-shell blender, a bin blender, or a continuous blender. The components may be blended for 10 minutes for batch blenders or continuously for a continuous blender.

Granulation Operation

Granulation Fluid—SLS and binder are added to purified water and mixed until dissolved. A suitable ratio is 2.5% w/w SLS and 10.0% w/w PVP K30 in water.

Granulation—The blend containing Compound 1 and excipients may be dosed into the twin screw granulator using a Loss in Weight feeder at a rate of 10 kg/hr. The granulation fluid may be added using a peristaltic pump at a rate of 3.5 kg/hr. The granulator may be run at a speed of 400 RPM. A notable advantage of the present twin screw wet granulation process is using a granulation fluid that comprises both a surfactant and the binder for better granulation through increased wettability. In one embodiment, the surfactant is SLS. Another notable advantage is that because the process is continuous and at any moment in time only a limited amount of material is processed, the process can be well controlled and results in a high quality product.

Milling

The granules may be reduced in size using a screen mill or a cone mill, either before drying or after drying, or both.

Drying

The granules may be dried using a vacuum oven, tray dryer, bi-conical dryer, or fluid bed drier.

Blending

The granules may be blended with extra-granular excipients. The granules have been blended using a 300 liter bin blender for 60 revolutions.

Compression

The compression blend has been compressed into tablets using a Courtoy Modul P rotary press Film Coating Tablets may be film coated using a pan coater, such as, for example an O'Hara Labcoat.

Printing

Film coated tablets may be printed with a monogram on one or both tablet faces with, for example, a Hartnett Delta printer.

Assays

Protocol 1

Assays for Detecting and Measuring ΔF508-CFTR Potentiation Properties of Compounds Membrane Potential Optical Methods for Assaying ΔF508-CFTR Modulation Properties of Compounds The assay utilizes fluorescent voltage sensing dyes to measure changes in membrane potential using a fluorescent plate reader (e.g., FLIPR III, Molecular Devices, Inc.) as a readout for increase in functional ΔF508-CFTR in NIH 3T3 cells. The driving force for the response is the creation of a chloride ion gradient in conjunction with channel activation by a single liquid addition step after the cells have previously been treated with compounds and subsequently loaded with a voltage sensing dye.

Identification of Potentiator Compounds

To identify potentiators of ΔF508-CFTR, a double-addition HTS assay format was developed. This HTS assay utilizes fluorescent voltage sensing dyes to measure changes in membrane potential on the FLIPR III as a measurement for increase in gating (conductance) of ΔF508 CFTR in temperature-corrected ΔF508 CFTR NIH 3T3 cells. The driving force for the response is a Cl⁻ ion gradient in conjunction with channel activation with forskolin in a single liquid addition step using a fluorescent plate reader such as FLIPR III after the cells have previously been treated with potentiator compounds (or DMSO vehicle control) and subsequently loaded with a redistribution dye.

Solutions

Bath Solution #1: (in mM) NaCl 160, KCl 4.5, $CaCl_2$ 2, $MgCl_2$ 1, HEPES 10, pH 7.4 with NaOH.

Chloride-free bath solution: Chloride salts in Bath Solution #1 (above) are substituted with gluconate salts.

Cell Culture

NIH3T3 mouse fibroblasts stably expressing ΔF508-CFTR are used for optical measurements of membrane potential. The cells are maintained at 37° C. in 5% $CO_2$ and 90% humidity in Dulbecco's modified Eagle's medium supplemented with 2 mM glutamine, 10% fetal bovine serum, 1×NEAA, P-ME, 1× pen/strep, and 25 mM HEPES in 175 cm² culture flasks. For all optical assays, the cells were seeded at ~20,000/well in 384-well matrigel-coated plates and cultured for 2 hrs at 37° C. before culturing at 27° C. for 24 hrs. for the potentiator assay. For the correction assays, the cells are cultured at 27° C. or 37° C. with and without compounds for 16-24 hours.

Electrophysiological Assays for assaying ΔF508-CFTR modulation properties of compounds.

Ussing Chamber Assay

Ussing chamber experiments were performed on polarized airway epithelial cells expressing ΔF508-CFTR to further characterize the ΔF508-CFTR augmenters or inducers identified in the optical assays. Non-CF and CF airway epithelia were isolated from bronchial tissue, cultured as previously described (Galietta, L. J. V., Lantero, S., Gazzolo, A., Sacco, O., Romano, L., Rossi, G. A., & Zegarra-Moran, O. (1998) *In Vitro Cell. Dev. Biol.* 34, 478-481), and plated onto Costar® Snapwell™ filters that were precoated with NIH3T3-conditioned media. After four days the apical media was removed and the cells were grown at an air liquid interface for >14 days prior to use. This resulted in a monolayer of fully differentiated columnar cells that were ciliated, features that are characteristic of airway epithelia. Non-CF HBE were isolated from non-smokers that did not have any known lung disease. CF-HBE were isolated from patients homozygous for ΔF508.

HBE grown on Costar® Snapwell™ cell culture inserts were mounted in an Using chamber (Physiologic Instruments, Inc., San Diego, Calif.), and the transepithelial resistance and short-circuit current in the presence of a basolateral to apical Cl⁻ gradient ($I_{SC}$) were measured using a voltage-clamp system (Department of Bioengineering, University of Iowa, Iowa). Briefly, HBE were examined under voltage-clamp recording conditions ($V_{hold}$=0 mV) at 37° C. The basolateral solution contained (in mM) 145 NaCl, 0.83 $K_2HPO_4$, 3.3 $KH_2PO_4$, 1.2 $MgCl_2$, 1.2 $CaCl_2$, 10 Glucose, 10 HEPES (pH adjusted to 7.35 with NaOH) and the apical solution contained (in mM) 145 NaGluconate, 1.2 $MgCl_2$, 1.2 $CaCl_2$, 10 glucose, 10 HEPES (pH adjusted to 7.35 with NaOH).

Identification of Potentiator Compounds

Typical protocol utilized a basolateral to apical membrane Cl⁻ concentration gradient. To set up this gradient, normal ringers was used on the basolateral membrane, whereas apical NaCl was replaced by equimolar sodium gluconate (titrated to pH 7.4 with NaOH) to give a large Cl⁻ concentration gradient across the epithelium. Forskolin (10 μM) and all test compounds were added to the apical side of the cell culture inserts. The efficacy of the putative ΔF508-CFTR potentiators was compared to that of the known potentiator, genistein.

Patch-Clamp Recordings

Total Cl⁻ current in ΔF508-NIH3T3 cells was monitored using the perforated-patch recording configuration as previously described (Rae, J., Cooper, K., Gates, P., & Watsky, M. (1991) *J. Neurosci. Methods* 37, 15-26). Voltage-clamp recordings were performed at 22° C. using an Axopatch 200B patch-clamp amplifier (Axon Instruments Inc., Foster City, Calif.). The pipette solution contained (in mM) 150 N-methyl-D-glucamine (NMDG)-Cl, 2 $MgCl_2$, 2 $CaCl_2$, 10 EGTA, 10 HEPES, and 240 μg/mL amphotericin-B (pH adjusted to 7.35 with HCl). The extracellular medium contained (in mM) 150 NMDG-Cl, 2 $MgCl_2$, 2 $CaCl_2$, 10 HEPES (pH adjusted to 7.35 with HCl). Pulse generation, data acquisition, and analysis were performed using a PC equipped with a Digidata 1320 A/D interface in conjunction with Clampex 8 (Axon Instruments Inc.). To activate ΔF508-CFTR, 10 μM forskolin and 20 μM genistein were added to the bath and the current-voltage relation was monitored every 30 sec.

Identification of Potentiator Compounds

The ability of ΔF508-CFTR potentiators to increase the macroscopic ΔF508-CFTR Cl⁻ current ($I_{\Delta F508}$) in NIH3T3 cells stably expressing ΔF508-CFTR was also investigated using perforated-patch-recording techniques. The potentiators identified from the optical assays evoked a dose-dependent increase in $I\Delta_{F508}$ with similar potency and efficacy observed in the optical assays. In all cells examined, the reversal potential before and during potentiator application was around −30 mV, which is the calculated $E_{Cl}$ (−28 mV).

Cell Culture

NIH3T3 mouse fibroblasts stably expressing ΔF508-CFTR are used for whole-cell recordings. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 cm² culture flasks. For whole-cell recordings, 2,500-5,000 cells were seeded on poly-L-lysine-coated glass coverslips and cultured for 24-48 hrs at 27° C. before use to test the activity of potentiators; and incubated with or without the correction compound at 37° C. for measuring the activity of correctors.

Single-Channel Recordings

Gating activity of wt-CFTR and temperature-corrected ΔF508-CFTR expressed in NIH3T3 cells was observed using excised inside-out membrane patch recordings as previously described (Dalemans, W., Barbry, P., Champigny, G., Jallat, S., Dott, K., Dreyer, D., Crystal, R. G., Pavirani, A., Lecocq, J-P., Lazdunski, M. (1991) *Nature* 354, 526-528) using an Axopatch 200B patch-clamp amplifier (Axon Instruments Inc.). The pipette contained (in mM): 150 NMDG, 150 aspartic acid, 5 $CaCl_2$, 2 $MgCl_2$, and 10 HEPES (pH adjusted to 7.35 with Tris base). The bath contained (in mM): 150 NMDG-Cl, 2 $MgCl_2$, 5 EGTA, 10 TES, and 14 Tris base (pH adjusted to 7.35 with HCl). After excision, both wt- and ΔF508-CFTR were activated by adding 1 mM Mg-ATP, 75 nM of the catalytic subunit of cAMP-dependent protein kinase (PKA; Promega Corp. Madison, Wis.), and 10 mM NaF to inhibit protein phosphatases, which prevented current rundown. The pipette potential was maintained at 80 mV. Channel activity was analyzed from membrane patches containing ≤2 active channels. The maximum number of simultaneous openings determined the number of active channels during the course of an experiment. To determine the single-channel current amplitude, the data recorded from 120 sec of ΔF508-CFTR activity was filtered "off-line" at 100 Hz and then used to construct all-point amplitude histograms that were fitted with multigaussian functions using Bio-Patch Analysis software (Bio-Logic Comp. France). The total microscopic current and open probability ($P_o$) were determined from 120 sec of channel activity. The $P_o$ was determined using the Bio-Patch software or from the relationship $P_o=I/i(N)$, where I=mean current, i=single-channel current amplitude, and N=number of active channels in patch.

Cell Culture

NIH3T3 mouse fibroblasts stably expressing ΔF508-CFTR are used for excised-membrane patch-clamp recordings. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 $cm^2$ culture flasks. For single channel recordings, 2,500-5,000 cells were seeded on poly-L-lysine-coated glass coverslips and cultured for 24-48 hrs at 27° C. before use.

Protocol 2

Assays for Detecting and Measuring ΔF508-CFTR Correction Properties of Compounds Membrane potential optical methods for assaying ΔF508-CFTR modulation properties of compounds.

The optical membrane potential assay utilized voltage-sensitive FRET sensors described by Gonzalez and Tsien (See Gonzalez, J. E. and R. Y. Tsien (1995) "Voltage sensing by fluorescence resonance energy transfer in single cells" *Biophys J* 69(4): 1272-80, and Gonzalez, J. E. and R. Y. Tsien (1997) "Improved indicators of cell membrane potential that use fluorescence resonance energy transfer" *Chem Biol* 4(4): 269-77) in combination with instrumentation for measuring fluorescence changes such as the Voltage/Ion Probe Reader (VIPR) (See. Gonzalez, J. E., K. Oades, et al. (1999) "Cell-based assays and instrumentation for screening ion-channel targets" *Drug Discov Today* 4(9): 431-439).

These voltage sensitive assays are based on the change in fluorescence resonant energy transfer (FRET) between the membrane-soluble, voltage-sensitive dye, $DiSBAC_2(3)$, and a fluorescent phospholipid, CC2-DMPE, which is attached to the outer leaflet of the plasma membrane and acts as a FRET donor. Changes in membrane potential ($V_m$) cause the negatively charged $DiSBAC_2(3)$ to redistribute across the plasma membrane and the amount of energy transfer from CC2-DMPE changes accordingly. The changes in fluorescence emission were monitored using VIPR™ II, which is an integrated liquid handler and fluorescent detector designed to conduct cell-based screens in 96- or 384-well microtiter plates.

Identification of Correction Compounds

To identify small molecules that correct the trafficking defect associated with ΔF508-CFTR; a single-addition HTS assay format was developed. The cells were incubated in serum-free medium for 16 hrs at 37° C. in the presence or absence (negative control) of test compound. As a positive control, cells plated in 384-well plates were incubated for 16 hrs at 27° C. to "temperature-correct" ΔF508-CFTR. The cells were subsequently rinsed 3× with Krebs Ringers solution and loaded with the voltage-sensitive dyes. To activate ΔF508-CFTR, 10 μM forskolin and the CFTR potentiator, genistein (20 μM), were added along with $Cl^-$-free medium to each well. The addition of $Cl^-$-free medium promoted $Cl^-$ efflux in response to ΔF508-CFTR activation and the resulting membrane depolarization was optically monitored using the FRET-based voltage-sensor dyes.

Identification of Potentiator Compounds

To identify potentiators of ΔF508-CFTR, a double-addition HTS assay format was developed. During the first addition, a $Cl^-$-free medium with or without test compound was added to each well. After 22 sec, a second addition of $Cl^-$-free medium containing 2-10 M forskolin was added to activate ΔF508-CFTR. The extracellular $Cl^-$ concentration following both additions was 28 mM, which promoted $Cl^-$ efflux in response to ΔF508-CFTR activation and the resulting membrane depolarization was optically monitored using the FRET-based voltage-sensor dyes.

Solutions

Bath Solution #1: (in mM) NaCl 160, KCl 4.5, $CaCl_2$ 2, $MgCl_2$ 1, HEPES 10, pH 7.4 with NaOH.

Chloride-free bath solution: Chloride salts in Bath Solution #1 (above) are substituted with gluconate salts.

CC2-DMPE: Prepared as a 10 mM stock solution in DMSO and stored at −20° C.

$DiSBAC_2(3)$: Prepared as a 10 mM stock in DMSO and stored at −20° C.

Cell Culture

NIH3T3 mouse fibroblasts stably expressing ΔF508-CFTR are used for optical measurements of membrane potential. The cells are maintained at 37° C. in 5% $CO_2$ and 90% humidity in Dulbecco's modified Eagle's medium supplemented with 2 mM glutamine, 10% fetal bovine serum, 1×NEAA, 13-ME, 1× pen/strep, and 25 mM HEPES in 175 $cm^2$ culture flasks. For all optical assays, the cells were seeded at 30,000/well in 384-well matrigel-coated plates and cultured for 2 hrs at 37° C. before culturing at 27° C. for 24 hrs for the potentiator assay. For the correction assays, the cells are cultured at 27° C. or 37° C. with and without compounds for 16-24 hours.

Electrophysiological Assays for assaying ΔF508-CFTR modulation properties of compounds Ussing Chamber Assay Using chamber experiments were performed on polarized epithelial cells expressing ΔF508-CFTR to further characterize the ΔF508-CFTR augmenters or inducers identified in the optical assays. $FRT^{\Delta F508-CFTR}$ epithelial cells grown on Costar Snapwell cell culture inserts were mounted in an Ussing chamber (Physiologic Instruments, Inc., San Diego, Calif.), and the monolayers were continuously short-circuited using a Voltage-clamp System (Department of Bioengineering, University of Iowa, Iowa, and, Physiologic Instruments, Inc., San Diego, Calif.). Transepithelial resistance was measured by applying a 2-mV pulse. Under these conditions, the FRT epithelia demonstrated resistances of 4 $K\Omega/cm^2$ or more. The solutions were maintained at 27° C. and bubbled with air. The electrode offset potential and fluid resistance were corrected using a cell-free insert. Under these conditions, the current reflects the flow of $Cl^-$ through ΔF508-CFTR expressed in the apical membrane. The $I_{SC}$ was digitally acquired using an MP100A-CE interface and AcqKnowledge software (v3.2.6; BIOPAC Systems, Santa Barbara, Calif.).

Identification of Correction Compounds

Typical protocol utilized a basolateral to apical membrane $Cl^-$ concentration gradient. To set up this gradient, normal ringer was used on the basolateral membrane, whereas apical NaCl was replaced by equimolar sodium gluconate (titrated to pH 7.4 with NaOH) to give a large Cl⁻ concentration gradient across the epithelium. All experiments were performed with intact monolayers. To fully activate ΔF508-CFTR, forskolin (10 µM) and the PDE inhibitor, IBMX (100 µM), were applied followed by the addition of the CFTR potentiator, genistein (50 µM).

As observed in other cell types, incubation at low temperatures of FRT cells stably expressing ΔF508-CFTR increases the functional density of CFTR in the plasma membrane. To determine the activity of correction compounds, the cells were incubated with 10 µM of the test compound for 24 hours at 37° C. and were subsequently washed 3× prior to recording. The cAMP- and genistein-mediated $I_{SC}$ in compound-treated cells was normalized to the 27° C. and 37° C. controls and expressed as percentage activity. Preincubation of the cells with the correction compound significantly increased the cAMP- and genistein-mediated $I_{SC}$ compared to the 37° C. controls.

Identification of Potentiator Compounds

Typical protocol utilized a basolateral to apical membrane Cl⁻ concentration gradient. To set up this gradient, normal ringers was used on the basolateral membrane and was permeabilized with nystatin (360 µg/ml), whereas apical NaCl was replaced with equimolar sodium gluconate (titrated to pH 7.4 with NaOH) to give a large Cl⁻ concentration gradient across the epithelium. All experiments were performed 30 min after nystatin permeabilization. Forskolin (10 µM) and all test compounds were added to both sides of the cell culture inserts. The efficacy of the putative ΔF508-CFTR potentiators was compared to that of the known potentiator, genistein.

Solutions

Basolateral solution (in mM): NaCl (135), CaCl₂ (1.2), MgCl₂ (1.2), K₂HPO₄ (2.4), KHPO₄ (0.6), N-2-hydroxyethylpiperazine-N'-2-ethanesulfonic acid (HEPES) (10), and dextrose (10). The solution was titrated to pH 7.4 with NaOH.

Apical solution (in mM): Same as basolateral solution with NaCl replaced with Na Gluconate (135).

Cell Culture

Fisher rat epithelial (FRT) cells expressing ΔF508-CFTR (FRT$^{\Delta F508-CFTR}$) were used for Ussing chamber experiments for the putative ΔF508-CFTR augmenters or inducers identified from our optical assays. The cells were cultured on Costar Snapwell cell culture inserts and cultured for five days at 37° C. and 5% CO₂ in Coon's modified Ham's F-12 medium supplemented with 5% fetal calf serum, 100 U/ml penicillin, and 100 µg/ml streptomycin. Prior to use for characterizing the potentiator activity of compounds, the cells were incubated at 27° C. for 16-48 hrs to correct for the ΔF508-CFTR. To determine the activity of corrections compounds, the cells were incubated at 27° C. or 37° C. with and without the compounds for 24 hours.

Whole-Cell Recordings

The macroscopic ΔF508-CFTR current ($I_{\Delta F508}$) in temperature- and test compound-corrected NIH3T3 cells stably expressing ΔF508-CFTR were monitored using the perforated-patch, whole-cell recording. Briefly, voltage-clamp recordings of $I_{\Delta F508}$ were performed at room temperature using an Axopatch 200B patch-clamp amplifier (Axon Instruments Inc., Foster City, Calif.). All recordings were acquired at a sampling frequency of 10 kHz and low-pass filtered at 1 kHz. Pipettes had a resistance of 5-6 MΩ when filled with the intracellular solution. Under these recording conditions, the calculated reversal potential for Cl⁻ ($E_{Cl}$) at room temperature was −28 mV. All recordings had a seal resistance >20 GΩ and a series resistance <15 MΩ. Pulse generation, data acquisition, and analysis were performed using a PC equipped with a Digidata 1320 A/D interface in conjunction with Clampex 8 (Axon Instruments Inc.). The bath contained <250 µl of saline and was continuously perifused at a rate of 2 ml/min using a gravity-driven perfusion system.

Identification of Correction Compounds

To determine the activity of correction compounds for increasing the density of functional ΔF508-CFTR in the plasma membrane, we used the above-described perforated-patch-recording techniques to measure the current density following 24-hr treatment with the correction compounds. To fully activate ΔF508-CFTR, 10 µM forskolin and 20 µM genistein were added to the cells. Under our recording conditions, the current density following 24-hr incubation at 27° C. was higher than that observed following 24-hr incubation at 37° C. These results are consistent with the known effects of low-temperature incubation on the density of ΔF508-CFTR in the plasma membrane. To determine the effects of correction compounds on CFTR current density, the cells were incubated with 10 µM of the test compound for 24 hours at 37° C. and the current density was compared to the 27° C. and 37° C. controls (% activity). Prior to recording, the cells were washed 3× with extracellular recording medium to remove any remaining test compound. Preincubation with 10 M of correction compounds significantly increased the cAMP- and genistein-dependent current compared to the 37° C. controls.

Identification of Potentiator Compounds

The ability of ΔF508-CFTR potentiators to increase the macroscopic ΔF508-CFTR Cl⁻ current ($I_{\Delta F508}$) in NIH3T3 cells stably expressing ΔF508-CFTR was also investigated using perforated-patch-recording techniques. The potentiators identified from the optical assays evoked a dose-dependent increase in $I_{\Delta F508}$ with similar potency and efficacy observed in the optical assays. In all cells examined, the reversal potential before and during potentiator application was around −30 mV, which is the calculated $E_{Cl}$ (−28 mV).

Solutions

Intracellular solution (in mM): Cs-aspartate (90), CsCl (50), MgCl₂ (1), HEPES (10), and 240 g/ml amphotericin-B (pH adjusted to 7.35 with CsOH).

Extracellular solution (in mM): N-methyl-D-glucamine (NMDG)-Cl (150), MgCl₂ (2), CaCl₂ (2), HEPES (10) (pH adjusted to 7.35 with HCl).

Cell Culture

NIH3T3 mouse fibroblasts stably expressing ΔF508-CFTR are used for whole-cell recordings. The cells are maintained at 37° C. in 5% CO₂ and 90% humidity in Dulbecco's modified Eagle's medium supplemented with 2 mM glutamine, 10% fetal bovine serum, 1×NEAA, β-ME, 1× pen/strep, and 25 mM HEPES in 175 cm² culture flasks. For whole-cell recordings, 2,500-5,000 cells were seeded on poly-L-lysine-coated glass coverslips and cultured for 24-48 hrs at 27° C. before use to test the activity of potentiators; and incubated with or without the correction compound at 37° C. for measuring the activity of correctors.

Single-Channel Recordings

The single-channel activities of temperature-corrected ΔF508-CFTR stably expressed in NIH3T3 cells and activities of potentiator compounds were observed using excised inside-out membrane patch. Briefly, voltage-clamp recordings of single-channel activity were performed at room temperature with an Axopatch 200B patch-clamp amplifier (Axon Instruments Inc.). All recordings were acquired at a sampling frequency of 10 kHz and low-pass filtered at 400 Hz. Patch pipettes were fabricated from Corning Kovar Sealing #7052 glass (World Precision Instruments, Inc., Sarasota, Fla.) and had a resistance of 5-8 MΩ when filled with the extracellular solution. The ΔF508-CFTR was activated after excision, by adding 1 mM Mg-ATP, and 75 nM of the cAMP-dependent protein kinase, catalytic subunit (PKA; Promega Corp. Madison, Wis.). After channel activity stabilized, the patch was perifused using a gravity-driven microperfusion system. The inflow was placed adjacent to the patch, resulting in complete solution exchange within 1-2 sec. To maintain ΔF508-CFTR activity during the rapid perifusion, the nonspecific phosphatase inhibitor $F^-$ (10 mM NaF) was added to the bath solution. Under these recording conditions, channel activity remained constant throughout the duration of the patch recording (up to 60 min). Currents produced by positive charge moving from the intra- to extracellular solutions (anions moving in the opposite direction) are shown as positive currents. The pipette potential ($V_p$) was maintained at 80 mV.

Channel activity was analyzed from membrane patches containing ≤2 active channels. The maximum number of simultaneous openings determined the number of active channels during the course of an experiment. To determine the single-channel current amplitude, the data recorded from 120 sec of ΔF508-CFTR activity was filtered "off-line" at 100 Hz and then used to construct all-point amplitude histograms that were fitted with multigaussian functions using Bio-Patch Analysis software (Bio-Logic Comp. France). The total microscopic current and open probability ($P_o$) were determined from 120 sec of channel activity. The $P_o$ was determined using the Bio-Patch software or from the relationship $P_o=I/i(N)$, where I=mean current, i=single-channel current amplitude, and N=number of active channels in patch.

Solutions

Extracellular solution (in mM): NMDG (150), aspartic acid (150), $CaCl_2$ (5), $MgCl_2$ (2), and HEPES (10) (pH adjusted to 7.35 with Tris base).

Intracellular solution (in mM): NMDG-Cl (150), $MgCl_2$ (2), EGTA (5), TES (10), and Tris base (14) (pH adjusted to 7.35 with HCl).

Cell Culture

NIH3T3 mouse fibroblasts stably expressing ΔF508-CFTR are used for excised-membrane patch-clamp recordings. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 $cm^2$ culture flasks. For single channel recordings, 2,500-5,000 cells were seeded on poly-L-lysine-coated glass coverslips and cultured for 24-48 hrs at 27° C. before use.

Compound 1 and Compound 2 of the invention are useful as augmenters or inducers of CFTR activity. Table 9 below illustrates the EC50 and relative efficacy of Compound 1 and Compound 2. In Table 9 below, the following meanings apply. EC50: "+++" means <10 uM; "++" means between 10 uM to 25 uM; "+" means between 25 uM to 60 uM. % Efficacy: "+" means <25%; "++" means between 25% to 100%; "+++" means >100%.

TABLE 9

| Cmpd. No. | EC50 (μM) | % Activity |
|---|---|---|
| 1 | +++ | +++ |
| 2 | +++ | ++ |

Other Embodiments

All publications and patents referred to in this disclosure are incorporated herein by reference to the same extent as if each individual publication or patent application were specifically and individually indicated to be incorporated by reference. Should the meaning of the terms in any of the patents or publications incorporated by reference conflict with the meaning of the terms used in this disclosure, the meaning of the terms in this disclosure are intended to be controlling. Furthermore, the foregoing discussion discloses and describes merely exemplary embodiments of the invention. One skilled in the art will readily recognize from such discussion and from the accompanying drawings and claims, that various changes, modifications and variations can be made therein without departing from the spirit and scope of the invention as defined in the following claims.

The invention claimed is:

1. A continuous process for preparing a tablet comprising 3-(6-(1-(2,2-difluorobenzo[d][1,3]dioxol-5-yl)cyclopropanecarboxamido)-3-methylpyridin-2-yl)benzoic acid ("Compound 1") Form I and a solid dispersion comprising substantially amorphous N-(5-hydroxy-2,4-ditert-butyl-phenyl)-4-oxo-1H-quinoline-3-carboxamide ("Compound 2") comprising the steps of:
   a) mixing Compound 1 Form I, a solid dispersion comprising substantially amorphous Compound 2, a filler, and a disintegrant in a blender to form a blend;
   b) preparing a granulation solution with water, a binder, and a surfactant;
   c) feeding the blend from step a) into a continuous twin screw granulator while adding the granulation solution from step b) to produce granules;
   d) drying the granules from step c) and milling them;
   e) blending the milled granules from step d) with a filler, disintegrant, and lubricant to form a blend; and
   f) compressing the blend from step e) into a tablet;
   wherein at least one of the above steps comprises process analytical technology; and
   wherein step f) comprises monitoring solid, form identity of Compound 1 and/or Compound 2 in the tablet using Raman spectroscopy.

2. The process of claim 1, wherein the process analytic technology comprises NIR and/or laser diffraction to monitor defined standards.

3. The process of claim 2, wherein the defined standard is selected from blend uniformity, granule uniformity, moisture, particle size distribution, active pharmaceutical ingredient solid form identity, weight, thickness, hardness, and coating thickness.

4. The process of claim 1, wherein step a) comprises monitoring blend uniformity using NIR.

5. The process of claim 1, wherein step c) comprises monitoring granule uniformity and/or moisture using NIR.

6. The process of claim 1, wherein step c) comprises monitoring particle size distribution using laser diffraction.

7. The process of claim 1, wherein step e) comprises monitoring blend uniformity and/or moisture using NIR.

8. The process of claim 1, wherein step f) further comprises monitoring tablet weight, thickness, and/or hardness using a tablet tester.

* * * * *